(12) United States Patent
Alberati-Giani et al.

(10) Patent No.: US 7,595,314 B2
(45) Date of Patent: Sep. 29, 2009

(54) BENZOYL-PIPERAZINE DERIVATIVES

(75) Inventors: Daniela Alberati-Giani, Zofingen (CH); Synese Jolidon, Blauen (CH); Robert Narquizian, St. Louis (FR); Matthias Heinrich Nettekoven, Grenzach-Wyhlen (DE); Roger David Norcross, Rheinfelden (CH); Emmanuel Pinard, Linsdorf (FR); Henri Stalder, Basel (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 12/177,386

(22) Filed: Jul. 22, 2008

(65) Prior Publication Data

US 2009/0192136 A1    Jul. 30, 2009

Related U.S. Application Data

(62) Division of application No. 10/933,103, filed on Sep. 2, 2004, now Pat. No. 7,427,612.

(30) Foreign Application Priority Data

Sep. 9, 2003    (EP) .................................. 03019686

(51) Int. Cl.
    A61K 31/5377    (2006.01)
    A61K 31/496     (2006.01)
    A61K 31/55      (2006.01)
    C07D 413/12     (2006.01)

(52) U.S. Cl. ............ 514/235.8; 514/236.5; 514/253.01; 514/252.02; 514/252.14; 540/575; 544/121; 544/194; 544/238; 544/295; 544/357; 544/360

(58) Field of Classification Search .................. None
    See application file for complete search history.

(56) References Cited

U.S. PATENT DOCUMENTS

| | | | |
|---|---|---|---|
| 3,933,802 | A | 1/1976 | Ferrini et al. |
| 4,244,871 | A | 1/1981 | Kosary et al. |
| 7,427,612 | B2 * | 9/2008 | Alberati-Giani et al. .......... 514/217.05 |
| 2005/0209241 | A1 | 9/2005 | Jolidon et al. |

FOREIGN PATENT DOCUMENTS

| | | |
|---|---|---|
| EP | 0 171 636 | 2/1986 |
| WO | WO 99/44596 | 9/1999 |
| WO | 2005/023260 | * 3/2005 |

OTHER PUBLICATIONS

Lewis D.A. & Lieberman J.A., Neuron. vol. 28, pp. 325-334 (2000).
Vandenberg R. J. & Aubrey K. R., Exp. Opin. Ther. Targets vol. 5(4) pp. 507-518 (2001).
Nakazato A. & Okuyama S., Exp. Opin. Ther. Patents vol. 10(1) pp. 75-98 (2000).
Sharma T., Br. J. Psychiatry, vol. 174 (Suppl. 38) pp. 44-51 (1999).
Javitt D. C. et al., Biol. Psychiatry, vol. 45 pp. 668-679 (1999).
Mohn A. R. et al., Cell vol. 98 pp. 427-436 (1999).
Bliss, T. V. & Collingridge G. L., Nature, vol. 361 pp. 31-39 (1993).
Tang J. P. et al., Nature, vol. 401, pp. 63-69 (1999).
Gainetdinov R. R. et al., Trends in Pharm. Sci. vol. 23(8) pp. 367-373 (2002).
Lopez-Corcuera B, et al., Mol. Mem. Biol. vol. 18 pp. 13-20 (2001).
Bergeron R. et al., Proc. Natl. Acad. Sci. USA vol. 95, pp. 15730-15734 (1998).
Chen et al., J. Neurophysiol. vol. 89(2) pp. 691-703 (2003).
Armer R. E. & Miller D. J., Exp. Opin. Ther. Patents vol. 11(4) pp. 563-572 (2001).
Pralong E. et al., Prog. Neurobiol. vol. 67, pp. 173-202 (2002).
Carlsson M. L., J. Neural Trans. vol. 105, pp. 525-535 (1998).
Chemical Abstracts Service, Apr. 23, 2003, XP002308402, Database accession No. 2003: 2142911 Chemcats & Catalog: AsInExExpress Gold.
Chemical Abstracts Service, Jun. 6, 2003, XP002308481 & Database Chemcats.
Chemical Abstracts Service, Jan. 1, 2004, XP002308405, Database accession No. 2003:2872406 Chemcats & Catalog: Ambinter Stock Screening Collection.
Chemical Abstracts Service, Jan. 1, 2004, XP002308403, Database accession No. 2004:591813 & Catalog: Ambinter Stock Screening Collection.
Chemical Abstracts Service, Jan. 1, 2004, XP002308404, Database accession No. 2004:660630 & Catalog: Ambinter Screening Library.

* cited by examiner

*Primary Examiner*—Emily Bernhardt
(74) *Attorney, Agent, or Firm*—George W. Johnston; Patricia S. Rocha-Tramaloni; Kimberly J. Prior

(57) ABSTRACT

A compound of formula wherein the substituents are as described in the specification for the treatment of psychoses, pain, neurodegenerative disfunction in memory and learning, schizophrenia, dementia and other diseases in which cognitive processes are impaired, such as attention deficit disorders or Alzheimer's disease.

28 Claims, No Drawings

BENZOYL-PIPERAZINE DERIVATIVES

PRIORITY TO RELATED APPLICATIONS

This application is a division of U.S. application Ser. No. 10/933,103, filed Sep. 2, 2004, now U.S. Pat. No. 7,427,612, which claims the benefit of European Application No. 03019686.9, filed Sep. 9, 2003. The entire contents of the above-identified applications are hereby incorporated by reference.

FIELD OF THE INVENTION

The present invention relates to the treatment of central nervous system diseases, such as psychoses, dysfunction in memory and learning, schizophrenia, dementia, attention deficit disorders, and Alzheimer's disease. More particularly, the invention relates to inhibition of Glyt-1 through activation of NMDA receptors.

BACKGROUND OF THE INVENTION

Schizophrenia is a progressive and devastating neurological disease characterized by episodic positive symptoms such as delusions, hallucinations, thought disorders and psychosis and persistent negative symptoms such as flattened affect, impaired attention and social withdrawal, and cognitive impairments (Lewis D A and Lieberman J A, Neuron, 28:325-33, 2000). For decades research has focused on the "dopaminergic hyperactivity" hypothesis which has led to therapeutic interventions involving blockade of the dopaminergic system (Vandenberg R J and Aubrey K R., Exp. Opin. Ther. Targets, 5(4): 507-518, 2001; Nakazato A and Okuyama S, et al., Exp. Opin. Ther. Patents, 10(1): 75-98, 2000). This pharmacological approach poorly address negative and cognitive symptoms which are the best redictors of functional outcome (Sharma T., Br. J. Psychiatry, 174 (suppl. 28): 44-51, 1999).

A complementary model of schizophrenia was proposed in the mid-1960' based upon the psychotomimetic action caused by the blockade of the glutamate system by compounds like phencyclidine (PCP) and related agents (ketamine) which are non-competitive NMDA receptor antagonists. Interestingly in healthy volunteers, PCP-induced psychotomimetic action incorporates positive and negative symptoms as well as cognitive dysfunction, thus closely resembling schizophrenia in patients (Javitt D C et al., Biol. Psychiatry, 45: 668-679, 1999). Furthermore transgenic mice expressing reduced levels of the NMDAR1 subunit displays behavioral abnormalities similar to those observed in pharmacologically induced models of schizophrenia, supporting a model in which reduced NMDA receptor activity results in schizophrenia-like behavior (Mohn A R et al., Cell, 98: 427-236, 1999).

Glutamate neurotransmission, in particular NMDA receptor activity, plays a critical role in synaptic plasticity, learning and memory, such as the NMDA receptors appears to serve as a graded switch for gating the threshold of synaptic plasticity and memory formation (Wiley, N Y; Bliss T V and Collingridge G L, Nature, 361: 31-39, 1993). Transgenic mice overexpressing the NMDA NR2B subunit exhibit enhanced synaptic plasticity and superior ability in learning and memory (Tang J P et al., Natur, 401-63-69, 1999).

Thus, if a glutamate deficit is implicate in the pathophysiology of schizophrenia, enhancing glutamate transmission, in particular via NMDA receptor activation, would be predicted to produce both anti-psychotic and cognitive enhancing effects.

The amino acid glycine is known to have at least two important functions in the CNS. It acts as an inhibitory amino acid, binding to strychnine sensitive glycine receptors, and it also influences excitatory activity, acting as an essential co-agonist with glutamate for N-methyl-D-aspartate (NMDA) receptor function. While glutamate is released in an activity-dependent manner from synaptic terminals, glycine is apparently present at a more constant level and seems to modulate/control the receptor for its response to glutamate.

One of the most effective ways to control synaptic concentrations of neurotransmitter is to influence their re-uptake at the synapses. Neurotransmitter transporters by removing neurotransmitters from the extracellular space, can control their extracellular lifetime and thereby modulate the magnitude of the synaptic transmission (Gainetdinov R R et al, Trends in Pharm. Sci., 23(8): 367-373, 2002).

Glycine transporters, which form part of the sodium and chloride family of neurotransmitter transporters, play an important role in the termination of post-synaptic glycinergic actions and maintenance of low extracellular glycine concentration by re-uptake of glycine into presynaptic nerve terminals and surrounding fine glial processes.

Two distinct glycine transporter genes have been cloned (GlyT-1 and GlyT-2) from mammalian brain, which give rise to two transporters with ~50% amino acid sequence homology. GlyT-1 presents four isoforms arising from alternative splicing and alternative promoter usage (1a, 1b, 1c and 1d). Only two of these isoforms have been found in rodent brain (GlyT-1a and GlyT-1b). GlyT-2 also presents some degree of heterogeneity. Two GlyT-2 isoforms (2a and 2b) have been identified in rodent brains. GlyT-1 is known to be located in CNS and in peripheral tissues, whereas GlyT-2 is specific to the CNS. GlyT-1 has a predominantly glial distribution and is found not only in areas corresponding to strychnine sensitive glycine receptors but also outside these areas, where it has been postulated to be involved in modulation of NMDA receptor function (Lopez-Corcuera B et al., Mol. Mem. Biol., 18: 13-20, 2001). Thus, one strategy to enhance NMDA receptor activity is to elevate the glycine concentration in the local microenvironment of synaptic NMDA receptors by inhibition of GlyT-1 transporter (Bergereon R. et al., Proc. Natl. Acad. Sci. USA, 95: 15730-15734, 1998; Chen L. et al., J. Neurophysiol., 89(2): 691-703, 2003).

Glycine transporters inhibitors are suitable for the treatment of neurological and neuropsychiatric disorders. The majority of diseases states implicated are psychoses, schizophrenia (Armer R E and Miller D J, Exp. Opin. Ther. Patents, 11 (4): 563-572, 2001), psychotic mood disorders such as severe major depressive disorder, mood disorders associated with psychotic disorders such as acute mania or depression, associated with bipolar disorders and mood disorders, associated with schizophrenia, (Pralong E T et al., Prog. Neurobiol., 67: 173-202, 2002), autistic disorders (Carlsson M L, J. Neural Trans,. 105: 525-535, 1998), cognitive disorders such as dementias, including age related dementia and senile dementia of the Alzheimer type, memory disorders in a mammal, including a human, attention deficit disorders and pain (Armer R E and Miller D J, Exp. Opin. Ther. Patents, 11 (4): 563-572, 2001).

Thus, increasing activation of NMDA receptors via GlyT-1 inhibition may lead to agents that treat psychosis, schizophrenia, dementia and other diseases in which cognitive processes are impaired, such as attention deficit disorders or Alzheimer's disease.

SUMMARY OF THE INVENTION

The present invention provides compounds of formula I per se and pharmaceutically acceptable salts thereof, as well as methods for the manufacture of such compounds. Furthermore, the invention includes all racemic mixtures, all their corresponding enantiomers and/or optical isomers. The invention also provides compositions containing compounds of formula I, and methods for preparing such compositions. The invention further provides methods for the treatment of diseases related to activation of NMDA receptors via Glyt-1 inhibition. In particular, the invention provides methods for the control or prevention of illnesses such as psychoses, disfunction in memory and learning, schizophrenia, dementia and other diseases in which cognitive processes are impaired, such as attention deficit disorders or Alzheimer's disease.

In particular, the present invention provides compounds of formula I wherein

Ar is unsubstituted or substituted aryl or 6-membered heteroaryl containing one, two or three nitrogen atoms, and wherein the substituted aryl and the substituted heteroaryl groups are substituted by one or more substituents selected from the group consisting of hydroxy, halogen, $NO_2$, CN, $(C_1-C_6)$-alkyl, $(C_1-C_6)$-alkyl substituted by halogen, $(C_1-C_6)$-alkoxy, $(C_1-C_6)$-alkoxy substituted by halogen, $NR^7R^8$, $C(O)R^9$ and $SO_2R^{10}$;

$R^1$ is hydrogen or $(C_1-C_6)$-alkyl;

$R^2$ and $R^{2'}$ are each independently hydrogen,
  $(CR_2)_n$-hydroxy wherein R is hydrogen or $(C_1-C_6)$-alkyl,
  $(C_1-C_6)$-alkyl,
  $(C_2-C_6)$-alkenyl,
  $(C_1-C_6)$-alkyl substituted by halogen,
  $(CH_2)_n$—$(C_3-C_6)$-cycloalkyl,
  $(CH_2)_n$-heterocycloalkyl,
  $(CH_2)_n$—O—$(C_1-C_6)$-alkyl
  or $(CH_2)_n$-aryl or $R^2$ and $R^{2'}$ form together with the N atom to which they are attached a heterocycloalkyl ring, optionally containing in addition to the N atom a further heteroatom selected from the group consisting of N, S and O, which ring is unsubstituted or substituted by $(CH_2)_n$-hydroxy, $(C_1-C_6)$-alkyl, $(C_1-C_6)$-alkoxy, $(CH_2)_n$—O—$(C_1-C_6)$-alkyl, or $R^2$ and $R^{2'}$ form together with the N atom to which they are attached a 5-membered heteroaryl group, optionally containing in addition to the N atom one, two or three further nitrogen atoms and wherein the heteroaryl group is optionally substituted by $(C_1-C_6)$-alkyl;

$R^3$, $R^4$ and $R^6$ are each independently hydrogen, halogen, $(C_1-C_6)$-alkyl or $(C_1-C_6)$-alkoxy;

$R^5$ is $NO_2$, CN, $C(O)R^9$, S—$(C_1-C_6)$-alkyl, $SO_2R^{10}$ or $NR^{11}R^{12}$;

$R^7$ and $R^8$ are each independently hydrogen, $(CH_2)_n$—$(C_3-C_6)$-cycloalkyl or $(C_1-C_6)$-alkyl, or form together with the N atom to which they are attached a heterocycloalkyl ring, optionally containing in addition to the N atom a further heteroatom selected from the group consisting of N, S and O;

$R^9$ is hydroxy, $(C_1-C_6)$-alkyl, $(C_3-C_6)$-cycloalkyl, $(C_1-C_6)$-alkoxy or $NR^7R^8$;

$R^{10}$ is $(C_1-C_6)$-alkyl, $(CH_2)_n$—$(C_3-C_6)$-cycloalkyl or $NR^7R^8$;

$R^{11}$ and $R^{12}$ are each independently hydrogen, C(O)—$(C_1-C_6)$-alkyl, $SO_2$—$(C_1-C_6)$-alkyl, or form together with the N-atom to which they are attached a 5-membered heteroaryl group optionally containing in addition to the N atom one, two or three nitrogen atoms and wherein the heteroaryl group is optionally substituted by halogen, $(C_1-C_6)$-alkyl or $(CH_2)_n(C_3-C_6)$-cycloalkyl;

n is 0, 1 or 2;

or a pharmaceutically acceptable acid addition salt thereof, with the proviso that 1-[5-(aminosulfonyl)-2-(4-morpholinyl)benzoyl]-4-phenyl-piperazine, 1-(4-methoxyphenyl)-4-[2-(4-morpholinyl)-5-nitrobenzoyl]-piperazine, 1-[2-(4-morpholinyl)-5-nitrobenzoyl]-4-[2-nitro-4-(trifluoromethyl)phenyl]-piperazine, 1-(4-methoxyphenyl)-4-[5-nitro-2-(1-pyrrolidinyl)benzoyl]-piperazine, 1-[2-[4-(2-hydroxyethyl)-1-piperazinyl]-5-nitrobenzoyl]-4-(4-methoxyphenyl)-piperazine, 1-[2-fluoro-4-(1-oxopropyl)phenyl]-4-[5-nitro-2-(1-piperidinyl)benzoyl]-piperazine, 1-[2-fluoro-4-(1-oxopropyl)phenyl]-4-[5-nitro-2-(1-pyrrolidinyl)benzoyl]-piperazine, 1-[2-fluoro-4-(1-oxopropyl)phenyl]-4-[2-(4-methyl-1-piperidinyl)-5-nitrobenzoyl]-piperazine, 1-[2-fluoro-4-(1-oxopropyl)phenyl]-4-[2-(4-methyl-1-piperazinyl)-5-nitrobenzoyl]-piperazine, 1-[2-fluoro-4-(1-oxopropyl)phenyl]-4-[2-(4-morpholinyl)-5-nitrobenzoyl]-piperazine, 1-[5-[[methyl(phenylmethyl)amino]sulfonyl]-2-(4-morpholinyl)benzoyl]-4-(4-nitrophenyl)-piperazine and 1-(4-acetyl-2-fluorophenyl)-4-[2-(4-morpholinyl)-5-nitrobenzoyl]-piperazine, are excluded.

The compound 1-[5-(aminosulfonyl)-2-(4-morpholinyl)benzoyl]-4-phenyl-piperazine has been described specifically in U.S. Pat. No. 4,244,871, which possess tyrosine-paralyzing activity, and the other compounds mentioned above are commercially available products.

It has surprisingly been found that the compounds of general formula I are good inhibitors of the glycine transporter 1 (GlyT-1), and that they have a good selectivity to glycine transporter 2 (GlyT-2) inhibitors. Therefore, the present invention provides compounds of general formula I, to pharmaceutical composition containing them and their use in the treatment of neurological and neuropsychiatric disorders.

DETAILED DESCRIPTION OF THE INVENTION

The following definitions of general terms used herein apply irrespective of whether the terms in question appear alone or in combination. It must be noted that, as used in the specification and the appended claims, the singular forms "a", "an," and "the" include plural forms unless the context clearly dictates otherwise.

As used herein, the term "alkyl" denotes a saturated straight- or branched-chain group containing from 1 to 6 carbon atoms, for example, methyl, ethyl, propyl, isopropyl, n-butyl, i-butyl, 2-butyl, t-butyl and the like. Preferred alkyl groups are groups with 1-4 carbon atoms.

The term "alkoxy" denotes the residue —O—R, wherein R is a lower alkyl residue as defined herein. Examples of alkoxy radicals include, but are not limited to, methoxy, ethoxy, isopropoxy, and the like.

The term "alkenyl" denotes an unsaturated straight- or branched-chain group containing from 2 to 6 carbon atoms. Preferred alkenyl group is allyl.

The term "halogen" denotes chlorine, iodine, fluorine and bromine.

The term "cycloalkyl" denotes a saturated carbocyclic group, containing 3 to 7 carbon atoms. For example, a cycloalkyl group is cyclopropyl, cyclobutyl, cyclopentyl, cyclohexyl and cycloheptyl.

The term "aryl" denotes a monovalent cyclic aromatic hydrocarbon radical consisting of one or more fused rings in which at least one ring is aromatic in nature, for example phenyl or naphthyl.

The term "6-membered heteroaryl containing one, two or three nitrogen atoms" denotes a monovalent aromatic carbocyclic radical, for example pyridyl, pyrazinyl, pyrimidinyl, pyridazinyl or triazinyl.

The term "5-membered heteroaryl group optionally containing in addition to the N atom one, two or three further nitrogen atoms" denotes a monovalent aromatic carbocyclic radical, for example pyrrolyl, 2,5-dihydro-pyrrol-1-yl, imidazolyl, pyrazolyl, triazolyl, tetrazolyl.

The term "heterocycloalkyl" denotes a non aromatic hydrocarbon radical, for example azepanyl, oxetanyl, tetrahydrofuranyl, tetrahydropyranyl, azetidinyl; pyrrolidinyl, piperidinyl, piperazinyl, morpholinyl or thiomorpholinyl.

The term "pharmaceutically acceptable," such as pharmaceutically acceptable carrier, excipient, etc., denotes pharmacologically acceptable and substantially non-toxic to the subject to which the particular compound is administered.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluene-sulfonic acid and the like.

The term "therapeutically effective amount" denotes an amount that is effective to prevent, alleviate or ameliorate symptoms of disease or prolong the survival of the subject being treated.

The present invention provides compounds of formula I

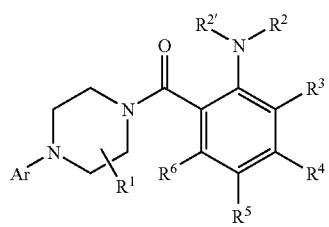

I wherein
Ar is unsubstituted or substituted aryl or 6-membered heteroaryl containing one, two or three nitrogen atoms, and wherein the substituted aryl and the substituted heteroaryl groups are substituted by one or more substituents selected from the group consisting of hydroxy, halogen, $NO_2$, CN, $(C_1-C_6)$-alkyl, $(C_1-C_6)$-alkyl substituted by halogen, $(C_1-C_6)$-alkoxy, $(C_1-C_6)$-alkoxy substituted by halogen, $NR^7R^8$, $C(O)R^9$ and $SO_2R^{10}$;

$R^1$ is hydrogen or $(C_1-C_6)$-alkyl;

$R^2$ and $R^{2'}$ are each independently hydrogen,
  $(CR_2)_n$-hydroxy wherein R is hydrogen or $(C_1-C_6)$-alkyl,
  $(C_1-C_6)$-alkyl,
  $(C_2-C_6)$-alkenyl,
  $(C_1-C_6)$-alkyl substituted by halogen,
  $(CH_2)_n$—$(C_3-C_6)$-cycloalkyl,
  $(CH_2)_n$-heterocycloalkyl,
  $(CH_2)_n$—O—$(C_1-C_6)$-alkyl
  or $(CH_2)_n$-aryl or $R^2$ and $R^{2'}$ form together with the N atom to which they are attached a heterocycloalkyl ring, optionally containing in addition to the N atom a further heteroatom selected from the group consisting of N, S and O, which ring is unsubstituted or substituted by $(CH_2)_n$-hydroxy, $(C_1-C_6)$-alkyl, $(C_1-C_6)$-alkoxy, $(CH_2)_n$—O—$(C_1-C_6)$-alkyl, or $R^2$ and $R^{2'}$ form together with the N atom to which they are attached a 5-membered heteroaryl group, optionally containing in addition to the N atom one, two or three further nitrogen atoms and wherein the heteroaryl group is optionally substituted by $(C_1-C_6)$-alkyl;

$R^3$, $R^4$ and $R^6$ are each independently hydrogen, halogen, $(C_1-C_6)$-alkyl or $(C_1-C_6)$-alkoxy;

$R^5$ is $NO_2$, CN, $C(O)R^9$, S—$(C_1-C_6)$-alkyl, $SO_2R^{10}$ or $NR^{11}R^{12}$;

$R^7$ and $R^8$ are each independently hydrogen, $(CH_2)_n$—$(C_3-C_6)$-cycloalkyl or $(C_1-C_6)$-alkyl, or form together with the N atom to which they are attached a heterocycloalkyl ring, optionally containing in addition to the N atom a further heteroatom selected from the group consisting of N, S and O;

$R^9$ is hydroxy, $(C_1-C_6)$-alkyl, $(C_3-C_6)$-cycloalkyl, $(C_1-C_6)$-alkoxy or $NR^7R^8$;

$R^{10}$ is $(C_1-C_6)$-alkyl, $(CH_2)_n$—$(C_3-C_6)$-cycloalkyl or $NR^7R^8$;

$R^{11}$ and $R^{12}$ are each independently hydrogen, C(O)—$(C_1-C_6)$-alkyl, $SO_2$—$(C_1-C_6)$-alkyl, or form together with the N-atom to which they are attached a 5-membered heteroaryl group optionally containing in addition to the N atom one, two or three nitrogen atoms and wherein the heteroaryl group is optionally substituted by halogen, $(C_1-C_6)$-alkyl or $(CH_2)_n(C_3-C_6)$-cycloalkyl;

n is 0, 1 or 2;

or a pharmaceutically acceptable acid addition salt thereof, with the proviso that 1-[5-(aminosulfonyl)-2-(4-morpholinyl)benzoyl]-4-phenyl-piperazine, 1-(4-methoxyphenyl)-4-[2-(4-morpholinyl)-5-nitrobenzoyl]-piperazine, 1-[2-(4-morpholinyl)-5-nitrobenzoyl-4-[2-nitro-4-(trifluoromethyl)phenyl]-piperazine, 1-(4-methoxyphenyl)-4-[5-nitro-2-(1-pyrrolidinyl)benzoyl]-piperazine, 1-[2-[4-(2-hydroxyethyl)-1-piperazinyl]-5-nitrobenzoyl]-4-(4-methoxyphenyl)-piperazine, 1-[2-fluoro-4-(1-oxopropyl)phenyl]-4-[5-nitro-2-(1-piperidinyl)benzoyl]-piperazine, 1-[2-fluoro-4-(1-oxopropyl)phenyl]-4-[5-nitro-2-(1-pyrrolidinyl)benzoyl]-piperazine, 1-[2-fluoro-4-(1-oxopropyl)phenyl]-4-[2-(4-methyl-1-piperidinyl)-5-nitrobenzoyl]-piperazine, 1-[2-fluoro-4-(1-oxopropyl)phenyl]-4-[2-(4-methyl-1-piperazinyl)-5-nitrobenzoyl]-piperazine, 1-[2-fluoro-4-(1-oxopropyl)phenyl]-4-[2-(4-morpholinyl)-5-nitrobenzoyl]-piperazine,
1-[5-[[methyl(phenylmethyl)amino]sulfonyl]-2-(4-morpholinyl)benzoyl]-4-(4-nitrophenyl)-piperazine and
1-(4-acetyl-2-fluorophenyl)-4-[2-(4-morpholinyl)-5-nitrobenzoyl]-piperazine, are excluded.

Preferred compounds of formula I are those of formula I-1 wherein
R' is hydroxy, halogen, $NO_2$, CN, $(C_1-C_6)$-alkyl, $(C_1-C_6)$-alkyl substituted by halogen, $(C_1-C_6)$-alkoxy, $(C_1-C_6)$-alkoxy substituted by halogen, $NR^7R^8$, $C(O)R^9$ or $SO_2R^{10}$;
m is 0, 1, 2 or 3;
$R^1$ is hydrogen or $(C_1-C_6)$-alkyl;
$R^2$ and $R^{2'}$ are each independently hydrogen,
  $(CR_2)_n$-hydroxy wherein R is hydrogen or $(C_1-C_6)$-alkyl,
  $(C_1-C_6)$-alkyl,
  $(C_2-C_6)$-alkenyl,
  $(C_1-C_6)$-alkyl substituted by halogen,
  $(CH_2)_n$—$(C_3-C_6)$-cycloalkyl,
  $(CH_2)_n$-heterocycloalkyl,
  $(CH_2)_n$—O—$(C_1-C_6)$-alkyl or
  $(CH_2)_n$-aryl;
$R^3$, $R^4$ and $R^6$ are each independently hydrogen, halogen, $(C_1-C_6)$-alkyl or $(C_1-C_6)$-alkoxy;
$R^5$ is $NO_2$, CN, $C(O)R^9$, S—$(C_1-C_6)$-alkyl, $SO_2R^{10}$ or $NR^{11}R^{12}$;
$R^7$ and $R^8$ are each independently hydrogen, $(CH_2)_n$—$(C_3-C_6)$-cycloalkyl or $(C_1-C_6)$-alkyl, or form together with the N atom to which they are attached a heterocycloalkyl ring, optionally containing in addition to the N atom a further heteroatom selected from the group consisting of N, S and O;
$R^9$ is hydroxy, $(C_1-C_6)$-alkyl, $(C_3-C_6)$-cycloalkyl, $(C_1-C_6)$-alkoxy or $NR^7R^8$;
$R^{10}$ is $(C_1-C_6)$-alkyl, $(CH_2)_n$—$(C_3-C_6)$-cycloalkyl or $NR^7R^8$;
$R^{11}$ and $R^{12}$ are each independently hydrogen, C(O)—$(C_1-C_6)$-alkyl, $SO_2$—$(C_1-C_6)$-alkyl, or form together with the N-atom to which they are attached a 5-membered heteroaryl group optionally containing in addition to the N atom one, two or three nitrogen atoms and wherein the heteroaryl group is optionally substituted by halogen, $(C_1-C_6)$-alkyl or $(CH_2)_n(C_3-C_6)$-cycloalkyl;
n is 0, 1 or 2;
or a pharmaceutically acceptable acid addition salt thereof.

The following compounds of formula I-1 are preferred:
1-(4-{4-[2-(cyclopropylmethyl-amino)-5-nitro-benzoyl]-piperazin-1-yl}-3-fluoro-phenyl)-ethanone,
1-{4-[4-(2-cyclohexylamino-5-nitro-benzoyl)-piperazin-1-yl]-3-fluoro-phenyl}-ethanone,
1-{4-[4-(2-diethylamino-5-nitro-benzoyl)-piperazin-1-yl]-3-fluoro-phenyl}-ethanone,
1-{3-fluoro-4-[4-(2-isobutylamino-5-nitro-benzoyl)-piperazin-1-yl]-phenyl}-ethanone,
1-{4-[4-(2-cyclobutylamino-5-nitro-benzoyl)-piperazin-1-yl]-3-fluoro-phenyl}-ethanone,
1-{4-[4-(2-cyclobutylamino-5-nitro-benzoyl)-piperazin-1-yl]-3-fluoro-phenyl}-ethanone,
1-{4-[4-(2-cyclopentylamino-5-nitro-benzoyl)-piperazin-1-yl]-3-fluoro-phenyl}-ethanone and
1-(4-{4-[2-(allyl-methyl-amino)-5-nitro-benzoyl]-piperazin-1-yl}-3-fluoro-phenyl)-ethanone.

Further preferred are compounds of formula I-2 wherein
R' is hydroxy, halogen, $NO_2$, CN, $(C_1-C_6)$-alkyl, $(C_1-C_6)$-alkyl substituted by halogen, $(C_1-C_6)$-alkoxy, $(C_1-C_6)$-alkoxy substituted by halogen, $NR^7R^8$, $C(O)R^9$ or $SO_2R^{10}$;
m is 0, 1, 2 or 3;
$R^1$ is hydrogen or $(C_1-C_6)$-alkyl;

is a heterocycloalkyl ring, optionally containing in addition to the N atom a further heteroatom, selected from the group consisting of N, S and O, which ring is unsubstituted or substituted by $(CH_2)_n$-hydroxy, $(C_1-C_6)$-alkyl, $(C_1-C_6)$-alkoxy, $(CH_2)_n$—O—$(C_1-C_6)$-alkyl, or is a 5-membered heteroaryl group, optionally containing in addition to the N atom one, two or three further nitrogen atoms and wherein the heteroaryl group is optionally substituted by $(C_1-C_6)$-alkyl;
$R^3$, $R^4$ and $R^6$ are each independently hydrogen, halogen, $(C_1-C_6)$-alkyl or $(C_1-C_6)$-alkoxy;
$R^5$ is $NO_2$, CN, $C(O)R^9$, S—$(C_1-C_6)$-alkyl, $SO_2R^{10}$ or $NR^{11}R^{12}$;
$R^7$ and $R^8$ are each independently hydrogen, $(CH_2)_n$—$(C_3-C_6)$-cycloalkyl or $(C_1-C_6)$-alkyl, or form together with the N atom to which they are attached a heterocycloalkyl ring, optionally containing in addition to the N atom a further heteroatom, selected from the group consisting of N, S and O;
$R^9$ is hydroxy, $(C_1-C_6)$-alkyl, $(C_3-C_6)$-cycloalkyl, $(C_1-C_6)$-alkoxy or $NR^7R^8$;
$R^{10}$ is $(C_1-C_6)$-alkyl, $(CH_2)_n$—$(C_3-C_6)$-cycloalkyl or $NR^7R^8$;
$R^{11}$ and $R^{12}$ are each independently hydrogen, C(O)—$(C_1-C_6)$-alkyl,
  $SO_2$—$(C_1-C_6)$-alkyl, or form together with the N-atom to which they are attached a 5-membered heteroaryl group optionally containing in addition to the N atom one, two or three nitrogen atoms and wherein the heteroaryl group is optionally substituted by halogen, $(C_1-C_6)$-alkyl or $(CH_2)_n(C_3-C_6)$-cycloalkyl;

n is 0, 1 or 2;

or a pharmaceutically acceptable acid addition salt thereof.

The following compounds of formula I-2 are preferred:

1-{4-[4-(2-morpholin-4-yl-5-nitro-benzoyl)-piperazin-1-yl]-3-fluoro-phenyl}-ethanone,
1-{3-fluoro-4-[4-(5-nitro-2-pyrrolidin-1-yl-benzoyl)-piperazin-1-yl]-phenyl}-ethanone,
1-{3-fluoro-4-[4-(5-nitro-2-piperidin-1-yl-benzoyl)-piperazin-1-yl]-phenyl}-ethanone,
1-{4-[4-(2-azepan-1-yl-5-nitro-benzoyl)-piperazin-1-yl]-3-fluoro-phenyl}-ethanone,
1-(3-fluoro-4-{4-[2-(2-methyl-piperidin-1-yl)-5-nitro-benzoyl]-piperazin-1-yl}-phenyl)-ethanone,
1-(3-fluoro-4-{4-[2-(4-methyl-piperidin-1-yl)-5-nitro-benzoyl]-piperazin-1-yl}-phenyl)-ethanone,
1-(3-fluoro-4-{4-[2-(3-methyl-piperidin-1-yl)-5-nitro-benzoyl]-piperazin-1-yl}-phenyl)-ethanone,
1-(3-fluoro-4-{4-[2-(2-methyl-pyrrolidin-1-yl)-5-nitro-benzoyl]-piperazin-1-yl}-phenyl)-ethanone,
1-(4-{4-[2-(2,5-dihydro-pyrrol-1-yl)-5-nitro-benzoyl]-piperazin-1-yl}-3-fluoro-phenyl)-ethanone,
1-{3-fluoro-4-[4-(5-nitro-2-thiomorpholin-4-yl-benzoyl)-piperazin-1-yl]-phenyl}-ethanone,
1-(3-fluoro-4-{4-[2-(3-hydroxy-piperidin-1-yl)-5-nitro-benzoyl]-piperazin-1-yl}-phenyl)-ethanone,
1-{4-[4-(2-azepan-1-yl-5-methanesulfonyl-benzoyl)-piperazin-1-yl]-3-fluoro-phenyl}-ethanone,
1-{3-fluoro-4-[4-(5-methanesulfonyl-2-pyrrolidin-1-yl-benzoyl)-piperazin-1-yl]-phenyl}-ethanone,
N-methyl-4-pyrrolidin-1-yl-3-[4-(4-trifluoromethyl-phenyl)-piperazine-1-carbonyl]-benzenesulfonamide,
N-methyl-4-morpholin-4-yl-3-[4-(4-trifluoromethyl-phenyl)-piperazine-1-carbonyl]-benzenesulfonamide,
3-[4-(4-acetyl-2-fluoro-phenyl)-piperazine-1-carbonyl]-N-methyl-4-pyrrolidin-1-yl-benzenesulfonamide,
1-(3-fluoro-4-{4-[2-(3-hydroxymethyl-pyrrolidin-1-yl)-5-nitro-benzoyl]-piperazin-1-yl}-phenyl)-ethanone,
2-[4-(2-morpholin-4-yl-5-nitro-benzoyl)-piperazin-1-yl]-5-trifluoromethyl-benzonitrile,
3-fluoro-4-[4-(5-methanesulfonyl-2-piperidin-1-yl-benzoyl)-piperazin-1-yl]-benzonitrile,
2-fluoro-4-[4-(5-methanesulfonyl-2-piperidin-1-yl-benzoyl)-piperazin-1-yl]-benzonitrile,
[4-(2-fluoro-4-trifluoromethyl-phenyl)-piperazin-1-yl]-(5-methanesulfonyl-2-piperidin-1-yl-phenyl)-methanone,
[4-(3-fluoro-4-trifluoromethyl-phenyl)-piperazin-1-yl]-(5-methanesulfonyl-2-piperidin-1-yl-phenyl)-methanone,
3-[4-(4-cyano-phenyl)-piperazine-1-carbonyl]-N-methyl-4-pyrrolidin-1-yl-benzenesulfonamide,
3-[4-(4-cyano-2-fluoro-phenyl)-piperazine-1-carbonyl]-N-methyl-4-pyrrolidin-1-yl-benzenesulfonamide,
3-[4-(2-fluoro-4-trifluoromethyl-phenyl)-piperazine-1-carbonyl]-N-methyl-4-pyrrolidin-1-yl-benzenesulfonamide,
3-[4-(3-fluoro-4-trifluoromethyl-phenyl)-piperazine-1-carbonyl]-N-methyl-4-pyrrolidin-1-yl-benzenesulfonamide,
3-[4-(4-acetyl-2-fluoro-phenyl)-piperazine-1-carbonyl]-N-methyl-4-piperidin-1-yl-benzenesulfonamide,
3-[4-(4-cyano-phenyl)-piperazine-1-carbonyl]-N-methyl-4-piperidin-1-yl-benzenesulfonamide,
3-[4-(4-cyano-2-fluoro-phenyl)-piperazine-1-carbonyl]-N-methyl-4-piperidin-1-yl-benzenesulfonamide,
3-[4-(4-cyano-3-fluoro-phenyl)-piperazine-1-carbonyl]-N-methyl-4-piperidin-1-yl-benzenesulfonamide,
N-methyl-4-piperidin-1-yl-3-[4-(4-trifluoromethyl-phenyl)-piperazine-1-carbonyl]-benzenesulfonamide,
3-[4-(2-fluoro-4-trifluoromethyl-phenyl)-piperazine-1-carbonyl]-N-methyl-4-piperidin-1-yl-benzenesulfonamide,
3-[4-(2-fluoro-4-trifluoromethyl-phenyl)-piperazine-1-carbonyl]-N-methyl-4-piperidin-1-yl-benzenesulfonamide,
3-[4-(2-fluoro-4-trifluoromethyl-phenyl)-piperazine-1-carbonyl]-N-methyl-4-morpholin-4-yl-benzenesulfonamide and
3-[4-(3-fluoro-4-trifluoromethyl-phenyl)-piperazine-1-carbonyl]-N-methyl-4-morpholin-4-yl-benzenesulfonamide.

Further preferred are compounds of formula I-3

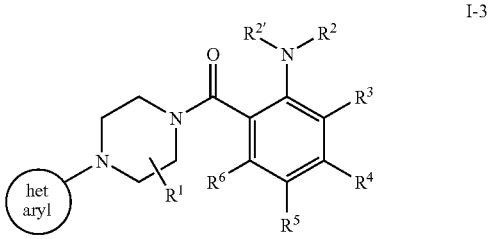

wherein hetaryl is a 6-membered heteroaryl containing one, two or three nitrogen atoms, optionally substituted by one or more substituents selected from the group consisting of hydroxy, halogen, $NO_2$, CN, ($C_1$-$C_6$)-alkyl, ($C_1$-$C_6$)-alkyl substituted by halogen, ($C_1$-$C_6$)-alkoxy, ($C_1$-$C_6$)-alkoxy substituted by halogen, $NR^7R^8$, $C(O)R^9$ or $SO_2R^{10}$;

$R^1$ is hydrogen or ($C_1$-$C_6$)-alkyl;

$R^2$ and $R^{2'}$ are each independently hydrogen,
  $(CR_2)_n$-hydroxy wherein R is hydrogen or $C_1$-$C_6$)-alkyl,
  ($C_1$-$C_6$)-alkyl,
  ($C_2$-$C_6$)-alkenyl,
  ($C_1$-$C_6$)-alkyl substituted by halogen,
  $(CH_2)_n$—($C_3$-$C_6$)-cycloalkyl,
  $(CH_2)_n$-heterocycloalkyl,
  $(CH_2)_n$—O—($C_1$-$C_6$)-alkyl or
  $(CH_2)_n$-aryl;

$R^3$, $R^4$ and $R^6$ are each independently hydrogen, halogen, ($C_1$-$C_6$)-alkyl or ($C_1$-$C_6$)-alkoxy;

$R^5$ is $NO_2$, CN, $C(O)R^9$, S—($C_1$-$C_6$)-alkyl, $SO_2R^{10}$ or $NR^{11}R^{12}$;

$R^7$ and $R^8$ are each independently hydrogen, $(CH_2)_n$—($C_3$-$C_6$)-cycloalkyl or
  ($C_1$-$C_6$)-alkyl, or form together with the N atom to which they are attached a heterocycloalkyl ring, optionally containing in addition to the N atom a further heteroatom selected from the group consisting of N, S and O;

$R^9$ is hydroxy, ($C_1$-$C_6$)-alkyl, ($C_3$-$C_6$)-cycloalkyl, ($C_1$-$C_6$)-alkoxy or $NR^7R^8$;

$R^{10}$ is ($C_1$-$C_6$)-alkyl, $(CH_2)_n$—($C_3$-$C_6$)-cycloalkyl or $NR^7R^8$;

$R^{11}$ and $R^{12}$ are each independently hydrogen, C(O)—($C_1$-$C_6$)-alkyl,
  $SO_2$—($C_1$-$C_6$)-alkyl, or form together with the N-atom to which they are attached a 5-membered heteroaryl group optionally containing in addition to the N atom one, two or three nitrogen atoms and wherein the heteroaryl group is optionally substituted by halogen, ($C_1$-$C_6$)-alkyl or $(CH_2)_n($C_3$-$C_6$)-cycloalkyl;

n is 0, 1 or 2;

or a pharmaceutically acceptable acid addition salt thereof.

Further preferred are compounds of formula I-4

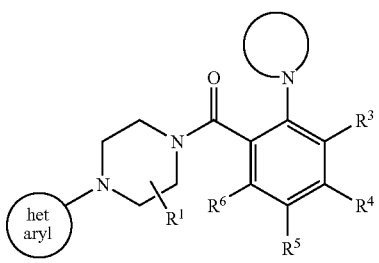

wherein hetaryl is a 6-membered heteroaryl, containing one, two or three nitrogen atoms, optionally substituted by one or more substituents selected from the group consisting of hydroxy, halogen, $NO_2$, CN, $(C_1-C_6)$-alkyl, $(C_1-C_6)$-alkyl substituted by halogen, $(C_1-C_6)$-alkoxy, $(C_1-C_6)$-alkoxy substituted by halogen, $NR^7R^8$, $C(O)R^9$ and $SO_2R^{10}$;

$R^1$ is hydrogen or $(C_1-C_6)$-alkyl;

is a heterocycloalkyl ring, optionally containing in addition to the N atom a further heteroatom, selected from the group consisting of N, S and O, which ring is unsubstituted or substituted by $(CH_2)_n$-hydroxy, $(C_1-C_6)$-alkyl, $(C_1-C_6)$-alkoxy, $(CH_2)_n$—O—$(C_1-C_6)$-alkyl, or is a 5-membered heteroaryl group, optionally containing in addition to the N atom one, two or three further nitrogen atoms and wherein the heteroaryl group is optionally substituted by $(C_1-C_6)$-alkyl;

$R^3$, $R^4$ and $R^6$ are each independently hydrogen, halogen, $(C_1-C_6)$-alkyl or $(C_1-C_6)$-alkoxy;

$R^5$ is $NO_2$, CN, $C(O)R^9$, S—$(C_1-C_6)$-alkyl, $SO_2R^{10}$ or $NR^{11}R^{12}$;

$R^7$ and $R^8$ are each independently hydrogen, $(CH_2)_n$—$(C_3-C_6)$-cycloalkyl or $(C_1-C_6)$-alkyl, or form together with the N atom to which they are attached a heterocycloalkyl ring, optionally containing in addition to the N atom a further heteroatom selected from the group consisting of N, S and O;

$R^9$ is hydroxy, $(C_1-C_6)$-alkyl, $(C_3-C_6)$-cycloalkyl, $(C_1-C_6)$-alkoxy or $NR^7R^8$;

$R^{10}$ is $(C_1-C_6)$-alkyl, $(CH_2)_n$—$(C_3-C_6)$-cycloalkyl or $NR^7R^8$;

$R^{11}$ and $R^{12}$ are each independently hydrogen, $C(O)$—$(C_1-C_6)$-alkyl, $SO_2$—$(C_1-C_6)$-alkyl, or form together with the N-atom to which they are attached a 5-membered heteroaryl group optionally containing in addition to the N atom one, two or three nitrogen atoms and wherein the heteroaryl group is optionally substituted by halogen, $(C_1-C_6)$-alkyl or $(CH_2)_n(C_3-C_6)$-cycloalkyl;

n is 0, 1 or 2;

or a pharmaceutically acceptable acid addition salt thereof.

The following compounds of formula I-4 are preferred:

3-[4-(3-fluoro-4-trifluoromethyl-phenyl)-piperazine-1-carbonyl]-N-methyl-4-morpholin-4-yl-benzenesulfonamide (2-morpholin-4-yl-5-nitro-phenyl)-[4-(5-trifluoromethyl-pyridin-2-yl)-piperazin-1-yl]-methanone

[4-(3-chloro-5-trifluoromethyl-pyridin-2-yl)-piperazin-1-yl]-(2-morpholin-4-yl-5-nitro-phenyl)-methanone 6-[4-(2-morpholin-4-yl-5-nitro-benzoyl)-piperazin-1-yl]-nicotinonitrile

[4-(3-chloro-pyridin-2-yl)-piperazin-1-yl]-(2-morpholin-4-yl-5-nitro-phenyl)-methanone (2-morpholin-4-yl-5-nitro-phenyl)-[4-(4-trifluoromethyl-pyridin-2-yl)-piperazin-1-yl]-methanone (2-morpholin-4-yl-5-nitro-phenyl)-[4-(6-trifluoromethyl-pyridin-2-yl)-piperazin-1-yl]-methanone

[4-(5-bromo-pyrimidin-2-yl)-piperazin-1-yl]-(2-morpholin-4-yl-5-nitro-phenyl)-methanone

[4-(6-chloro-5-trifluoromethyl-pyridin-2-yl)-piperazin-1-yl]-(2-morpholin-4-yl-5-nitro-phenyl)-methanone (5-methanesulfonyl-2-morpholin-4-yl-phenyl)-[4-(2-trifluoromethyl-pyrimidin-4-yl)-piperazin-1-yl]-methanone (5-methanesulfonyl-2-morpholin-4-yl-phenyl)-[4-(6-trifluoromethyl-pyrimidin-4-yl)-piperazin-1-yl]-methanone (5-methanesulfonyl-2-morpholin-4-yl-phenyl)-[4-(5-trifluoromethyl-pyrimidin-2-yl)-piperazin-1-yl]-methanone 6-[4-(5-methanesulfonyl-2-morpholin-4-yl-benzoyl)-piperazin-1-yl]-nicotinonitrile (5-methanesulfonyl-2-morpholin-4-yl-phenyl)-[4-(5-trifluoromethyl-pyridin-2-yl)-piperazin-1-yl]-methanone

[4-(3-chloro-5-trifluoromethyl-pyridin-2-yl)-piperazin-1-yl]-(5-methanesulfonyl-2-morpholin-4-yl-phenyl)-methanone

[4-(5-chloro-pyridin-2-yl)-piperazin-1-yl]-(5-methanesulfonyl-2-morpholin-4-yl-phenyl)-methanone (5-methanesulfonyl-2-morpholin-4-yl-phenyl)-[4-(6-trifluoromethyl-pyridin-3-yl)-piperazin-1-yl]-methanone

[4-(3-fluoro-5-trifluoromethyl-pyridin-2-yl)-piperazin-1-yl]-(5-methanesulfonyl-2-morpholin-4-yl-phenyl)-methanone (5-methanesulfonyl-2-morpholin-4-yl-phenyl)-[4-(6-methyl-pyridin-3-yl)-piperazin-1-yl]-methanone (5-methanesulfonyl-2-morpholin-4-yl-phenyl)-[4-(5-methyl-pyridin-2-yl)-piperazin-1-yl]-methanone (5-methanesulfonyl-2-morpholin-4-yl-phenyl)-[4-(4-trifluoromethyl-pyridin-2-yl)-piperazin-1-yl]-methanone (5-methanesulfonyl-2-morpholin-4-yl-phenyl)-[4-(6-trifluoromethyl-pyridin-2-yl)-piperazin-1-yl]-methanone (5-methanesulfonyl-2-morpholin-4-yl-phenyl)-[4-(2-trifluoromethyl-pyrimidin-5-yl)-piperazin-1-yl]-methanone (5-methanesulfonyl-2-morpholin-4-yl-phenyl)-[4-(6-trifluoromethyl-pyridazin-3-yl)-piperazin-1-yl]-methanone

[4-(4-dimethylamino-[1,3,5]triazin-2-yl)-piperazin-1-yl]-(5-methanesulfonyl-2-morpholin-4-yl-phenyl)-methanone and (5-methanesulfonyl-2-morpholin-4-yl-phenyl)-(5'-trifluoromethyl-2,3,5,6-tetrahydro-[1,2']bipyrazinyl-4-yl)-methanone.

In one embodiment, the invention provides compounds of formula

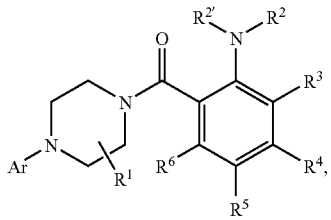

wherein

Ar is unsubstituted or substituted aryl or 6-membered heteroaryl containing one, two or three nitrogen atoms, and wherein the substituted aryl and the substituted heteroaryl groups are substituted by one or more substituents selected from the group consisting of hydroxy, halogen, $NO_2$, CN, $(C_1-C_6)$-alkyl, $(C_1-C_6)$-alkyl substituted by halogen, $(C_1-C_6)$-alkoxy, $(C_1-C_6)$-alkoxy substituted by halogen, $NR^7R^8$, $C(O)R^9$ and $SO_2R^{10}$;

$R^1$ is hydrogen or $(C_1-C_6)$-alkyl;

$R^2$ and $R^{2'}$ are each independently hydrogen, hydroxy, $(C_1-C_6)$-alkyl,
  $(C_3-C_6)$-alkenyl, $(C_2-C_6)$-alkyl substituted by halogen, $(C_3-C_6)$-cycloalkyl, heterocycloalkyl, $(C_1-C_6)$-alkyl-$(C_3-C_6)$-cycloalkyl, $(C_1-C_6)$-alkyl-heterocycloalkyl, $(C_1-C_6)$-alkyl-C(O)—$R^9$, $(C_1-C_6)$-alkyl-CN, $(C_2-C_6)$-alkyl-O—$R^3$, $(C_2-C_6)$-alkyl-$NR^7R^8$, aryl or 6-membered heteroaryl containing one, two or three nitrogen atoms, $(C_1-C_6)$-alkyl-aryl or $(C_1-C_6)$-alkyl-5 or -6-membered heteroaryl containing one, two or three heteroatoms selected from the group consisting of oxygen, sulphur and nitrogen, wherein aryl, heterocycloalkyl and heteroaryl are unsubstituted or substituted by one or more substituents selected from the group consisting of hydroxy, halogen, $(C_1-C_6)$-alkyl and $(C_1-C_6)$-alkoxy; or $R^2$ and $R^{2'}$ form together with the N atom to which they are attached a heterocycloalkyl ring, optionally containing in addition to the N atom a further heteroatom selected from the group consisting of N, S and O, which rings are unsubstituted or substituted by hydroxy, $(C_1-C_6)$-alkyl, $(C_1-C_6)$-alkoxy, or $(C_1-C_6)$-alkyl-O—$R^3$, or $R^2$ and $R^{2'}$ form together with the N atom to which they are attached a 5-membered heteroaryl group, optionally containing in addition to the N atom one, two or three further nitrogen atoms and wherein the heteroaryl group is optionally substituted by halogen, $(C_1-C_6)$-alkyl, $(C_1-C_6)$-alkyl substituted by halogen or $(C_3-C_6)$-cycloalkyl;

$R^3$, $R^4$ and $R^6$ are each independently hydrogen, hydroxy, halogen, CN, $(C_1-C_6)$-alkyl, $(C_1-C_6)$-alkoxy or $NR^7R^8$;

$R^5$ is $NO_2$, CN, $C(O)R^9$, S—$(C_1-C_6)$-alkyl, $SO_2R^{10}$ or $NR^{11}R^{12}$;

$R^7$ and $R^8$ are each independently hydrogen, $(C_1-C_6)$-alkyl-$(C_3-C_6)$-cycloalkyl, $(C_1-C_6)$-alkyl, or $(C_3-C_6)$-cycloalkyl, or form together with the N atom to which they are attached a heterocycloalkyl ring, optionally containing in addition to the N atom a further heteroatom selected from the group consisting of N, S and O;

$R^9$ is hydroxy, $(C_1-C_6)$-alkyl, $(C_3-C_6)$-cycloalkyl, $(C_1-C_6)$-alkoxy or $NR^7R^8$;

$R^{10}$ is $(C_1-C_6)$-alkyl, $(C_3-C_6)$-cycloalkyl, $(C_1-C_6)$-alkyl-$(C_3-C_6)$-cycloalkyl or $NR^7R^8$;

$R^{11}$ and $R^{12}$ are each independently from each other hydrogen, C(O)—$(C_1-C_6)$-alkyl, $SO_2$—$(C_1-C_6)$-alkyl, or form together with the N-atom to which they are attached a 5-membered heteroaryl group optionally containing in addition to the N atom one, two or three nitrogen atoms and wherein the heteroaryl group is optionally substituted by halogen, $(C_1-C_6)$-alkyl, $(C_1-C_6)$-alkyl substituted by halogen or $(C_3-C_6)$-cycloalkyl;

$R^{13}$ is hydrogen, $(C_1-C_6)$-alkyl or $(C_3-C_6)$-cycloalkyl;

or a pharmaceutically acceptable acid addition salt thereof, with the proviso that 1-[5-(aminosulfonyl)-2-(4-morpholinyl)benzoyl]-4-phenyl-piperazine, 1-(4-methoxyphenyl)-4-[2-(4-morpholinyl)-5-nitrobenzoyl]-piperazine, 1-[2-(4-morpholinyl)-5-nitrobenzoyl]-4-[2-nitro-4-(trifluoromethyl)phenyl]-piperazine, 1-(4-methoxyphenyl)-4-[5-nitro-2-(1-pyrrolidinyl)benzoyl]-piperazine, 1-[2-[4-(2-hydroxyethyl)-1-piperazinyl]-5-nitrobenzoyl]-4-(4-methoxyphenyl)-piperazine, 1-[2-fluoro-4-(1-oxopropyl)phenyl]-4-[5-nitro-2-(1-piperidinyl)benzoyl]-piperazine, 1-[2-fluoro-4-(1-oxopropyl)phenyl]-4-[5-nitro-2-(1-pyrrolidinyl)benzoyl]-piperazine, 1-[2-fluoro-4-(1-oxopropyl)phenyl]-4-[2-(4-methyl-1-piperidinyl)-5-nitrobenzoyl]-piperazine, 1-[2-fluoro-4-(1-oxopropyl)phenyl]-4-[2-(4-methyl-1-piperazinyl)-5-nitrobenzoyl]-piperazine, 1-[2-fluoro-4-(1-oxopropyl)phenyl]-4-[2-(4-morpholinyl)-5-nitrobenzoyl]-piperazine, 1-[5-[[methyl(phenylmethyl)amino]sulfonyl]-2-(4-morpholinyl)benzoyl]-4-(4-nitrophenyl)-piperazine and 1-(4-acetyl-2-fluorophenyl)-4-[2-(4-morpholinyl)-5-nitrobenzoyl]-piperazine, are excluded.

In another embodiment, the invention provides compounds of formula Ia

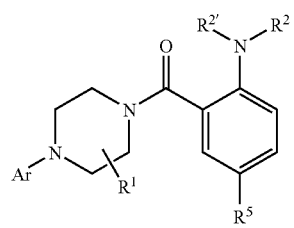

wherein

Ar is unsubstituted or substituted phenyl or 6-membered heteroaryl, containing one or two nitrogen atoms, and wherein the substituted phenyl and the substituted heteroaryl groups are optionally substituted by one or two substituents selected from the group consisting of halogen, $NO_2$, CN, $(C_1-C_6)$-alkyl, $(C_1-C_6)$-alkyl substituted by halogen, $(C_1-C_6)$-alkoxy, $(C_1-C_6)$-alkoxy substituted by halogen, $NR^7R^8$, $C(O)R^9$ and $SO_2R^{10}$;

$R^1$ is hydrogen or $(C_1-C_6)$-alkyl;

$R^2$ and $R^{2'}$ are each independently hydrogen, hydroxy, $(C_1-C_6)$-alkyl,
  $(C_3-C_6)$-alkenyl, $(C_3-C_6)$-cycloalkyl, heterocycloalkyl, $(C_1-C_6)$-alkyl-$(C_3-C_6)$-cycloalkyl, $(C_1-C_6)$-alkyl-aryl, or $(C_2-C_6)$-alkyl-O—$R^{13}$, or R² and R²' form together with the N atom to which they are attached a heterocycloalkyl ring, optionally containing in addition to the N atom a further heteroatom selected from the group consisting of N, S and O, which ring is unsubstituted or substituted by hydroxy, $(C_1-C_6)$-alkyl, $(C_1-C_6)$-alkoxy, or $(C_1-C_6)$-alkyl-O—$R^{13}$, or R² and R²' form together with the N atom to which they are attached a 5-membered heteroaryl group optionally containing in addition to the N atom one or two nitrogen atoms;

$R^5$ is $NO_2$, CN, $C(O)R^9$, S—$(C_1-C_6)$-alkyl, $SO_2R^{10}$ or $NR^{11}R^{12}$;

$R^7$ and $R^8$ are each independently hydrogen, $(C_1-C_6)$-alkyl-$(C_3-C_6)$-cycloalkyl, or $(C_1-C_6)$-alkyl or form together with the N atom to which they are attached a heterocycloalkyl ring, optionally containing in addition to the N atom a further heteroatom selected from the group consisting of oxygen;

$R^9$ is $(C_1-C_6)$-alkyl, $(C_1-C_6)$-alkoxy or $NR^7R^8$;

$R^{10}$ is $(C_1-C_6)$-alkyl, $(C_1-C_6)$-alkyl-$(C_3-C_6)$-cycloalkyl or $NR^7R^8$;

$R^{11}$ and $R^{12}$ are each independently $SO_2$—$(C_1-C_6)$-alkyl, or form together with the N-atom to which they are attached a 5-membered heteroaryl group containing in addition to the N atom one, two or three nitrogen atoms;

$R^{13}$ is hydrogen or $(C_1-C_6)$-alkyl;

or a pharmaceutically acceptable acid addition salt thereof, with the proviso that 1-[5-(aminosulfonyl)-2-(4-morpholinyl)benzoyl]-4-phenyl-piperazine, 1-(4-methoxyphenyl)-4-[2-(4-morpholinyl)-5-nitrobenzoyl]-piperazine, 1-[2-(4-morpholinyl)-5-nitrobenzoyl]-4-[2-nitro-4-(trifluoromethyl)phenyl]-piperazine, 1-(4-methoxyphenyl)-4-[5-nitro-2-(1-pyrrolidinyl)benzoyl]-piperazine, 1-[2-[4-(2-hydroxyethyl)-1-piperazinyl]-5-nitrobenzoyl]-4-(4-methoxyphenyl)-piperazine, 1-[2-fluoro-4-(1-oxopropyl)phenyl]-4-[5-nitro-2-(1-piperidinyl)benzoyl]-piperazine, 1-[2-fluoro-4-(1-oxopropyl)phenyl]-4-[5-nitro-2-(1-pyrrolidinyl)benzoyl]-piperazine, 1-[2-fluoro-4-(1-oxopropyl)phenyl]-4-[2-(4-methyl-1-piperidinyl)-5-nitrobenzoyl]-piperazine, 1-[2-fluoro-4-(1-oxopropyl)phenyl]-4-[2-(4-methyl-1-piperazinyl)-5-nitrobenzoyl]-piperazine, 1-[2-fluoro-4-(1-oxopropyl)phenyl]-4-[2-(4-morpholinyl)-5-nitrobenzoyl]-piperazine, 1-[5-[[methyl(phenylmethyl)amino]sulfonyl]-2-(4-morpholinyl)benzoyl]-4-(4-nitrophenyl)-piperazine and 1-(4-acetyl-2-fluorophenyl)-4-[2-(4-morpholinyl)-5-nitrobenzoyl]-piperazine, are excluded.

In another embodiment are those compounds of formula Ia,

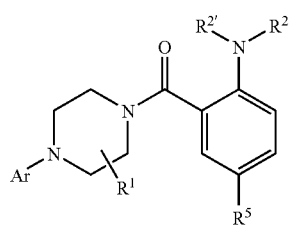

Ia wherein

Ar is unsubstituted or substituted phenyl, pyridyl or pyrimidinyl, optionally substituted by one or two substituents selected from the group consisting of halogen, $NO_2$, CN, methyl, $CF_3$, methoxy, $OCF_3$, $NH_2$, $C(O)CH_3$, $C(O)OCH_3$, $C(O)OCH_2CH_3$, $SO_2NH_2$ and $SO_2CH_3$;

$R^1$ is hydrogen or methyl;

R² and R²' are each independently hydrogen, hydroxy, $(C_1-C_6)$-alkyl,
—$CH_2CH=CH_2$, —$CH_2CH_2OH$, —$CH(CH_3)CH_2OH$, cyclopropyl, cyclopentyl, cyclohexyl, tetrahydropyranyl, —$CH_2$-cyclopropyl, or $(CH_2)_2OCH_3$, benzyl, or R² and R²' form together with the N atom to which they are attached a heterocycloalkyl ring selected from the group consisting of morpholinyl, thiomorpholinyl, azetidinyl, pyrrolidinyl, piperidinyl and azepanyl, which ring is unsubstituted or substituted by hydroxy, methyl, methoxy, ethoxy, or $CH_2OH$, or R² and R²' form together with the N atom to which they are attached a 5-membered heteroaryl ring selected from the group consisting of imidazolyl, triazolyl and dihydro-pyrrolyl;

$R^5$ is $NO_2$, CN, —$C(O)NH_2$, —$C(O)NHCH_3$, —$C(O)N(CH_3)_2$, —$C(O)CH_3$, —$SCH_3$, —$SO_2$—$(C_1-C_6)$-alkyl, —$SO_2$—NH—$(C_1-C_6)$-alkyl, —$SO_2$—N—$[(C_1-C_6)$-alkyl$]_2$, —$SO_2NH_2$, —$NHSO_2CH_3$, —$SO_2$—$NHCH_2$-cycloalkyl, —$SO_2$—$CH_2$-cycloalkyl, —$SO_2$-pyrrolidin-1-yl, —$SO_2$-morpholidin-1-yl, imidazolyl or tetrazolyl, or a pharmaceutically acceptable acid addition salt thereof, with the proviso that 1-[5-(aminosulfonyl)-2-(4-morpholinyl)benzoyl]-4-phenyl-piperazine, 1-(4-methoxyphenyl)-4-[2-(4-morpholinyl)-5-nitrobenzoyl]-piperazine, 1-[2-(4-morpholinyl)-5-nitrobenzoyl]-4-[2-nitro-4-(trifluoromethyl)phenyl]-piperazine, 1-[2-[4-(2-hydroxyethyl)-1-piperazinyl]-5-nitrobenzoyl]-4-(4-methoxyphenyl)-piperazine and 1-(4-acetyl-2-fluorophenyl)-4-[2-(4-morpholinyl)-5-nitrobenzoyl]-piperazine, are excluded.

Still another embodiment are compounds, wherein R² and R²' form together with the N atom to which they are attached a morpholine ring, for example the following compounds:

1-{4-[4-(2-morpholin-4-yl-5-nitro-benzoyl)-piperazin-1-yl]-3-fluoro-phenyl}-ethanone, N-methyl-4-morpholin-4-yl-3-[4-(4-trifluoromethyl-phenyl)-piperazine-1-carbonyl]-benzenesulfonamide and 2-[4-(2-morpholin-4-yl-5-nitro-benzoyl)-piperazin-1-yl]-5-trifluoromethyl-benzonitrile.

Another embodiment encompasses compounds wherein R² and R²' form together with the N atom to which they are attached a pyrrolidin- or 2,5-dihydropyrrol ring, which is optionally substituted by methyl or $CH_2OH$, for example the following compounds:

1-{3-fluoro-4-[4-(5-nitro-2-pyrrolidin-1-yl-benzoyl)-piperazin-1-yl]-phenyl}-ethanone, 1-(3-fluoro-4-{4-[2-(2-methyl-pyrrolidin-1-yl)-5-nitro-benzoyl]-piperazin-1-yl}-phenyl)-ethanone, 1-(4-{4-[2-(2,5-dihydro-pyrrol-1-yl)-5-nitro-benzoyl]-piperazin-1-yl}-3-fluoro-phenyl)-ethanone, 1-{3-fluoro-4-[4-(5-methanesulfonyl-2-pyrrolidin-1-yl-benzoyl)-piperazin-1-yl]-phenyl}-ethanone, N-methyl-4-pyrrolidin-1-yl-3-[4-(4-trifluoromethyl-phenyl)-piperazine-1-carbonyl]-benzenesulfonamide, 3-[4-(4-acetyl-2-fluoro-phenyl)-piperazine-1-carbonyl]-N-methyl-4-pyrrolidin-1-yl-benzenesulfonamide and 1-(3-fluoro-4-{4-[2-(3-hydroxymethyl-pyrrolidin-1-yl)-5-nitro-benzoyl]-piperazin-1-yl}-phenyl)-ethanone.

Still another embodiment encompasses compounds wherein $R^2$ and $R^{2'}$ form together with the N atom to which they are attached a piperidine ring, which is optionally substituted by methyl or hydroxy, for example the following compounds:

1-{3-fluoro-4-[4-(5-nitro-2-piperidin-1-yl-benzoyl)-piperazin-1-yl]-phenyl}-ethanone, 1-(3-fluoro-4-{4-[2-(2-methyl-piperidin-1-yl)-5-nitro-benzoyl]-piperazin-1-yl}-phenyl)-ethanone, 1-(3-fluoro-4-{4-[2-(4-methyl-piperidin-1-yl)-5-nitro-benzoyl]-piperazin-1-yl}-phenyl)-ethanone, 1-(3-fluoro-4-{4-[2-(3-methyl-piperidin-1-yl)-5-nitro-benzoyl]-piperazin-1-yl}-phenyl)-ethanone and 1-(3-fluoro-4-{4-[2-(3-hydroxy-piperidin-1-yl)-5-nitro-benzoyl]-piperazin-1-yl}-phenyl)-ethanone.

In another embodiment, the invention provides compounds wherein $R^2$ and $R^{2'}$ form together with the N atom to which they are attached an azepane ring, for example the following compounds:

1-{4-[4-(2-azepan-1-yl-5-nitro-benzoyl)-piperazin-1-yl]-3-fluoro-phenyl}-ethanone and 1-{4-[4-(2-azepan-1-yl-5-methanesulfonyl-benzoyl)-piperazin-1-yl]-3-fluoro-phenyl}-ethanone.

Compounds of the invention are further those wherein $R^2$ and $R^{2'}$ form together with the N atom to which they are attached a thiomorpholine ring, for example the following compound:

1-{3-fluoro-4-[4-(5-nitro-2-thiomorpholin-4-yl-benzoyl)-piperazin-1-yl]-phenyl}-ethanone.

A further embodiment of the invention provides compounds wherein $R^2$ or $R^{2'}$ is CH$_2$-cycloalkyl or cycloalkyl, for example the following compounds:

1-(4-{4-[2-(cyclopropylmethyl-amino)-5-nitro-benzoyl]-piperazin-1-yl}-3-fluoro-phenyl)-ethanone, 1-{4-[4-(2-cyclohexylamino-5-nitro-benzoyl)-piperazin-1-yl]-3-fluoro-phenyl}-ethanone, 1-{4-[4-(2-cyclobutylamino-5-nitro-benzoyl)-piperazin-1-yl]-3-fluoro-phenyl}-ethanone and 1-{4-[4-(2-cyclopentylamino-5-nitro-benzoyl)-piperazin-1-yl]-3-fluoro-phenyl}-ethanone.

Another embodiment of the invention provides compounds wherein one of $R^2$ or $R^{2'}$ is (C$_1$-C$_6$)-alkyl and the other is hydrogen, or both of $R^2$ or $R^{2'}$ are (C$_1$-C$_6$)-alkyl, for example the following compounds:

1-{3-fluoro-4-[4-(2-isopropylamino-5-nitro-benzoyl)-piperazin-1-yl]-phenyl}-ethanone, 1-{3-fluoro-4-[4-(2-isobutylamino-5-nitro-benzoyl)-piperazin-1-yl]-phenyl}-ethanone, 1-{3-fluoro-4-[4-(2-tert.-butylamino-5-nitro-benzoyl)-piperazin-1-yl]-phenyl}-ethanone and 1-{4-[4-(2-diethylamino-5-nitro-benzoyl)-piperazin-1-yl]-3-fluoro-phenyl}-ethanone.

Compounds of the invention are further those wherein one of $R^2$ or R is (C$_2$-C$_6$)-alkenyl, and the other is (C$_1$-C$_6$)-alkyl, for example the following compound:

1-(4-{4-[2-(allyl-methyl-amino)-5-nitro-benzoyl]-piperazin-1-yl}-3-fluoro-phenyl)-ethanone.

The present compounds of formula I and their pharmaceutically acceptable salts can be prepared by methods known in the art, for example, by processes described below, which processes comprise a) reacting a compound of formula

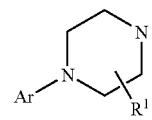

II with a compound of formula

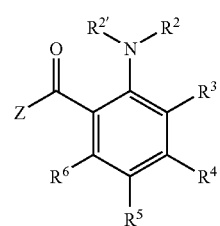

III to produce a compound of formula

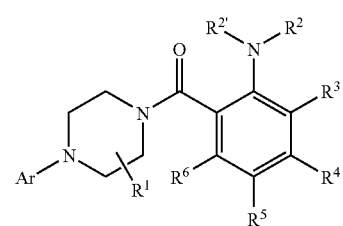

I wherein Z is OH or halogen and the other substituents are as defined above, or b) reacting a compound of formula

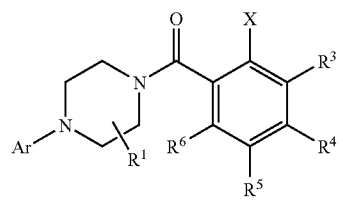

V with a compound of formula $R^2R^{2'}NH$ to produce a compound of formula

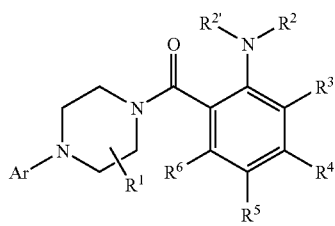

I wherein X is halogen and the other substituents are as defined above, c) reacting a compound of formula

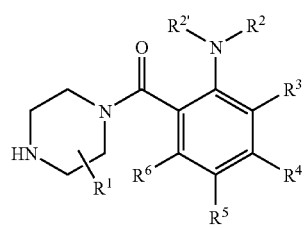

VII with a compound of formula

ArX to produce a compound of formula

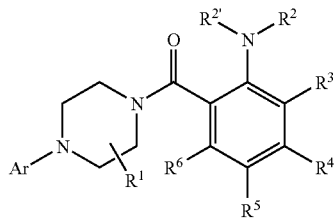

I wherein X is halogen and the other substituents are as defined above, d) reacting a compound of formula

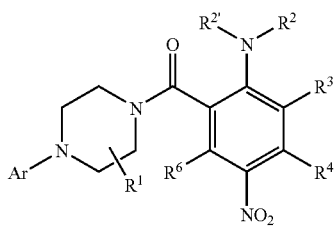

IA with hydrogen on Pd/C to produce a compound of formula

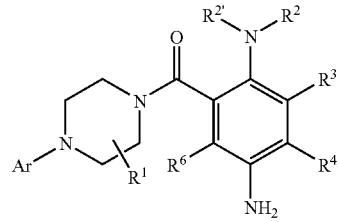

IB wherein the substituents are as defined above, e) reacting a compound of formula

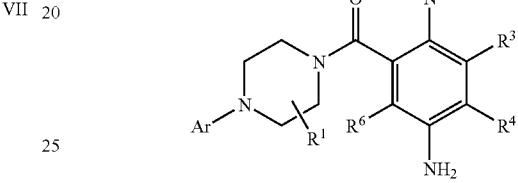

IB with a compound of formula

R$^{14}$AX to produce a compound of formula

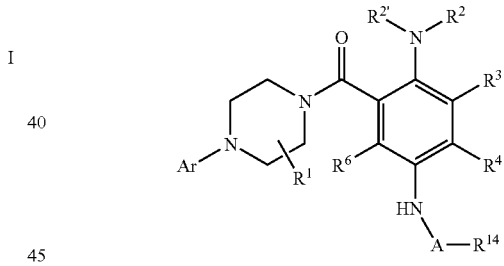

IC wherein X is halogen, A is —C(O)— or —SO$_2$—, R$^{14}$ is (C$_1$-C$_6$)-alkyl and the other substituents are as defined above, f) reacting a compound of formula

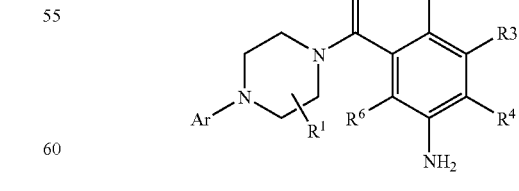

IB with a compound of formula

R$^{15}$C(OEt)$_3$ to produce a compound of formula

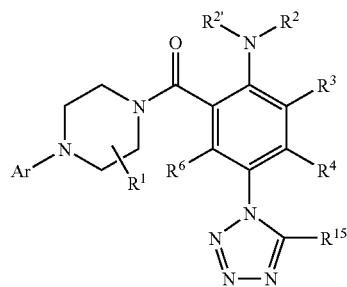

wherein $R^{15}$ is hydrogen, halogen, $(C_1-C_6)$-alkyl, $(C_1-C_6)$-alkyl substituted by halogen or $(C_3-C_6)$-cycloalkyl and the other substituents are as defined above, g) reacting a compound of formula

IE

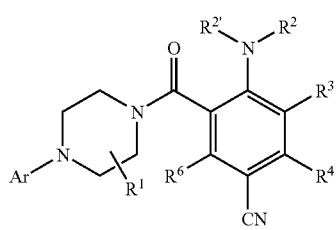

with a base
to produce a compound of formula

IF

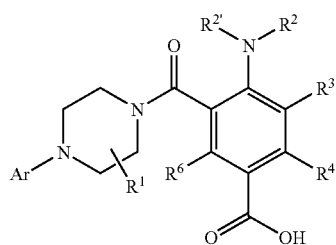

wherein the substituents are as defined above,
h) reacting a compound of formula

IF

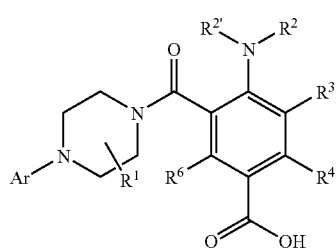

with a compound of formula $R^7R^8NH$ to produce a compound of formula

ID

IG

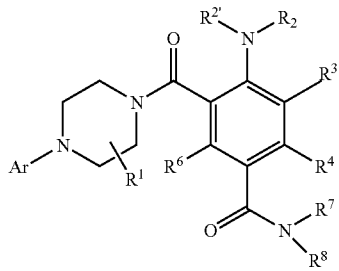

wherein the substituents are as defined above,
i) reacting a compound of formula

X

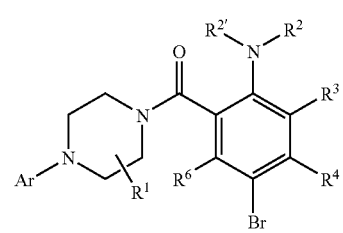

with a compound of formula

XI

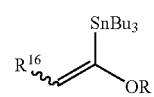

to produce a compound of formula

IH

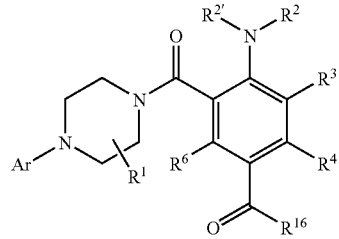

wherein R is $(C_1-C_6)$-alkyl, $R^{16}$ is $(C_1-C_6)$-alkyl or $(C_3-C_6)$-cycloalkyl and the other substituents are as defined above, j) reacting a compound of formula

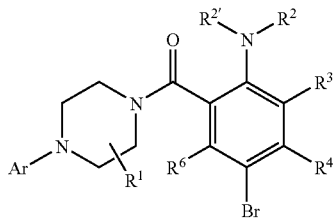

with a compound of formula

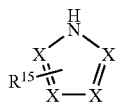

to produce a compound of formula

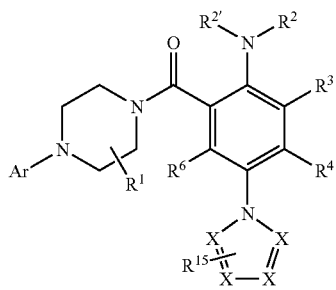

wherein X is CH or N and the heteroaryl ring is selected from the group consisting of imidazole, pyrazole or triazole, $R^{15}$ is hydrogen, halogen, $(C_1-C_6)$-alkyl, $(C_1-C_6)$-alkyl substituted by halogen, or $(C_3-C_6)$-cycloalkyl and the other substituents are as defined above, and if desired, converting the compounds obtained into pharmaceutically acceptable acid addition salts.

The compounds of formula I may be prepared in accordance with process variants a) to j) and with the following schemes 1 to 6.

The starting material is commercially available or may be prepared in accordance with known methods.

Scheme 1

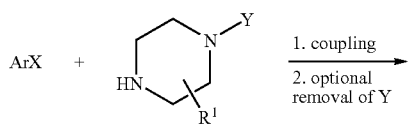

X: halogen
Y: H, protective group (i.e. boc)
Z: OH, halogen (i.e.: Cl)

-continued

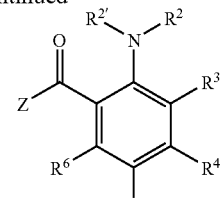

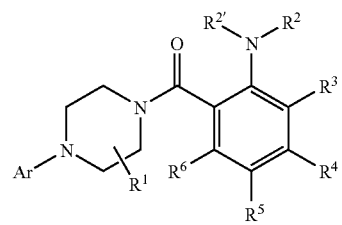

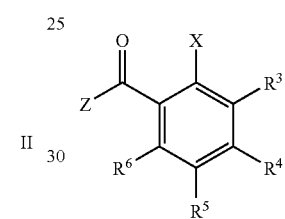

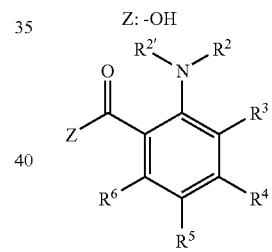 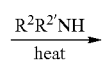 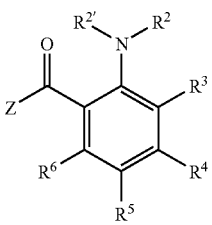

III  
Z: -OH

III  
Z: -Cl

Compounds of general formula I can be prepared by reacting of a piperazine of formula II with a compound of formula III (Z: Cl) or III (Z: OH) in the presence of an activating agent like CDI (N,N-carbonyldiimidazole) or TBTU (2-(1H-benzotriazole-1-yl)-1,1,3,3-tetramethyluroniumtetrafluoroborate).

A compound of formula III (Z: Cl) can be prepared from a compound of formula III (Z: OH) in the presence of an activating agent like thionylchloride. In turn the acid of formula III (Z: OH) can be prepared by heating a mixture of an acid of formula IV and an amino derivative of formula $R^2R^{2'}NH$.

The piperazine of formula II can be prepared by heating of a corresponding piperazine with ArX or by reacting of a N-protected piperazine with ArX in the presence of palladium catalyst followed by cleavage of the protective group. The protective group is typically tert-butoxycarbonyl (Boc).

Scheme 2

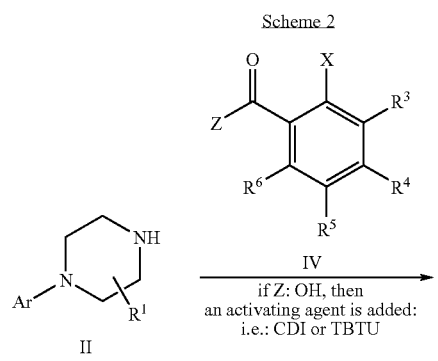

X: halogen
Z: OH, halogen (i.e.: Cl)

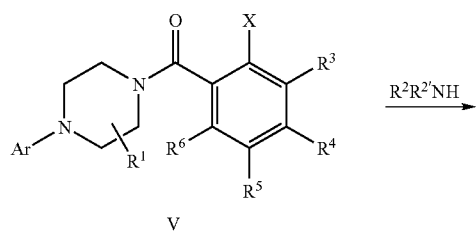

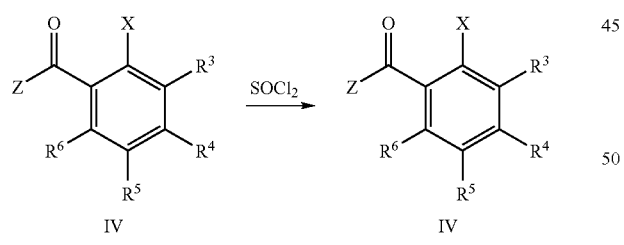

Alternatively, compounds of general formula I can be prepared by reaction of a derivative of formula V with a corresponding amine of formula $R^2R^{2'}NH$. Compounds of formula V can be prepared by reacting of derivatives of formula II with compounds of formula IV (Z: Cl) or with compounds of formula IV(Z: OH) in the presence of an activating agent like CDI (N-carbonyldiimidazole) or TBTU (2-(1H-benzotriazole-1-yl)-1,1,3,3-tetramethyluroniumtetrafluoroborate).

Scheme 3

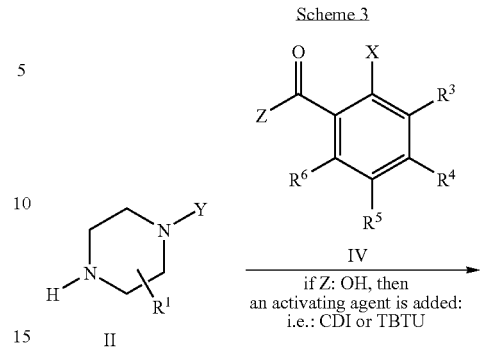

X: halogen
Y: H, protective group (i.e. boc)
Z: OH, halogen (i.e.: Cl)

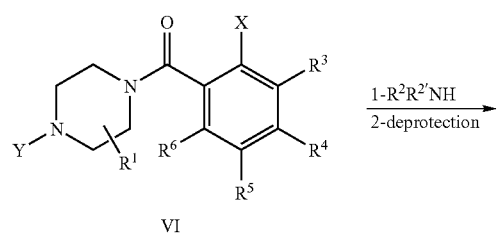

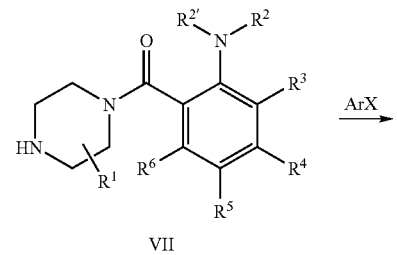

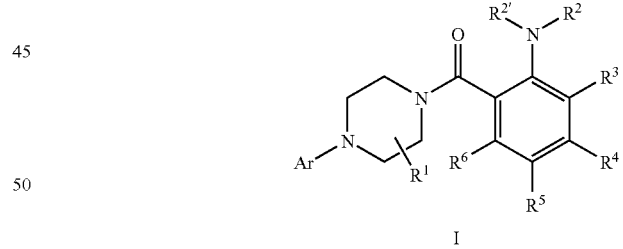

Alternatively, compounds of general formula I can be prepared by reaction of a compound of formula VII with ArX. A compound of formula VII can be prepared by reacting of a N-protected derivative of formula VI with an amine of formula $R^2R^{2'}NH$, followed by cleavage of the protective group. The protective group is typically tert-butoxycarbonyl (Boc). In turn, a compound of formula VI can be prepared by reacting of a piperazine of formula II with a compound of formula IV (Z: Cl) or with a compound of formula IV (Z: OH) in the presence of an activating agent like CDI (N-carbonyl-diimidazole) or TBTU (2-(1H-benzotriazole-1-yl)-1,1,3,3-tetramethyluronium-tetrafluoroborate).

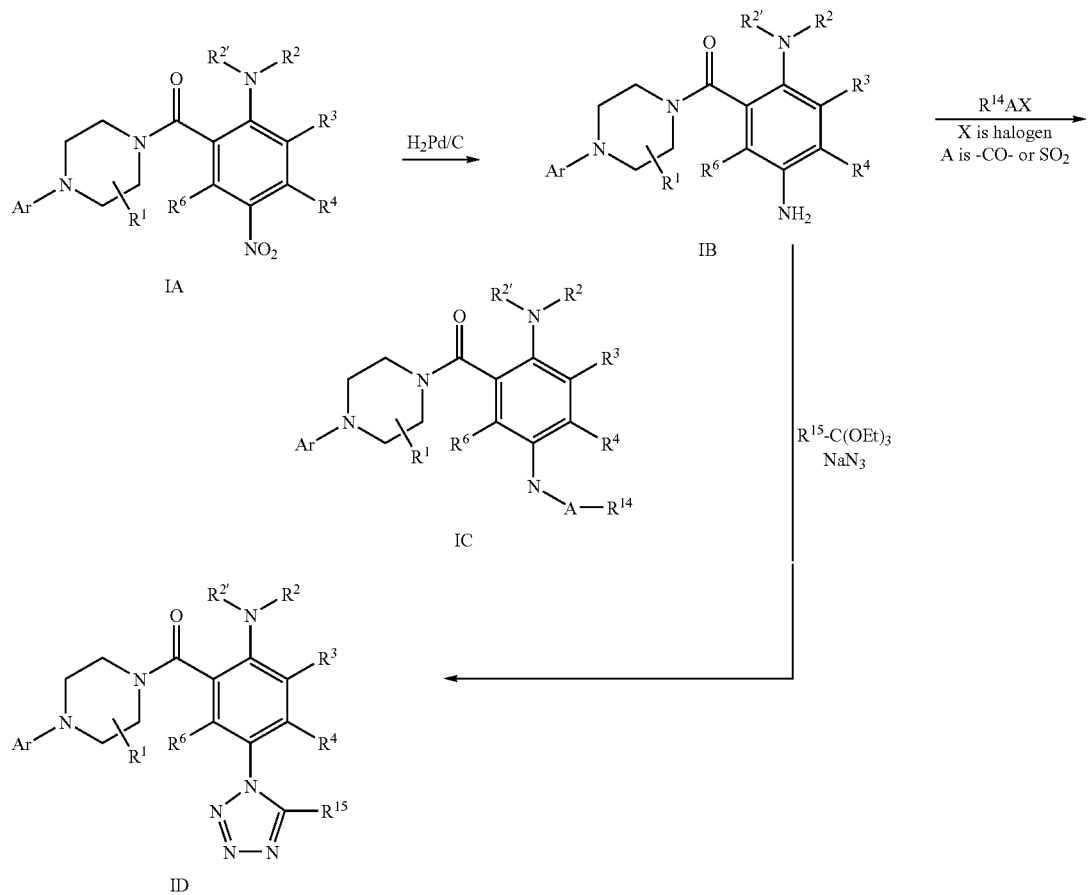

Compounds of formula IC (A is —CO—) and IC (A is —SO$_2$—) can be prepared respectively by carbonylation or sulfonylation of a corresponding amino derivative IB in the presence of a compound of formula R$^{14}$AX. In turn, a compound of formula IB can be prepared by hydrogenation of a compound of formula IA.

Heterocyclic compounds of formula ID can be prepared by reaction of a compound of formula IB with a substituted triethyl orthoformate derivative of formula R$^{15}$—C(OEt)$_3$ in the presence of sodium azide.

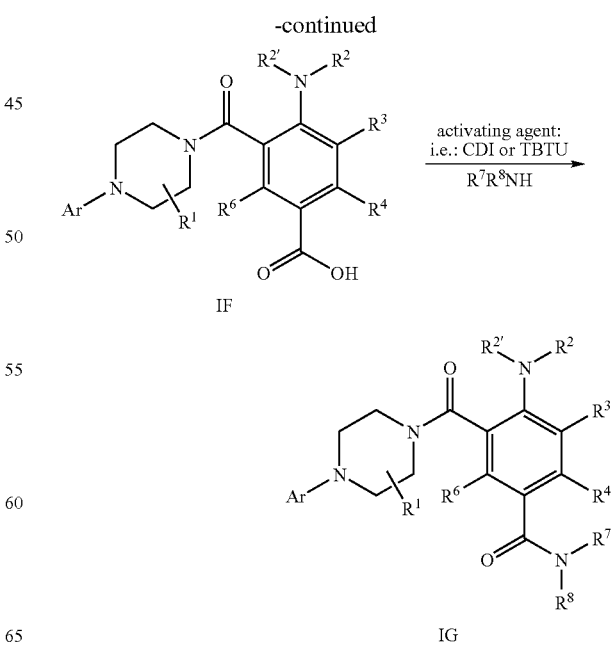

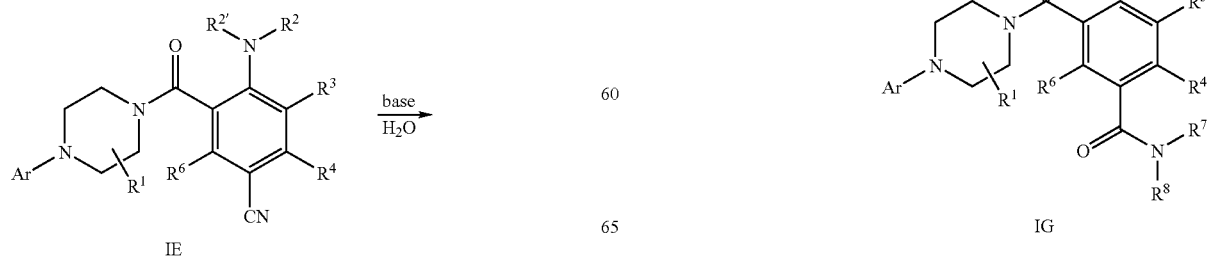

Compounds of formula IG can be prepared by reaction of an acid derivative of formula IF with an amine of formula R⁷R⁸NH in the presence of an activating agent like CDI (N-carbonyldiimidazole) or TBTU (2-(1H-benzotriazole-1-yl)-1,1,3,3-tetramethyluronium tetrafluoroborate). A compound of formula IF can be prepared by hydrolysis of a compound of formula IE in the presence of base like sodium hydroxide.

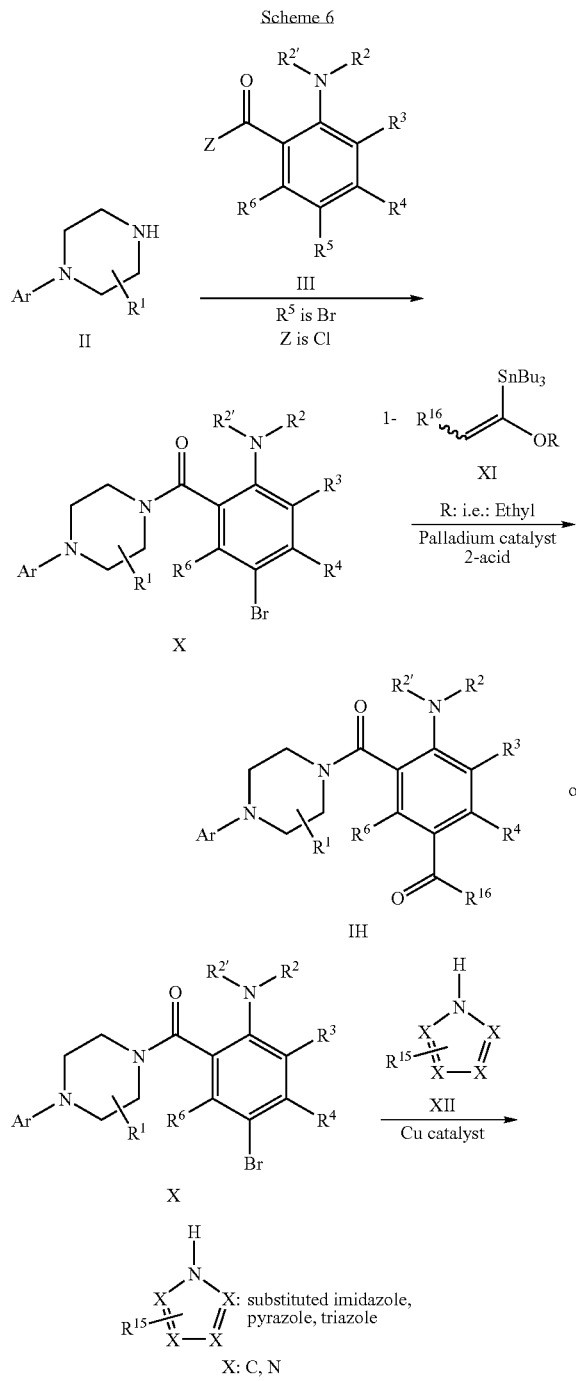

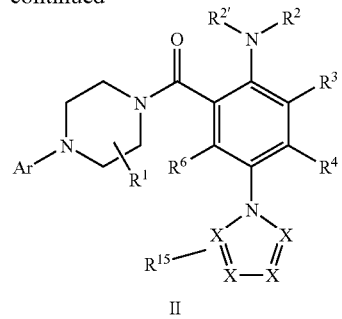

A compound of formula IH can be prepared by reacting under Stille conditions with an aryl-bromo derivative of formula X and with a corresponding vinyl stannane of formula XI in the presence of a palladium catalyst like dichlorobis(triphenylphosphine) palladium(II). A compound of formula II can be prepared by reacting of a compound of formula X with a compound of formula XII in the presence of a Cu catalyst like CuI. A compound of formula X can be prepared by coupling an acid chloride III with a piperazine derivative of formula II.

The acid addition salts of the basic compounds of formula I may be converted to the corresponding free bases by treatment with at least a stoichiometric equivalent of a suitable base such as sodium or potassium hydroxide, potassium carbonate, sodium bicarbonate, ammonia, and the like.

The compounds of formula I and their pharmaceutically usable addition salts possess valuable pharmacological properties. Specifically, it has been found that the compounds of the present invention are good inhibitors of the glycine transporter I (GlyT-1).

The compounds were investigated in accordance with the test given hereinafter.

Solutions and Materials

DMEM complete medium: Nutrient mixture F-12 (Gibco Life-technologies), fetal bovine serum (FBS) 5%, (Gibco life technologies), Penicillin/Streptomycin1 % (Gibco life technologies), Hygromycin 0.6 mg/ml (Gibco life technologies), Glutamine 1 mM Gibco life technologies)

Uptake buffer (UB): 150 mM NaCl, 10 mM Hepes-Tris, pH 7.4, 1 mM $CaCl_2$, 2.5 mM KCl, 2.5 mM $MgSO_4$, 10 mM (+) D-glucose. Flp-in™-CHO (Invitrogen Cat no. R758-07) cells stably transfected with mGlyT1b cDNA.

Glycine Uptake Inhibition Assay (mGlyT-1b)

On day 1 mammalian cells, (Flp-in™-CHO), transfected with mGlyT-1b cDNA, were plated at the density of 40,000 cells/well in complete F-12 medium, without hygromycin in 96-well culture plates. On day 2, the medium was aspirated and the cells were washed twice with uptake buffer (UB). The cells were then incubated for 20 min at 22° C. with either (i) no potential competitor, (ii) 10 mM non-radioactive glycine, (iii) a concentration of a potential inhibitor. A range of concentrations of the potential inhibitor was used to generate data for calculating the concentration of inhibitor resulting in 50% of the effect (e.g. $IC_{50}$, the concentration of the competitor inhibiting glycine uptake of 50%). A solution was then immediately added containing [³H]-glycine 60 nM (11-16 Ci/mmol) and 25 μM non-radioactive glycine. The plates were incubated with gentle shaking and the reaction was stopped by aspiration of the mixture and washing (three times) with ice-cold UB. The cells were lysed with scintillation liquid, shaken 3 hours and the radioactivity in the cells was counted using a scintillation counter.

The compounds in the above table show an $IC_{50}$ (EM) at mGlyT-1<0.02 (μM)

| Example No. | $IC_{50}$ (μM) | Example No. | $IC_{50}$ (μM) |
|---|---|---|---|
| 1 | 0.015 | 131 | 0.008 |
| 4 | 0.013 | 133 | 0.009 |
| 6 | 0.01 | 175 | 0.0097 |
| 11 | 0.015 | 176 | 0.02 |
| 16 | 0.012 | 186 | 0.015 |
| 18 | 0.0025 | 216 | 0.012 |
| 19 | 0.003 | 217 | 0.016 |
| 20 | 0.0021 | 219 | 0.017 |
| 21 | 0.0023 | 220 | 0.019 |
| 27 | 0.0012 | 233 | 0.016 |
| 28 | 0.0033 | 234 | 0.01 |
| 35 | 0.006 | 235 | 0.0065 |
| 36 | 0.014 | 236 | 0.004 |
| 37 | 0.007 | 245 | 0.018 |
| 38 | 0.008 | 246 | 0.011 |
| 41 | 0.014 | 247 | 0.014 |
| 42 | 0.0035 | 248 | 0.01 |
| 43 | 0.009 | 250 | 0.015 |
| 45 | 0.019 | 251 | 0.019 |
| 76 | 0.019 | 263 | 0.01 |
| 83 | 0.019 | 264 | 0.012 |
| 129 | 0.005 | | |

The present invention also provides pharmaceutical compositions containing compounds of the invention or pharmaceutically acceptable salts thereof and a pharmaceutically acceptable carrier. Such pharmaceutical compositions can be in the form of tablets, coated tablets, dragées, hard and soft gelatine capsules, solutions, emulsions or suspensions. The pharmaceutical compositions also can be in the form of suppositories, or injectable solutions.

The pharmaceutical compositions of the invention, in addition to one or more compounds of the invention, contain a pharmaceutically acceptable carrier. Suitable pharmaceutically acceptable carriers include pharmaceutically inert, inorganic or organic carriers for the production of pharmaceutical preparations. Lactose, corn starch or derivatives thereof, talc, stearic acids or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like. Depending on the nature of the active substance no carriers are however usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

In addition, the pharmaceutical compositions can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The compounds and compositions of the present invention can be administered in a conventional manner, for example, orally, rectally, or parenterally. The pharmaceutical compositions of the invention can be administered orally, for example, in the form of tablets, coated tablets, dragées, hard and soft gelatine capsules, solutions, emulsions, or suspensions. The pharmaceutical compositions also can be administered rectally, for example, in the form of suppositories, or parenterally, for example, in the form of injectable solutions.

The present invention also provides a method for the manufacture of pharmaceutical compositions. Such process comprises bringing one or more compounds of formula I and/or pharmaceutically acceptable acid addition salts thereof and, if desired, one or more other therapeutically valuable substances into a galenical administration form together with one or more therapeutically inert carriers.

The compound of the present invention are inhibitors of the glycine transporter 1 (GlyT-1), and have good selectivity to glycine transporter 2 (GlyT-2) inhibitors. Therefore, the compounds of formula I are useful in the treatment of neurological and neuropsychiatric disorders. The invention provides methods for the treatment of diseases related to activation of NMDA receptors via Glyt-1 inhibition. In particular, the invention provides methods for the treatment of central nervous system diseases, such as psychoses, dysfunction in memory and learning, schizophrenia, dementia, attention deficit disorders, and Alzheimer's disease.

The most preferred indications in accordance with the present invention are those, which include disorders of the central nervous system, for example the treatment or prevention of schizophrenia, cognitive impairment and Alzheimer's disease. Thus, the invention provides a method for the treatment of schizophrenia which comprises administering to a patient having schizophrenia a therapeutically effective amount of a compound of formula I or a pharmaceutically acceptable acid addition salt thereof. The invention also provides a method for the treatment of cognitive impairment which comprises administering to a patient having cognitive impairment a therapeutically effective amount of a compound of formula I or a pharmaceutically acceptable acid addition salt thereof. The invention further provides a method for the treatment of Alzheimer's disease which comprises administering to a patient having Alzheimer's disease a therapeutically effective amount of a compound of formula I or a pharmaceutically acceptable acid addition salt thereof.

The dosage at which the compounds of the invention can be administered varies within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt thereof. The daily dosage may be administered as single dose or in divided doses and, in addition, the upper limit can also be exceeded when this is found to be indicated.

The following examples illustrate the present invention without limiting it. All temperatures are given in degree Celsius.

The following abbreviations were used in the examples:

RT: room temperature;

n-Boc-piperazine: tert-Butyl 1-piperazinecarboxylate,

Oxone®: (potassium peroxymonosulfate) 2 $KHSO_5.KHSO_4.K_2SO_4$,

EtOAc: ethyl acetate;

THF: tetrahydrofuran;

TBTU: 2-(1H-benzotriazole-1-yl)-1,1,3,3-tetramethyluroniumtetrafluoroborate;

DIPEA: diisopropylethylamine,

DMF: N,N-dimetyhylformamide

Example A

1-{3-Fluoro-4-[4-(2-fluoro-5-nitro-benzoyl)-piperazin-1-yl]-phenyl}-ethanone

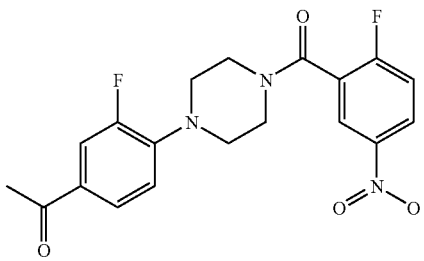

A solution of 2-Fluoro-5-nitro-benzoyl chloride (CAS: 7304-32-7; Feng, Y.; Burgess, K.; Chem. Europ. J.; EN; 5; 11; 1999; 3261-3272) (0.054 g, 0.261 mmol) in dioxane (1 ml) was treated with triethylamine (0.073 ml, 0.522 mmol) and then with a solution of 1-(3-Fluoro-4-piperazin-1-yl-phenyl)-ethanone (CAS: 189763-57-3; WO9714690) (58 mg, 0.261 mmol) in dioxane (1 ml). The mixture was stirred at room temperature for 30 minutes. The solvent was removed in vacuo. The crude oil was taken in water. The aqueous layer was extracted 3 times with $CH_2Cl_2$. The combined extracts were dried over $Na_2SO_4$, filtered and the solvent was removed in vacuo. The crude gum was purified on silicagel (eluent: heptane/ethylacetate 0%-20% (10 minutes) to provide the title compound (69 mg, 68%) as a light yellow solid, MS (m/e): 390.2 ($MH^+$, 100%)

Example 1

1-{4-[4-(2-Morpholin-4-yl-5-nitro-benzoyl)-piperazin-1-yl]-3-fluoro-phenyl}-ethanone Known Compound, RN 310415

A solution of 1-{3-Fluoro-4-[4-(2-fluoro-5-nitro-benzoyl)-piperazin-1-yl]-phenyl}-ethanone (0.065 g, 0.167 mmol) in morpholine (0.29 ml) was heated for 30 minutes at 100° C. then cooled to room temperature and diluted with water. The resulting solid was filtered and dried to provide the title compound (71 mg, 93%) as a yellow solid, MS (m/e): 457.3 ($M+H^+$, 100%)

According to the procedure described for the synthesis of Example 1 further derivatives have been synthesised and comprise Examples 179, 180, 189, 190, 191, 196, 197, 198 in Table 1.

Example 2

1-{4-[4-(2-Ethylamino-5-nitro-benzoyl)-piperazin-1-yl]-3-fluoro-phenyl}-ethanone A mixture of 27.4 mg (0.07 mmol) 1-{3-Fluoro-4-[4-(2-fluoro-5-nitro-benzoyl)-piperazin-1-yl]-phenyl}-ethanone, 91 ul (0.091 mmol) of a 1N solution of ethylamine in DMF and 30 ul (0.175 mmol) DIPEA in 2 ml THF was heated to 80° C. for 16 h. After evaporation of the volatiles the residue was taken up in 2 ml methanol/formic acid 6/1 and subjected to preparative HPLC purification on reversed phase eluting with an acetonitrile/water gradient to yield after evaporation of the product fractions 20.2 mg (70%) of the title compound. MS (m/e): 415.2 ($MH^+$, 100%)

According to the procedure described for the synthesis of Example 2 further derivatives have been synthesised from 1-{3-Fluoro-4-[4-(2-fluoro-5-nitro-benzoyl)-piperazin-1-yl]-phenyl}-ethanone and amines and comprise Examples 2-45 in Table 1.

Example B

2-Morpholin-4-yl-5-nitro-benzoyl chloride

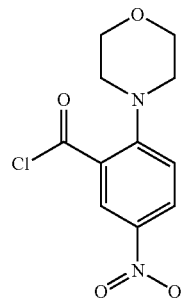

Step 1: 2-Morpholin-4-yl-5-nitro-benzoic acid

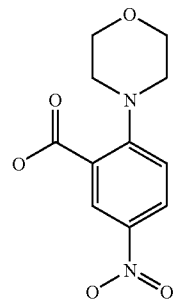

To a solution of 2-Fluoro-5-nitrobenzoic acid (4.86 g, 26.2 mmol) in dioxane (50 ml) was added morpholine (11.5 ml). The mixture was stirred at room temperature for 2 hours. The solvent was removed in vacuo. The residue was dissolved in water and the mixture was acidified with HCl 2N. The solid was filtered, washed with water and dried to provide the title compound (6.2 g, 93%) as a yellow solid, MS (m/e): 251.2 (M−H, 100%).

Step 2: 2-Morpholin-4-yl-5-nitro-benzoyl chloride

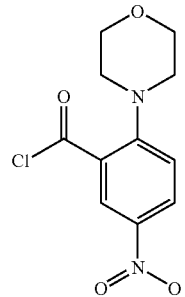

To a suspension of 2-Morpholin-4-yl-5-nitro-benzoic acid (4.0 g, 16 mmol) in toluene were added 2 drops of DMF and thionylchloride (5.7 ml, 79.3 mmol). The mixture was heated to 80° C. for 50 minutes. The solvent was removed in vacuo, and the resulting solid was stirred in ether, filtered and dried to provide the title compound (4.0 g, 93%) as a yellow solid.

Example C 1-(3-Chloro-4-piperazin-1-yl-phenyl)-ethanone

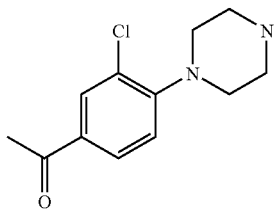

A mixture of 5.0 g (29 mmol) 3-Chloro-4-fluoroacetophenon and 12.5 g (145 mmol) piperazine in 10 ml N,N-dimethyl-acetamide was heated to 120° C. for 23 h. All volatiles were removed under vacuum and the residue was purified by flash column chromatography on silica eluting with a mixture of DCM/methanol/5% NH$_3$ aq. to yield 3.47 g (50%) of the title compound as yellow amorphous solid.

1-H-NMR (300 MHz, CDCl$_3$) δ=7.96 (d, J$_1$=8.4 Hz, J$_2$=2.1 Hz, H-2, 1H), 7.82 (dd, J$_1$=8.4 Hz, J$_2$=2.1 Hz, H-6, 1H), 7.04 (d, J$_1$=8.4 Hz, H-5, 1H), 3.03 (m, 4H, piperazine), 2.88 (m, 4H, piperazine), 2.55 (s, 3H, COMe).

MS (m/e): 239.2 (MH$^+$, 100%)

Example D 1-(2-Chloro-4-trifluoromethyl-phenyl)-piperazine

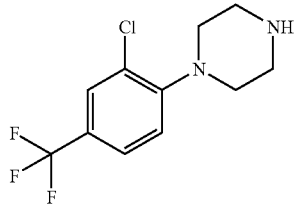

Step 1: 4-(2-Chloro-4-trifluoromethyl-phenyl)-piperazine-1-carboxylic acid tert-butyl ester

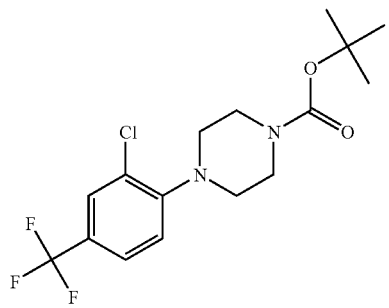

A mixture of 0.5 g (1.6 mmol) of 3-chloro-4-iodobenzotrifluoride 0.7 g (3.8 mmol), N-Boc-piperazine, 41 mg (0.04 mmol) Tris(dibenzylideneacetone)dipalladium chloroform complex, 0.44 g (4.43 mmol) sodium-t-butoxide and 48 mg (0.16 mmol) tri-o-tolylphosphine in 6 ml dioxane was heated overnight at 100° C. The solution was allowed to cool to room temperature, taken up in ether (30 ml) and washed with brine (25 ml). The organic layer was dried over Na$_2$SO$_4$, filtered and the solvent was removed in vacuo. The crude oil was chromatographed over on silica gel: Eluent: Heptane-AcOEt 0-10% over 15 min to provide the title compound (0.06 g, 10%) as a brown oil, MS (m/e): 365.1 (MH$^+$, 100%).

Step 2:
1-(2-Chloro-4-trifluoromethyl-phenyl)-piperazine

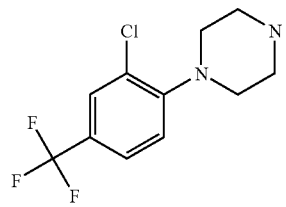

A solution of 4-(2-Chloro-4-trifluoromethyl-phenyl)-piperazine-1-carboxylic acid tert-butyl ester (60 mg, 0.164 mmol) in MeCl$_2$ (0.8 ml) was treated with trifluoroacetic acid (63 μl), heated up to 40° C. and stirred for 4 h. The solvent was removed in vacuo. The residue was dissolved in water and basified with NaOH 1N. The aqueous layer was extracted twice with MeCl$_2$. The combined organic layers were dried over Na$_2$SO$_4$, filtered and the solvent was removed in vacuo to provide the title compound (20 mg, 46%) as a yellow oil, MS (m/e): 265.0 (MH$^+$, 100%).

Example E 2-piperazin-1-yl-5-trifluoromethyl-benzonitrile

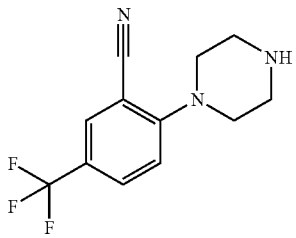

Step 1: 4-(2-Cyano-4-trifluoromethyl-phenyl)-piperazine-1-carboxylic acid tert-butyl ester

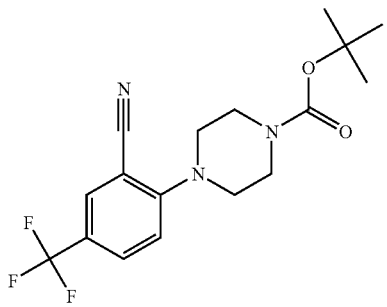

Title compound was prepared according to the procedure described in example G from N-Boc-piperazine and 2-Chloro-5-trifluoromethylbenzonitrile (CAS: 328-87-0) (15% yield, yellow oil, MS (m/e): 373.1 (M+NH$_4^+$, 100%).

Step 2: 2-piperazin-1-yl-5-trifluoromethyl-benzonitrile

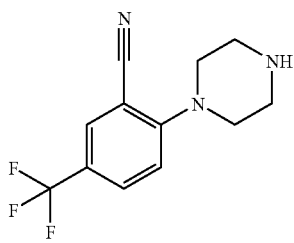

Title compound was prepared according to procedure described in example D/step 2, (82% yield, yellow oil, MS (m/e): 256.0 (M+H$^+$, 100%).

Example F 1-(2-Bromo-5-trifluoromethyl-phenyl)-piperazine

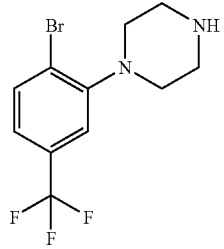

A mixture of 2 g (8 mmol) 1-Bromo-2-fluoro-4-trifluoromethyl-benzene and 2.13 g (25 mmol) piperazine in 2 ml N,N-dimethylacetamide was heated to 100° C. for 2 h and subsequently all volatiles were removed under vacuum. The residue was purified by flash column chromatography on silica eluting with DCM/methanol/1% NH$_3$ aq. to yield 0.765 g (37%) of the title compound as colourless oil.

1-H-NMR (300 MHz, CDCl$_3$) δ=7.81 (d, J=8 Hz, 1H, H-4), 7.30 (m, 2H, H-3/H-6), 3.2-3.5 (s, br, 1H, NH), 2.93 (m, 4H, piperazine) 2.86 (m, 4H, piperazine).

MS (m/e): 309.1 (MH$^+$, 100%)

Example G 4-(2-Fluoro-4-trifluoromethyl-phenyl)-piperazine-1-carboxylic acid tert-butyl ester

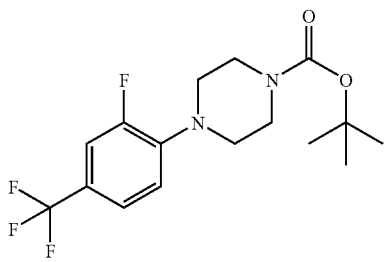

A mixture of 5 g (20 mmol) 1-Bromo-2-fluoro-4-trifluoromethyl-benzene, 4.6 g (24.7 mmol) n-Boc-piperazine, 106 mg (0.1 mmol) Tris(dibenzylideneacetone)dipalladium chloroform complex 2.77 g (28.8 mmol) sodium-t-butoxide and 144 mg (0.4 mmol) 2-(Dicyclohexylphosphino)biphenyl in 50 ml toluene was heated for 16 h at 80° C. After cooling to room temperature the mixture was treated with 15 g Isolute HM-N and all volatiles were removed under vacuum. The residue was purified on silica eluting with a gradient of heptane/EtOAc to yield after evaporation 4.54 g (63%) of the title compound as white amorphous solid.

1-H-NMR (300 MHz, CDCl$_3$) δ=7.50 (d, J=12 Hz, 1H, H-3), 7.48 (d, J=8 Hz, 1H, H-5), 7.2 (dd, J$_1$=8 Hz, J$_2$=8 Hz, 1H, H-6), 3.49 (m, 4H, piperazine), 3.08 (m, 4H, piperazine).

MS (m/e): 349.2 (MH$^+$, 100%)

Example H 1-(2-Fluoro-4-trifluoromethyl-phenyl)-piperazine

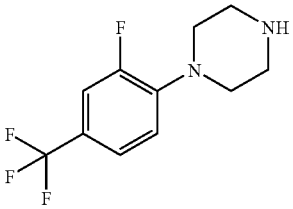

A mixture of 3.11 g (9 mmol) 4-(2-Fluoro-4-trifluoromethyl-phenyl)-piperazine-1-carboxylic acid tert-butyl ester in 20 ml dioxane was treated with 8.93 ml 4N HCl in dioxane for 2 h at 80° C. The mixture was concentrated and treated with 20 ml water, 20 ml 2M Na$_2$CO$_3$ and extracted with 50 ml EtOAc. The organic phase was washed with 30 ml saturated NaCl. All aqueous phases were combined and extracted with 50 ml EtOAc. The combined organic phases were dried with MgSO$_4$ and evaporated to yield 2.1 g (95%) of the title compound as brownish crystals.

1-H-NMR (300 MHz, CDCl$_3$) δ=7.50 (d, J=13.3 Hz, 1H, H-3), 7.45 (d, J=8.8 Hz, 1H, H-5), 7.16 (dd, J$_1$=8.8 Hz, J$_2$=8.8

Hz, 1H, H-6), 3.5-3.2 (s, br, 1H, NH), 3.04 (m, 4H, piperazine), 2.87 (m, 4H, piperazine).

MS (m/e): 249.2 (MH+, 100%)

Example I

3-Fluoro-4-piperazin-1-yl-benzoic acid ethyl ester

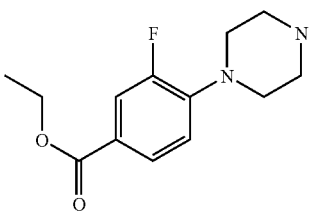

A mixture of 5 g (27 mmol) 3,4-Difluoro-benzoic acid ethyl ester and 11.56 g (134 mmol) piperazine in 15 ml N,N-dimethylacetamide was heated to 120° C. for 1.5 h and subsequently all volatiles were removed under vacuum. The residue was purified by flash column chromatography on silica eluting with DCM/methanol to yield 6.19 g (91%) of the title compound as white amorphous solid.

1-H-NMR (300 MHz, DMSO-d6) δ=7.69 (dd, $J_1$=8.4 Hz, $J_2$=1.9 Hz, 1H, H-6), 7.57 (dd, $J_1$=12.1 Hz, $J_2$=2.0 Hz, 1H, H-2), 7.07 (dd, $J_1$=8.7 Hz, $J_2$=8.7 Hz, 1H, H-5), 4.26 (q, $J_1$=7.1 Hz, 2H, O—CH$_2$), 3.06 (m, 4H, piperazine), 2.83 (m, 4H, piperazine), 1.30 (t, $J_1$=7.1 Hz, 3H, CH$_3$).

MS (m/e): 253.2 (MH+, 100%)

Example J

3-Fluoro-4-piperazin-1-yl-benzenesulfonamide

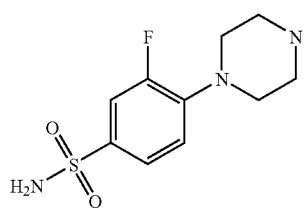

A mixture of 0.5 g (3 mmol) 3,4-Difluoro-benzenesulfonamide and 1.15 g (13 mmol) piperazine in 2.3 ml water was heated to 110° C. for 3 h and subsequently the precipitate was filtered off and washed with water and toluene. The residue was dried under high vacuum to yield 0.578 g (86%) of the title compound as white crystals.

1-H-NMR (300 MHz, DMSO-d6) δ=7.53 (dd, $J_1$=8.6 Hz, $J_2$=2 Hz, 1H, H-6), 7.48 (dd, $J_1$=15 Hz, $J_2$=2 Hz, 1H, H-2), 7.2-7.4 (s, br, 2H, NH$_2$), 7.13 (dd, $J_1$=8.6 Hz, $J_2$=8.6 Hz 1H, H-5), 3.2-3.5 (s, br, 1H, NH), 3.03 (m, 4H, piperazine), 2.83 (m, 4H, piperazine).

MS (m/e): 260.0 (MH+, 100%)

Example 46

[4-(2-Chloro-phenyl)-piperazin-1-yl]-(2-morpholin-4-yl-5-nitro-phenyl)-methanone A mixture of 18.9 mg (0.07 mmol) 2-Morpholin-4-yl-5-nitro-benzoyl chloride, 16.5 mg (0.084 mmol) 1-(2-Chlorophenyl)-piperazine and 34 ul (0.245 mmol) NEt$_3$ in 2 ml DCM was stirred at room temperature for 16 h. After evaporation of the volatiles the residue was taken up in 2 ml CH$_3$CN/MeOH/HCOOH 2/2/1 and subjected to preparative HPLC purification on reversed phase eluting with an acetonitrile/water gradient to yield after evaporation of the product fractions 23.2 mg (77%) of the title compound.

MS (m/e): 431.2 (MH+, 100%)

According to the procedure described for the synthesis of Example 46 further derivatives have been synthesised from 2-morpholin-4-yl-5-nitro-benzoyl chloride and piperazine derivatives and comprise Examples 46-74, 177, 184, 185, 186, 187, 188, 192, 200, 201 in Table 1.

Example K

1-{4-[4-(2-Chloro-5-methanesulfonyl-benzoyl)-piperazin-1-yl]-3-fluoro-phenyl}-ethanone

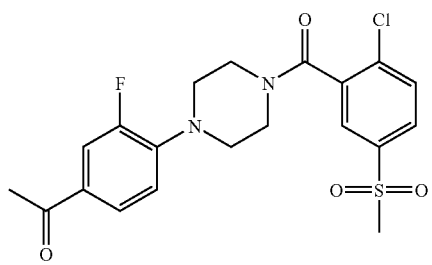

Step 1: 2-Chloro-5-methanesulfonyl-benzoic acid

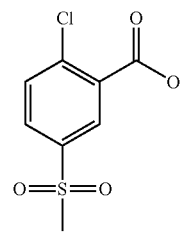

A solution of 2-Chloro-5-(methylthio)benzoic acid (CAS: 51546-12-4; 2.5 g, 11.8 mmol) was dissolved in methanol (50 ml) and cooled to 0° C. Oxone (21.9 g, 35.5 mmol) was added portionwise within 5 minutes. The mixture was stirred at 0° C. for 30 minutes and then at room temperature for 22 hours. The mixture was filtered. The filtrate was poured onto water (200 ml). The aqueous layer was extracted with dichloromethane (5×50 ml). The combined extracts were dried over Na$_2$SO$_4$, filtered and the solvent was removed in vacuo. The solid was stirred in ether (30 ml), filtered and dried to provide the title compound (1.96 g, 70%) as a beige solid, MS (m/e): 232.9 (M−H+, 100%).

Step 2: 1-{4-[4-(2-Chloro-5-methanesulfonyl-benzoyl)-piperazin-1-yl]-3-fluoro-phenyl}-ethanone Example L 3-[4-(4-Acetyl-2-fluoro-phenyl)-piperazine-1-carbonyl]-4-bromo-benzonitrile

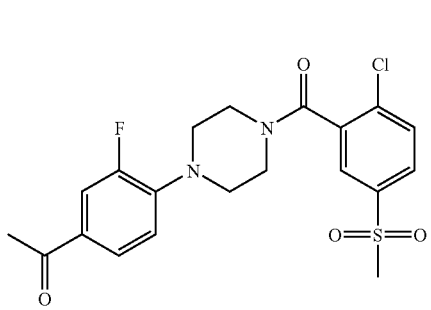

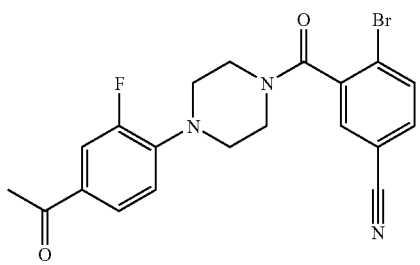

Step 1: 2-bromo-5-cyano-benzoic acid

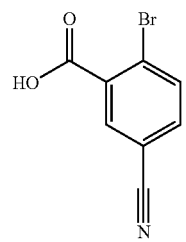

To a solution of 2-Chloro-5-methanesulfonyl-benzoic acid (200 mg, 0.852 mmol) in DMF (3 ml) was added dropwise 1,1'-Carbonyldiimidazole (142 mg, 0.852 mmol). When the $CO_2$ evolution ceased, the mixture was heated to 50° C. for 15 minutes. The mixture was cooled to room temperature. 1-(3-Fluoro-4-piperazin-1-yl-phenyl)-ethanone (189 mg, 0.852 mmol) was added portionwise. The mixture was stirred at room temperature for 1 hour. The solvent was removed in vacuo. The residue was dissolved in ethyl acetate. The solution was washed twice with water, dried over $Na_2SO_4$, filtered and the solvent was removed in vacuo. The crude oil was purified on silica gel (Heptane/AcOEt 0%-50% (15 minutes) to provide the title compound (185 mg, 49%) as a white solid, MS (m/e): 439.1 (M+H$^+$, 100%).

Example 75

1-(3-Fluoro-4-{4-[5-methanesulfonyl-2-(2-methyl-pyrrolidin-1-yl)-benzoyl]-piperazin-1-yl}-phenyl)-ethanone A mixture of 30.7 mg (0.7 mmol) 1-{4-[4-(2-Chloro-5-methanesulfonyl-benzoyl)-piperazin-1-yl]-3-fluoro-phenyl}-ethanone, 30 ul (0.175 mmol) DIPEA and 91 ul (0.91 mmol) of a 1M solution of 2-Methyl-pyrrolidine in DMF was heated to 100° C. for 24 h. After removal of THF 2 ml dioxane, 180 ul of a 1M solution of 2-Methyl-pyrrolidine in DMF and 30 ul (0.175 mmol) DIPEA were added and the mixture was heated to 120° C. for 16 h. After evaporation of all volatiles the residue was taken up in 1 ml MeOH/formic acid 6/1 and subjected to reversed phase HPLC purification eluting with an acetonitrile/water gradient to yield after evaporation of the product fractions 4.7 mg (14%) of the title compound. MS (m/e): 488.2 (MH$^+$, 100%)

According to the procedure described for the synthesis of Example 75 further derivatives have been synthesised from 1-{4-[4-(2-Chloro-5-methanesulfonyl-benzoyl)-piperazin-1-yl]-3-fluoro-phenyl}-ethanone and amines and comprise Examples 75-89 in Table 1.

To a suspension of copper (II) bromide (1.6 g, 7.1 mmol) in acetonitrile (30 ml) was added dropwise tert-butylnitrite (1.15 ml, 8.63 mmol) at 0° C. within 2 minutes. 2-Amino-5-cyano-benzoic acid (CAS: 99767-45-0; WO9518097) (1.0 g, 6.17 mmol) was added portionwise within 10 minutes at 0° C. The mixture was stirred at 0° C. for 2 hours and then at room temperature overnight. Half of the solvent was removed in vacuo. The residue was taken in HCl 1N (15 ml) and ethyl acetate (30 ml). The organic layer was extracted with NaOH 1N (3×10 ml). The aqueous layer was acidified with HCl 2N. The resulting solid was filtered, washed with water and dried (high vacuum, 50° C.) to provide the title compound (0.92 g, 66%) as a yellow solid.

Step 2: 3-[4-(4-acetyl-2-fluoro-phenyl)-piperazine-1-carbonyl]-4-bromo benzonitrile

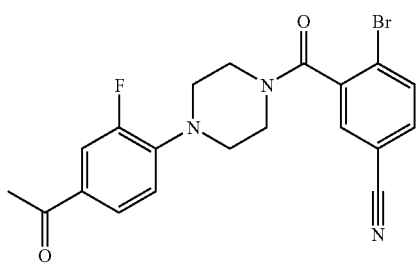

Title compound was prepared according to procedure described in example K/step 2 from 1-(3-Fluoro-4-piperazin-1-yl-phenyl)-ethanone and 2-bromo-5-cyano-benzoic acid, (49% yield, white solid, MS (m/e): 430 (M$^+$, 100%).

Example 90

3-[4-(4-Acetyl-2-fluoro-phenyl)-piperazine-1-carbonyl]-4-azepan-1-yl-benzonitrile A mixture of 30.1 mg (0.7 mmol) 3-[4-(4-Acetyl-2-fluoro-phenyl)-piperazine-1-carbonyl]-4-bromo-benzonitrile, 30 ul (0.175 mmol) DIPEA and 91 ul (0.91 mmol) of a 1M solution of azepane in DMF was heated to 100° C. for 24 h. After removal of THF 2 ml dioxane, 180 ul of a 1M solution of azepane in DMF and 30 ul (0.175 mmol) DIPEA were added and the mixture was heated to 120° C. for 16 h. After evaporation of all volatiles the residue was taken up in 1 ml MeOH/formic acid 6/1 and subjected to reversed phase HPLC purification eluting with an acetonitrile/water gradient to yield after evaporation of the product fractions 9.3 mg (30%) of the title compound. MS (m/e): 449.2 (MH+, 100%)

According to the procedure described for the synthesis of Example 90 further derivatives have been synthesised from 3-[4-(4-Acetyl-2-fluoro-phenyl)-piperazine-1-carbonyl]-4-bromo-benzonitrile and amines and comprise Examples 90-103 in Table 1.

Example 104

3-Chloro-4-[4-(2-morpholin-4-yl-5-nitro-benzoyl)-piperazin-1-yl]-benzonitrile

A mixture of 40.6 mg (0.15 mmol) 2-Morpholin-4-yl-5-nitro-benzoyl chloride, 39.9 mg (0.18 mmol) 3-Chloro-4-piperazin-1-yl-benzonitrile (WO9625414) and 62.5 ul (0.45 mmol) NEt₃ in 1 ml DCM was stirred at room temperature for 16 h. After evaporation of the volatiles the residue was taken up in 1 ml CH₃CN/DMF/HCOOH 3/5/2 and subjected to preparative HPLC purification on reversed phase eluting with an acetonitrile/water gradient to yield after evaporation of the product fractions 4.9 mg (8%) of the title compound.

MS (m/e): 456.2 (MH+, 100%)

According to the procedure described for the synthesis of Example 104 further derivatives have been synthesised from 2-Morpholin-4-yl-5-nitro-benzoyl chloride and piperazine derivatives and comprise Examples 104-122 in Table 1.

Example M

2-Chloro-5-sulfino-benzoic acid

A solution of 33.59 g (267 mmol) sodium sulfite in 100 ml water at 0° C. is treated with 21.2 g (89 mmol) 2-Chloro-5-fluorosulfonyl-benzoic acid and 26.6 ml of a 10M aqueous NaOH solution (267 mmol). The mixture was allowed to stir for 3 h at room temperature, acidified with HCl conc. (pH=4) and water was removed under vacuum. Methanol was added, the precipitate filtered off and the filtrate concentrated. Methanol and diethylether were added and the precipitate was filtered off washed with ether and dried to yield 15 g (76.5%) of the title compound as white gum. MS (m/e): 219.1 (MH−, 100%)

Example N

2-Chloro-5-methanesulfonyl-benzoic acid

A mixture of 1 g (4 mmol) 2-Chloro-5-sulfino-benzoic acid in 20 ml Methanol and 20 ml water was treated with 10N NaOH to pH=9 before adding 1.7 g (12 mmol) Methyliodide. The mixture was heated for 48 h to 80° C. with occasional addition of NaOH to maintain pH=9. After removal of all volatiles HCl conc. was added and the mixture was extracted with ethyl acetate. The combined organic layers were dried with MgSO₄ and evaporated to dryness. The residue was taken up in methanol and subjected to reversed phase HPLC purification eluting with an acetonitrile/water gradient to yield after evaporation of the product fractions 323 mg (34%) of the title compound. MS (m/e): 233.0 (MH−, 100%).

Example O

2-Chloro-5-ethanesulfonyl-benzoic acid

The title compound was synthesised according to the procedure described for the synthesis of 2-Chloro-5-methanesulfonyl-benzoic acid from 2-Chloro-5-sulfino-benzoic acid and ethyl iodide in 20 ml ethanol/20 ml water and obtained in 27% yield. MS (m/e): 247.1 (MH⁻, 100%).

Example P

2-Chloro-5-(propane-2-sulfonyl)-benzoic acid

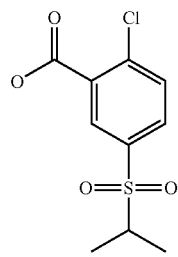

The title compound was synthesised according to the procedure described for the synthesis of 2-Chloro-5-methanesulfonyl-benzoic acid from 2-Chloro-5-sulfino-benzoic acid and 2-iodopropane in 20 ml isopropanol/20 ml water and obtained in 42% yield. MS (m/e): 261.1 (MH⁻, 100%).

Example O

2-Chloro-5-cyclopropylmethanesulfonyl-benzoic acid

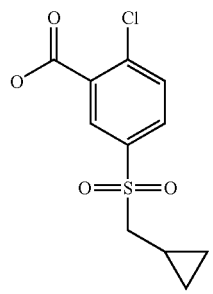

The title compound was synthesised according to the procedure described for the synthesis of 2-Chloro-5-methanesulfonyl-benzoic acid from 2-Chloro-5-sulfino-benzoic acid and Bromomethyl-cyclopropane (+catalytic amount I2) in 20 ml cyclopropyl methanol/20 ml water and obtained in 8% yield. MS (m/e): 273.1 (MH⁻, 100%).

Example R

2-Chloro-5-(propane-1-sulfonyl)-benzoic acid

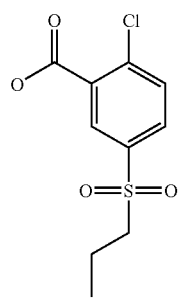

The title compound was synthesised according to the procedure described for the synthesis of 2-Chloro-5-methanesulfonyl-benzoic acid from 2-Chloro-5-sulfino-benzoic acid and 1-iodopropane in 20 ml propanol/20 ml water and obtained in 3% yield. MS (m/e): 261.1 (MH⁻, 100%).

Example S

2-Chloro-5-methylsulfamoyl-benzoic acid

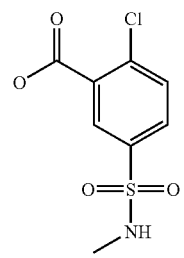

A mixture of 1 g (4 mmol) 2-Chloro-5-sulfino-benzoic acid and 0.62 g (20 mmol) Methylamine in 10 ml dioxane was stirred for 3 h at room temperature. After evaporation of the volatiles 15 ml 5N HCl was added and the mixture was extracted 3× with ethylacetate. The solvent was removed under vacuum to yield 0.724 g (72%) of the title compound as amorphous white solid. MS (m/e): 248.1 (MH⁻, 100%).

Example T

2-Chloro-5-ethylsulfamoyl-benzoic acid

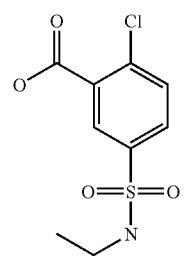

The title compound was synthesised according to the procedure described for 2-Chloro-5-methylsulfamoyl-benzoic acid from 2-Chloro-5-sulfino-benzoic acid and ethylamine and obtained in 78% yield. MS (m/e): 262.2 (MH⁻, 100%).

Example U

2-Chloro-5-isopropylsulfamoyl-benzoic acid

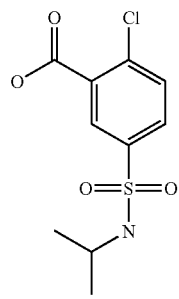

The title compound was synthesised according to the procedure described for 2-Chloro-5-methylsulfamoyl-benzoic acid from 2-Chloro-5-sulfino-benzoic acid and isopropylamine and obtained in 74% yield. MS (m/e): 276.1 (MH⁻, 100%).

Example V

2-Chloro-5-(cyclopropylmethyl-sulfamoyl)-benzoic acid

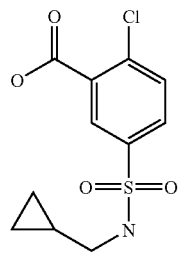

The title compound was synthesised according to the procedure described for 2-Chloro-5-methylsulfamoyl-benzoic acid from 2-Chloro-5-sulfino-benzoic acid and cyclopropylmethylamine and obtained in 81% yield. MS (m/e): 288.0 (MH⁻, 100%).

Example W

2-Chloro-5-(pyrrolidine-1-sulfonyl)-benzoic acid

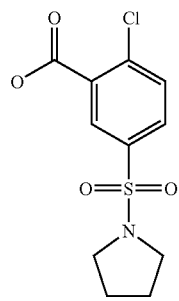

The title compound was synthesised according to the procedure described for 2-Chloro-5-methylsulfamoyl-benzoic acid from 2-Chloro-5-sulfino-benzoic acid and pyrrolidine and obtained in 91% yield. MS (m/e): 288.0 (MH⁻, 100%).

Example X

2-Chloro-5-(morpholine-4-sulfonyl)-benzoic acid

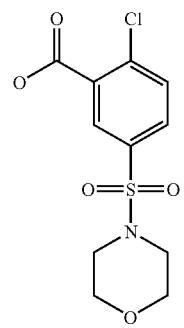

The title compound was synthesised according to the procedure described for 2-Chloro-5-methylsulfamoyl-benzoic acid from 2-Chloro-5-sulfino-benzoic acid and morpholine and obtained in 100% yield. MS (m/e): 304.0 (MH⁻, 100%).

Example Y

5-Methanesulfonyl-2-pyrrolidin-1-yl-benzoic acid

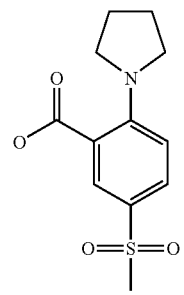

A mixture of 163.8 mg (0.7 mmol) 2-Chloro-5-methanesulfonyl-benzoic acid in 2 ml pyrrolidine was heated for 16 h to 100° C. After evaporation of all volatiles the residue was taken up in 2 ml methanol/formic acid 3/1 and subjected to reversed phase HPLC purification eluting with an acetonitrile/water gradient to yield after evaporation of the product fractions 143.4 mg (77%) of the title compound. MS (m/e): 268.1 (MH⁻, 100%).

Example Z

5-Ethanesulfonyl-2-pyrrolidin-1-yl-benzoic acid

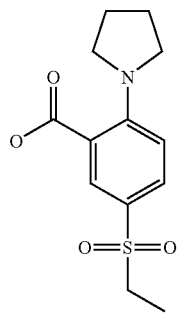

The title compound was synthesised according to the procedure described for the synthesis of 5-Methanesulfonyl-2-pyrrolidin-1-yl-benzoic acid from 2-Chloro-5-(ethane-2-sulfonyl)-benzoic acid and pyrrolidine and obtained in 73% yield. MS (m/e): 282.2 (MH$^-$, 100%).

Example AA 5-(Propane-1-sulfonyl)-2-pyrrolidin-1-yl-benzoic acid

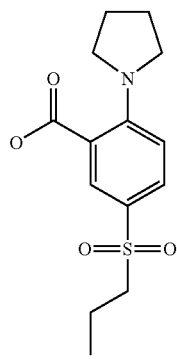

The title compound was synthesised according to the procedure described for the synthesis of 5-Methanesulfonyl-2-pyrrolidin-1-yl-benzoic acid from 2-Chloro-5-(propane-2-sulfonyl)-benzoic acid and pyrrolidine and obtained in 63% yield. MS (m/e): 296.2 (MH$^-$, 100%).

Example AB 5-(Propane-2-sulfonyl)-2-pyrrolidin-1-yl-benzoic acid

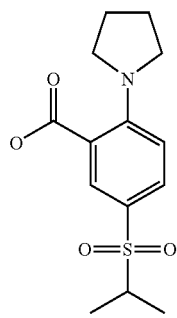

The title compound was synthesised according to the procedure described for the synthesis of 5-Methanesulfonyl-2-pyrrolidin-1-yl-benzoic acid from 2-Chloro-5-(propane-2-sulfonyl)-benzoic acid and pyrrolidine and obtained in 72% yield. MS (m/e): 296.2 (MH$^-$, 100%).

Example AC

5-Methylsulfamoyl-2-pyrrolidin-1-yl-benzoic acid

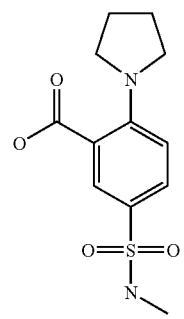

The title compound was synthesised according to the procedure described for the synthesis of 5-Methanesulfonyl-2-pyrrolidin-1-yl-benzoic acid from 2-Chloro-5-methylsulfamoyl-benzoic acid and pyrrolidine and obtained in 45% yield. MS (m/e): 283.1 (MH$^-$, 100%).

Example AD

5-Ethylsulfamoyl-2-pyrrolidin-1-yl-benzoic acid

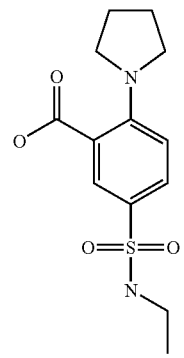

The title compound was synthesised according to the procedure described for the synthesis of 5-Methanesulfonyl-2-pyrrolidin-1-yl-benzoic acid from 2-Chloro-5-ethylsulfa-

Example AE

5-Isopropylsulfamoyl-2-pyrrolidin-1-yl-benzoic acid

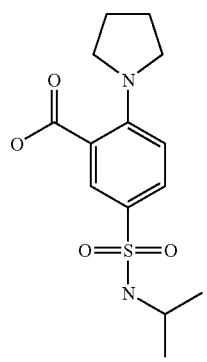

The title compound was synthesised according to the procedure described for the synthesis of 5-Methanesulfonyl-2-pyrrolidin-1-yl-benzoic acid from 2-Chloro-5-isopropylsulfamoyl-benzoic acid and pyrrolidine and obtained in 40% yield. MS (m/e): 311.2 (MH−, 100%).

Example AF 5-(Cyclopropylmethyl-sulfamoyl)-2-pyrrolidin-1-yl-benzoic acid

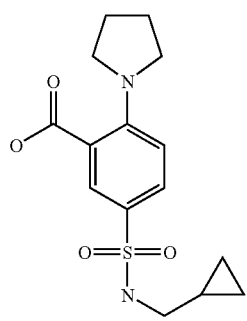

The title compound was synthesised according to the procedure described for the synthesis of 5-Methanesulfonyl-2-pyrrolidin-1-yl-benzoic acid from 2-Chloro-5-(cyclopropylmethyl-sulfamoyl)-benzoic acid and pyrrolidine and obtained in 38% yield.
MS (m/e): 323.2 (MH−, 100%).

Example AG

5-Methanesulfonyl-2-morpholin-4-yl-benzoic acid

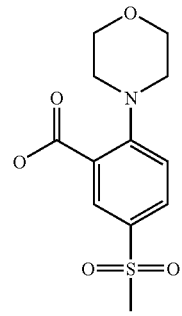

The title compound was synthesised according to the procedure described for the synthesis of 5-Methanesulfonyl-2-pyrrolidin-1-yl-benzoic acid from 2-Chloro-5-(methane-2-sulfonyl)-benzoic acid and morpholine and obtained in 80% yield. MS (m/e): 284.1 (MH−, 100%).

Example AH

5-Ethanesulfonyl-2-morpholin-4-yl-benzoic acid

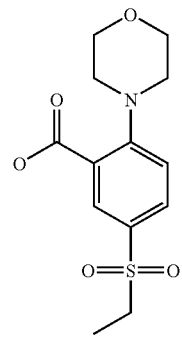

The title compound was synthesised according to the procedure described for the synthesis of 5-Methanesulfonyl-2-pyrrolidin-1-yl-benzoic acid from 2-Chloro-5-(ethane-2-sulfonyl)-benzoic acid and morpholine and obtained in 77% yield. MS (m/e): 298.2 (MH−, 100%).

Example AI

2-Morpholin-4-yl-5-(propane-2-sulfonyl)-benzoic acid

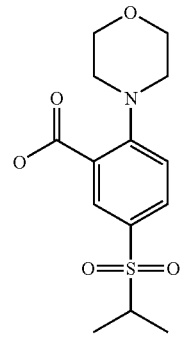

The title compound was synthesised according to the procedure described for the synthesis of 5-Methanesulfonyl-2- pyrrolidin-1-yl-benzoic acid from 2-Chloro-5-(isopropane-2-sulfonyl)-benzoic acid and morpholine and obtained in 53% yield. MS (m/e): 312.1 (MH⁻, 100%).

Example AJ

5-Cyclopropylmethanesulfonyl-2-morpholin-4-yl-benzoic acid

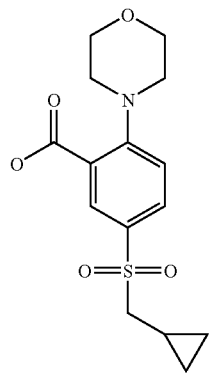

The title compound was synthesised according to the procedure described for the synthesis of 5-Methanesulfonyl-2-pyrrolidin-1-yl-benzoic acid from 2-Chloro-5-cyclopropyl-methanesulfonyl-benzoic acid and morpholine and obtained in 27% yield. MS (m/e): 324.2 (MH⁻, 100%).

Example AK

2-Morpholin-4-yl-5-(propane-1-sulfonyl)-benzoic acid

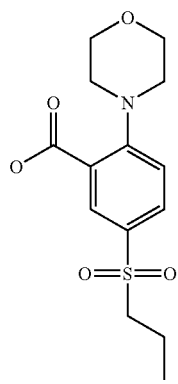

The title compound was synthesised according to the procedure described for the synthesis of 5-Methanesulfonyl-2-pyrrolidin-1-yl-benzoic acid from 2-Chloro-5-(propane-2-sulfonyl)-benzoic acid and morpholine and obtained in 62% yield. MS (m/e): 312.2 (MH⁻, 100%).

Example AL

5-Methylsulfamoyl-2-morpholin-4-yl-benzoic acid

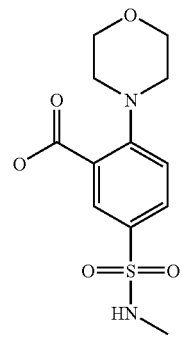

The title compound was synthesised according to the procedure described for the synthesis of 5-Methanesulfonyl-2-pyrrolidin-1-yl-benzoic acid from 2-Chloro-5-methylsulfamoyl-benzoic acid and morpholine and obtained in 40% yield. MS (m/e): 299.2 (MH⁻, 100%).

Example AM

5-Ethylsulfamoyl-2-morpholin-4-yl-benzoic acid

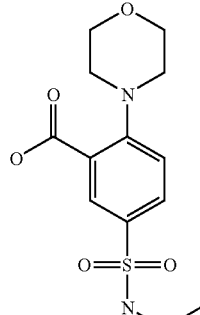

The title compound was synthesised according to the procedure described for the synthesis of 5-Methanesulfonyl-2-pyrrolidin-1-yl-benzoic acid from 2-Chloro-5-ethylsulfamoyl-benzoic acid and morpholine and obtained in 42% yield. MS (m/e): 313.2 (MH⁻, 100%).

Example AN

5-Isopropylsulfamoyl-2-morpholin-4-yl-benzoic acid

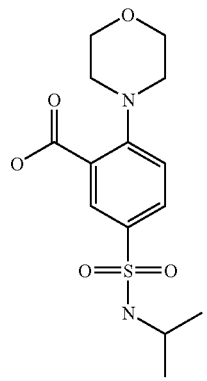

The title compound was synthesised according to the procedure described for the synthesis of 5-Methanesulfonyl-2-pyrrolidin-1-yl-benzoic acid from 2-Chloro-5-isopropylsulfamoyl-benzoic acid and morpholine and obtained in 38% yield. MS (m/e): 327.2 (MH⁻, 100%).

Example AO 5-(Cyclopropylmethyl-sulfamoyl)-2-morpholin-4-yl-benzoic acid

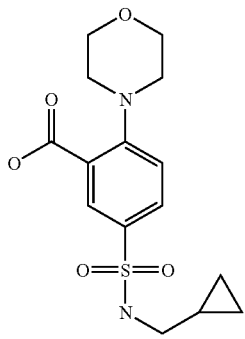

The title compound was synthesised according to the procedure described for the synthesis of 5-Methanesulfonyl-2-pyrrolidin-1-yl-benzoic acid from 2-Chloro-5-(cyclopropylmethyl-sulfamoyl)-benzoic acid and morpholine and obtained in 33% yield.

MS (m/e): 339.2 (MH⁻, 100%).

Example AP

2-Morpholin-4-yl-5-(pyrrolidine-1-sulfonyl)-benzoic acid

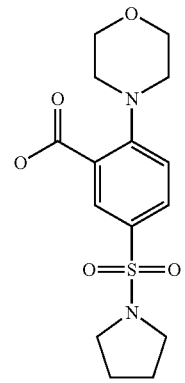

The title compound was synthesised according to the procedure described for the synthesis of 5-Methanesulfonyl-2-pyrrolidin-1-yl-benzoic acid from 2-Chloro-5-(pyrrolidine-1-sulfonyl)-benzoic acid and morpholine and obtained in 34% yield. MS (m/e): 339.2 (MH⁻, 100%).

Example AQ 5-(Morpholine-4-sulfonyl)-2-morpholin-4-yl-benzoic acid

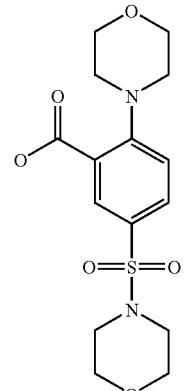

The title compound was synthesised according to the procedure described for the synthesis of 5-Methanesulfonyl-2-pyrrolidin-1-yl-benzoic acid from 2-Chloro-5-(morpholine-1-sulfonyl)-benzoic acid and morpholine and obtained in 22% yield. MS (m/e): 355.2 (MH⁻, 100%).

Example 123

4-Fluoro-2-[4-(5-methanesulfonyl-2-pyrrolidin-1-yl-benzoyl)-piperazin-1-yl]-benzonitrile A mixture of 13.6 mg (0.05 mmol) 5-Methanesulfonyl-2-pyrrolidin-1-yl-benzoic acid, 15.7 mg (0.06 mmol) 2-Fluoro-4-piperazin-1-yl-benzonitrile (Org. Proc. Res. Dev. 1999, 460), 17.9 mg (0.06 mmol) TBTU and 43 ul (0.25 mmol) DIPEA in 1 ml DMF was stirred for 16 h at room temperature. After addition of 100 ul formic acid the mixture was subjected to preparative HPLC purification on reversed phase eluting with an acetonitrile/water gradient to yield after evaporation of the product fractions 10.6 mg (33%) of the title compound. MS (m/e): 457.2 (MH+, 100%)

According to the procedure described for the synthesis of Example 123 further derivatives have been synthesised from acid derivatives and piperazine derivatives and comprise Examples 123-173 in Table 1.

Example 174

1-(4-{4-[2-(4-Methyl-piperazin-1-yl)-5-nitro-benzoyl]-piperazin-1-yl}-phenyl)-ethanone A stirred mixture of 150 mg (0.39 mmol) 1-{3-fluoro-4-[4-(2-fluoro-5-nitro-benzoyl)-piperazin-1-yl]-phenyl}-ethanone, 200 mg (2.0 mmol) 1-methylpiperazine in 4 ml THF was heated to 80° C. for 1 h. Water was added to the reaction mixture, the precipitate isolated, dried and purified by flash-chromatography on silica gel with heptane/AcOEt as eluent. The title compound was obtained as a light yellow powder, MS (m/e): 471.2 (MH+, 100%).

According to the procedure described for the synthesis of Example 174 further derivatives have been synthesised from 1-{3-fluoro-4-[4-(2-fluoro-5-nitro-benzoyl)-piperazin-1-yl]-phenyl}-ethanone and amines and comprise Examples 174 to 176 in Table 1.

Example AR 4-(2-Fluoro-4-methyl-phenyl)-piperazine-1-carboxylic acid tert-butyl ester

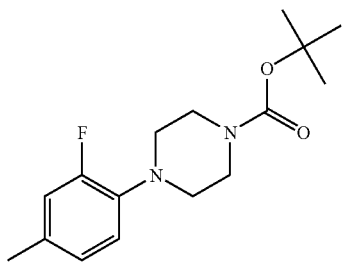

Title compound was prepared according to the procedure described in example G from N-Boc-piperazine and 4-bromo-3-fluorotoluene (40% yield, yellow oil, MS (m/e): 295.2 (M+H+, 100%).

Example AS 1-(2-Fluoro-4-methyl-phenyl)-piperazine

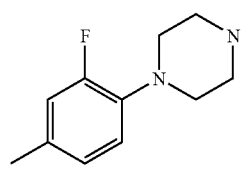

Title compound was prepared according to procedure described in example D/step 2, (99% yield, yellow oil, MS (m/e): 195.3 (M+H+, 100%).

Example 177

[4-(2-Fluoro-4-methyl-phenyl)-piperazin-1-yl]-(2-morpholin-4-yl-5-nitro-phenyl)-methanone Title compound was prepared according to procedure described in example 46 from 1-(2-Fluoro-4-methyl-phenyl)-piperazine and 2-morpholin-4-yl-5-nitro-benzoyl chloride (70% yield, yellow oil, MS (m/e): 429.2 (M+H+, 100%).

Example AT (5-Amino-2-morpholin-4-yl-phenyl)-[4-(4-trifluoromethyl-phenyl)-piperazin-1-yl]-methanone

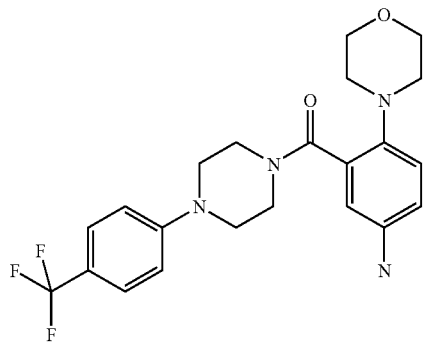

To a solution of (2-Morpholin-4-yl-5-nitro-phenyl)-[4-(4-trifluoromethyl-phenyl)-piperazin-1-yl]-methanone (preparation described in example 57, 150 mg, 0.323 mmol) in methanol (3 ml) was added Pd/C 10% (6.9 mg). The mixture was stirred under an atmosphere of hydrogen at room temperature for 1 hour. Catalyst was filtered and the filtrate was concentrated in vacuo. The residue was chromatographed over silicagel (Eluent: Heptane/Ethylacetate (0-100% in 20 minutes)) to provide the title compound (111 mg, 79% yield) as a yellow solid, MS (m/e): 435.2 (M+H+, 100%).

Example 178

(2-Morpholin-4-yl-5-tetrazol-1-yl-phenyl)-[4-(4-trifluoromethyl-phenyl)-piperazin-1-yl]-methanone A suspension of (5-Amino-2-morpholin-4-yl-phenyl)-[4-(4-trifluoromethyl-phenyl)-piperazin-1-yl]-methanone (50 mg, 0.115 mmol) in Acetic acid (1 ml) was heated to 75° C. under nitrogen and then triethylorthoformate (36.76 ul, 0.34 mmol) was slowly added. After 1 hour, sodium azide (22.4 mg, 0.34 mmol) was added portionwise and the reaction mixture was stirred at 75° C. for 1 h30. The reaction mixture was cooled to room temperature, diluted with water and basified with 1N NaOH solution. The aqueous phase was extracted with ethyl acetate. The organic phases were combined, dried over Na2SO4, filtered and evaporated to dryness. The residue was chromatographed on silica gel: Eluent: Heptane/Ethylacetate 0% to 60% (10 minutes) to provide the title compound (29 mg, 52%) as yellow solid, MS (m/e): 488.2 (M+H+, 100%)

Example AU

3-[4-(4-Acetyl-2-fluoro-phenyl)-piperazine-1-carbonyl]-4-chloro-N-methyl-benzenesulfonamide

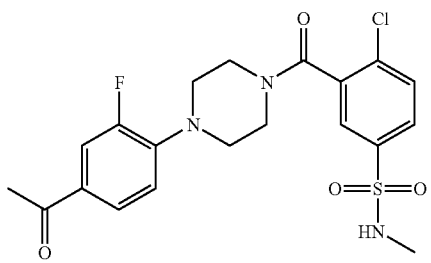

The title compound was prepared according to the procedure described for example K/step 2 from 1-(3-Fluoro-4-piperazin-1-yl-phenyl)-ethanone and 2-Chloro-5-methylsulfamoyl-benzoic acid (CAS: 68901-09-7; BE 620741) (69%, light yellow foam, MS (m/e): 452.1 (M−H, 100%)

Example 179

3-[4-(4-Acetyl-2-fluoro-phenyl)-piperazine-1-carbonyl]-N-methyl-4-morpholin-4-yl-benzenesulfonamide The title compound was prepared according to the procedure described for example 1 from 3-[4-(4-Acetyl-2-fluoro-phenyl)-piperazine-1-carbonyl]-4-chloro-N-methyl-benzenesulfonamide and morpholine (58%, light yellow solid, MS (m/e): 503.1 (M−H, 100%)

Example AV

3-[4-(4-Acetyl-2-fluoro-phenyl)-piperazine-1-carbonyl]-4-chloro-N,N-dimethyl-benzenesulfonamide

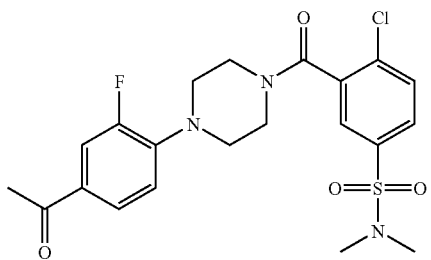

The title compound was prepared according to the procedure described for example K/step 2 from 1-(3-Fluoro-4-piperazin-1-yl-phenyl)-ethanone and 2-Chloro-5-dimethylsulfamoyl-benzoic acid (CAS: 37088-27-0; BE 620741) (64%, light yellow foam, MS (m/e): 468.1 (M+H+, 100%)

Example 180

3-[4-(4-Acetyl-2-fluoro-phenyl)-piperazine-1-carbonyl]-N,N-dimethyl-4-morpholin-4-yl-benzenesulfonamide The title compound was prepared according to the procedure described for example 1 from 3-[4-(4-Acetyl-2-fluoro-phenyl)-piperazine-1-carbonyl]-4-chloro-N,N-dimethyl-benzenesulfonamide and morpholine (60%, light yellow solid, MS (m/e): 519.2 (M+H, 100%)

Example AW

3-[4-(4-Acetyl-2-fluoro-phenyl)-piperazine-1-carbonyl]-4-morpholin-4-yl-benzoic acid

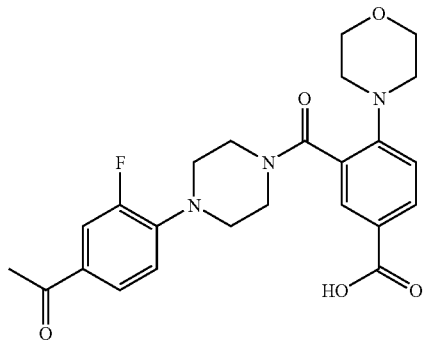

A suspension of 3-[4-(4-Acetyl-2-fluoro-phenyl)-piperazine-1-carbonyl]-4-morpholin-4-yl-benzonitrile (example 196, 469 mg, 1.07 mmol) in ethanol (6 ml) and NaOH 2N (6 ml) was heated to 85° C. for 17 hours. The reaction mixture was cooled to room temperature, diluted with water and acidified with 2N HCl. The resulting solid was filtered, washed with water and dried to provide the title compound (0.47 g, 96%) as an orange solid.

Example 181

3-[4-(4-Acetyl-2-fluoro-phenyl)-piperazine-1-carbonyl]-4-morpholin-4-yl-benzamide The title compound was prepared according to the procedure described for example K/step 2 from 3-[4-(4-Acetyl-2-fluoro-phenyl)-piperazine-1-carbonyl]-4-morpholin-4-yl-benzoic acid and ammonia (10%, white solid, MS (m/e): 455.2 (M+H, 100%)

Example 182

3-[4-(4-Acetyl-2-fluoro-phenyl)-piperazine-1-carbonyl]-N-methyl-4-morpholin-4-yl-benzamide The title compound was prepared according to the procedure described for example K/step 2 from 3-[4-(4-Acetyl-2-fluoro-phenyl)-piperazine-1-carbonyl]-4-morpholin-4-yl-benzoic acid and methylamine (43%, white solid, MS (m/e): 469.3 (M+H, 100%)

Example 183

3-[4-(4-Acetyl-2-fluoro-phenyl)-piperazine-1-carbonyl]-N,N-dimethyl-4-morpholin-4-yl-benzamide The title compound was prepared according to the procedure described for example K/step 2 from 3-[4-(4-Acetyl-2-fluoro-phenyl)-piperazine-1-carbonyl]-4-morpholin-4-yl-benzoic acid and dimethylamine (44%, yellow solid, MS (m/e): 483.2 (M+H, 100%)

Example 184

[4-(2-Chloro-4-trifluoromethyl-phenyl)-piperazin-1-yl]-(2-morpholin-4-yl-5-nitro-phenyl)-methanone The title compound was prepared according to the procedure described for example 46 from 1-(2-Chloro-4-trifluoromethyl-phenyl)-piperazine and 2-Morpholin-4-yl-5-nitro-benzoyl chloride (74%, yellow solid, MS (m/e): 499.2 (M+H, 100%)

Example AX 4-(4-Trifluoromethoxy-phenyl)-piperazine-1-carboxylic acid tert-butyl ester

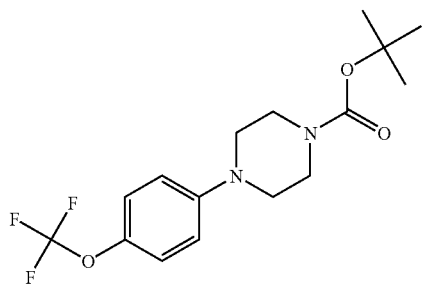

To a mixture of cesium carbonate (1.88 g, 5.7 mmol), palladium(II) acetate (46.1 mg, 0.205 mmol), rac-2,2'-Bis(diphenylphosphino)-1,1'-binaphthyl (192 mg, 0.31 mmol), tert-Butyl-1-piperazine carboxylate (928 mg, 4.93 mmol) and 1-Bromo-4-(trifluoromethoxy)benzene (1 g, 4.11 mmol) was added degazed toluene (10 ml). The mixture was heated to 100° C. for 4 hours. The mixture was cool to room temperature, diluted with ethylacetate, filtered and the solvent was removed in vacuo. The crude oil was chromatographed over silica gel: eluent: heptane/ethylacetate 0-10% over 20 minutes to provide the title compound (180 mg, 13%) as a yellow solid, MS (m/e): 347.4 (M+H, 100%).

Example AY 1-(4-Trifluoromethoxy-phenyl)-piperazine

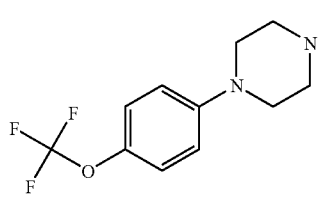

The title compound was prepared according to the procedure described for example D step 2 from 4-(4-trifluoromethoxy-phenyl)-piperazine-1-carboxylic acid tert-butyl ester (44%, brown oil, MS (m/e): 247.1 (M+H, 100%)

Example 185

(2-Morpholin-4-yl-5-nitro-phenyl)-[4-(4-trifluoromethoxy-phenyl)-piperazin-1-yl]-methanone The title compound was prepared according to the procedure described for example 46 from 1-(4-Trifluoromethoxy-phenyl)-piperazine and 2-Morpholin-4-yl-5-nitro-benzoyl chloride (74%%, yellow solid, MS (m/e): 481.2 (M+H, 100%)

Example 186

2-[4-(2-Morpholin-4-yl-5-nitro-benzoyl)-piperazin-1-yl]-5-trifluoromethyl-benzonitrile The title compound was prepared according to the procedure described for example 46 from 2-piperazin-1-yl-5-trifluoromethyl-benzonitrile and 2-Morpholin-4-yl-5-nitro-benzoyl chloride (69%, yellow solid, MS (m/e): 490.2 (M+H, 100%)

Example AZ 4-(4-Methanesulfonyl-phenyl)-piperazine-1-carboxylic acid tert-butyl ester

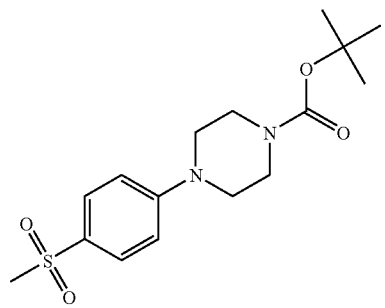

The title compound was prepared according to the procedure described for example AX from 4-bromophenyl methyl sulfone and N-Boc-piperazine (31%, white solid, MS (m/e): 241.2 (M−Boc, 100%)

Example BA 1-(4-Methanesulfonyl-phenyl)-piperazine

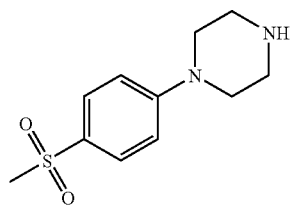

The title compound was prepared according to the procedure described for example D step 2 from 4-(4-Methanesulfonyl-phenyl)-piperazine-1-carboxylic acid tert-butyl ester (99%, brown solid, MS (m/e): 241.2 (M+H, 100%)

Example 187

[4-(4-Methanesulfonyl-phenyl)-piperazin-1-yl]-(2-morpholin-4-yl-5-nitro-phenyl)-methanone The title compound was prepared according to the procedure described for example 46 from 1-(4-Methanesulfonyl-phenyl)-piperazine and 2-Morpholin-4-yl-5-nitro-benzoyl chloride (76%, yellow solid, MS (m/e): 475.1 (M+H, 100%)

Example BB 4-(3-Fluoro-4-trifluoromethyl-phenyl)-piperazine-1-carboxylic acid tert-butyl ester

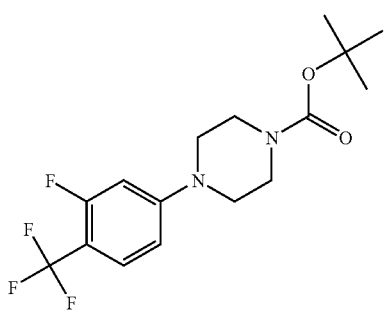

To a mixture of sodium tert-butoxide (0.68 g, 6.9 mmol), palladium(II) acetate (11 mg, 0.05 mmol), 2-(di-t-butylphosphino)biphenyl (149 mg, 0.49 mmol), tert-Butyl-1-piperazine carboxylate (1.1 g, 5.9 mmol) and 4-chloro-2-fluorobenzotrifluoride (1 g, 4.94 mmol) was added degazed toluene (10 ml). The mixture was heated to 80° C. overnight. The mixture was cool to room temperature, diluted with ether, filtered and the filtrate was concentrated in vacuo. The residue was chromatographed over silica gel: eluent: Heptane/Ethylacetate 0-10% over 15 minutes to provide the title compound (1.05 g, 61%) as a white solid, MS (m/e): 349.2 (M+H, 100%).

Example BC 1-(3-Fluoro-4-trifluoromethyl-phenyl)-piperazine

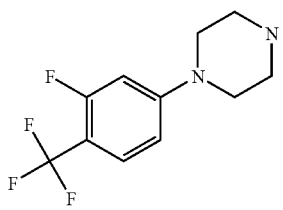

The title compound was prepared according to the procedure described for example D step 2 from 4-(3-Fluoro-4-trifluoromethyl-phenyl)-piperazine-1-carboxylic acid tert-butyl ester (98%, brown solid, MS (m/e): 249.2 (M+H, 100%)

Example 188

[4-(3-Fluoro-4-trifluoromethyl-phenyl)-piperazin-1-yl]-(2-morpholin-4-yl-5-nitro-phenyl)-methanone The title compound was prepared according to the procedure described for example 46 from 1-(3-Fluoro-4-trifluoromethyl-phenyl)-piperazine and 2-Morpholin-4-yl-5-nitro-benzoyl chloride (62%, yellow solid, MS (m/e): 483.2 (M+H, 100%)

Example BD

1-{4-[4-(2-Fluoro-5-nitro-benzoyl)-piperazin-1-yl]-phenyl}-ethanone

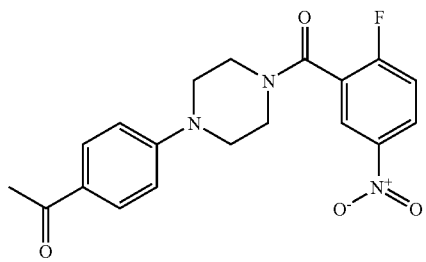

The title compound was prepared according to the procedure described for example K step 2 from 4'-piperazino-acetophenone and 2-fluoro-5-nitrobenzoic acid (16%, yellow solid, MS (m/e): 372.1 (M+H, 100%)

Example 189

1-{4-[4-(2-Morpholin-4-yl-5-nitro-benzoyl)-piperazin-1-yl]-phenyl}-ethanone

The title compound was prepared according to the procedure described for example 1 from 1-{4-[4-(2-Fluoro-5-nitro-benzoyl)-piperazin-1-yl]-phenyl}-ethanone and morpholine (85%, yellow solid, MS (m/e): 439.3 (M+H, 100%)

Example BE (2-Fluoro-5-nitro-phenyl)-[4-(2-fluoro-phenyl)-piperazin-1-yl]-methanone

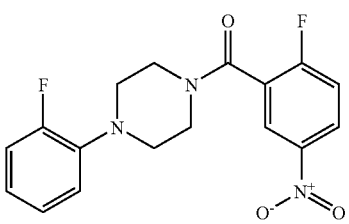

The title compound was prepared according to the procedure described for example 46 from 2-Fluoro-5-nitro-benzoyl chloride and 1-(2-fluorophenyl)-piperazine (52%, orange solid, MS (m/e): 348.1 (M+H, 100%)

Example 190

[4-(2-Fluoro-phenyl)-piperazin-1-yl]-(2-morpholin-4-yl-5-nitro-phenyl)-methanone The title compound was prepared according to the procedure described for example 1 from (2-Fluoro-5-nitro-phenyl)-[4-(2-fluoro-phenyl)-piperazin-1-yl]-methanone and morpholine (87%, yellow solid, MS (m/e): 415.2 (M+H, 100%)

Example BF (2-Fluoro-5-nitro-phenyl)-(4-phenyl-piperazin-1-yl)-methanone

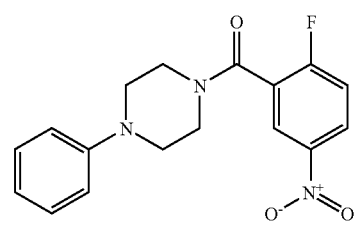

The title compound was prepared according to the procedure described for example 46 from 2-Fluoro-5-nitro-benzoyl chloride and 1-phenyl-piperazine (70%, orange solid, MS (m/e): 330.1 (M+H, 100%)

Example 191

(2-Morpholin-4-yl-5-nitro-phenyl)-(4-phenyl-piperazin-1-yl)-methanone

The title compound was prepared according to the procedure described for example 1 from (2-Fluoro-5-nitro-phenyl)-(4-phenyl-piperazin-1-yl)-methanone and morpholine (87%, yellow solid, MS (m/e): 397.3 (M+H, 100%)

Example 192

[4-(4-Chloro-phenyl)-piperazin-1-yl]-(2-morpholin-4-yl-5-nitro-phenyl)-methanone The title compound was prepared according to the procedure described for example 46 from 2-morpholin-4-yl-5-nitro-benzoyl chloride and 4-chloro-phenyl-piperazine (orange solid), MS (m/e): 449.2 (M+H, 100%).

Example BG

1-{4-[4-(5-Amino-2-morpholin-4-yl-benzoyl)-piperazin-1-yl]-3-fluoro-phenyl}-ethanone

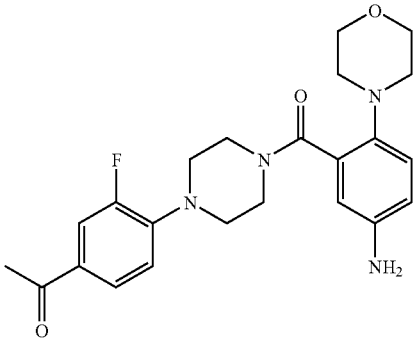

The title compound was prepared according to the procedure described for example AT from 1-{4-[4-(2-Morpholin-4-yl-5-nitro-benzoyl)-piperazin-1-yl]-3-fluoro-phenyl}-ethanone (72%, yellow solid, MS (m/e): 427.2 (M+H, 100%)

Example 193

N-{3-[4-(4-Acetyl-2-fluoro-phenyl)-piperazine-1-carbonyl]-4-morpholin-4-yl-phenyl}-methanesulfonamide To a solution of 1-{4-[4-(5-Amino-2-morpholin-4-yl-benzoyl)-piperazin-1-yl]-3-fluoro-phenyl}-ethanone (50 mg, 0.12 mmol) and triethylamine (33 ul, 0.234 mmol) in dioxane (1.5 ml) was added a solution of methanesulfonyl chloride (15 mg, 0.13 mmol) in dioxane (0.5 ml). The mixture was stirred at room temperature for 3 hours. The reaction mixture was stirred in water. The yellow solid was filtered, washed with water and dissolved in $CH_2Cl_2$. The solution was dried over $Na_2SO_4$, filtered and the solvent was removed in vacuo. The residue was chromatographed over silica gel eluent: Heptane/ethyl acetate 0%-100% (5 minutes) to provide the title compound (35 mg, 59%) as a yellow solid MS (m/e): 505.3 (M+H, 100%)

Example BH

5-Bromo-2-morpholin-4-yl-benzoic acid

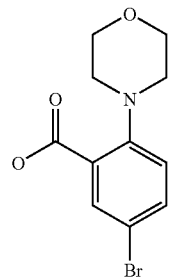

The title compound was prepared according to the procedure described for example B step 1 from 5-Bromo-2-fluorobenzoic acid and morpholine except that the mixture was heated at 130° C. for 48 hours (77%, white solid), 1-H-NMR (300 MHz, CDCl₃) δ=8.45 (d), 7.74 (dxd, 7.33 (d)

Example BI

5-Bromo-2-morpholin-4-yl-benzoyl chloride

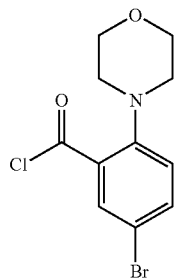

The title compound was prepared according to the procedure described for example B step 2 from 5-Bromo-2-morpholin-4-yl-benzoic acid (100%, yellow oil, MS (m/e): 305.0 (M+H, 100%)

Example BJ

1-{4-[4-(5-Bromo-2-morpholin-4-yl-benzoyl)-piperazin-1-yl]-3-fluoro-phenyl}-ethanone

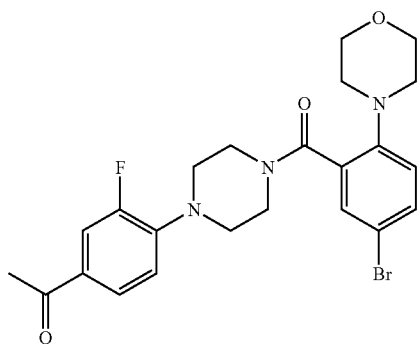

The title compound was prepared according to the procedure described for example 46 from 5-Bromo-2-morpholin-4-yl-benzoyl chloride and 1-(3-Fluoro-4-piperazin-1-yl-phenyl)-ethanone (94%, yellow foam, MS (m/e): 490.3 (M+, 100%)

Example 194

1-{4-[4-(5-Acetyl-2-morpholin-4-yl-benzoyl)-piperazin-1-yl]-3-fluoro-phenyl}-ethanone To a suspension of 1-{4-[4-(5-Bromo-2-morpholin-4-yl-benzoyl)-piperazin-1-yl]-3-fluoro-phenyl}-ethanone (160 mg, 0.33 mmol) in toluene (2 ml) were added PdCl₂(PPh₃)₂ (5 mg, 0.0065 mmol) and tributyl(1-ethoxyvinyl) tin (125 ul, 0.36 mmol). The mixture was heated to 100° C. for 6 hours. The mixture was cooled in an ice bath and 2N HCl (0.55 ml) was added. The mixture was stirred at room temperature overnight. The mixture was filtered. The organic layer was separated and 10% aqueous KF solution was added. The mixture was stirred at room temperature for 3 hours and filtered. The organic layer was dried over Na₂SO₄, filtered and the solvent was removed in vacuo. The crude gum was chromatographed on silica gel, eluent: heptane/ethylacetate 0%-50% (10 minutes) to provide the title compound (15 mg, 10%) as a white solid MS (m/e): 454.2 (M+H, 100%).

Example BK

5-Methylsulfanyl-2-morpholin-4-yl-benzoic acid

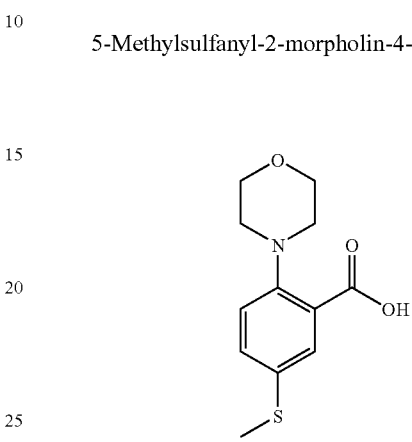

A mixture of 2-Chloro-5-(methylthio)-benzoic acid (1 g, 4.7 mmol), morpholine (620 ul, 7.1 mmol), potassium carbonate (1.05 g, 7.6 mmol) and Copper (24 mg, 0.38 mmol) in pentanol (6 ml) was stirred for 1 h at room temperature. The mixture was heated to 100° C. and stirred for 40 minutes. The solvent was evaporated. The residue was taken up in water and acidified to pH 2. The aqueous layer was extracted twice with ethylacetate. The organic layers were combined, dried over Na₂SO₄, filtered and the solvent was removed in vacuo. The crude oil was chromatographed over silicagel: eluent: heptane/ethylacetate 0-20% over 15 minutes to provide the title compound as a brown solid (120 mg, 10%), MS (m/e): 252.1 (M–H, 100%)

Example 195

1-{3-Fluoro-4-[4-(5-methylsulfanyl-2-morpholin-4-yl-benzoyl)-piperazin-1-yl]-phenyl}-ethanone The title compound was prepared according to the procedure described for example K step 2 from 5-Methylsulfanyl-2-morpholin-4-yl-benzoic acid and 1-(3-Fluoro-4-piperazin-1-yl-phenyl)-ethanone (8%, white solid), MS (m/e): 458.2 (M+, 100%)

Example 196

3-[4-(4-Acetyl-2-fluoro-phenyl)-piperazine-1-carbonyl]-4-morpholin-4-yl-benzonitrile The title compound was prepared according to the procedure described for example 1 from 3-[4-(4-Acetyl-2-fluorophenyl)-piperazine-1-carbonyl]-4-bromo-benzonitrile (example L) and morpholine (71%, white solid), MS (m/e): 437.2 (M+H, 100%)

Example 197

1-{3-Fluoro-4-[4-(5-methanesulfonyl-2-morpholin-4-yl-benzoyl)-piperazin-1-yl]-phenyl}-ethanone The title compound was prepared according to the procedure described for example 1 from 1-{4-[4-(2-Chloro-5-methanesulfonyl-benzoyl)-piperazin-1-yl]-3-fluoro-phenyl}-ethanone (example K) and morpholine (57%, white solid), MS (m/e): 490.2 (M+H, 100%)

Example BL

3-[4-(4-Acetyl-2-fluoro-phenyl)-piperazine-1-carbonyl]-4-chloro-benzenesulfonamide

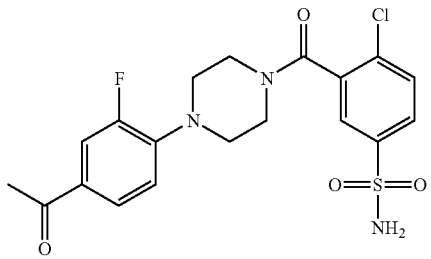

The title compound was prepared according to the procedure described for example K/step 2 from 1-(3-Fluoro-4-piperazin-1-yl-phenyl)-ethanone and 2-Chloro-5-sulfamoyl-benzoic acid (CAS: 97-04-1; Basu; D.-G.; J.Indian Chem. Soc.; 16; 1939; 100, 106) (42%, white solid), MS (m/e): 438.1 (M–H, 100%)

Example 198

3-[4-(4-Acetyl-2-fluoro-phenyl)-piperazine-1-carbonyl]-4-morpholin-4-yl-benzenesulfonamide The title compound was prepared according to the procedure described for example 1 from 3-[4-(4-Acetyl-2-fluoro-phenyl)-piperazine-1-carbonyl]-4-chloro-benzenesulfonamide and morpholine (39%, yellow solid), MS (m/e): 489.4 (M–H, 100%)

Example 199

1-{3-Fluoro-4-[4-(5-imidazol-1-yl-2-morpholin-4-yl-benzoyl)-piperazin-1-yl]-phenyl}-ethanone In a tube were added successively 1-{4-[4-(5-Bromo-2-morpholin-4-yl-benzoyl)-piperazin-1-yl]-3-fluoro-phenyl}-ethanone (example BJ, 0.05 g, 0.1 mmol), imidazole (8.4 mg, 0.12 mmol), cesium carbonate (70 mg, 0.21 mmol), CuI (4 mg, 0.02 mmol), 1,10-phenanthroline (7.3 mg, 0.04 mmol) and dioxane (0.2 ml). The mixture was heated under argon at 120° C. for 12 hours. The reaction mixture was cooled to room temperature and quenched with water/ethyl acetate. The aqueous layer was extracted twice with ethylacetate. The organic layers were combined, dried over Na$_2$SO$_4$, filtered and the solvent was removed in vacuo. The crude oil was chromatographed over silicagel: eluent: CH$_2$Cl$_2$/methanol: 0-5% to provide the title compound as a brown solid (20 mg, 40%), MS (m/e): 478.4 (M+H, 100%)

Example 200

[4-(2,4-Difluoro-phenyl)-piperazin-1-yl]-(2-morpholin-4-yl-5-nitro-phenyl)-methanone The title compound was prepared according to the procedure described for example 46 from 2-Morpholin-4-yl-5-nitro-benzoyl chloride and 1-(2,4-difluorophenyl)-piperazine (87%, yellow solid, MS (m/e): 433.4 (M+H, 100%)

Example BM 4-(2-Chloro-4-fluoro-phenyl)-piperazine-1-carboxylic acid tert-butyl ester

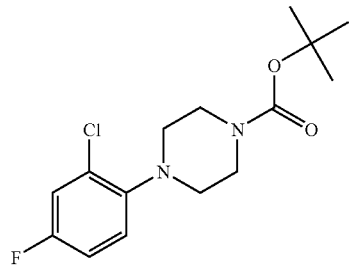

The title compound was prepared according to the procedure described for example AX from 1-bromo-2-chloro-4-fluorobenzene and N-Boc-piperazine (10%, off white solid, MS (m/e): 315.1 (M+H, 100%)

Example BN 1-(2-Chloro-4-fluoro-phenyl)-piperazine

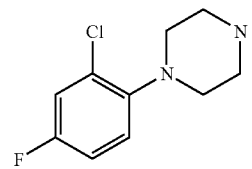

The title compound was prepared according to the procedure described for example D step 2 from 4-(2-Chloro-4-fluoro-phenyl)-piperazine-1-carboxylic acid tert-butyl ester (91%, light yellow oil, MS (m/e): 215.2 (M+H, 100%)

Example 201

[4-(2-Chloro-4-fluoro-phenyl)-piperazin-1-yl]-(2-morpholin-4-yl-5-nitro-phenyl)-methanone The title compound was prepared according to the procedure described for example 46 from 2-Morpholin-4-yl-5-nitro-benzoyl chloride and 1-(2-Chloro-4-fluoro-phenyl)-piperazine (70%, yellow solid, MS (m/e): 449.2 (M+H, 100%)

Example BO (2-Chloro-5-methanesulfonyl-phenyl)-[4-(4-trifluoromethyl-phenyl)-piperazin-1-yl]-methanone

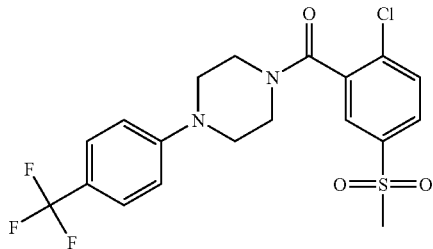

To a solution of 2-Chloro-5-methanesulfonyl-benzoic acid (102 mg, 0.43 mmol) in dimethylformamide (20 ml) were successively added TBTU (153 mg, 0.48 mmol), N-ethyldiisopropylamine (0.28 ml, 2.17 mmol) and 1-(4-trifluoromethylphenyl)piperazine (ABCR F07741NB, [30459-17-7], 100 mg, 0.43 mmol). The reaction was then stirred at room temperature for two hours, then concentrated in vacuo and purified by column chromatography (SiO$_2$, 50 g, heptane/ethylacetate=0 to 100%), to give the title compound as a colorless gum (170 mg, 0.38 mmol). MS (m/e): 464.3 (M+NH$_4^+$, 100%)

Example 202

5-Methanesulfonyl-2-morpholin-4-yl-phenyl)-[4-(4-trifluoromethyl-phenyl)-piperazin-1-yl]-methanone To a solution of (2-Chloro-5-methanesulfonyl-phenyl)-[4-(4-trifluoromethyl-phenyl)-piperazin-1-yl]-methanone (0.28 mmol, 130 mg) was added morpholine (0.5 ml). The reaction mixture was then stirred at 100° C. for 48 hours before being concentrated in vacuo. The residue was then purified by column chromatography (SiO$_2$, 20 g, Heptane/EtOAc 0-100%) to give the title compound as a white solid (118 mg, 85%). MS (m/e): 497.5 (M+H$^+$, 100%).

Example BP rac-3-Methyl-4-(4-trifluoromethyl-phenyl)-piperazine-1-carboxylic acid tert-butyl ester

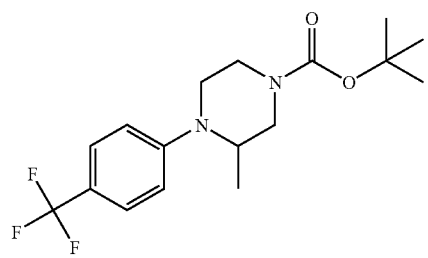

To a solution of 3-Methyl-piperazine-1-carboxylic acid tert-butyl ester (1.0 g, 5.3 mmol) and of 1-Bromo-4-trifluoromethyl-benzene (1.0 g, 4.4 mmol) in toluene (10 ml) were added sodium-tert butylate (0.6 g, 6.2 mmol), 2-(dicyclohexylphosphino)biphenyl (31 mg, 89 mmol), and tris(dibenzylideneacetone)dipalladium-chloroform complex (23 mg, 22 mmol). The reaction mixture was then stirred for 16 hours at 80° C. After allowing to cool to room temperature the reaction mixture was concentrated in vacuo and purified by column chromatography (SiO$_2$, 70 g, heptane/ethyl acetate 0-30%) to give the title compound as a light brown solid (0.47 g, 31%). MS (m/e): 345.2 (M+H$^+$, 100%).

Example BO

2-Iodo-5-methanesulfonyl-benzoic acid

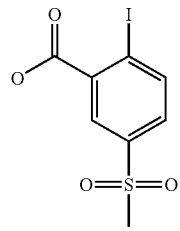

(a) 2-Amino-5-methanesulfonyl-benzoic acid

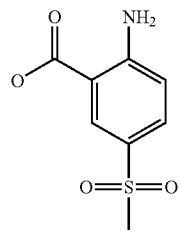

A mixture of 4.26 mmol 2-chloro-5-methanesulfonyl-benzoic acid (see example K, step 1), 0.39 mmol Copper powder and 10 ml ammonium hydroxide 25% was heated at 125-130° C. with stirring for 18 hours. Mixture was cooled to room temperature and filtered. The solid was washed with methanol. The filtrate was concentrated in vacuo. The residue was acidified with HCl 1N to pH=2. The obtained solid was washed with water and dried (HV, 50° C., 1 hour) to yield the title compound. MS (m/e): 214.1 (M−H, 100%)

(b) 2-Iodo-5-methanesulfonyl-benzoic acid

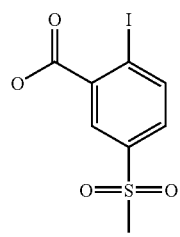

To a suspension of 3.0 mmol 2-amino-5-methanesulfonyl-benzoic acid in a mixture of 1.7 ml sulfuric acid and 1.7 ml water was added dropwise a solution of 3.92 mmol sodium nitrite in 1.7 ml water at such rate that the temperature did not exceed 3° C. The mixture was stirred at 0° C. for 1 hour. A solution of 3.0 mmol KI in 1.7 ml water was added dropwise at 0° C. The brown suspension was allowed to warm to rt and stirred for 30 minutes. Excess iodine was destroyed by addition of a few drops of a sodium hydrogenosulfite solution. The solid was filtered, washed with water and dried (HV, 50° C., 1 hour) to yield the title compound. MS (m/e): 325.0 (M−H, 100%)

Example BR rac-(2-Iodo-5-methanesulfonyl-phenyl)-[3-methyl-4-(4-trifluoromethyl-phenyl)-piperazin-1-yl]-methanone

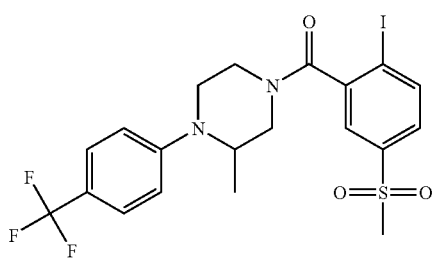

To a solution of rac-3-Methyl-4-(4-trifluoromethyl-phenyl)-piperazine-1-carboxylic acid tert-butyl ester (95 mg, 0.27 mmol) in dichloromethane (2 ml) was added trifluoroacetic acid (1 ml) and the reaction mixture was stirred at room temperature for 30 min. After such time the reaction mixture was concentrated in vacuo, and the residue was dissolved in dimethylformamide (3 ml). To the solution were added 2-Iodo-5-methanesulfonyl-benzoic acid (81 mg, 0.25 mmol), N-ethyldiisopropylamine (0.29 ml, 1.7 mmol), and TBTU (99 mg, 0.3 mmol). The reaction mixture was then allowed to stir at room temperature for 2 hours. The reaction mixture was then concentrated in vacuo and the residue was purified by column chromatography (SiO$_2$, 20 g, Heptane/EtOAc 0-100%) to give the title compound as a light brown solid (135 mg, 90%). MS (m/e): 553.1 (M+H$^+$).

Example 203 rac-(5-Methanesulfonyl-2-morpholin-4-yl-phenyl)-[3-methyl-4-(4-trifluoromethyl-phenyl)-piperazin-1-yl]-methanone (2-Iodo-5-methanesulfonyl-phenyl)-[3-methyl-4-(4-trifluoromethyl-phenyl)-piperazin-1-yl]-methanone (50 mg, 0.09 mmol) was poured into morpholine (2.0 ml) and the reaction mixture was stirred for 24 h at 100° C. before being concentrated in vacuo. The residue was then purified by column chromatography (SiO$_2$, 20 g, Heptane/EtOAc 0-100%) to give the title compound as a light brown solid (43.5 mg, 94%). MS (m/e): 512.3 (M+H$^+$).

Example BS rac-4-(2-Iodo-5-methanesulfonyl-benzoyl)-3-methyl-piperazine-1-carboxylic acid tert-butyl ester

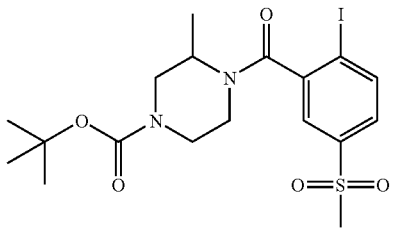

To a solution of rac-3-Methyl-piperazine-1-carboxylic acid tert-butyl ester (350 mg, 1.75 mmol) in dimethylformamide (3 ml) were added 2-Iodo-5-methanesulfonyl-benzoic acid (540 mg, 1.67 mmol), N-ethyldiisopropylamine (1.8 ml, 10.5 mmol), and TBTU (630 mg, 1.92 mmol). The reaction mixture was then allowed to stir at room temperature for 16 hours. The reaction mixture was then concentrated in vacuo and the residue was purified by column chromatography (SiO$_2$, 20 g, Heptane/EtOAc 0-100%) to give the title compound (400 mg, 45%). MS (m/e): 526.2 (M+NH$_4^+$).

Example BT rac-4-(5-Methanesulfonyl-2-morpholin-4-yl-benzoyl)-3-methyl-piperazine-1-carboxylic acid tert-butyl ester

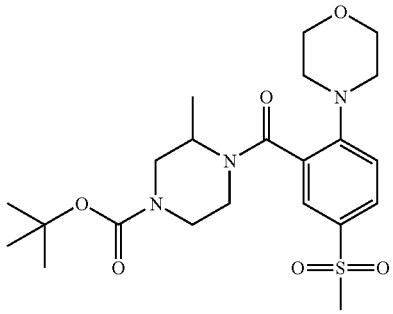

rac-4-(2-Iodo-5-methanesulfonyl-benzoyl)-3-methyl-piperazine-1-carboxylic acid tert-butyl ester (400 mg, 0.78 mmol) was poured into morpholine (5.0 ml) and the reaction mixture was stirred for 15 h at 100° C. before being concentrated in vacuo. The residue was then purified by column chromatography (SiO$_2$, 20 g, dichloromethane/methanol=0-5%) to give the title compound as a colorless foam (322 mg, 88%). MS (m/e): 468.3 (M+H$^+$).

Example 204 rac-(5-Methanesulfonyl-2-morpholin-4-yl-phenyl)-[2-methyl-4-(4-trifluoromethyl-phenyl)-piperazin-1-yl]-methanone To a solution of rac-4-(5-Methanesulfonyl-2-morpholin-4-yl-benzoyl)-3-methyl-piperazine-1-carboxylic acid tert-butyl ester (250 mg, 0.54 mmol) in dichloromethane (2 ml) was added trifluoroacetic acid (1 ml) and the reaction mixture was stirred at room temperature for 30 min. After such time the reaction mixture was concentrated in vacuo, and the residue was dissolved in toluene (5 ml). To the solution were added 1-Bromo-4-trifluoromethyl-benzene (0.15 ml, 1.1 mmol), sodium-tert butylate (128 mg, 1.4 mmol), 2-(dicyclohexylphosphino)biphenyl (3.8 mg, 0.011 mmol), and tris(dibenzylidene-acetone)dipalladium-chloroform complex (5.5 mg, 0.005 mmol). The reaction mixture was then stirred for 16 hours at 80° C. After allowing to cool to room temperature the reaction mixture was concentrated in vacuo and purified by column chromatography (SiO$_2$, 70 g, dichloromethane/methanol 0-5%) to give the title compound (83 mg, 30%). MS (m/e): 512.3 (M+H$^+$)

TABLE 1

| No. | Structure | MW | Systematic Name | Starting materials | MW found (MH$^+$) |
|---|---|---|---|---|---|
| 1 | 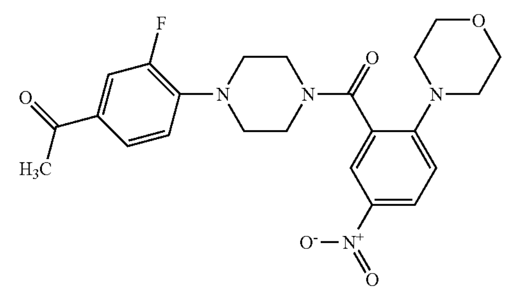 | 456.5 | 1-{4-[4-(2-Morpholin-4-yl-5-nitro-benzoyl)-piperazin-1-yl]-3-fluoro-phenyl}-ethanone | 1-{3-Fluoro-4-[4-(2-fluoro-5-nitro-benzoyl)-piperazin-1-yl]-phenyl}-ethanone and morpholine | 457.3 |
| 2 | 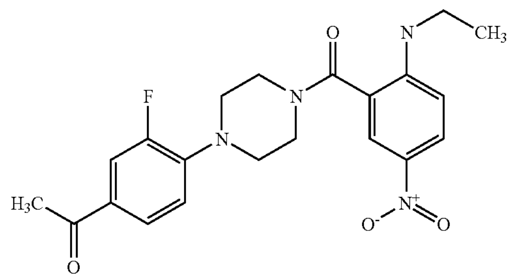 | 414.4 | 1-{4-[4-(2-Ethylamino-5-nitro-benzoyl)-piperazin-1-yl]-3-fluoro-phenyl}-ethanone | 1-{3-Fluoro-4-[4-(2-fluoro-5-nitro-benzoyl)-piperazin-1-yl]-phenyl}-ethanone and ethylamine (commerically available) | 415.2 |
| 3 | 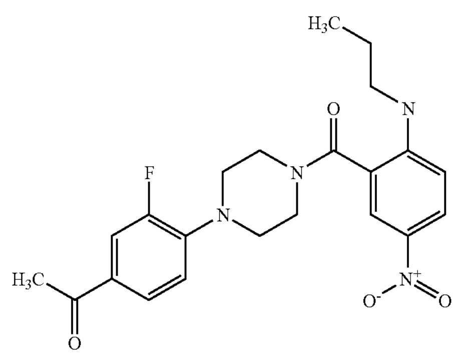 | 428.5 | 1-{3-Fluoro-4-[4-(5-nitro-2-propylamino-benzoyl)-piperazin-1-yl]-phenyl}-ethanone | 1-{3-Fluoro-4-[4-(2-fluoro-5-nitro-benzoyl)-piperazin-1-yl]-phenyl}-ethanone and propylamine (commerically available) | 429.2 |
| 4 | 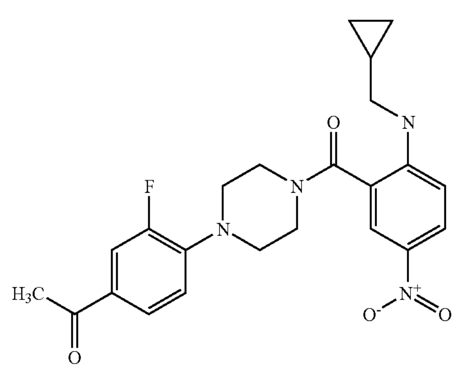 | 440.5 | 1-(4-{4-[2-(Cyclopropylmethyl-amino)-5-nitro-benzoyl]-piperazin-1-yl}-3-fluoro-phenyl)-ethanone | 1-{3-Fluoro-4-[4-(2-fluoro-5-nitro-benzoyl)-piperazin-1-yl]-phenyl}-ethanone and cyclopropylmethylamine (commerically available) | 441.2 |

TABLE 1-continued

| No. | Structure | MW | Systematic Name | Starting materials | MW found (MH+) |
|---|---|---|---|---|---|
| 5 | 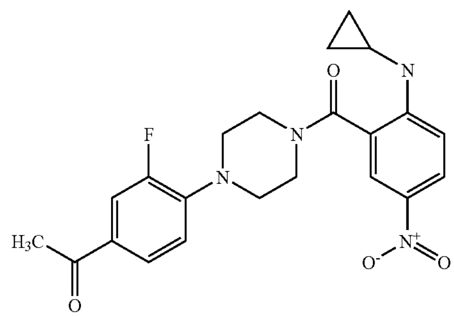 | 426.5 | 1-(4-{4-[2-(Cyclopropylamino-5-nitro-benzoyl]-piperazin-1-yl]-3-fluoro-phenyl}-ethanone | 1-{3-Fluoro-4-[4-(2-fluoro-5-nitro-benzoyl)-piperazin-1-yl]-phenyl}-ethanone and cyclopropylamine (commerically available) | 427.2 |
| 6 | 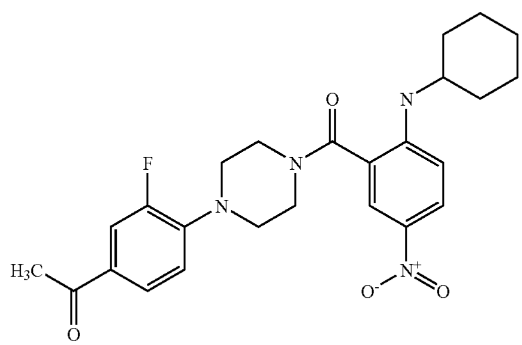 | 468.5 | 1-(4-{4-[2-(Cyclohexylamino-5-nitro-benzoyl]-piperazin-1-yl]-3-fluoro-phenyl}-ethanone | 1-{3-Fluoro-4-[4-(2-fluoro-5-nitro-benzoyl)-piperazin-1-yl]-phenyl}-ethanone and cyclohexylamine (commerically available) | 469.2 |
| 7 | 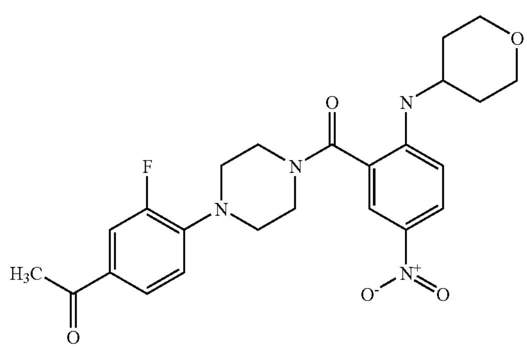 | 470.5 | 1-(3-Fluoro-4-{4-[5-nitro-2-(tetrahydro-pyran-4-ylamino)-benzoyl]-piperazin-1-yl}-phenyl)-ethanone | 1-{3-Fluoro-4-[4-(2-fluoro-5-nitro-benzoyl)-piperazin-1-yl]-phenyl}-ethanone and tetrahydro-pyran-4-ylamine (commerically available) | 471.2 |
| 8 | 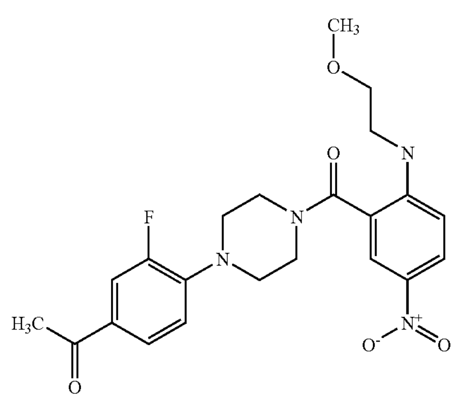 | 444.5 | 1-(3-Fluoro-4-{4-[2-(2-methoxy-ethylamino)-5-nitro-benzoyl]-piperazin-1-yl}-phenyl)-ethanone | 1-{3-Fluoro-4-[4-(2-fluoro-5-nitro-benzoyl)-piperazin-1-yl]-phenyl}-ethanone and 2-Methoxy-ethylamine (commerically available) | 445.2 |

TABLE 1-continued

| No. | Structure | MW | Systematic Name | Starting materials | MW found (MH+) |
|---|---|---|---|---|---|
| 9 | 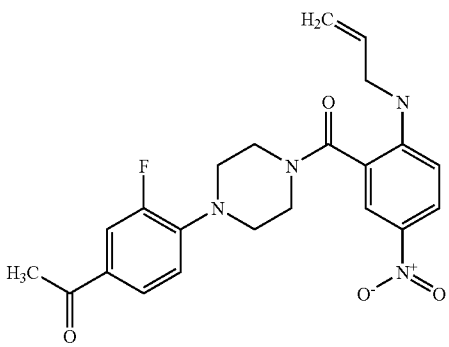 | 426.5 | 1-{4-[4-(2-Allylamino-5-nitro-benzoyl)-piperazin-1-yl]-3-fluoro-phenyl}-ethanone | 1-{3-Fluoro-4-[4-(2-fluoro-5-nitro-benzoyl)-piperazin-1-yl]-phenyl}-ethanone and allylamine ethylamine (commerically available) | 427.1 |
| 10 | 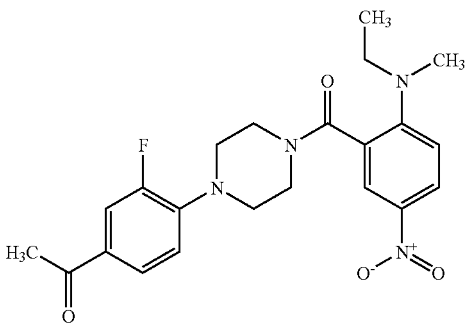 | 428.5 | 1-(4-{4-[2-(Ethyl-methyl-amino)-5-nitro-benzoyl]-piperazin-1-yl}-3-fluoro-phenyl)-ethanone | 1-{3-Fluoro-4-[4-(2-fluoro-5-nitro-benzoyl)-piperazin-1-yl]-phenyl}-ethanone and methyl ethylamine (commerically available) | 429.2 |
| 11 | 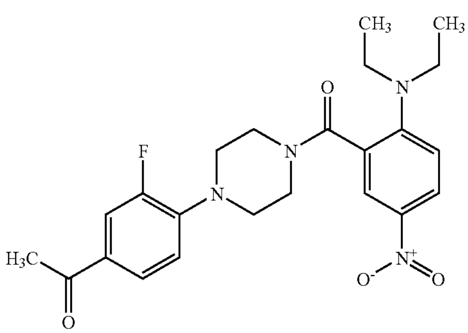 | 442.5 | 1-{4-[4-(2-Diethylamino-5-nitro-benzoyl)-piperazin-1-yl]-3-fluoro-phenyl}-ethanone | 1-{3-Fluoro-4-[4-(2-fluoro-5-nitro-benzoyl)-piperazin-1-yl]-phenyl}-ethanone and diethylamine (commerically available) | 443.2 |
| 12 | 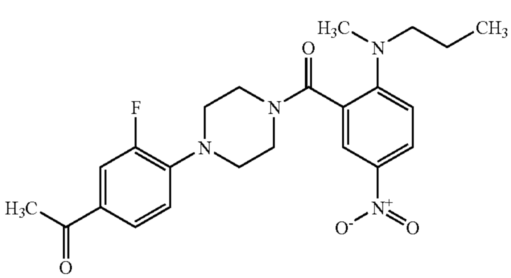 | 442.5 | 1-(3-Fluoro-4-{4-[2-(methyl-propyl-amino)-5-nitro-benzoyl]-piperazin-1-yl}-phenyl)-ethanone | 1-{3-Fluoro-4-[4-(2-fluoro-5-nitro-benzoyl)-piperazin-1-yl]-phenyl}-ethanone and methylpropylamine (commerically available) | 443.2 |

TABLE 1-continued

| No. | Structure | MW | Systematic Name | Starting materials | MW found (MH+) |
|---|---|---|---|---|---|
| 13 | 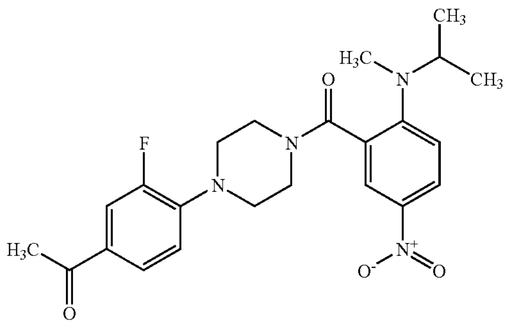 | 442.5 | 1-(3-Fluoro-4-{4-[2-(isopropyl-methyl-amino)-5-nitro-benzoyl]-piperazin-1-yl}-phenyl)-ethanone | 1-{3-Fluoro-4-[4-(2-fluoro-5-nitro-benzoyl)-piperazin-1-yl]-phenyl}-ethanone and isopropylmethylpropylamine (commerically available) | 443.2 |
| 14 | 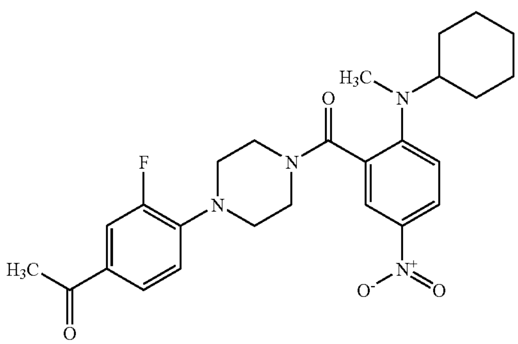 | 482.6 | 1-(4-{4-[2-(Cyclohexyl-methyl-amino)-5-nitro-benzoyl]-piperazin-1-yl}-3-fluoro-phenyl)-ethanone | 1-{3-Fluoro-4-[4-(2-fluoro-5-nitro-benzoyl)-piperazin-1-yl]-phenyl}-ethanone and cyclohexylmethylamine (commerically available) | 483.3 |
| 15 | 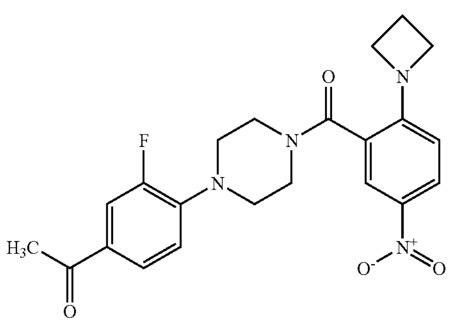 | 426.5 | 1-{4-[4-(2-Azetidin-1-yl-5-nitro-benzoyl)-piperazin-1-yl]-3-fluoro-phenyl}-ethanone | 1-{3-Fluoro-4-[4-(2-fluoro-5-nitro-benzoyl)-piperazin-1-yl]-phenyl}-ethanone and azetidine (commerically available) | 427.1 |
| 16 | 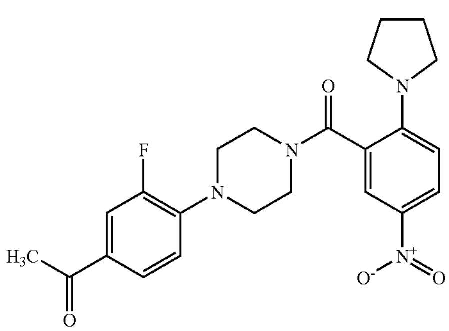 | 440.5 | 1-{3-Fluoro-4-[4-(5-nitro-2-pyrrolidin-1-yl-benzoyl)-piperazin-1-yl]-phenyl}-ethanone | 1-{3-Fluoro-4-[4-(2-fluoro-5-nitro-benzoyl)-piperazin-1-yl]-phenyl}-ethanone and pyrrolidine (commerically available) | 441.2 |

TABLE 1-continued

| No. | Structure | MW | Systematic Name | Starting materials | MW found (MH+) |
|---|---|---|---|---|---|
| 17 | 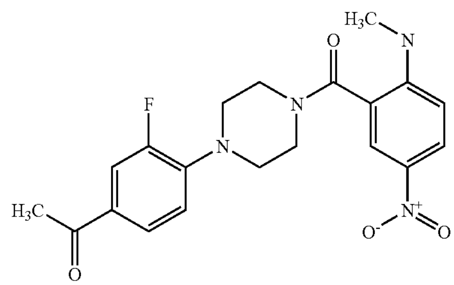 | 400.4 | 1-{3-Fluoro-4-[4-(2-methylamino-5-nitro-benzoyl)-piperazin-1-yl]-phenyl}-ethanone | 1-{3-Fluoro-4-[4-(2-fluoro-5-nitro-benzoyl)-piperazin-1-yl]-phenyl}-ethanone and methylamine (commerically available) | 401.2 |
| 18 | 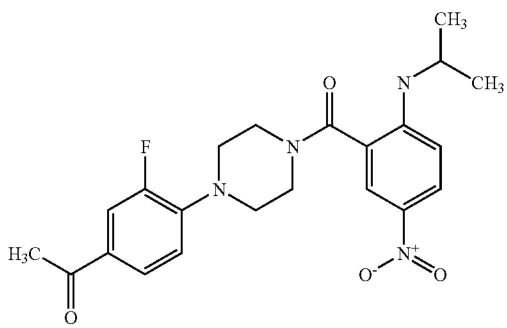 | 428.5 | 1-{3-Fluoro-4-[4-(2-isopropylamino-5-nitro-benzoyl)-piperazin-1-yl]-phenyl}-ethanone | 1-{3-Fluoro-4-[4-(2-fluoro-5-nitro-benzoyl)-piperazin-1-yl]-phenyl}-ethanone and isopropylamine (commerically available) | 429.2 |
| 19 | 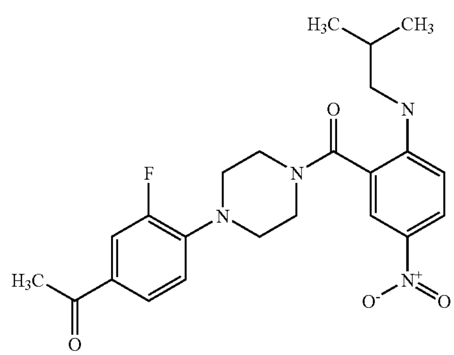 | 442.5 | 1-{3-Fluoro-4-[4-(2-isobutylamino-5-nitro-benzoyl)-piperazin-1-yl]-phenyl}-ethanone | 1-{3-Fluoro-4-[4-(2-fluoro-5-nitro-benzoyl)-piperazin-1-yl]-phenyl}-ethanone and isobutylamine (commerically available) | 443.2 |
| 20 | 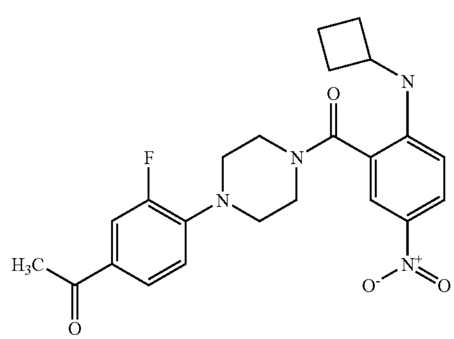 | 440.5 | 1-(4-{4-[2-(Cyclobutylamino-5-nitro-benzoyl)-piperazin-1-yl]-3-fluoro-phenyl}-ethanone | 1-{3-Fluoro-4-[4-(2-fluoro-5-nitro-benzoyl)-piperazin-1-yl]-phenyl}-ethanone and cyclobutylamine (commerically available) | 441.2 |

TABLE 1-continued

| No. | Structure | MW | Systematic Name | Starting materials | MW found (MH+) |
|---|---|---|---|---|---|
| 21 | 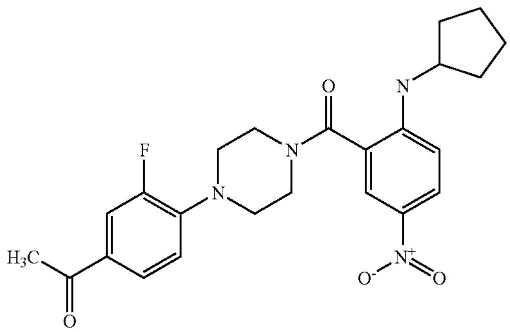 | 454.5 | 1-(4-{4-[2-(Cyclopentylamino-5-nitro-benzoyl]-piperazin-1-yl]-3-fluoro-phenyl}-ethanone | 1-{3-Fluoro-4-[4-(2-fluoro-5-nitro-benzoyl)-piperazin-1-yl]-phenyl}-ethanone and cyclopentylamine (commerically available) | 455.2 |
| 22 | 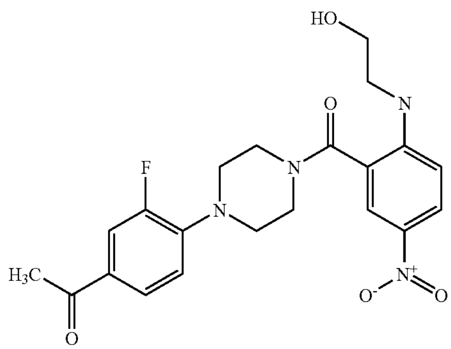 | 430.4 | 1-(3-Fluoro-4-{4-[2-(2-hydroxy-ethylamino)-5-nitro-benzoyl]-piperazin-1-yl}-phenyl)-ethanone | 1-{3-Fluoro-4-[4-(2-fluoro-5-nitro-benzoyl)-piperazin-1-yl]-phenyl}-ethanone and hydroxyethylamine (commerically available) | 431.2 |
| 23 | 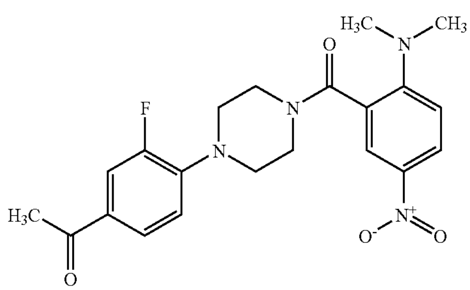 | 414.4 | 1-{4-[4-(2-Dimethylamino-5-nitro-benzoyl]-piperazin-1-yl]-3-fluoro-phenyl}-ethanone | 1-{3-Fluoro-4-[4-(2-fluoro-5-nitro-benzoyl)-piperazin-1-yl]-phenyl}-ethanone and dimethylamine (commerically available) | 415.2 |
| 24 | 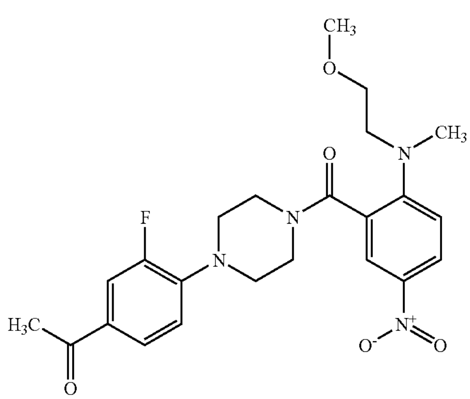 | 458.5 | 1-[3-Fluoro-4-(4-{2-[(2-methoxy-ethyl)-methyl-amino]-5-nitro-benzoyl}-piperazin-1-yl)-phenyl]-ethanone | 1-{3-Fluoro-4-[4-(2-fluoro-5-nitro-benzoyl)-piperazin-1-yl]-phenyl}-ethanone and (2-Methoxy-ethyl)-methyl-amine (commerically available) | 459.2 |

TABLE 1-continued

| No. | Structure | MW | Systematic Name | Starting materials | MW found (MH+) |
|---|---|---|---|---|---|
| 25 | 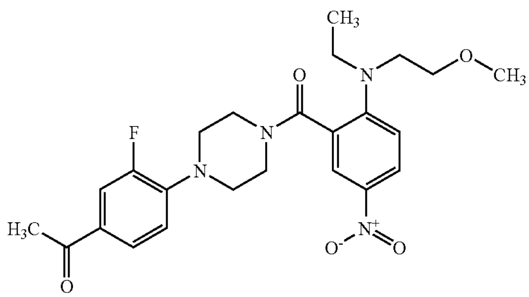 | 472.5 | 1-[4-(4-{2-[Ethyl-(2-methoxy-ethyl)-amino]-5-nitro-benzoyl}-piperazin-1-yl)-3-fluoro-phenyl]-ethanone | 1-{3-Fluoro-4-[4-(2-fluoro-5-nitro-benzoyl)-piperazin-1-yl]-phenyl}-ethanone and (2-Methoxy-ethyl)-ethyl-amine (commerically available) | 473.2 |
| 26 | 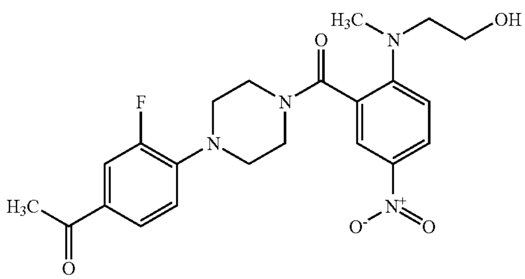 | 444.5 | 1-[3-Fluoro-4-(4-{2-[(2-hydroxy-ethyl)-methyl-amino]-5-nitro-benzoyl}-piperazin-1-yl)-phenyl]-ethanone | 1-{3-Fluoro-4-[4-(2-fluoro-5-nitro-benzoyl)-piperazin-1-yl]-phenyl}-ethanone and (2-hydroxy-ethyl)-methyl-amine (commerically available) | 445.2 |
| 27 | 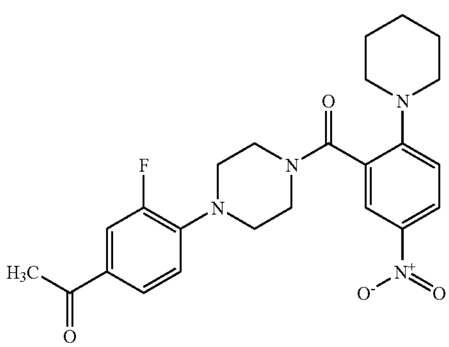 | 454.5 | 1-{3-Fluoro-4-[4-(5-nitro-2-piperidin-1-yl-benzoyl)-piperazin-1-yl]-phenyl}-ethanone | 1-{3-Fluoro-4-[4-(2-fluoro-5-nitro-benzoyl)-piperazin-1-yl]-phenyl}-ethanone and piperidine (commerically available) | 455.2 |
| 28 | 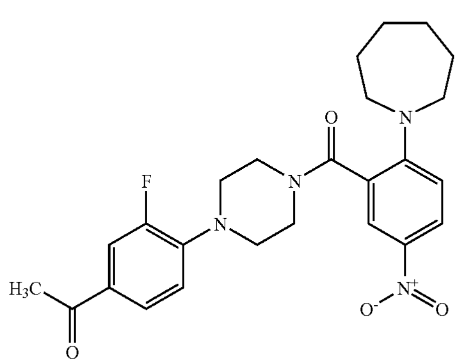 | 468.5 | 1-{4-[4-(2-Azepan-1-yl-5-nitro-benzoyl)-piperazin-1-yl]-3-fluoro-phenyl}-ethanone | 1-{3-Fluoro-4-[4-(2-fluoro-5-nitro-benzoyl)-piperazin-1-yl]-phenyl}-ethanone and azepan (commerically available) | 469.2 |

TABLE 1-continued

| No. | Structure | MW | Systematic Name | Starting materials | MW found (MH+) |
|---|---|---|---|---|---|
| 29 | 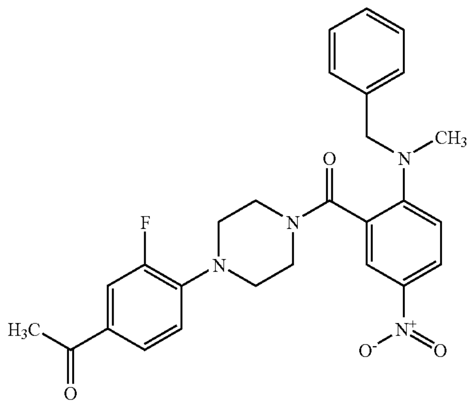 | 490.5 | 1-(4-{4-[2-(Benzyl-methyl-amino)-5-nitro-benzoyl]-piperazin-1-yl}-3-fluoro-phenyl)-ethanone | 1-{3-Fluoro-4-[4-(2-fluoro-5-nitro-benzoyl)-piperazin-1-yl]-phenyl}-ethanone and benzylmethylamine (commerically available) | 491.3 |
| 30 | 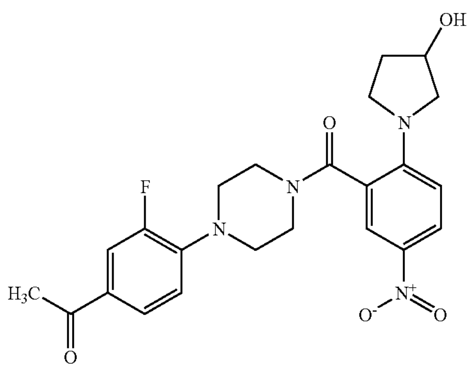 | 456.5 | 1-(3-Fluoro-4-{4-[2-(3-hydroxy-pyrrolidin-1-yl)-5-nitro-benzoyl]-piperazin-1-yl}-phenyl)-ethanone | 1-{3-Fluoro-4-[4-(2-fluoro-5-nitro-benzoyl)-piperazin-1-yl]-phenyl}-ethanone and 3-hydroxypyrrolidine (commerically available) | 457.2 |
| 31 | 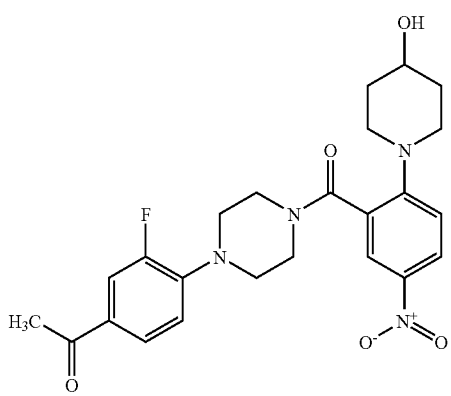 | 470.5 | 1-(3-Fluoro-4-{4-[2-(4-hydroxy-piperidin-1-yl)-5-nitro-benzoyl]-piperazin-1-yl}-phenyl)-ethanone | 1-{3-Fluoro-4-[4-(2-fluoro-5-nitro-benzoyl)-piperazin-1-yl]-phenyl}-ethanone and 4-hydroxy-piperidine (commerically available) | 471.2 |
| 32 | Chiral | 484.5 | 1-(3-Fluoro-4-{4-[2-((S)-2-methoxymethyl-pyrrolidin-1-yl)-5-nitro-benzoyl]-piperazin-1-yl}-phenyl)-ethanone | 1-{3-Fluoro-4-[4-(2-fluoro-5-nitro-benzoyl)-piperazin-1-yl]-phenyl}-ethanone and 2-((S)-2-methoxymethyl-pyrrolidine (commerically available) | 485.3 |

TABLE 1-continued

| No. | Structure | MW | Systematic Name | Starting materials | MW found (MH+) |
|---|---|---|---|---|---|
| 33 | 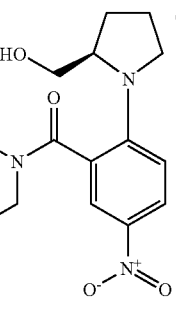 | 470.5 | 1-(3-Fluoro-4-{4-[2-((R)-2-hydroxymethyl-pyrrolidin-1-yl)-5-nitro-benzoyl]-piperazin-1-yl}-phenyl)-ethanone | 1-{3-Fluoro-4-[4-(2-fluoro-5-nitro-benzoyl)-piperazin-1-yl]-phenyl}-ethanone and 2-((R)-2-methoxymethyl-pyrrolidine (commerically available) | 471.2 |
| 34 | 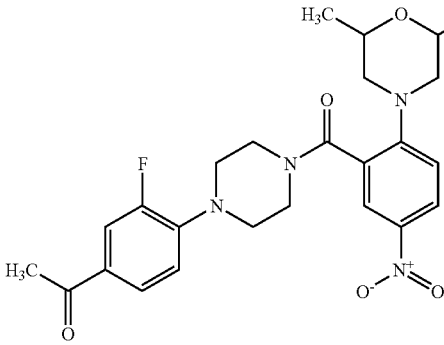 | 484.5 | 1-(4-{4-[2-(2,6-Dimethyl-morpholin-4-yl)-5-nitro-benzoyl]-piperazin-1-yl}-3-fluoro-phenyl)-ethanone | 1-{3-Fluoro-4-[4-(2-fluoro-5-nitro-benzoyl)-piperazin-1-yl]-phenyl}-ethanone and 2,6-Dimethylmorpholine (commerically available) | 485.3 |
| 35 | 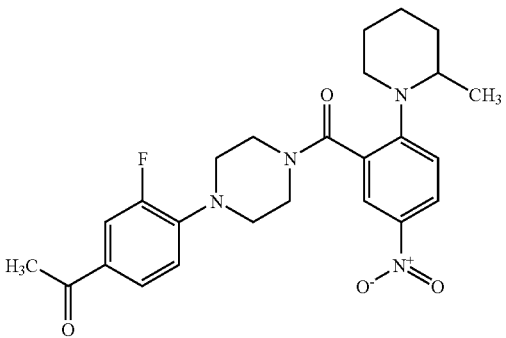 | 468.5 | 1-(3-Fluoro-4-{4-[2-(2-methyl-piperidin-1-yl)-5-nitro-benzoyl]-piperazin-1-yl}-phenyl)-ethanone | 1-{3-Fluoro-4-[4-(2-fluoro-5-nitro-benzoyl)-piperazin-1-yl]-phenyl}-ethanone and 2-methyl-piperidine (commerically available) | 469.2 |
| 36 | 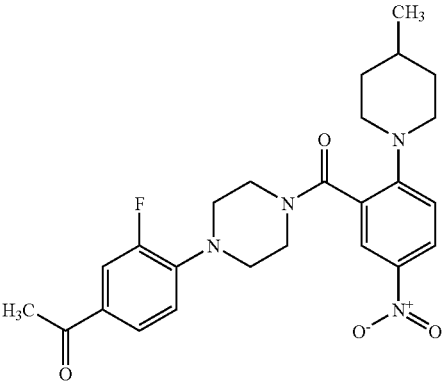 | 468.5 | 1-(3-Fluoro-4-{4-[2-(4-methyl-piperidin-1-yl)-5-nitro-benzoyl]-piperazin-1-yl}-phenyl)-ethanone | 1-{3-Fluoro-4-[4-(2-fluoro-5-nitro-benzoyl)-piperazin-1-yl]-phenyl}-ethanone and 4-methyl-piperidine (commerically available) | 469.2 |

TABLE 1-continued

| No. | Structure | MW | Systematic Name | Starting materials | MW found (MH+) |
|---|---|---|---|---|---|
| 37 | 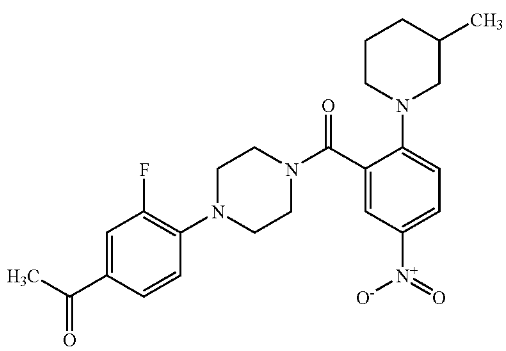 | 468.5 | 1-(3-Fluoro-4-{4-[2-(3-methyl-piperidin-1-yl)-5-nitro-benzoyl]-piperazin-1-yl}-phenyl)-ethanone | 1-{3-Fluoro-4-[4-(2-fluoro-5-nitro-benzoyl)-piperazin-1-yl]-phenyl}-ethanone and 3-methyl-piperidine (commerically available) | 469.2 |
| 38 | 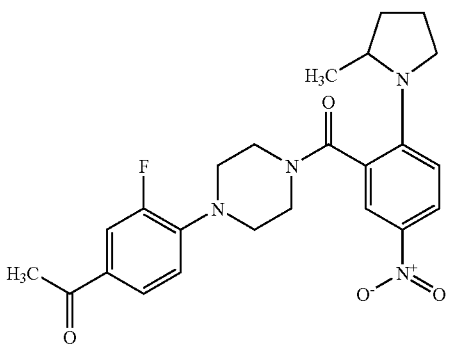 | 454.5 | 1-(3-Fluoro-4-{4-[2-(2-methyl-pyrrolidin-1-yl)-5-nitro-benzoyl]-piperazin-1-yl}-phenyl)-ethanone | 1-{3-Fluoro-4-[4-(2-fluoro-5-nitro-benzoyl)-piperazin-1-yl]-phenyl}-ethanone and 2-methyl-pyrrolidine (commerically available) | 455.2 |
| 39 | 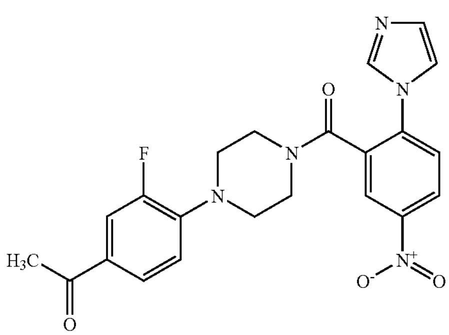 | 437.4 | 1-{3-Fluoro-4-[4-(2-imidazol-1-yl-5-nitro-benzoyl)-piperazin-1-yl]-phenyl}-ethanone | 1-{3-Fluoro-4-[4-(2-fluoro-5-nitro-benzoyl)-piperazin-1-yl]-phenyl}-ethanone and imidazole (commerically available) | 438.1 |
| 40 | 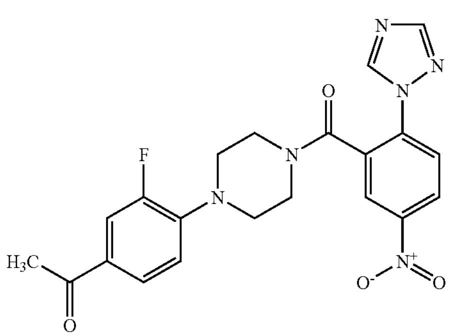 | 438.4 | 1-{3-Fluoro-4-[4-(5-nitro-2-[1,2,4]triazol-1-yl-benzoyl)-piperazin-1-yl]-phenyl}-ethanone | 1-{3-Fluoro-4-[4-(2-fluoro-5-nitro-benzoyl)-piperazin-1-yl]-phenyl}-ethanone and triazole (commerically available) | 439.2 |

TABLE 1-continued

| No. | Structure | MW | Systematic Name | Starting materials | MW found (MH+) |
|---|---|---|---|---|---|
| 41 | 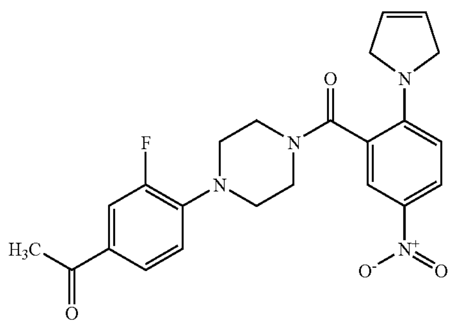 | 438.5 | 1-(4-{4-[2-(2,5-Dihydro-pyrrol-1-yl)-5-nitro-benzoyl]-piperazin-1-yl}-3-fluoro-phenyl)-ethanone | 1-{3-Fluoro-4-[4-(2-fluoro-5-nitro-benzoyl)-piperazin-1-yl]-phenyl}-ethanone and 2,5 Dihydro-pyrrol (commerically available) | 439.2 |
| 42 | 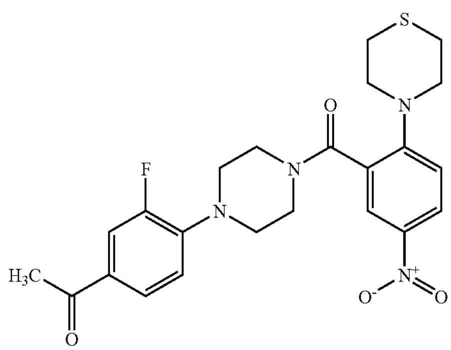 | 472.5 | 1-{3-Fluoro-4-[4-(5-nitro-2-thiomorpholin-4-yl-benzoyl)-piperazin-1-yl]-phenyl}-ethanone | 1-{3-Fluoro-4-[4-(2-fluoro-5-nitro-benzoyl)-piperazin-1-yl]-phenyl}-ethanone and thiomorpholine | 473.1 |
| 43 | 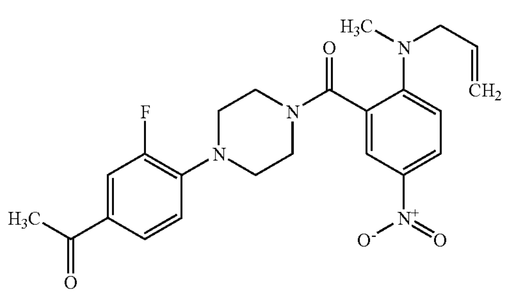 | 440.5 | 1-(4-{4-[2-(Allyl-methyl-amino)-5-nitro-benzoyl]-piperazin-1-yl}-3-fluoro-phenyl)-ethanone | 1-{3-Fluoro-4-[4-(2-fluoro-5-nitro-benzoyl)-piperazin-1-yl]-phenyl}-ethanone and allylmethylamine (commerically available) | 441.2 |
| 44 | 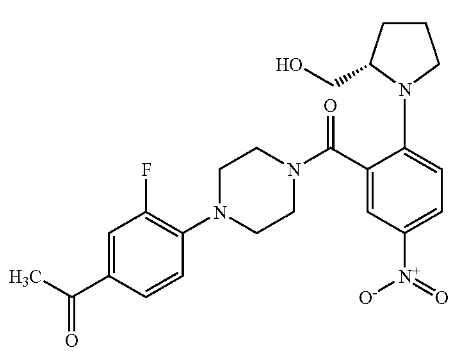 | 470.5 | 1-(3-Fluoro-4-{4-[2-[2(S)-(2-hydroxymethyl-pyrrolidin-1-yl)-5-nitro-benzoyl]-piperazin-1-yl}-phenyl)-ethanone | 1-{3-Fluoro-4-[4-(2-fluoro-5-nitro-benzoyl)-piperazin-1-yl]-phenyl}-ethanone and 2(S)-(2-hydroxymethyl-pyrrolidin (commerically available) | 471.2 |

TABLE 1-continued

| No. | Structure | MW | Systematic Name | Starting materials | MW found (MH+) |
|---|---|---|---|---|---|
| 45 | 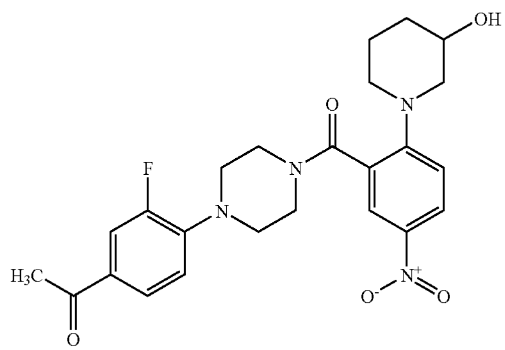 | 470.5 | 1-(3-Fluoro-4-{4-[2-(3-hydroxy-piperidin-1-yl)-5-nitro-benzoyl]-piperazin-1-yl}-phenyl)-ethanone | 1-{3-Fluoro-4-[4-(2-fluoro-5-nitro-benzoyl)-piperazin-1-yl]-phenyl}-ethanone and 3-hydroxy-piperidine (commerically available) | 471.2 |
| 46 | 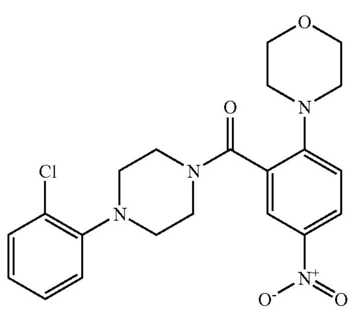 | 430.9 | [4-(2-Chloro-phenyl)-piperazin-1-yl]-(2-morpholin-4-yl-5-nitro-phenyl)-methanone | 1-(2-Chloro-phenyl)-piperazine (commercially available) and 2-Morpholin-4-yl-5-nitro-benzoyl chloride | 431.2 |
| 47 | 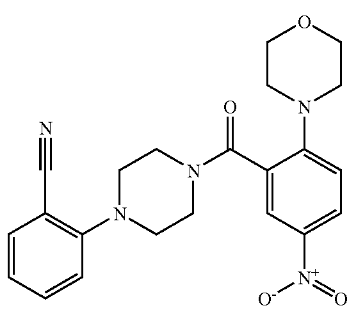 | 421.5 | 2-[4-(2-Morpholin-4-yl-5-nitro-benzoyl)-piperazin-1-yl]-benzonitrile | 1-(2-Cyano-phenyl)-piperazine (commercially available) and 2-Morpholin-4-yl-5-nitro-benzoyl chloride | 422.2 |
| 48 | 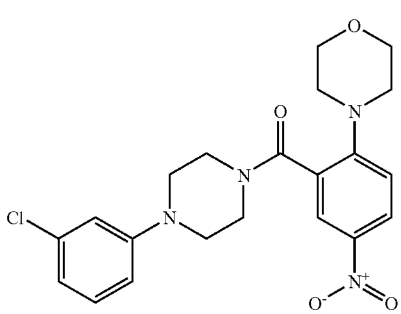 | 430.9 | [4-(3-Chloro-phenyl)-piperazin-1-yl]-(2-morpholin-4-yl-5-nitro-phenyl)-methanone | 1-(3-Chloro-phenyl)-piperazine (commercially available) and 2-Morpholin-4-yl-5-nitro-benzoyl chloride | 431.2 |

TABLE 1-continued

| No. | Structure | MW | Systematic Name | Starting materials | MW found (MH+) |
|---|---|---|---|---|---|
| 49 | 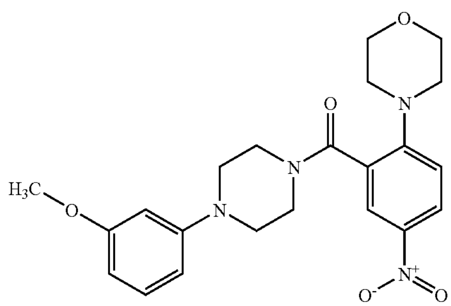 | 426.5 | [4-(3-Methoxy-phenyl)-piperazin-1-yl]-(2-morpholin-4-yl-5-nitro-phenyl)-methanone | 1-(3-Methoxy-phenyl)-piperazine (commercially available) and 2-Morpholin-4-yl-5-nitro-benzoyl chloride | 427.2 |
| 50 | 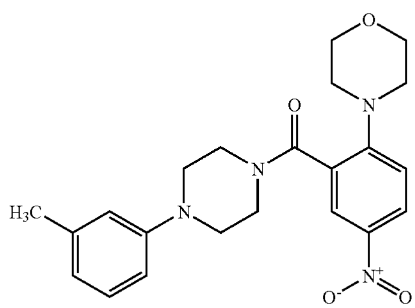 | 410.5 | (2-Morpholin-4-yl-5-nitro-phenyl)-(4-m-tolyl-piperazin-1-yl)-methanone | 1-(3-Methyl-phenyl)-piperazine (commercially available) and 2-Morpholin-4-yl-5-nitro-benzoyl chloride | 411.2 |
| 51 | 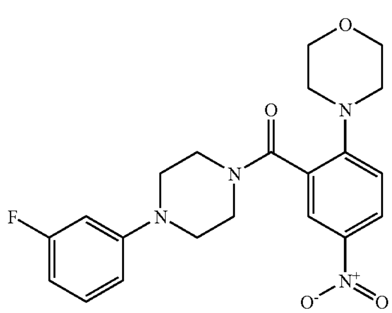 | 414.4 | [4-(3-Fluoro-phenyl)-piperazin-1-yl]-(2-morpholin-4-yl-5-nitro-phenyl)-methanone | 1-(3-Fluoro-phenyl)-piperazine (commercially available) and 2-Morpholin-4-yl-5-nitro-benzoyl chloride | 415.2 |
| 52 | 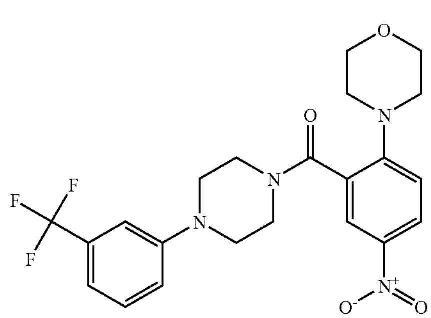 | 464.4 | (2-Morpholin-4-yl-5-nitro-phenyl)-[4-(3-trifluoromethyl-phenyl)-piperazin-1-yl]-methanone | 1-(3-Trifluoromethyl-phenyl)-piperazine (commercially available) and 2-Morpholin-4-yl-5-nitro-benzoyl chloride | 465.2 |

TABLE 1-continued

| No. | Structure | MW | Systematic Name | Starting materials | MW found (MH+) |
|---|---|---|---|---|---|
| 53 | 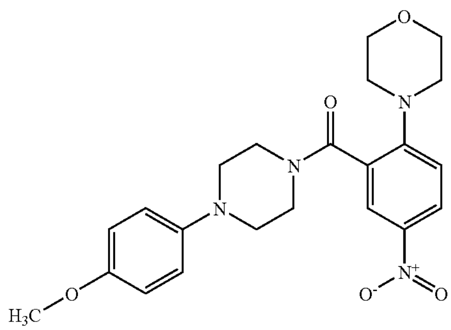 | 426.5 | [4-(4-Methoxy-phenyl)-piperazin-1-yl]-(2-morpholin-4-yl-5-nitro-phenyl)-methanone Known compound, RN 433242-97-8 | 1-(4-Methoxy-phenyl)-piperazine (commercially available) and 2-Morpholin-4-yl-5-nitro benzoyl chloride | 427.2 |
| 54 | 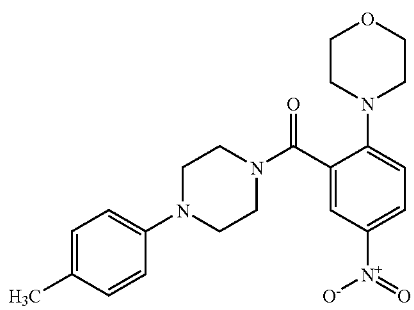 | 410.5 | (2-Morpholin-4-yl-5-nitro-phenyl-(4-p-tolyl-piperazin-1-yl)-methanone | 1-(4-Methyl-phenyl)-piperazine (commercially available) and 2-Morpholin-4-yl-5-nitro benzoyl chloride | 411.2 |
| 55 | 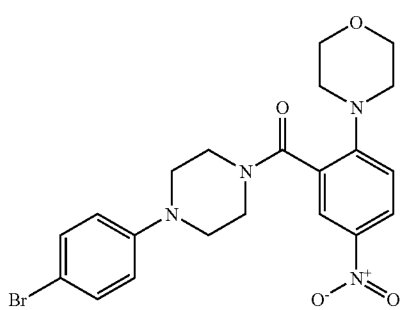 | 475.3 | [4-(4-Bromo-phenyl)-piperazin-1-yl]-(2-morpholin-4-yl-5-nitro-phenyl)-methanone | 1-(4-Bromo-phenyl)-piperazine (commercially available) and 2-Morpholin-4-yl-5-nitro benzoyl chloride | 477.0 |
| 56 | 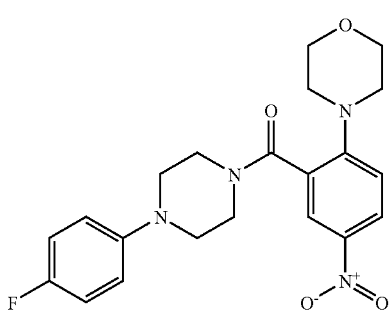 | 414.4 | [4-(4-Fluoro-phenyl)-piperazin-1-yl]-(2-morpholin-4-yl-5-nitro-phenyl)-methanone | 1-(4-Fluoro-phenyl)-piperazine (commercially available) and 2-Morpholin-4-yl-5-nitro benzoyl chloride | 415.2 |

TABLE 1-continued

| No. | Structure | MW | Systematic Name | Starting materials | MW found (MH+) |
|---|---|---|---|---|---|
| 57 | 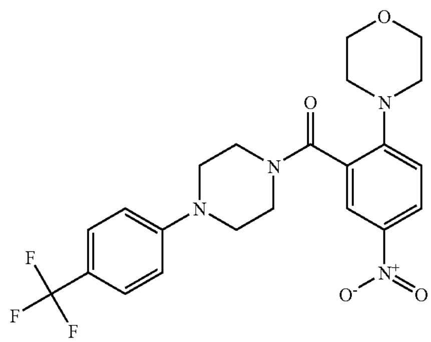 | 464.4 | (2-Morpholin-4-yl-5-nitro-phenyl)-[4-(4-trifluoromethyl-phenyl)-piperazin-1-yl]-methanone | 1-(4-Trifluoromethyl-phenyl)-piperazine (commercially available) and 2-Morpholin-4-yl-5-nitro-benzoyl chloride | 465.2 |
| 58 | 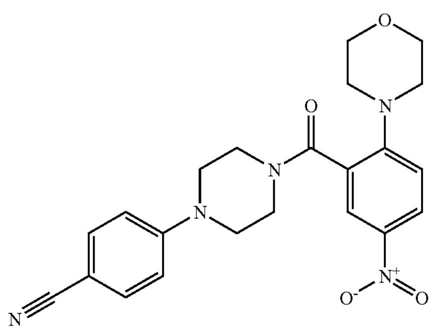 | 421.5 | 4-[4-(2-Morpholin-4-yl-5-nitro-benzoyl)-piperazin-1-yl]-benzonitrile | 1-(4-Cyano-phenyl)-piperazine (commercially available) and 2-Morpholin-4-yl-5-nitro benzoyl chloride | 422.2 |
| 59 | 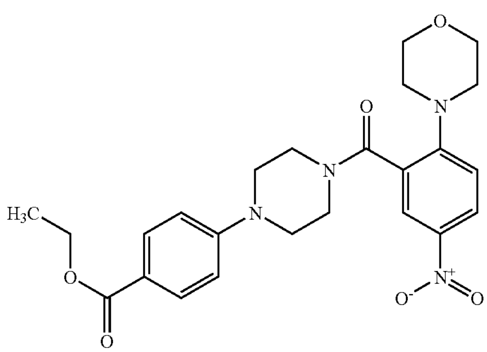 | 468.5 | 4-[4-(2-Morpholin-4-yl-5-nitro-benzoyl)-piperazin-1-yl]-benzoic acid ethyl ester | 4-Piperazin-1-yl-benzoic acid ethyl ester (WO9938849) and 2-Morpholin-4-yl-5-nitro-benzoyl chloride | 469.2 |
| 60 | 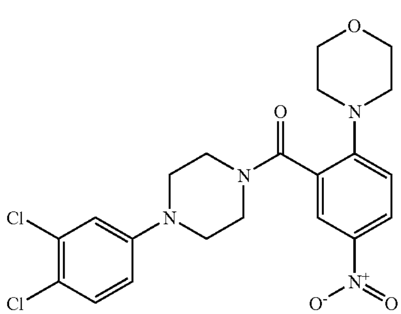 | 465.3 | [4-(3,4-Dichloro-phenyl)-piperazin-1-yl]-(2-morpholin-4-yl-5-nitro-phenyl)-methanone | 1-(3,4-Dichloro-phenyl)-piperazine (commercially available) and 2-Morpholin-4-yl-5-nitro benzoyl chloride | 466.2 |

TABLE 1-continued

| No. | Structure | MW | Systematic Name | Starting materials | MW found (MH+) |
|---|---|---|---|---|---|
| 61 | 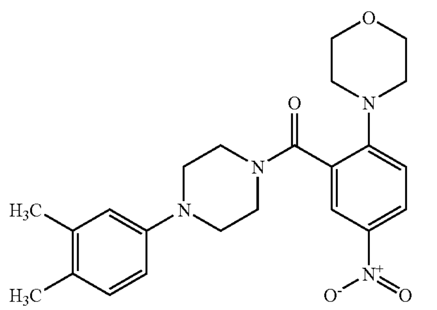 | 424.4 | [4-(3,4-Dimethyl-phenyl)-piperazin-1-yl]-(2-morpholin-4-yl-5-nitro-phenyl)-methanone | 1-(3,4-Dimethyl-phenyl)-piperazine (commercially available) and 2-Morpholin-4-yl-5-nitro benzoyl chloride | 425.2 |
| 62 | 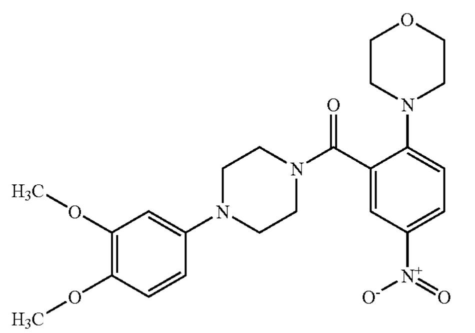 | 456.5 | [4-(3,4-Dimethoxy-phenyl)-piperazin-1-yl]-(2-morpholin-4-yl-5-nitro-phenyl)-methanone | 1-(3,4-Dimethoxy-phenyl)-piperazine (commercially available) and 2-Morpholin-4-yl-5-nitro benzoyl chloride | 457.2 |
| 63 | 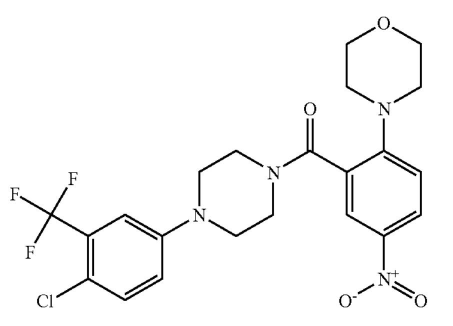 | 498.9 | [4-(4-Chloro-3-trifluoromethyl-phenyl)-piperazin-1-yl]-(2-morpholin-4-yl-5-nitro-phenyl)-methanone | 1-(4-Chloro-3-trifluoromethyl-phenyl)-piperazine (commercially available) and 2-Morpholin-4-yl-5-nitro benzoyl chloride | 499.3 |
| 64 | 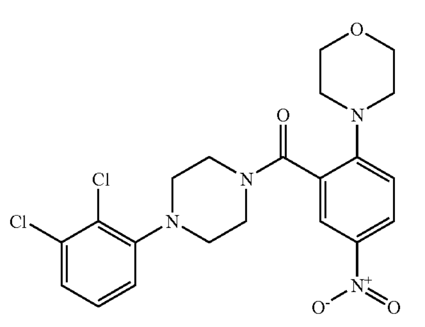 | 465.3 | [4-(2,3-Dichloro-phenyl)-piperazin-1-yl]-(2-morpholin-4-yl-5-nitro-phenyl)-methanone | 1-(2,3-Dichloro-phenyl)-piperazine (commercially available) and 2-Morpholin-4-yl-5-nitro benzoyl chloride | 465.1 |

TABLE 1-continued

| No. | Structure | MW | Systematic Name | Starting materials | MW found (MH+) |
|---|---|---|---|---|---|
| 65 | 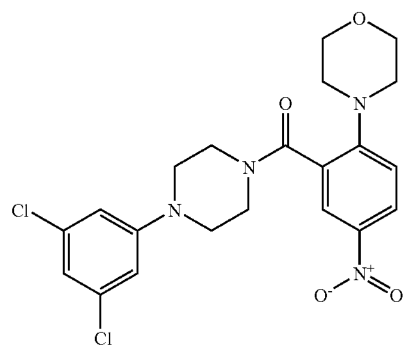 | 465.3 | [4-(3,5-Dichloro-phenyl)-piperazin-1-yl]-(2-morpholin-4-yl-5-nitro-phenyl)-methanone | 1-(3,5-Dichloro-phenyl)-piperazine (commercially available) and 2-Morpholin-4-yl-5-nitro benzoyl chloride | 464.9 |
| 66 | 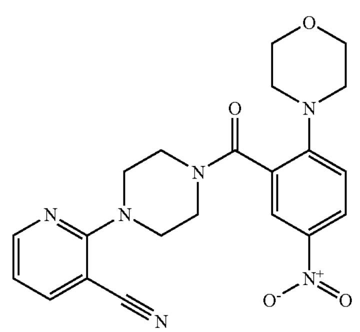 | 422.4 | 4-[4-(2-Morpholin-4-yl-5-nitro-benzoyl)-piperazin-1-yl]-nicotinonitrile | 2-Piperazin-1-yl-nicotinonitrile and 2-Morpholin-4-yl-5-nitro-benzoyl chloride | 423.2 |
| 67 | 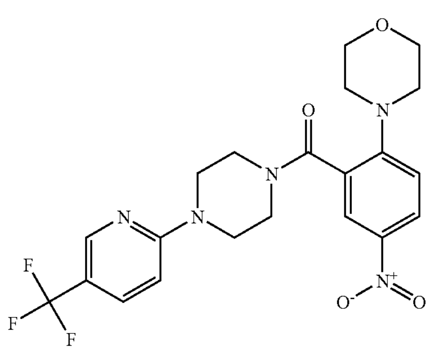 | 465.4 | (2-Morpholin-4-yl-5-nitro-phenyl)-[4-(5-trifluoromethyl-pyridin-2-yl)-piperazin-1-yl]-methanone | 1-(5-Trifluoromethyl-pyridin-2-yl)-piperazine and 2-Morpholin-4-yl-5-nitro-benzoyl chloride | 466.2 |
| 68 | 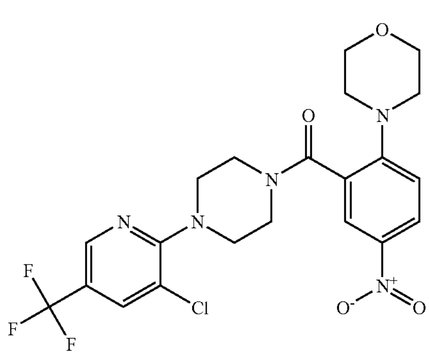 | 499.9 | [4-(3-Chloro-5-trifluoromethyl-pyridin-2-yl)-piperazin-1-yl]-(2-morpholin-4-yl-5-nitro-phenyl)-methanone | 1-(3-Chloro-5-trifluoromethyl-pyridin-2-yl)-piperazine and 2-Morpholin-4-yl-5-nitro benzoyl chloride | 500.1 |

TABLE 1-continued

| No. | Structure | MW | Systematic Name | Starting materials | MW found (MH+) |
|---|---|---|---|---|---|
| 69 | 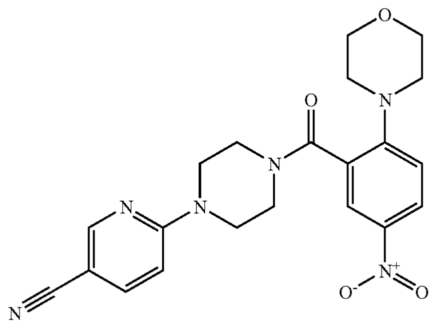 | 422.4 | 6-[4-(2-Morpholin-4-yl-5-nitro-benzoyl)-piperazin-1-yl]-nicotinonitrile | 6-Piperazin-1-yl-nicotinonitrile and 2-Morpholin-4-yl-5-nitro-benzoyl chloride | 423.2 |
| 70 | 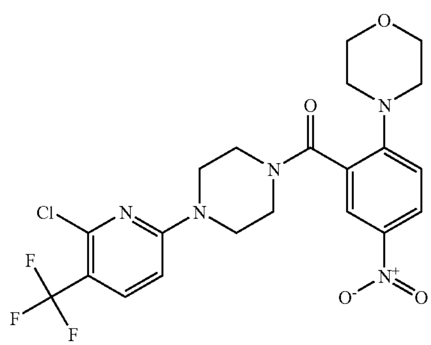 | 499.9 | [4-(6-Chloro-5-trifluoromethyl-pyridin-2-yl)-piperazin-1-yl]-(2-morpholin-4-yl-5-nitro-phenyl)-methanone | 1-(6-Chloro-5-trifluoromethyl-pyridin-2-yl)-piperazine and 2-Morpholin-4-yl-5-nitro benzoyl chloride | 500.1 |
| 71 | 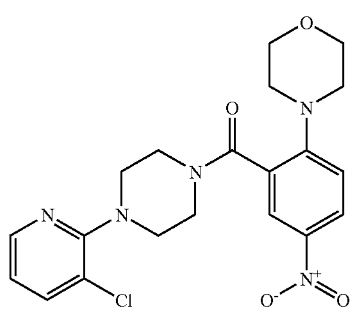 | 431.9 | [4-(3-Chloro-pyridin-2-yl)-piperazin-1-yl]-(2-morpholin-4-yl-5-nitro-phenyl)-methanone | 1-(3-Chloro-pyridin-2-yl)-piperazine and 2-Morpholin-4-yl-5-nitro benzoyl chloride | 432.2 |
| 72 | 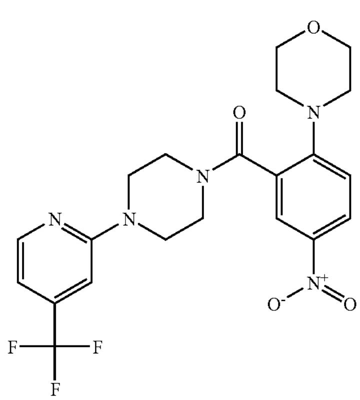 | 465.4 | (2-Morpholin-4-yl-5-nitro-phenyl)-[4-(4-trifluoromethyl-pyridin-2-yl)-piperazin-1-yl]-methanone | 1-(4-Trifluoromethyl-pyridin-2-yl)-piperazine and 2-Morpholin-4-yl-5-nitro-benzoyl chloride | 466.2 |

TABLE 1-continued

| No. | Structure | MW | Systematic Name | Starting materials | MW found (MH+) |
|---|---|---|---|---|---|
| 73 | 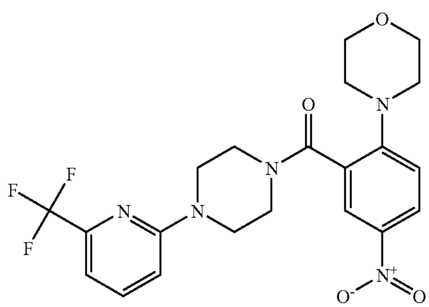 | 465.4 | (2-Morpholin-4-yl-5-nitro-phenyl)-[4-(6-trifluoromethyl-pyridin-2-yl)-piperazin-1-yl]-methanone | 1-(6-Trifluoromethyl-pyridin-2-yl)-piperazine and 2-Morpholin-4-yl-5-nitro-benzoyl chloride | 466.2 |
| 74 | 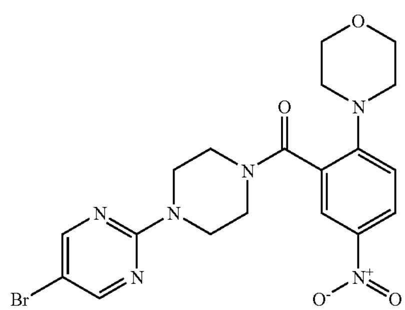 | 477.3 | [4-(5-Bromo-pyrimidin-2-yl)-piperazin-1-yl]-(2-morpholin-4-yl-5-nitro-phenyl)-methanone | 5-Bromo-2-piperazin-1-yl-pyrimidine and 2-Morpholin-4-yl-5-nitro-benzoyl chloride | 477.0 |
| 75 | 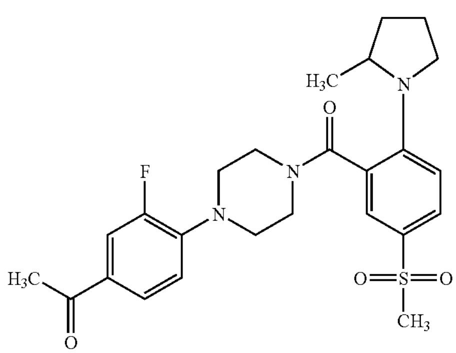 | 487.6 | 1-(3-Fluoro-4-{4-[5-methanesulfonyl-2-(2-methyl-pyrrolidin-1-yl)-benzoyl]-piperazin-1-yl}-phenyl)-ethanone | 1-{4-[4-(2-Chloro-5-methanesulfonyl-benzoyl)-piperazin-1-yl]-3-fluoro-phenyl}-ethanone and 2-methyl-pyrrolidin (commercially available) | 488.2 |
| 76 | 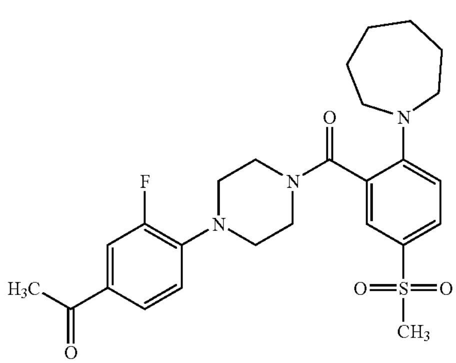 | 501.6 | 1-{4-[4-(2-Azepan-1-yl-5-methanesulfonyl-benzoyl)-piperazin-1-yl]-3-fluoro-phenyl}-ethanone | 1-{4-[4-(2-Chloro-5-methanesulfonyl-benzoyl)-piperazin-1-yl]-3-fluoro-phenyl}-ethanone and azepane (commercially available) | 502.2 |

TABLE 1-continued

| No. | Structure | MW | Systematic Name | Starting materials | MW found (MH+) |
|---|---|---|---|---|---|
| 77 | 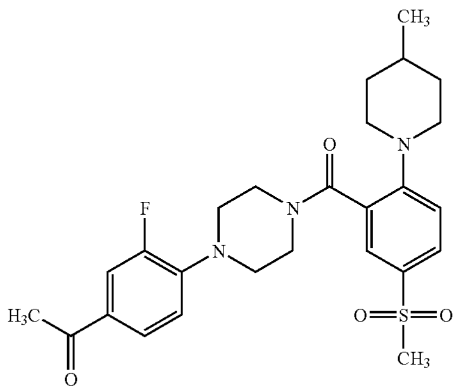 | 501.6 | 1-(3-Fluoro-4-{4-[5-methanesulfonyl-2-(4-methyl-piperidin-1-yl)-benzoyl)-piperazin-1-yl}-phenyl)-ethanone | 1-{4-[4-(2-Chloro-5-methanesulfonyl-benzoyl)-piperazin-1-yl]-3-fluoro-phenyl}-ethanone and 4-methylpiperidine (commercially available) | 502.2 |
| 78 | 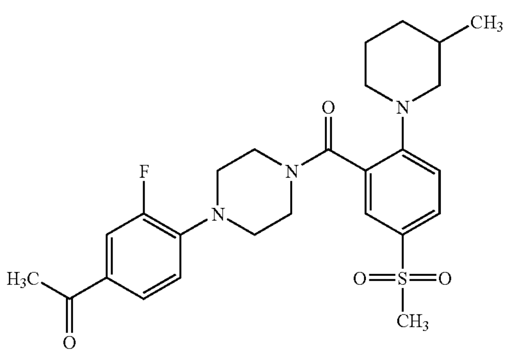 | 501.6 | 1-(3-Fluoro-4-{4-[5-methanesulfonyl-2-(3-methyl-piperidin-1-yl)-benzoyl)-piperazin-1-yl}-phenyl)-ethanone | 1-{4-[4-(2-Chloro-5-methanesulfonyl-benzoyl)-piperazin-1-yl]-3-fluoro-phenyl}-ethanone and 3-methylpiperidine (commercially available) | 502.2 |
| 79 | 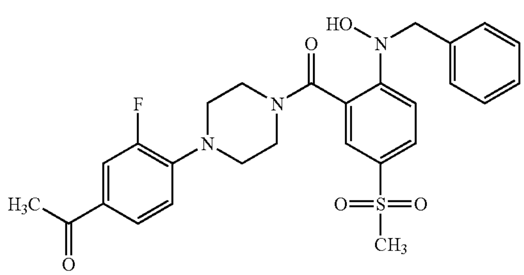 | 525.6 | 1-(4-{4-[2-(Benzyl-hydroxy-amino)-5-methanesulfonyl-benzoyl]-piperazin-1-yl}-3-fluoro-phenyl)-ethanone | 1-{4-[4-(2-Chloro-5-methanesulfonyl-benzoyl)-piperazin-1-yl]-3-fluoro-phenyl}-ethanone and benzylhydroxylamine (commercially available) | 527.1 |
| 80 | 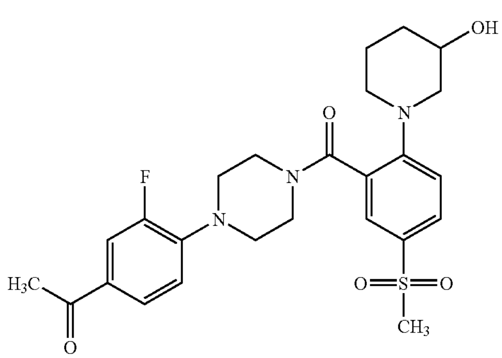 | 503.6 | 1-(3-Fluoro-4-{4-[2-(3-hydroxy-piperidin-1-yl)-5-methanesulfonyl-benzoyl]-piperazin-1-yl}-phenyl)-ethanone | 1-{4-[4-(2-Chloro-5-methanesulfonyl-benzoyl)-piperazin-1-yl]-3-fluoro-phenyl}-ethanone and 3-hydroxypiperidine (commercially available) | 504.2 |

TABLE 1-continued

| No. | Structure | MW | Systematic Name | Starting materials | MW found (MH+) |
|---|---|---|---|---|---|
| 81 | 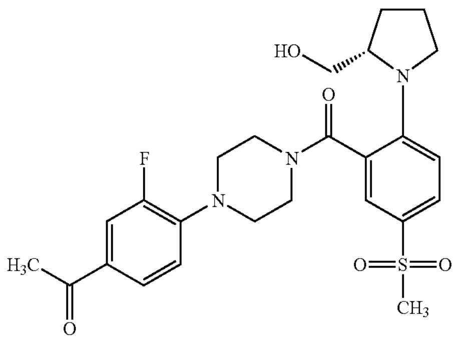 | Chiral 503.6 | 1-(3-Fluoro-4-{4-[2(S)-(2-hydroxymethyl-pyrrolidin-1-yl)-5-methanesulfonyl-benzoyl]-piperazin-1-yl}-phenyl)-ethanone | 1-{4-[4-(2-Chloro-5-methanesulfonyl-benzoyl)-piperazin-1-yl]-3-fluoro-phenyl}-ethanone and 2(S)-(2-hydroxymethyl-pyrrolidine (commercially available) | 504.2 |
| 82 | 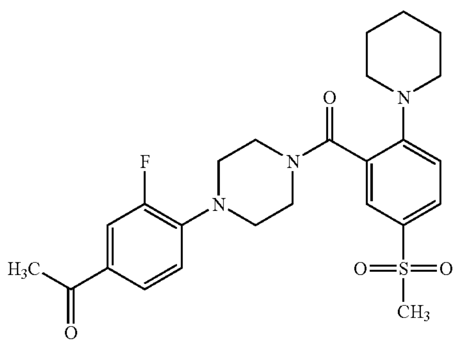 | 487.6 | 1-{3-Fluoro-4-[4-(5-methanesulfonyl-2-piperidin-1-yl-benzoyl)-piperazin-1-yl]-phenyl}-ethanone | 1-{4-[4-(2-Chloro-5-methanesulfonyl-benzoyl)-piperazin-1-yl]-3-fluoro-phenyl}-ethanone and piperidine (commercially available) | 488.2 |
| 83 | 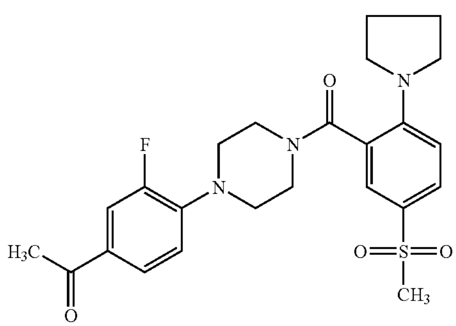 | 473.6 | 1-{3-Fluoro-4-[4-(5-methanesulfonyl-2-pyrrolidin-1-yl-benzoyl)-piperazin-1-yl]-phenyl}-ethanone | 1-{4-[4-(2-Chloro-5-methanesulfonyl-benzoyl)-piperazin-1-yl]-3-fluoro-phenyl}-ethanone and pyrrolidine (commercially available) | 474.1 |
| 84 | 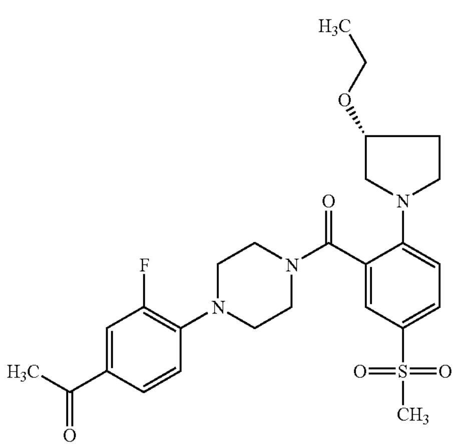 | Chiral 517.6 | 1-(4-{4-[2-(R)-(3-Ethoxy-pyrrolidin-1-yl)-5-methanesulfonyl-benzoyl]-piperazin-1-yl}-3-fluoro-phenyl)-ethanone | 1-{4-[4-(2-Chloro-5-methanesulfonyl-benzoyl)-piperazin-1-yl]-3-fluoro-phenyl}-ethanone and 2-(R)-3-Ethoxy-pyrrolidine (commercially available) | 518.2 |

TABLE 1-continued

| No. | Structure | MW | Systematic Name | Starting materials | MW found (MH+) |
|---|---|---|---|---|---|
| 85 | 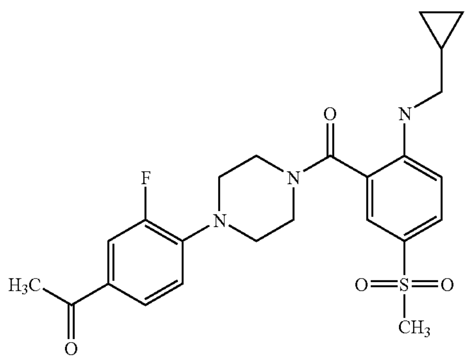 | 473.6 | 1-(4-{4-[2-(Cyclopropylmethyl-amino)-5-methanesulfonyl-benzoyl]-piperazin-1-yl}-3-fluoro-phenyl)-ethanone | 1-{4-[4-(2-Chloro-5-methanesulfonyl-benzoyl)-piperazin-1-yl]-3-fluoro-phenyl}-ethanone and cyclopropylmethylamine (commercially available) | 474.2 |
| 86 | 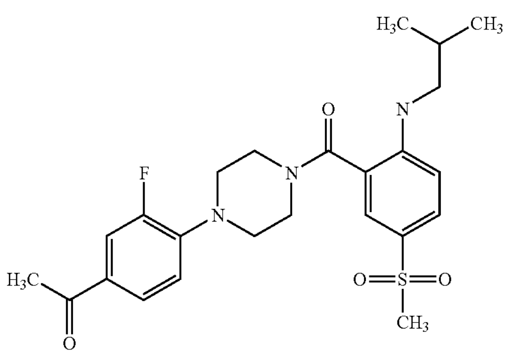 | 475.6 | 1-{3-Fluoro-4-[4-(2-isobutylamino-5-methanesulfonyl-benzoyl)-piperazin-1-yl]-phenyl}-ethanone | 1-{4-[4-(2-Chloro-5-methanesulfonyl-benzoyl)-piperazin-1-yl]-3-fluoro-phenyl}-ethanone and isobutylamine (commercially available) | 476.3 |
| 87 | 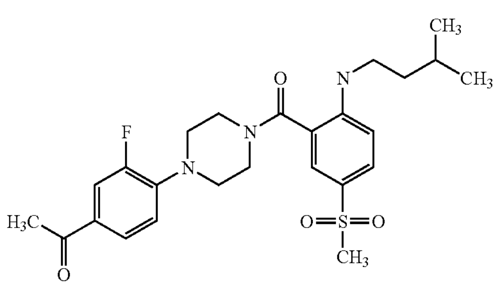 | 489.6 | 1-{3-Fluoro-4-{4-[5-methanesulfonyl-2-(3-methyl-butylamino)-benzoyl]-piperazin-1-yl}-phenyl)-ethanone | 1-{4-[4-(2-Chloro-5-methanesulfonyl-benzoyl)-piperazin-1-yl]-3-fluoro-phenyl}-ethanone and 3-methylbutylamine (commercially available) | 490.4 |
| 88 | 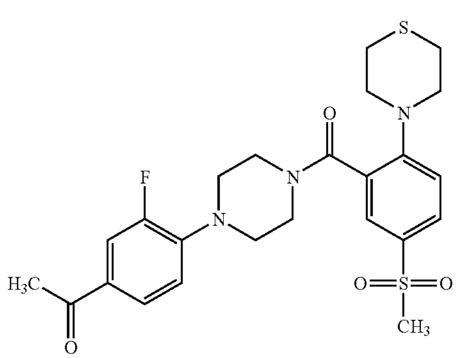 | 505.6 | 1-{3-Fluoro-4-[4-(5-methanesulfonyl-2-thiomorpholin-4-yl-benzoyl)-piperazin-1-yl]-phenyl}-ethanone | 1-{4-[4-(2-Chloro-5-methanesulfonyl-benzoyl)-piperazin-1-yl]-3-fluoro-phenyl}-ethanone and thiomorpholine (commercially available) | 506.3 |

TABLE 1-continued

| No. | Structure | MW | Systematic Name | Starting materials | MW found (MH+) |
|---|---|---|---|---|---|
| 89 | 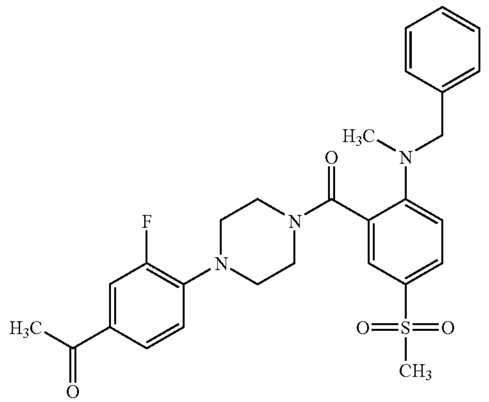 | 523.6 | 1-(4-{4-[2-(Benzyl-methyl-amino)-5-methanesulfonyl-benzoyl]-piperazin-1-yl}-3-fluoro-phenyl)-ethanone | 1-{4-[4-(2-Chloro-5-methanesulfonyl-benzoyl)-piperazin-1-yl]-3-fluoro-phenyl}-ethanone and benzylmethylamine (commercially available) | 524.2 |
| 90 | 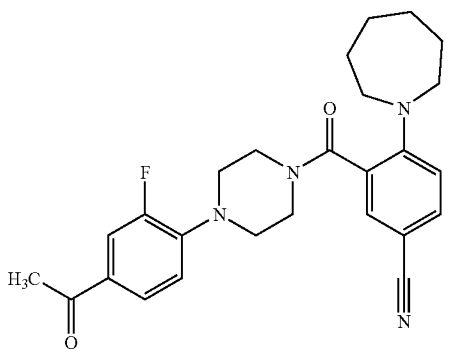 | 448.5 | 3-[4-(4-Acetyl-2-fluoro-phenyl)-piperazine-1-carbonyl]-4-azepan-1-yl-benzonitrile | 3-[4-(4-Acetyl-2-fluoro-phenyl)-piperazine-1-carbonyl]-4-bromo-benzonitrile and azepane (commercially available) | 449.2 |
| 91 | 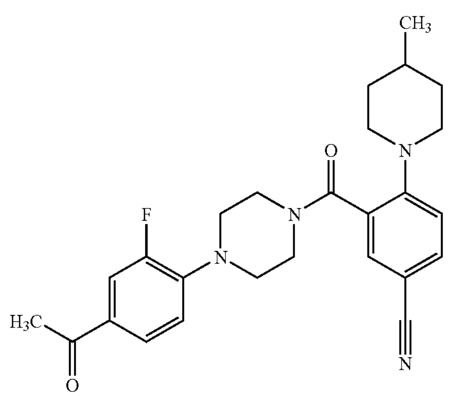 | 448.5 | 3-[4-(4-Acetyl-2-fluoro-phenyl)-piperazine-1-carbonyl]-4-(4-methyl-piperidin-1-yl)-benzonitrile | 3-[4-(4-Acetyl-2-fluoro-phenyl)-piperazine-1-carbonyl]-4-bromo-benzonitrile and 4-methyl-piperidine (commercially available) | 449.2 |
| 92 | 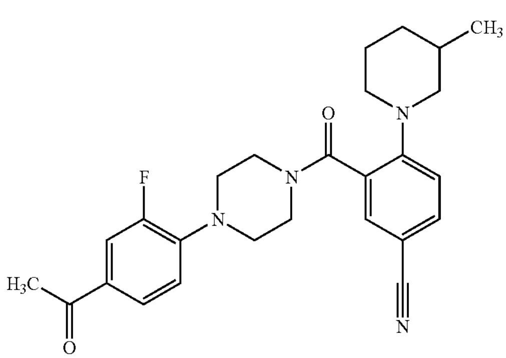 | 448.5 | 3-[4-(4-Acetyl-2-fluoro-phenyl)-piperazine-1-carbonyl]-4-(3-methyl-piperidin-1-yl)-benzonitrile | 3-[4-(4-Acetyl-2-fluoro-phenyl)-piperazine-1-carbonyl]-4-bromo-benzonitrile and 3-methyl-piperidine (commercially available) | 449.2 |

TABLE 1-continued

| No. | Structure | MW | Systematic Name | Starting materials | MW found (MH+) |
|---|---|---|---|---|---|
| 93 | 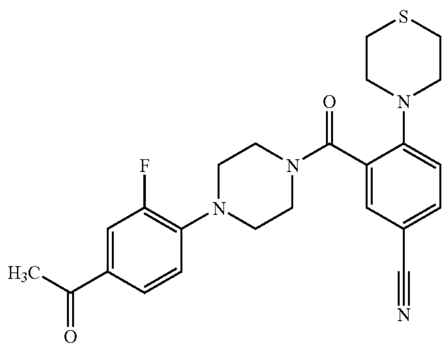 | 452.6 | 3-[4-(4-Acetyl-2-fluoro-phenyl)-piperazine-1-carbonyl]-4-thiomorpholin-4-yl-benzonitrile | 3-[4-(4-Acetyl-2-fluoro-phenyl)-piperazine-1-carbonyl]-4-bromo-benzonitrile and thiomorpholine (commercially available) | 453.1 |
| 94 | 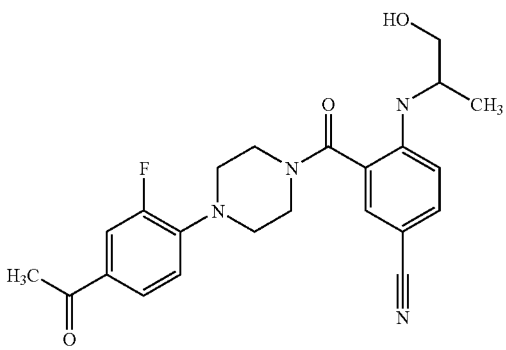 | 424.5 | 3-[4-(4-Acetyl-2-fluoro-phenyl)-piperazine-1-carbonyl]-4-(2-hydroxy-1-methyl-ethylamine)-benzonitrile | 3-[4-(4-Acetyl-2-fluoro-phenyl)-piperazine-1-carbonyl]-4-bromo-benzonitrile and 2-hydroxy-1-methyl-ethylamine (commercially available) | 425.1 |
| 95 | 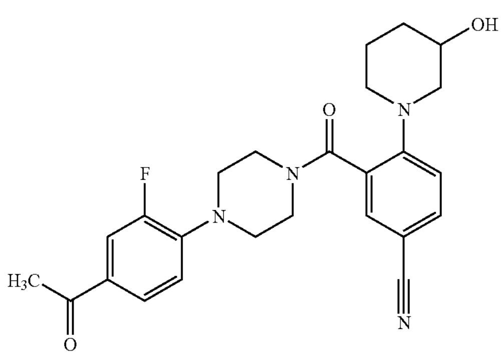 | 450.5 | 3-[4-(4-Acetyl-2-fluoro-phenyl)-piperazine-1-carbonyl]-4-(3-hydroxy-piperidin-1-yl)-benzonitrile | 3-[4-(4-Acetyl-2-fluoro-phenyl)-piperazine-1-carbonyl]-4-bromo-benzonitrile and 3-hydroxy-piperidine (commercially available) | 451.2 |
| 96 | 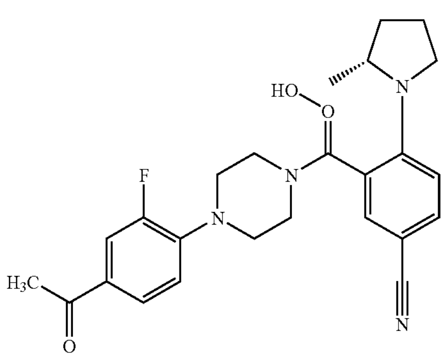 | 450.5 | 3-[4-(4-Acetyl-2-fluoro-phenyl)-piperazine-1-carbonyl]-4-(2-(S)-hydroxymethyl-pyrrolidin-1-yl)-benzonitrile | 3-[4-(4-Acetyl-2-fluoro-phenyl)-piperazine-1-carbonyl]-4-bromo-benzonitrile and 2-(S)-hydroxymethyl-pyrrolidine (commercially available) | 451.2 |

TABLE 1-continued

| No. | Structure | MW | Systematic Name | Starting materials | MW found (MH+) |
|---|---|---|---|---|---|
| 97 | 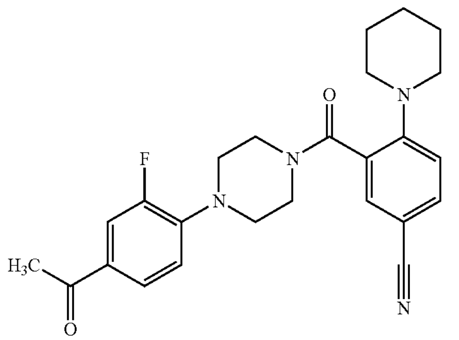 | 434.5 | 3-[4-(4-Acetyl-2-fluoro-phenyl)-piperazine-1-carbonyl]-4-piperidin-1-yl-benzonitrile | 3-[4-(4-Acetyl-2-fluoro-phenyl)-piperazine-1-carbonyl]-4-bromo-benzonitrile and piperidine (commercially available) | 435.2 |
| 98 | 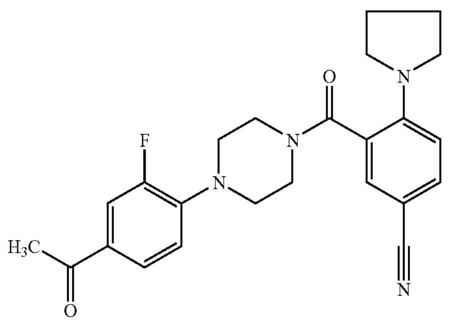 | 420.5 | 3-[4-(4-Acetyl-2-fluoro-phenyl)-piperazine-1-carbonyl]-4-pyrrolidin-1-yl-benzonitrile | 3-[4-(4-Acetyl-2-fluoro-phenyl)-piperazine-1-carbonyl]-4-bromo-benzonitrile and pyrrolididne (commercially available) | 421.1 |
| 99 | 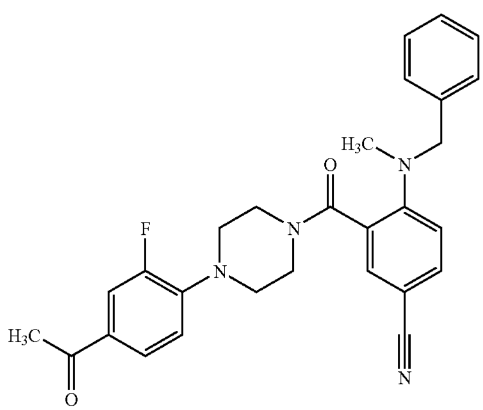 | 470.6 | 3-[4-(4-Acetyl-2-fluoro-phenyl)-piperazine-1-carbonyl]-4-(benzyl-methyl-amino)-benzonitrile | 3-[4-(4-Acetyl-2-fluoro-phenyl)-piperazine-1-carbonyl]-4-bromo-benzonitrile and benzylmethylamine (commercially available) | 471.2 |
| 100 | 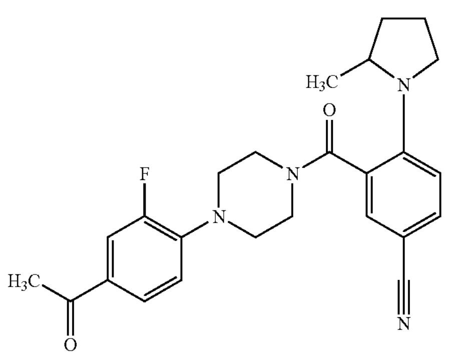 | 434.5 | 3-[4-(4-Acetyl-2-fluoro-phenyl)-piperazine-1-carbonyl]-4-(2-methyl-pyrrolidin-1-yl)-benzonitrile | 3-[4-(4-Acetyl-2-fluoro-phenyl)-piperazine-1-carbonyl]-4-bromo-benzonitrile and 2-methylpyrrolidine (commercially available) | 435.2 |

TABLE 1-continued

| No. | Structure | MW | Systematic Name | Starting materials | MW found (MH+) |
|---|---|---|---|---|---|
| 101 | 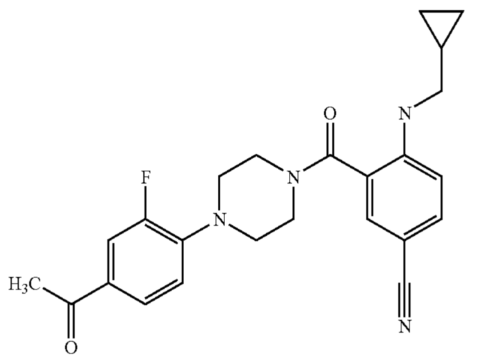 | 420.5 | 3-[4-(4-Acetyl-2-fluoro-phenyl)-piperazine-1-carbonyl]-4-(cyclopropylmethyl-amino)-benzonitrile | 3-[4-(4-Acetyl-2-fluoro-phenyl)-piperazine-1-carbonyl]-4-bromo-benzonitrile and cyclopropylmethylamine (commercially available) | 421.2 |
| 102 | 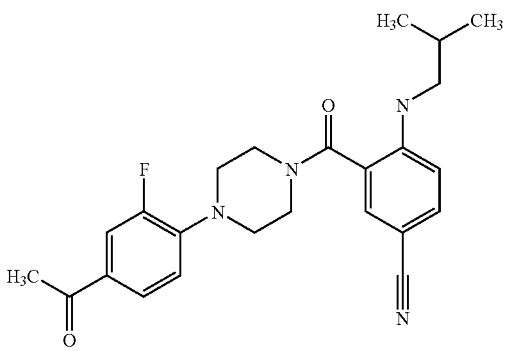 | 422.5 | 3-[4-(4-Acetyl-2-fluoro-phenyl)-piperazine-1-carbonyl]-4-isobutylamino-benzonitrile | 3-[4-(4-Acetyl-2-fluoro-phenyl)-piperazine-1-carbonyl]-4-bromo-benzonitrile and isobutylamine (commercially available) | 423.2 |
| 103 | 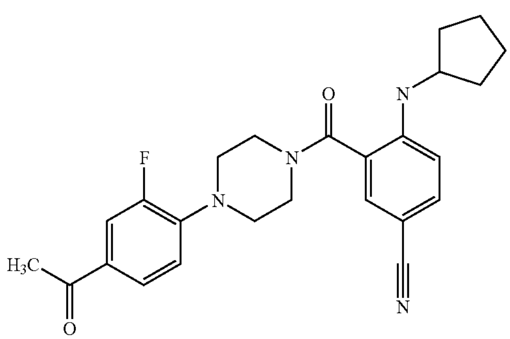 | 434.5 | 3-[4-(4-Acetyl-2-fluoro-phenyl)-piperazine-1-carbonyl]-4-cyclopentylamino-benzonitrile | 3-[4-(4-Acetyl-2-fluoro-phenyl)-piperazine-1-carbonyl]-4-bromo-benzonitrile and cyclopentylamine (commercially available) | 435.2 |
| 104 | 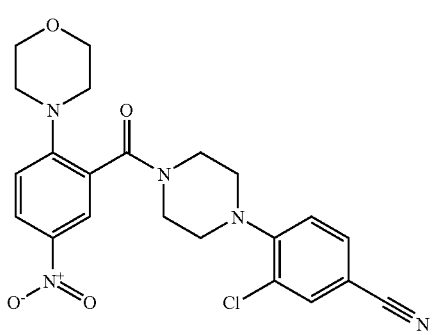 | 455.9 | 3-Chloro-4-[4-(2-morpholin-4-yl-5-nitro-benzoyl)-piperazin-1-yl]-benzonitrile | 3-Chloro-4-piperazin-1-yl-benzonitrile (WO9625414) and 2-Morpholin-4-yl-5-nitro-benzoyl chloride | 456.2 |

TABLE 1-continued

| No. | Structure | MW | Systematic Name | Starting materials | MW found (MH+) |
|---|---|---|---|---|---|
| 105 | 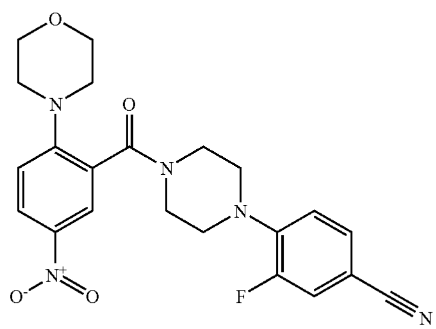 | 439.5 | 3-Fluoro-4-[4-(2-morpholin-4-yl-5-nitro-benzoyl)-piperazin-1-yl]-benzonitrile | 3-Fluoro-4-piperazin-1-yl-benzonitrile (commercially available) and 2-Morpholin-4-yl-5-nitro-benzoyl chloride | 440.3 |
| 106 | 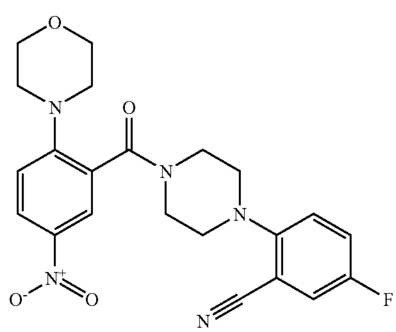 | 439.5 | 5-Fluoro-4-[4-(2-morpholin-4-yl-5-nitro-benzoyl)-piperazin-1-yl]-benzonitrile | 5-Fluoro-2-piperazin-1-yl-benzonitrile (commercially available) and 2-Morpholin-4-yl-5-nitro-benzoyl chloride | 440.3 |
| 107 | 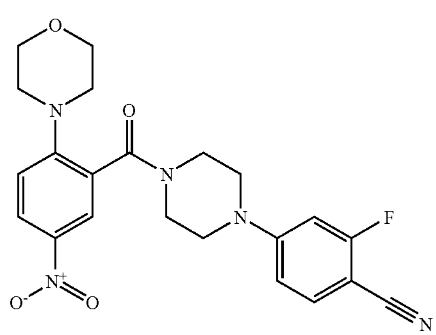 | 439.5 | 2-Fluoro-4-[4-(2-morpholin-4-yl-5-nitro-benzoyl)-piperazin-1-yl]-benzonitrile | 2-Fluoro-4-piperazin-1-yl-benzonitrile (Org. Proc. Res. Dev. 1999, 460) and 2-Morpholin-4-yl-5-nitro-benzoyl chloride | 440.3 |
| 108 | 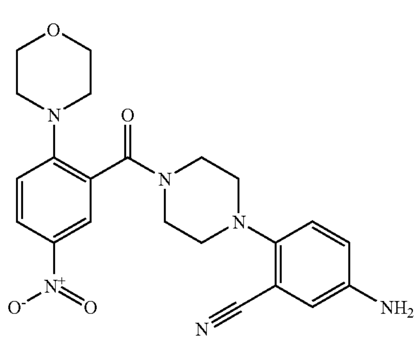 | 436.5 | 5-Amino-4-[4-(2-morpholin-4-yl-5-nitro-benzoyl)-piperazin-1-yl]-benzonitrile | 5-Amino-2-piperazin-1-yl-benzonitrile (commercially available) and 2-Morpholin-4-yl-5-nitro-benzoyl chloride | 437.2 |

TABLE 1-continued

| No. | Structure | MW | Systematic Name | Starting materials | MW found (MH+) |
|---|---|---|---|---|---|
| 109 | 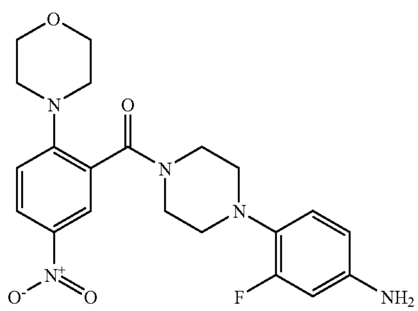 | 429.5 | [4-(4-Amino-2-fluoro-phenyl)-piperazin-1-yl]-(2-morpholin-4-yl-5-nitro-phenyl)-methanone | 3-Fluoro-4-piperazin-1-yl-phenylamine (DE190798440) and 2-Morpholin-4-yl-5-nitro-benzoyl chloride | 430.3 |
| 110 | 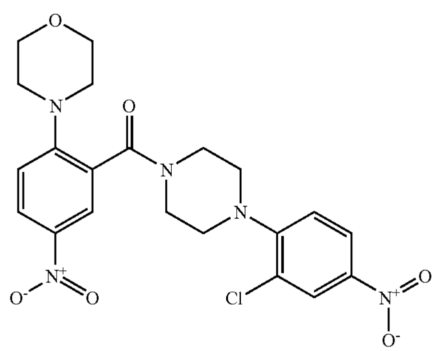 | 475.9 | [4-(2-Chloro-4-nitro-phenyl)-piperazin-1-yl]-(2-morpholin-4-yl-5-nitro-phenyl)-methanone | 1-(2-Chloro-4-nitro-phenyl)-piperazine (commercially available) and 2-Morpholin-4-yl-5-nitro-benzoyl chloride | 476.1 |
| 111 | 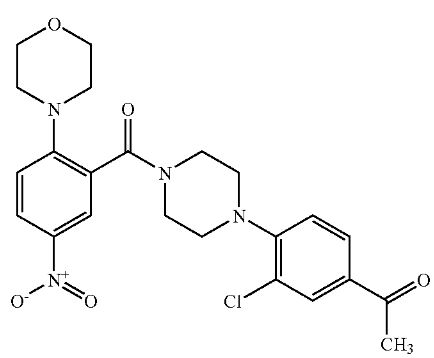 | 472.9 | 1-{3-Chloro-4-[4-(2-morpholin-4-yl-5-nitro-benzoyl)-piperazin-1-yl]-phenyl}-ethanone | 1-(3-Chloro-4-piperazin-1-yl-phenyl)-ethanone and 2-Morpholin-4-yl-5-nitro-benzoyl chloride | 473.1 |
| 112 | 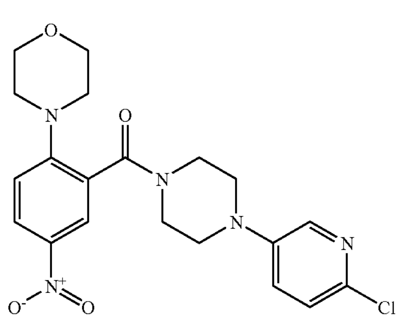 | 431.9 | [4-(6-Chloro-pyridin-3-yl)-piperazin-1-yl]-(2-morpholin-4-yl-5-nitro-phenyl)-methanone | 1-(6-Chloro-pyridin-3-yl)-piperazin-(WO0230405) and 2-Morpholin-4-yl-5-nitro-benzoyl chloride | 432.2 |

TABLE 1-continued

| No. | Structure | MW | Systematic Name | Starting materials | MW found (MH+) |
|---|---|---|---|---|---|
| 113 | 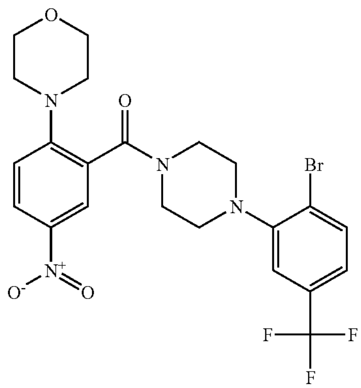 | 543.3 | [4-(2-Bromo-5-trifluoromethyl-phenyl)-piperazin-1-yl]-(2-morpholin-4-yl-5-nitro-phenyl)-methanone | 1-(2-Bromo-5-trifluoromethyl-phenyl)-piperazine and 2-Morpholin-4-yl-5-nitro-benzoyl chloride | 545.0 |
| 114 | 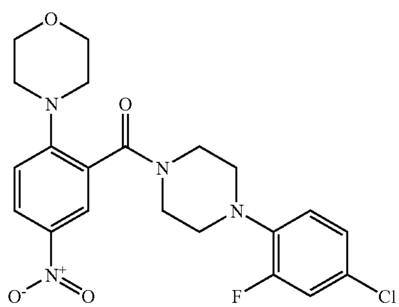 | 448.9 | [4-(4-Chloro-2-fluoro-phenyl)-piperazin-1-yl]-(2-morpholin-4-yl-5-nitro-phenyl)-methanone | 1-Chloro-2-fluoro-phenyl)-piperazine (commercially available) and 2-Morpholin-4-yl-5-nitro-benzoyl chloride | 449.2 |
| 115 | 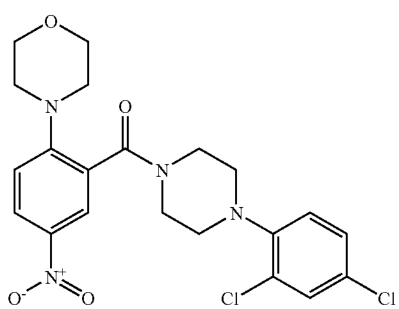 | 465.3 | [4-(2,4-Dichloro-phenyl)-piperazin-1-yl]-(2-morpholin-4-yl-5-nitro-phenyl)-methanone | 1-(2,4-Dichloro-phenyl)-piperazine (commercially available and 2-Morpholin-4-yl-5-nitro-benzoyl chloride | 465.1 |
| 116 | 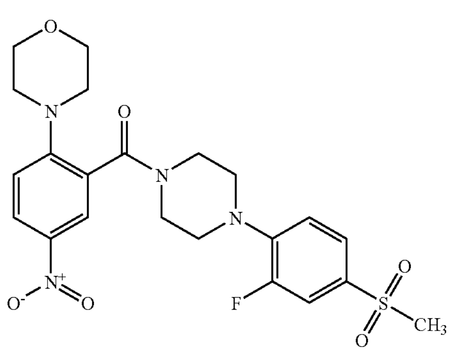 | 492.5 | [4-(2-Fluoro-4-methanesulfonyl-phenyl)-piperazin-1-yl]-(2-morpholin-4-yl-5-nitro-phenyl)-methanone | 1-(2-Fluoro-4-methanesulfonyl-phenyl)-piperazine and 2-Morpholin-4-yl-5-nitro-benzoyl chloride | 492.5 |

TABLE 1-continued

| No. | Structure | MW | Systematic Name | Starting materials | MW found (MH+) |
|---|---|---|---|---|---|
| 117 | 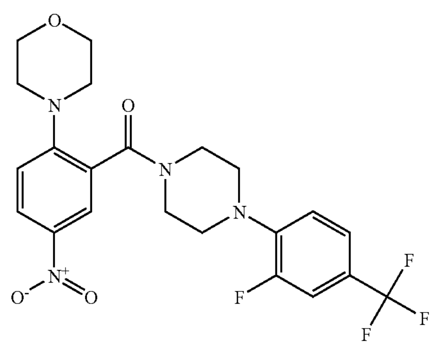 | 482.4 | [4-(2-Fluoro-4-trifluoromethyl-phenyl)-piperazin-1-yl]-(2-morpholin-4-yl-5-nitro-phenyl)-methanone | 1-(2-Fluoro-4-trifluoromethyl-phenyl)-piperazine and 2-Morpholin-4-yl-5-nitro-benzoyl chloride | 482.4 |
| 118 | 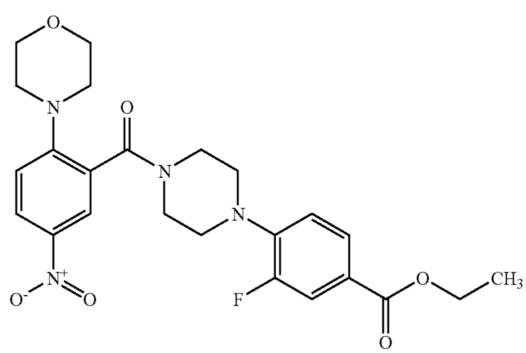 | 486.5 | 3-Fluoro-4-[4-(2-morpholin-4-yl-5-nitro-benzoyl)-piperazin-1-yl]-benzoic acid ethyl ester | 3-Fluoro-4-piperazin-1-yl-benzoic acid ethyl ester and 2-Morpholin-4-yl-5-nitro-benzoyl chloride | 487.3 |
| 119 | 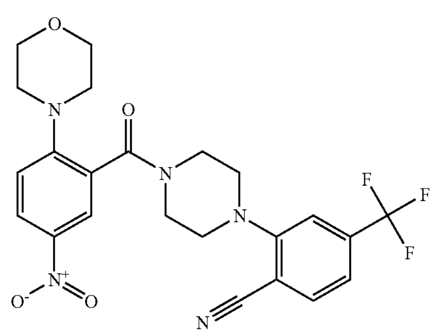 | 489.5 | 2-[4-(2-Morpholin-4-yl-5-nitro-benzoyl)-piperazin-1-yl]-4-trifluoromethyl-benzonitrile | 2-Piperazin-1-yl-4-trifluoromethyl-benzonitrile (WO0259108) and 2-Morpholin-4-yl-5-nitro-benzoyl chloride | 490.3 |
| 120 | 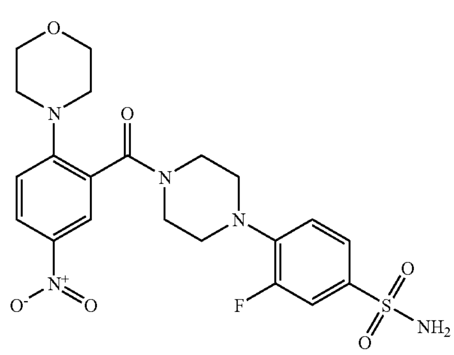 | 493.5 | 3-Fluoro-4-[4-(2-morpholin-4-yl-5-nitro-benzoyl)-piperazin-1-yl]-benzenesulfonamide | 3-Fluoro-4-piperazin-1-yl-benzenesulfonamide and 2-Morpholin-4-yl-5-nitro-benzoyl chloride | 494.4 |

TABLE 1-continued

| No. | Structure | MW | Systematic Name | Starting materials | MW found (MH+) |
|---|---|---|---|---|---|
| 121 | 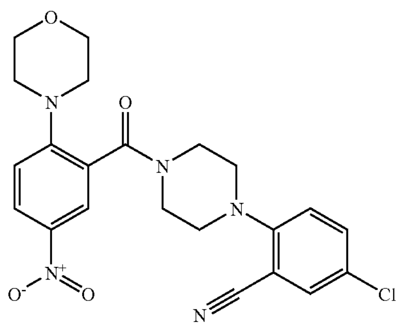 | 455.9 | 5-Chloro-2-[4-(2-morpholin-4-yl-5-nitro-benzoyl)-piperazin-1-yl]-benzonitrile | 5-Chloro-2-piperazin-1-yl-benzonitrile (WO9625414) and 2-Morpholin-4-yl-5-nitro-benzoyl chloride | 455.8 |
| 122 | 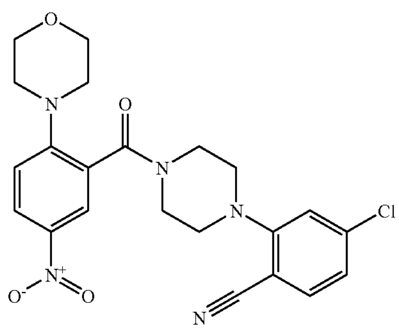 | 455.9 | 4-Chloro-2-[4-(2-morpholin-4-yl-5-nitro-benzoyl)-piperazin-1-yl]-benzonitrile | 4-Chloro-2-piperazin-1-yl-benzonitrile (WO0105765) and 2-Morpholin-4-yl-5-nitro-benzoyl chloride | 455.8 |
| 123 | 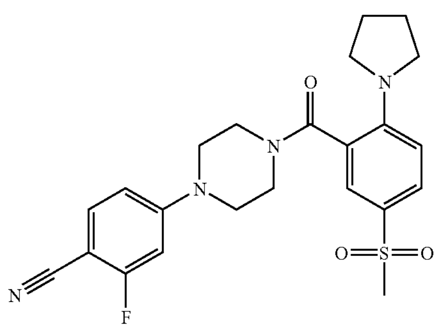 | 456.5 | 2-Fluoro-4-[4-(5-methanesulfonyl-2-pyrrolidin-1-yl-benzoyl)-piperazin-1-yl]-benzonitrile | 2-Fluoro-4-piperazin-1-yl-benzonitrile (Org. Proc. Res. Dev. 1999, 460) and 5-Methanesulfonyl-2-pyrrolidin-1-yl-benzoic acid | 457.2 |
| 124 | 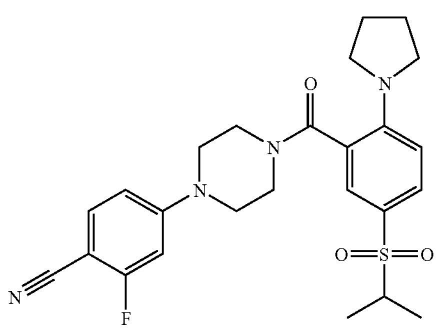 | 484.6 | 2-Fluoro-4-{4-[5-(propane-2-sulfonyl)-2-pyrrolidin-1-yl-benzoyl]-piperazin-1-yl}-benzonitrile | 2-Fluoro-4-piperazin-1-yl-benzonitrile (Org. Proc. Res. Dev. 1999, 460) and 5-(Propane-2-sulfonyl)-2-pyrrolidin-1-yl-benzoic acid | 485.3 |

TABLE 1-continued

| No. | Structure | MW | Systematic Name | Starting materials | MW found (MH+) |
|---|---|---|---|---|---|
| 125 | 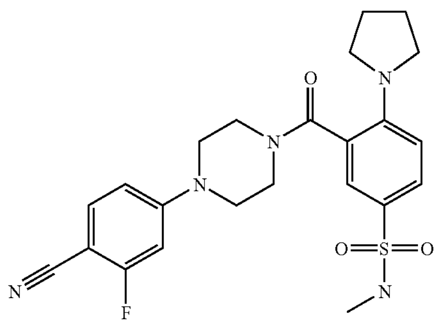 | 471.6 | 3-[4-(4-Cyano-3-fluoro-phenyl)-piperazine-1-carbonyl]-N-methyl-4-pyrrolidin-1-yl-benzenesulfonamide | 2-Fluoro-4-piperazin-1-yl-benzonitrile (Org. Proc. Res. Dev. 1999, 460) and 5-Methylsulfamoyl-2-pyrrolidin-1-yl-benzoic acid | 472.2 |
| 126 | 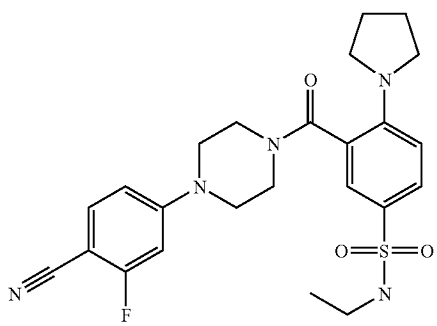 | 485.6 | 3-[4-(4-Cyano-3-fluoro-phenyl)-piperazine-1-carbonyl]-N-ethyl-4-pyrrolidin-1-yl-benzenesulfonamide | 2-Fluoro-4-piperazin-1-yl-benzonitrile (Org. Proc. Res. Dev. 1999, 460) and 5-Ethylsulfamoyl-2-pyrrolidin-1-yl-benzoic acid | 486.3 |
| 127 | 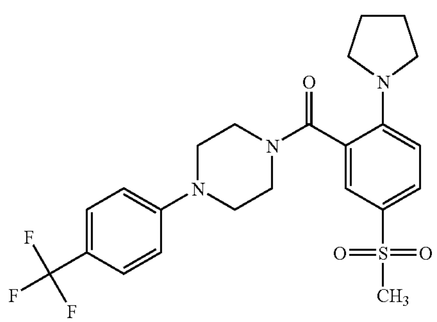 | 481.5 | (5-Methanesulfonyl-2-pyrrolidin-1-yl-phenyl)-[4-(4-trifluoromethyl-phenyl)-piperazin-1-yl]-methanone | 1-(4-Trifluoromethyl-phenyl)-piperazine (commercially available) and 5-Methanesulfonyl-2-pyrrolidin-1-yl-benzoic acid | 482.2 |
| 128 | 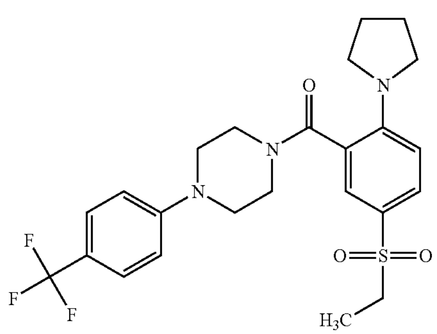 | 495.6 | (5-Ethanesulfonyl-2-pyrrolidin-1-yl-phenyl)-[4-(4-trifluoromethyl-phenyl)-piperazin-1-yl]-methanone | 1-(4-Trifluoromethyl-phenyl)-piperazine (commercially available) and 5-Ethanesulfonyl-2-pyrrolidin-1-yl-benzoic acid | 496.2 |

TABLE 1-continued

| No. | Structure | MW | Systematic Name | Starting materials | MW found (MH+) |
|---|---|---|---|---|---|
| 129 | 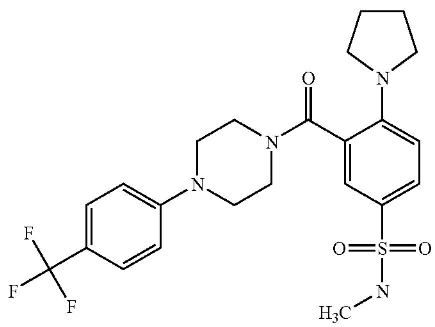 | 496.6 | N-Methyl-4-pyrrolidin-1-yl-3-[4-(4-trifluoromethyl-phenyl)-piperazine-1-carbonyl]-benzenesulfonamide | 1-(4-Trifluoromethyl-phenyl)-piperazine (commercially available) and 5-Methylsulfamoyl-2-pyrrolidin-1-yl-benzoic acid | 497.2 |
| 130 | 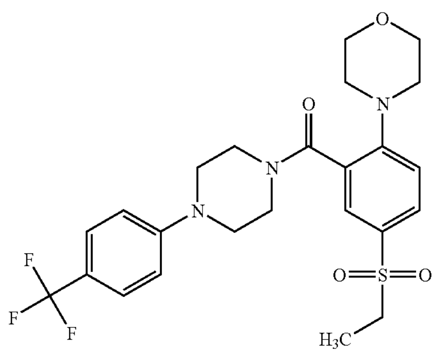 | 511.6 | (5-Ethanesulfonyl-2-morpholin-4-yl-phenyl)-[4-(4-trifluoromethyl-phenyl)-piperazin-1-yl]-methanone | 1-(4-Trifluoromethyl-phenyl)-piperazine (commercially available) and 5-Ethanesulfonyl-2-morpholin-1-yl-benzoic acid | 512.3 |
| 131 | 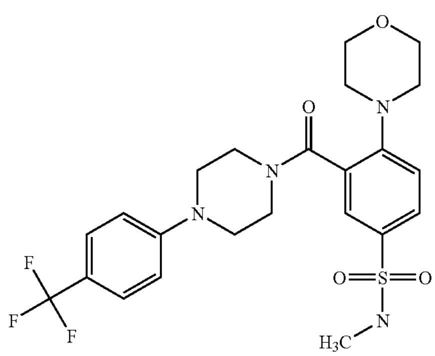 | 512.6 | N-Methyl-4-morpholin-4-yl-3-[4-(4-trifluoromethyl-phenyl)-piperazine-1-carbonyl]-benzenesulfonamide | 1-(4-Trifluoromethyl-phenyl)-piperazine (commercially available) and 5-Methylsulfamoyl-2-morpholin-1-yl-benzoic acid | 513.3 |
| 132 | 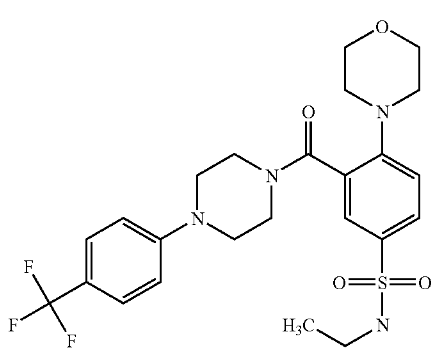 | 526.6 | N-Ethyl-4-morpholin-4-yl-3-[4-(4-trifluoromethyl-phenyl)-piperazine-1-carbonyl]-benzenesulfonamide | 1-(4-Trifluoromethyl-phenyl)-piperazine (commercially available) and 5-Ethylsulfamoyl-2-morpholin-1-yl-benzoic acid | 527.2 |

TABLE 1-continued

| No. | Structure | MW | Systematic Name | Starting materials | MW found (MH+) |
|---|---|---|---|---|---|
| 133 | 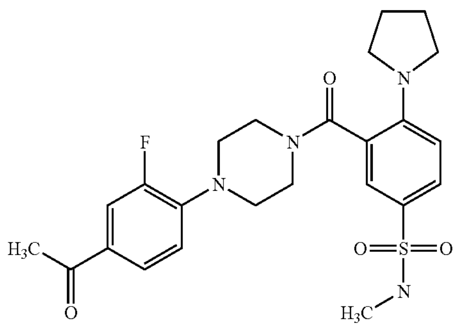 | 488.6 | 3-[4-(4-Acetyl-2-fluoro-phenyl)-piperazine-1-carbonyl]-N-methyl-4-pyrrolidin-1-yl-benzenesulfonamide | 1-(3-Fluoro-4-piperazin-1-yl-phenyl)-ethanone (comercially available) and 5-Methylsulfamoyl-2-pyrrolidin-1-yl-benzoic acid | 489.2 |
| 134 | 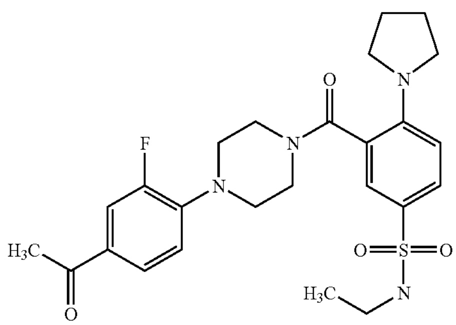 | 502.6 | 3-[4-(4-Acetyl-2-fluoro-phenyl)-piperazine-1-carbonyl]-N-ethyl-4-pyrrolidin-1-yl-benzenesulfonamide | 1-(3-Fluoro-4-piperazin-1-yl-phenyl)-ethanone (comercially available) and 5-Ethylsulfamoyl-2-pyrrolidin-1-yl-benzoic acid | 503.1 |
| 135 | 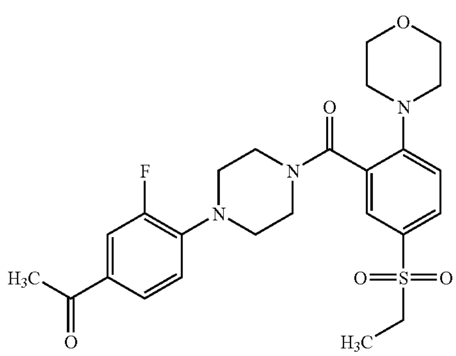 | 503.6 | 1-{4-[4-(5-Ethanesulfonyl-2-morpholin-4-yl-benzoyl)-piperazin-1-yl]-3-fluoro-phenyl}-ethanone | 1-(3-Fluoro-4-piperazin-1-yl-phenyl)-ethanone (comercially available) and 5-Ethanesulfonyl-2-morpholin-4-yl-benzoic acid | 504.2 |
| 136 | 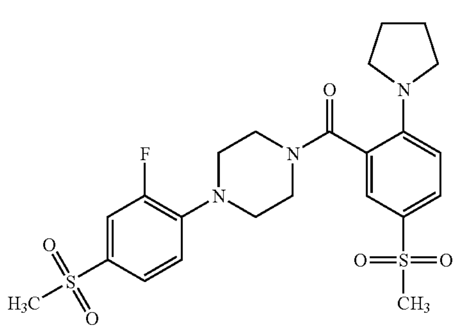 | 509.6 | [4-(2-Fluoro-4-methanesulfonyl-phenyl)-piperazin-1-yl]-(5-methanesulfonyl-2-pyrrolidin-1-yl-phenyl)-methanone | 1-(2-Fluoro-4-methanesulfonyl-phenyl)-piperazine and 5-Methanesulfonyl-2-pyrrolidin-1-yl-benzoic acid | 510.2 |

TABLE 1-continued

| No. | Structure | MW | Systematic Name | Starting materials | MW found (MH+) |
|---|---|---|---|---|---|
| 137 | 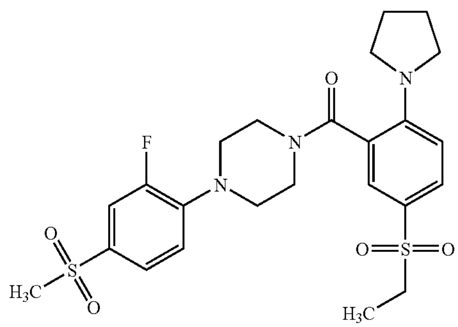 | 523.7 | (5-Ethanesulfonyl-2-pyrrolidin-1-yl-phenyl)-[4-(2-Fluoro-4-methanesulfonyl-phenyl)-piperazin-1-yl]-methanone | 1-(2-Fluoro-4-methanesulfonyl-phenyl)-piperazine and 5-Ethanesulfonyl-2-pyrrolidin-1-yl-benzoic acid | 524.3 |
| 138 | 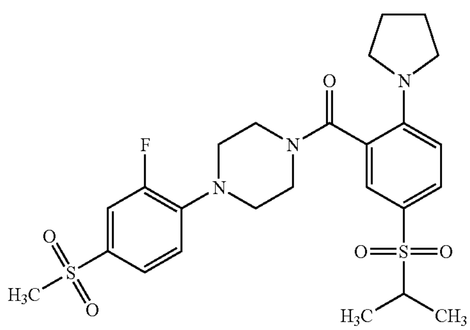 | 537.7 | [4-(2-Fluoro-4-methanesulfonyl-phenyl)-piperazin-1-yl]-[5-(propane-2-sulfonyl)-2-pyrrolidin-1-yl-phenyl]-methanone | 1-(2-Fluoro-4-methanesulfonyl-phenyl)-piperazine and 5-(Propane-2-sulfonyl)-2-pyrrolidin-1-yl-benzoic acid | 538.3 |
| 139 | 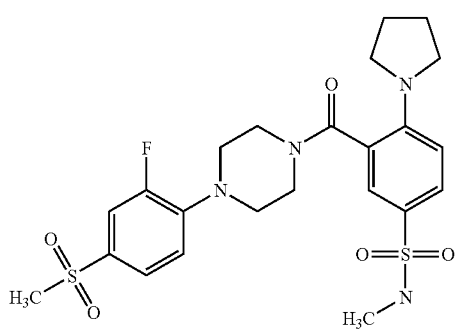 | 524.6 | 3-[4-(2-Fluoro-4-methanesulfonyl-phenyl)-piperazine-1-carbonyl]-N-methyl-4-pyrrolidin-1-yl-benzenesulfonamide | 1-(2-Fluoro-4-methanesulfonyl-phenyl)-piperazine and 5-Methylsulfamoyl-2-pyrrolidin-1-yl-benzoic acid | 525.2 |
| 140 | 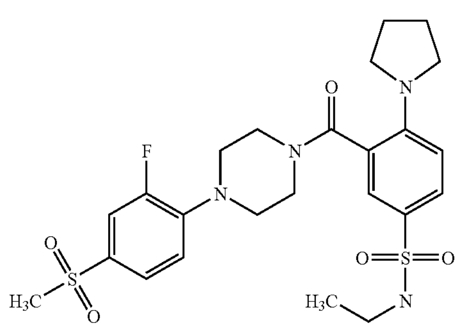 | 538.7 | N-Ethyl-3-[4-(2-fluoro-4-methanesulfonyl-phenyl)-piperazine-1-carbonyl]-4-pyrrolidin-1-yl-benzenesulfonamide | 1-(2-Fluoro-4-methanesulfonyl-phenyl)-piperazine and 5-Ethylsulfamoyl-2-pyrrolidin-1-yl-benzoic acid | 539.3 |

TABLE 1-continued

| No. | Structure | MW | Systematic Name | Starting materials | MW found (MH+) |
|---|---|---|---|---|---|
| 141 | 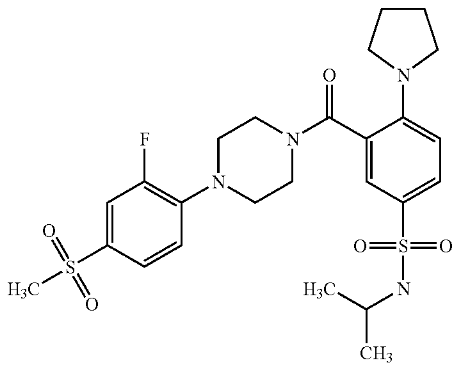 | 552.7 | 3-[4-(2-Fluoro-4-methanesulfonyl-phenyl)-piperazine-1-carbonyl]-N-isopropyl-4-pyrrolidin-1-yl-benzenesulfonamide | 1-(2-Fluoro-4-methanesulfonyl-phenyl)-piperazine and 5-Isopropylsulfamoyl-2-pyrrolidin-1-yl-benzoic acid | 553.3 |
| 142 | 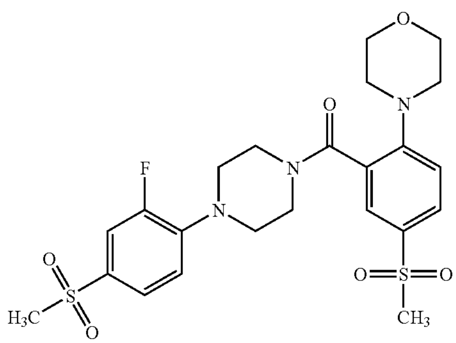 | 525.6 | [4-(2-Fluoro-4-methanesulfonyl-phenyl)-piperazin-1-yl]-(5-methanesulfonyl-2-morpholin-4-yl-phenyl)-methanone | 1-(2-Fluoro-4-methanesulfonyl-phenyl)-piperazine and 5-Methanesulfonyl-2-morpholin-4-yl-benzoic acid | 526.2 |
| 143 | 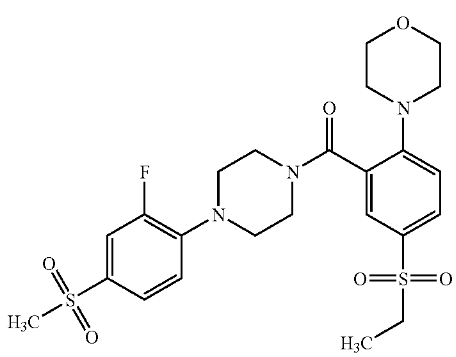 | 539.6 | (5-Ethanesulfonyl-2-morpholin-4-yl-phenyl)-[4-(2-fluoro-4-methanesulfonyl-phenyl)-piperazin-1-yl]-methanone | 1-(2-Fluoro-4-methanesulfonyl-phenyl)-piperazine and 5-Ethanesulfonyl-2-morpholin-4-yl-benzoic acid | 540.3 |
| 144 | 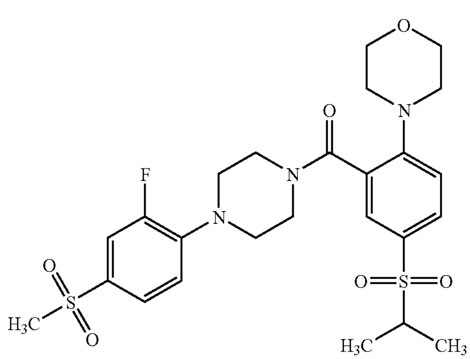 | 553.7 | [4-(2-Fluoro-4-methanesulfonyl-phenyl)-piperazin-1-yl]-[2-morpholin-4-yl-5-(propane-2-sulfonyl)-phenyl]-methanone | 1-(2-Fluoro-4-methanesulfonyl-phenyl)-piperazine and 2-Morpholin-4-yl-5-(propane-2-sulfonyl)-benzoic acid | 554.2 |

TABLE 1-continued

| No. | Structure | MW | Systematic Name | Starting materials | MW found (MH+) |
|---|---|---|---|---|---|
| 145 | 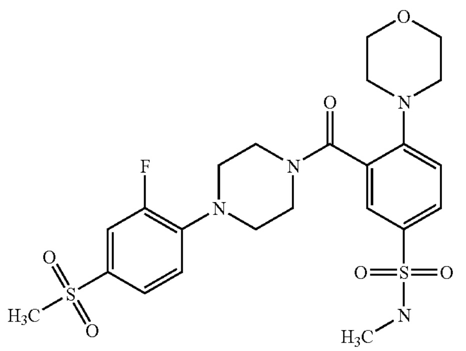 | 540.6 | 3-[4-(2-Fluoro-4-methanesulfonyl-phenyl)-piperazine-1-carbonyl]-N-methyl-4-morpholin-4-yl-benzenesulfonamide | 1-(2-Fluoro-4-methanesulfonyl-phenyl)-piperazine and 5-Methylsulfamoyl-2-morpholin-4-yl-benzoic acid | 541.2 |
| 146 | 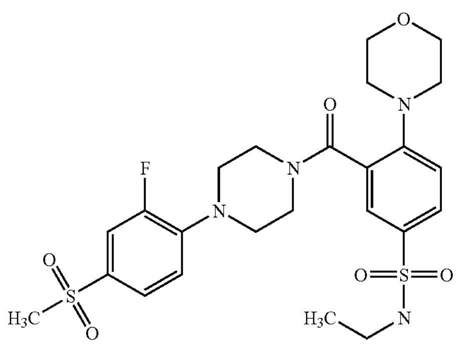 | 554.7 | N-Ethyl-3-[4-(2-fluoro-4-methanesulfonyl-phenyl)-piperazine-1-carbonyl]-4-morpholin-4-yl-benzenesulfonamide | 1-(2-Fluoro-4-methanesulfonyl-phenyl)-piperazine and 5-Ethylsulfamoyl-2-morpholin-4-yl-benzoic acid | 555.2 |
| 147 | 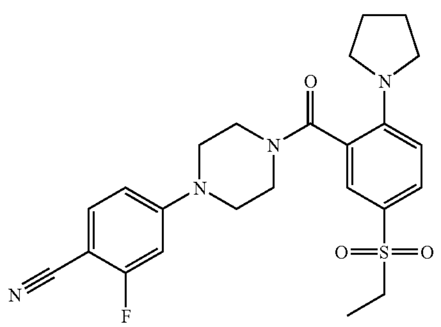 | 470.6 | 4-[4-(5-Ethanesulfonyl-2-pyrrolidin-1-yl-benzoyl)-piperazin-1-yl]-2-fluoro-benzonitrile | 2-Fluoro-4-piperazin-1-yl-benzonitrile (Org. Proc. Res. Dev. 1999, 460) and 5-Ethanesulfonyl-2-pyrrolidin-1-yl-benzoic acid | 471.2 |
| 148 | 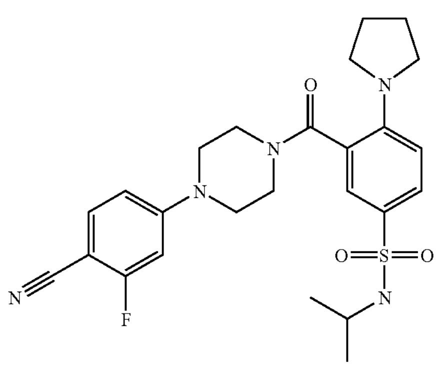 | 499.6 | 3-[4-(4-Cyano-3-fluoro-phenyl)-piperazine-1-carbonyl]-N-isopropyl-4-pyrrolidin-1-yl-benzenesulfonamide | 2-Fluoro-4-piperazin-1-yl-benzonitrile (Org. Proc. Res. Dev. 1999, 460) and Isopropylsulfamoyl-2-pyrrolidin-1-yl-benzoic acid | 500.2 |

TABLE 1-continued

| No. | Structure | MW | Systematic Name | Starting materials | MW found (MH+) |
|---|---|---|---|---|---|
| 149 | 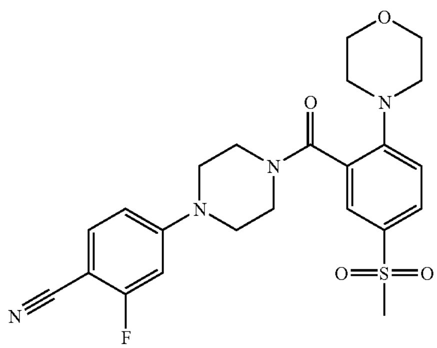 | 472.5 | 2-Fluoro-4-[4-(5-methanesulfonyl-2-morpholin-4-yl-benzoyl)-piperazin-1-yl]-benzonitrile | 2-Fluoro-4-piperazin-1-yl-benzonitrile (Org. Proc. Res. Dev. 1999, 460) and 5-Methanesulfonyl-2-morpholin-4-yl-benzoic acid | 473.1 |
| 150 | 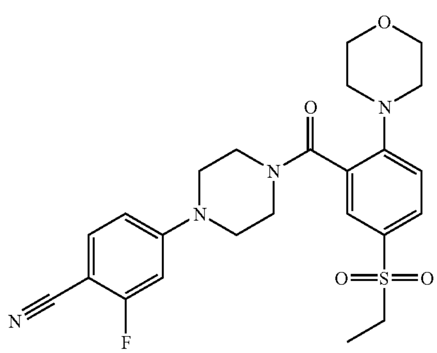 | 486.6 | 4-[4-(5-Ethanesulfonyl-2-morpholin-4-yl-benzoyl)-piperazin-1-yl]-2-fluoro-benzonitrile | 2-Fluoro-4-piperazin-1-yl-benzonitrile (Org. Proc. Res. Dev. 1999, 460) and 5-Ethanesulfonyl-2-morpholin-4-yl-benzoic acid | 487.3 |
| 151 | 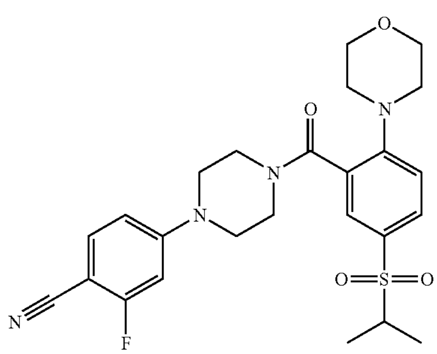 | 500.6 | 2-Fluoro-4-{4-[2-morpholin-4-yl-5-(propane-2-sulfonyl)-benzoyl]-piperazin-1-yl}-benzonitrile | 2-Fluoro-4-piperazin-1-yl-benzonitrile (Org. Proc. Res. Dev. 1999, 460) and 2-Morpholin-4-yl-5-(propane-2-sulfonyl)-benzoic acid | 501.2 |
| 152 | 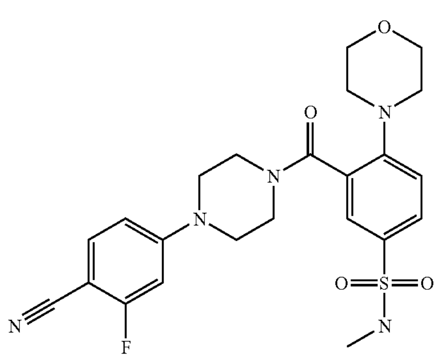 | 487.6 | 3-[4-(4-Cyano-3-fluoro-phenyl)-piperazine-1-carbonyl]-N-methyl-4-morpholin-4-yl-benzenesulfonamide | 2-Fluoro-4-piperazin-1-yl-benzonitrile (Org. Proc. Res. Dev. 1999, 460) and 5-Methylsulfamoyl-2-morpholin-4-yl-benzoic acid | 488.2 |

TABLE 1-continued

| No. | Structure | MW | Systematic Name | Starting materials | MW found (MH+) |
|---|---|---|---|---|---|
| 153 | 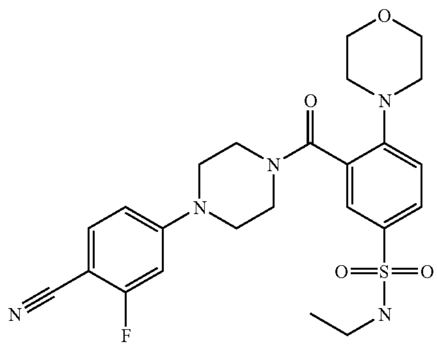 | 501.6 | 3-[4-(4-Cyano-3-fluoro-phenyl)-piperazine-1-carbonyl]-N-ethyl-4-morpholin-4-yl-benzenesulfonamide | 2-Fluoro-4-piperazin-1-yl-benzonitrile (Org. Proc. Res. Dev. 1999, 460) and 5-Ethylsufamoyl-2-morpholin-4-yl-benzoic acid | 502.2 |
| 154 | 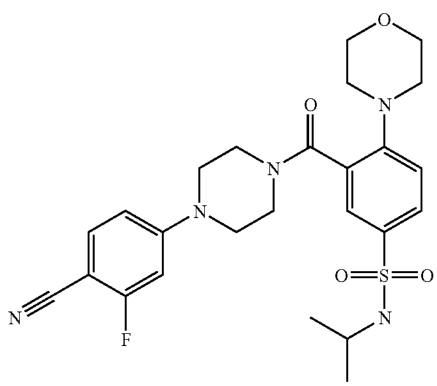 | 515.6 | 3-[4-(4-Cyano-3-fluoro-phenyl)-piperazine-1-carbonyl]-N-isopropyl-4-morpholin-4-yl-benzenesulfonamide | 2-Fluoro-4-piperazin-1-yl-benzonitrile (Org. Proc. Res. Dev. 1999, 460) and Isopropylsufamoyl-2-morpholin-1-yl-benzoic acid | 516.2 |
| 155 | 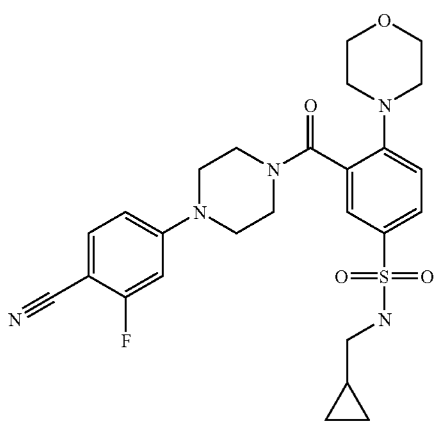 | 527.6 | 3-[4-(4-Cyano-3-fluoro-phenyl)-piperazine-1-carbonyl]-N-cyclopropylmethyl-4-morpholin-4-yl-benzenesulfonamide | 2-Fluoro-4-piperazin-1-yl-benzonitrile (Org. Proc. Res. Dev. 1999, 460) and 5-(Cyclopropylmethyl-sufamoyl)-2-morpholin-4-yl-benzoic acid | 528.2 |
| 156 | 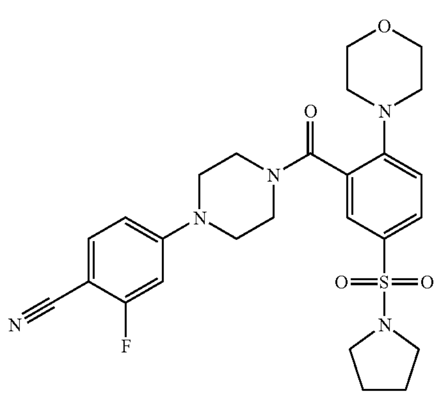 | 527.6 | 2-Fluoro-4-{4-[2-morpholin-4-yl-5-(pyrrolidine-1-sulfonyl)-benzoyl]-piperazin-1-yl}-benzonitrile | 2-Fluoro-4-piperazin-1-yl-benzonitrile (Org. Proc. Res. Dev. 1999, 460) and 2-Morpholin-4-yl-5-(pyrrolidine-1-sulfonyl)-benzoic acid | 528.2 |

TABLE 1-continued

| No. | Structure | MW | Systematic Name | Starting materials | MW found (MH+) |
|---|---|---|---|---|---|
| 157 | 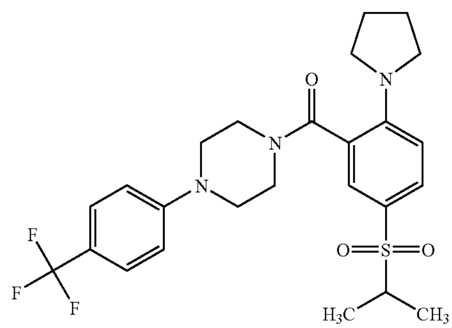 | 509.6 | [5-(Propane-2-sulfonyl)-2-pyrrolidin-1-yl-phenyl]-[4-(4-trifluoromethyl-phenyl)-piperazin-1-yl]-methanone | 1-(4-Trifluoromethyl-phenyl)-piperazine (commercially available) and 5-(Propane-2-sulfonyl)-2-pyrrolidin-1-yl-benzoic acid | 510.2 |
| 158 | 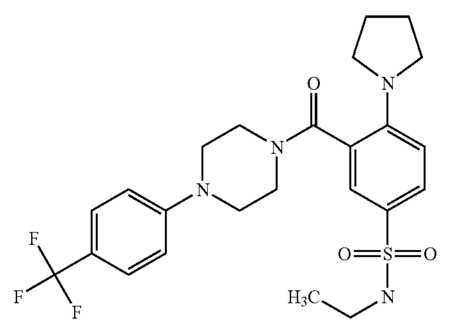 | 510.6 | N-Ethyl-4-pyrrolidin-1-yl-3-[4-(4-trifluoromethyl-phenyl)-piperazine-1-carbonyl]-benzenesulfonamide | 1-(4-Trifluoromethyl-phenyl)-piperazine (commercially available) and 5-Ethylsulfamoyl-2-pyrrolidin-1-yl-benzoic acid | 511.3 |
| 159 | 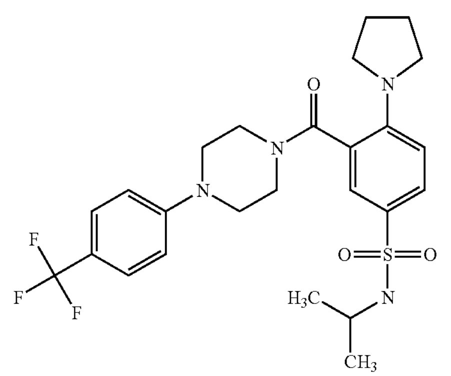 | 524.6 | N-Isopropyl-4-pyrrolidin-1-yl-3-[4-(4-trifluoromethyl-phenyl)-piperazine-1-carbonyl]-benzenesulfonamide | 1-(4-Trifluoromethyl-phenyl)-piperazine (commercially available) and Isopropylsulfamoyl-2-pyrrolidin-1-yl-benzoic acid | 525.3 |
| 160 | 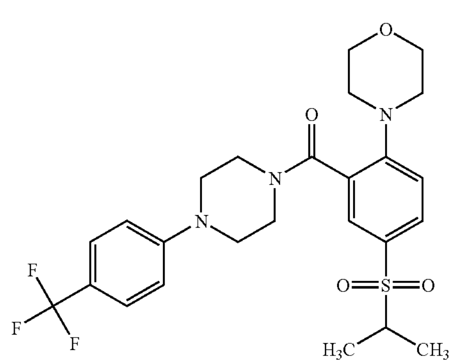 | 525.6 | [2-Morpholin-4-yl-5-(propane-2-sulfonyl)-phenyl]-[4-(4-trifluoromethyl-phenyl)-piperazin-1-yl]-methanone | 1-(4-Trifluoromethyl-phenyl)-piperazine (commercially available) and 2-Morpholin-4-yl-5-(propane-2-sulfonyl)-benzoic acid | 526.2 |

TABLE 1-continued

| No. | Structure | MW | Systematic Name | Starting materials | MW found (MH+) |
|---|---|---|---|---|---|
| 161 | 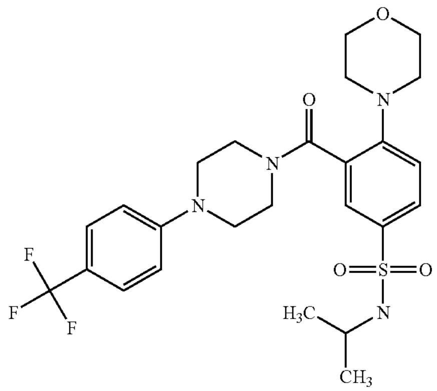 | 540.6 | N-Isopropyl-4-morpholin-4-yl-3-[4-(4-trifluoromethyl-phenyl)-piperazine-1-carbonyl]-benzenesulfonamide | 1-(4-Trifluoromethyl-phenyl)-piperazine (commercially available) and Isopropylsulfamoyl-2-morpholin-1-yl-benzoic acid | 541.3 |
| 162 | 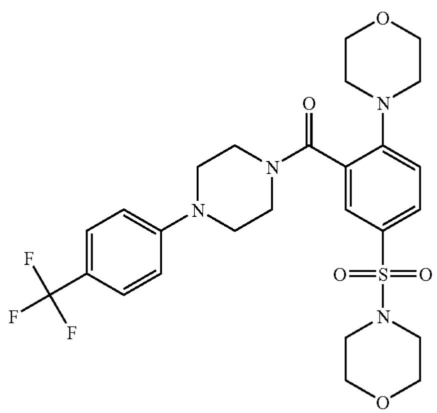 | 568.6 | [5-Morpholine-4-sulfonyl)-2-morpholin-4-yl-phenyl]-[4-(4-trifluoromethyl-phenyl)-piperazin-1-yl]-methanone | 1-(4-Trifluoromethyl-phenyl)-piperazine (commercially available) and 5-(morpholine-4-sulfonyl)-2-morpholin-4-yl-benzoic acid | 569.3 |
| 163 | 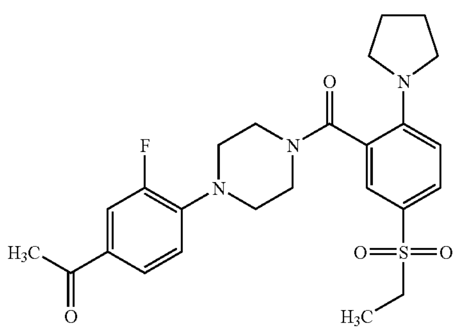 | 487.6 | 1-{4-[4-(5-Ethanesulfonyl-2-pyrrolidin-1-yl-benzoyl)-piperazin-1-yl]-3-fluoro-phenyl}-ethanone | 1-(3-Fluoro-4-piperazin-1-yl-phenyl)-ethanone (commercially available) and 5-Ethylsulfamoyl-2-pyrrolidin-1-yl-benzoic acid | 488.2 |
| 164 | 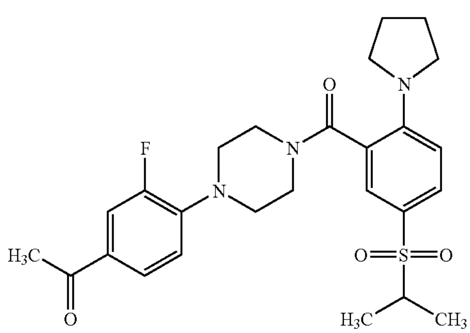 | 501.6 | 1-(3-Fluoro-4-{4-[5-(propane-2-sulfonyl)-2-pyrrolidin-1-yl-benzoyl]-piperazin-1-yl}-phenyl)-ethanone | 1-(3-Fluoro-4-piperazin-1-yl-phenyl)-ethanone (comercially available) and 5-(Propane-2-sulfonyl)-2-pyrrolidin-1-yl-benzoic acid | 502.2 |

TABLE 1-continued

| No. | Structure | MW | Systematic Name | Starting materials | MW found (MH+) |
|---|---|---|---|---|---|
| 165 | 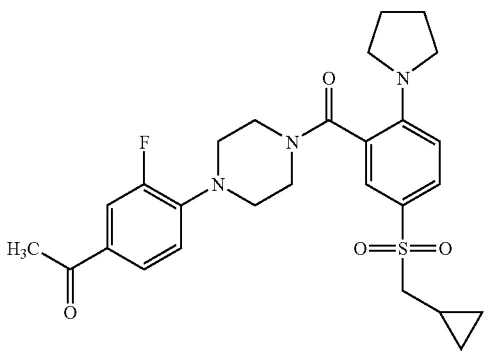 | 513.6 | 1-{4-[4-(5-Cyclopropylmethanesulfonyl-2-pyrrolidin-1-yl-benzoyl)-piperazin-1-yl]-3-fluoro-phenyl}-ethanone | 1-(3-Fluoro-4-piperazin-1-yl-phenyl)-ethanone (comercially available) and 5-Cyclopropylmethanesulfonyl-2-pyrrolidin-4-yl-benzoic acid | 514.3 |
| 166 | 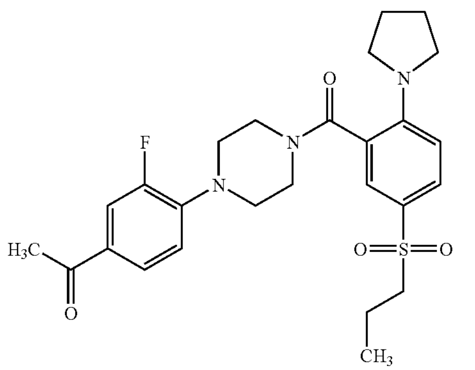 | 501.6 | 1-(3-Fluoro-4-{4-[5-(propane-1-sulfonyl)-2-pyrrolidin-1-yl-benzoyl]-piperazin-1-yl}-phenyl)-ethanone | 1-(3-Fluoro-4-piperazin-1-yl-phenyl)-ethanone (comercially available) and 5-(Propane-1-sulfonyl)-2-pyrrolidin-1-yl-benzoic acid | 502.2 |
| 167 | 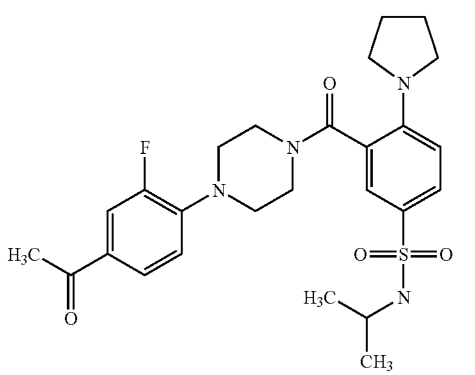 | 516.6 | 3-[4-(4-Acetyl-2-fluoro-phenyl)-piperazine-1-carbonyl]-N-isopropyl-4-pyrrolidin-1-yl-benzenesulfonamide | 1-(3-Fluoro-4-piperazin-1-yl-phenyl)-ethanone (comercially available) and Isopropylsulfamoyl-2-pyrrolidin-1-yl-benzoic acid | 517.3 |
| 168 | 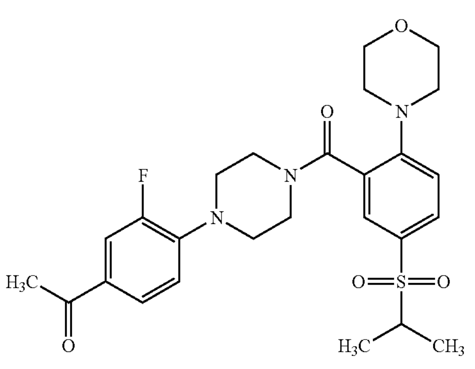 | 517.6 | 1-(3-Fluoro-4-{4-[2-morpholin-4-yl-5-(propane-2-sulfonyl)-benzoyl]-piperazin-1-yl}-phenyl)-ethanone | 1-(3-Fluoro-4-piperazin-1-yl-phenyl)-ethanone (comercially available) and 5-(Propane-2-sulfonyl)-2-morpholin-1-yl-benzoic acid | 518.3 |

TABLE 1-continued

| No. | Structure | MW | Systematic Name | Starting materials | MW found (MH+) |
|---|---|---|---|---|---|
| 169 | 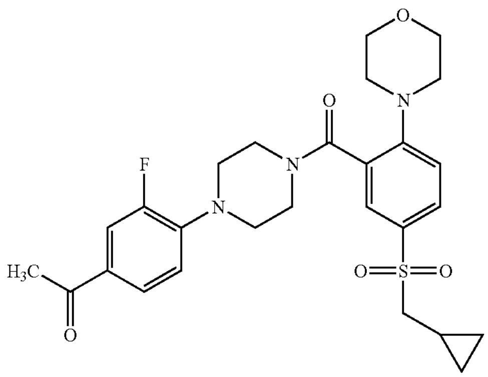 | 529.6 | 1-{4-[4-(5-Cyclopropylmethanesulfonyl-2-morpholin-4-yl-benzoyl)-piperazin-1-yl]-3-fluoro-phenyl}-ethanone | 1-(3-Fluoro-4-piperazin-1-yl-phenyl)-ethanone (comercially available) and 5-Cyclopropylmethanesulfonyl-2-morpholin-4-yl-benzoic acid | 530.1 |
| 170 | 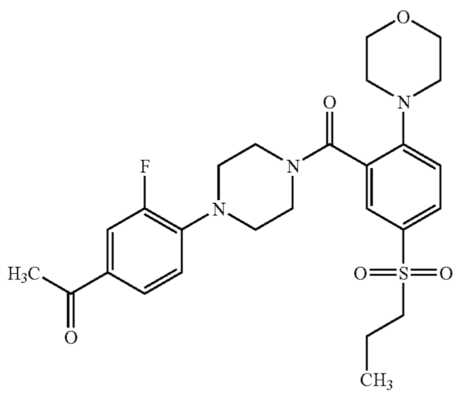 | 517.6 | 1-(3-Fluoro-4-{4-[2-morpholin-4-yl-5-(propane-1-sulfonyl)-benzoyl]-piperazin-1-yl}-phenyl)-ethanone | 1-(3-Fluoro-4-piperazin-1-yl-phenyl)-ethanone (comercially available) and 5-(Propane-1-sulfonyl)-2-morpholin-1-yl-benzoic acid | 518.3 |
| 171 | 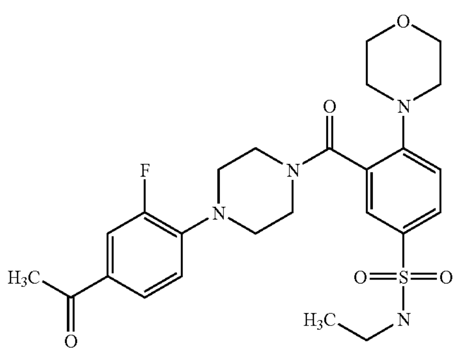 | 518.6 | 3-[4-(4-Acetyl-2-fluoro-phenyl)-piperazine-1-carbonyl]-N-ethyl-4-morpholin-4-yl-benzenesulfonamide | 1-(3-Fluoro-4-piperazin-1-yl-phenyl)-ethanone (comercially available) and 5-Ethylsulfamoyl-2-morpholin-4-yl-benzoic acid | 519.2 |
| 172 | 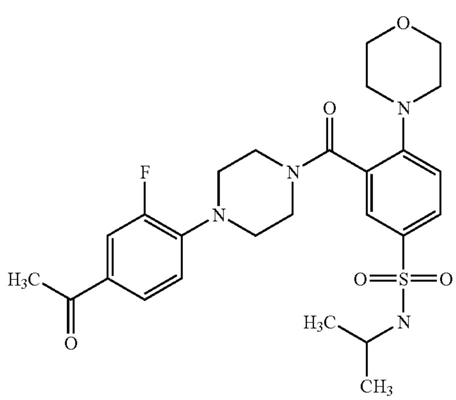 | 532.6 | 3-[4-(4-Acetyl-2-fluoro-phenyl)-piperazine-1-carbonyl]-N-isopropyl-4-morpholin-4-yl-benzenesulfonamide | 1-(3-Fluoro-4-piperazin-1-yl-phenyl)-ethanone (comercially available) and Isopropylsulfamoyl-2-morpholin-1-yl-benzoic acid | 533.2 |

TABLE 1-continued

| No. | Structure | MW | Systematic Name | Starting materials | MW found (MH+) |
|---|---|---|---|---|---|
| 173 | 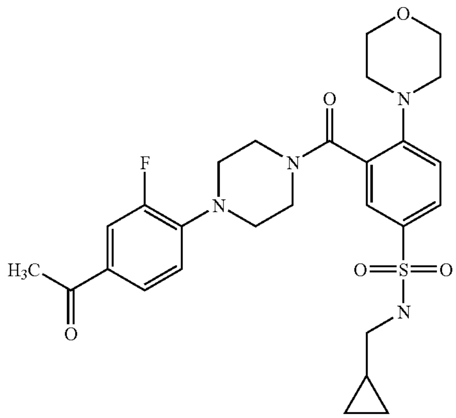 | 544.7 | 3-[4-(4-Acetyl-2-fluoro-phenyl)-piperazine-1-carbonyl]-N-cyclpropylmethyl-4-morpholin-4-yl-benzenesulfonamide | 1-(3-Fluoro-4-piperazin-1-yl-phenyl)-ethanone (comercially available) and 5-(Cyclopropylmethyl-sulfamoyl)-2-morpholin-4-yl-benzoic acid | 545.2 |
| 174 | 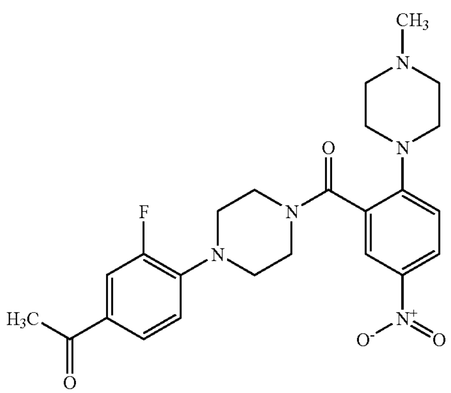 | 469.5 | 1-(4-{4-[2-(4-Methyl-piperazin-1-yl)-5-nitro-benzoyl]-piperazin-1-yl}-phenyl)-ethanone | 1-{3-fluoro-4-[4-(2-fluoro-5-nitro-benzoyl)-piperazin-1-yl]-phenyl}-ethanone and 1-methylpiperazine | 471.2 |
| 175 | 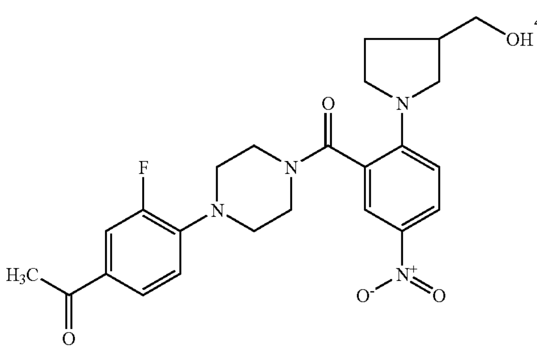 | 470.5 | 1-(3-Fluoro-4-{4-[2-(3-hydroxymethyl-pyrrolidin-1-yl)-5-nitro-benzoyl]-piperazin-1-yl}-phenyl)-ethanone | 1-{3-fluoro-4-[4-(2-fluoro-5-nitro-benzoyl)-piperazin-1-yl]-phenyl}-ethanone and rac-pyrrolidin-3-yl-methanol | 472.1 |
| 176 | 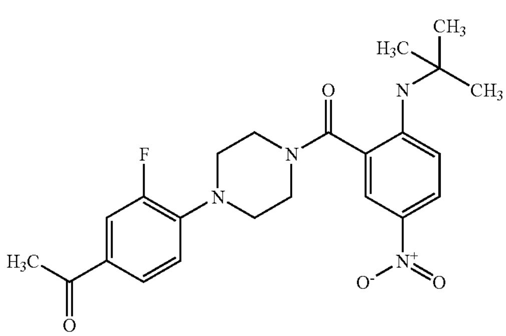 | 442.5 | 1-{3-Fluoro-4-[4-(2-tert.-butylamino-5-nitro-benzoyl)-piperazin-1-yl]-phenyl}-ethanone | 1-{3-fluoro-4-[4-(2-fluoro-5-nitro-benzoyl)-piperazin-1-yl]-phenyl}-ethanone ethanone and tert.-butylamine | 443.1 |

TABLE 1-continued

| No. | Structure | MW | Systematic Name | Starting materials | MW found (MH+) |
|---|---|---|---|---|---|
| 177 | 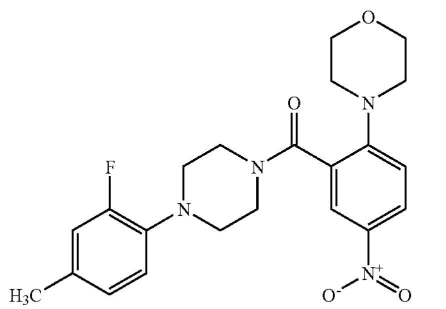 | 428.5 | [4-(2-Fluoro-4-methyl-phenyl)-piperazin-1-yl]-(2-morpholin-4-yl-5-nitro-phenyl)-methanone | 1-(2-Fluoro-4-methyl-phenyl)-piperazine and 2-morpholin-4-yl-5-nitro-benzoyl chloride | 429.2 |
| 178 | 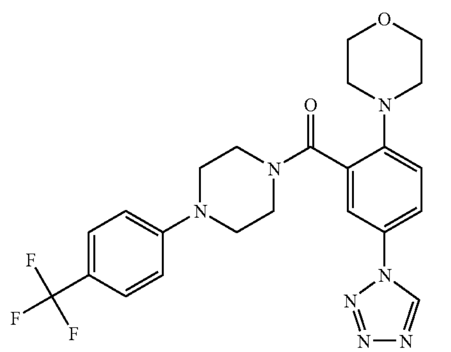 | 487.5 | (2-Morpholin-4-yl-5-tetrazol-1-yl-phenyl)-[4-(4-trifluoromethyl-phenyl)-piperazin-1-yl]-methanone | (5-Amino-2-morpholin-4-yl-phenyl)-[4-(4-trifluoromethyl-phenyl)-piperazin-1-yl]-methanone | 488.2 |
| 179 | 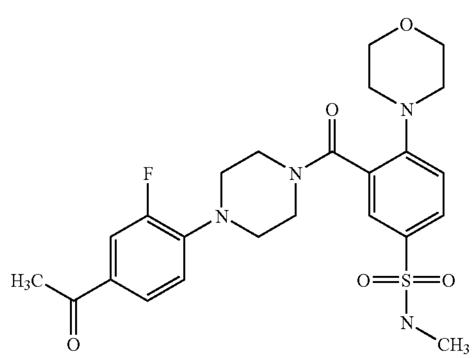 | 504.6 | 3-[4-(4-Acetyl-2-fluoro-phenyl)-piperazine-1-carbonyl]-N-methyl-4-morpholin-4-yl-benzenesulfonamide | 3-[4-(4-Acetyl-2-fluoro-phenyl)-piperazine-1-carbonyl]-4-chloro-N-methyl-benzenesulfonamide and morpholine | 503.1 |
| 180 | 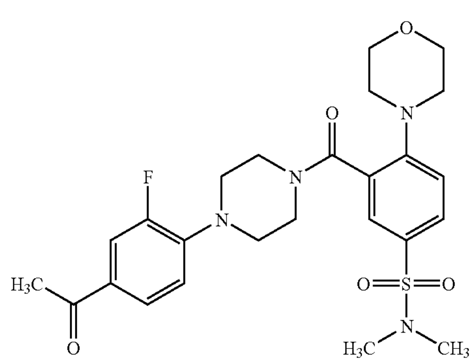 | 518.6 | 3-[4-(4-Acetyl-2-fluoro-phenyl)-piperazine-1-carbonyl]-N,N-dimethyl-4-morpholin-4-yl-benzenesulfonamide | 3-[4-(4-Acetyl-2-fluoro-phenyl)-piperazine-1-carbonyl]-4-chloro-N,N-dimethyl-benzenesulfonamide and morpholine | 519.2 |

TABLE 1-continued

| No. | Structure | MW | Systematic Name | Starting materials | MW found (MH+) |
|---|---|---|---|---|---|
| 181 | 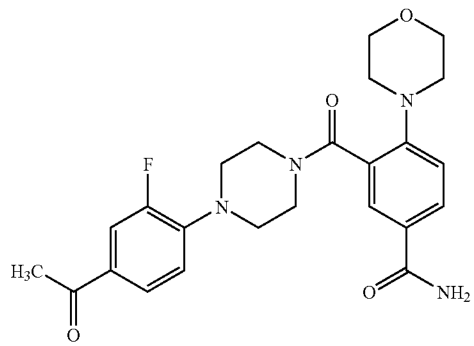 | 454.3 | 3-[4-(4-Acetyl-2-fluoro-phenyl)-piperazine-1-carbonyl]-4-morpholin-4-yl-benzamide | 3-[4-(4-Acetyl-2-fluoro-phenyl)-piperazine-1-carbonyl]-4-morpholin-4-yl-benzoic acid ammonia | 455.2 |
| 182 | 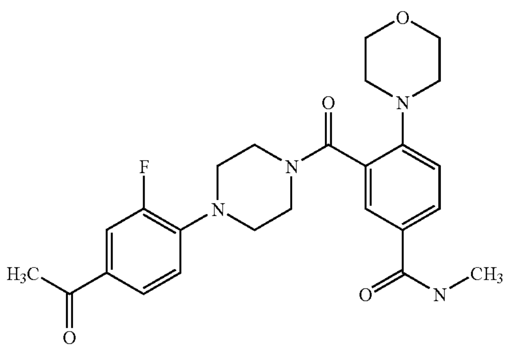 | 468.5 | 3-[4-(4-Acetyl-2-fluoro-phenyl)-piperazine-1-carbonyl]-N-methyl-4-morpholin-4-yl-benzamide | 3-[4-(4-Acetyl-2-fluoro-phenyl)-piperazine-1-carbonyl]-4-morpholin-4-yl-benzoic acid methylamine | 469.3 |
| 183 | 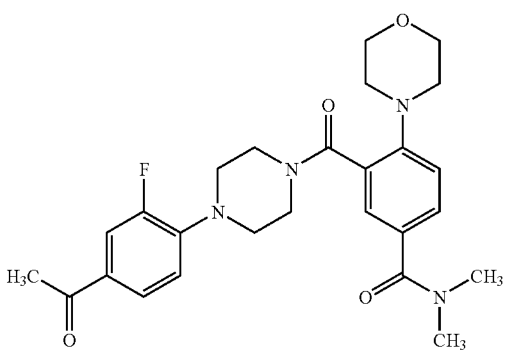 | 482.6 | 3-[4-(4-Acetyl-2-fluoro-phenyl)-piperazine-1-carbonyl]-N,N-dimethyl-4-morpholin-4-yl-benzamide | 3-[4-(4-Acetyl-2-fluoro-phenyl)-piperazine-1-carbonyl]-4-morpholin-4-yl-benzoic acid dimethylamine | 483.2 |
| 184 | 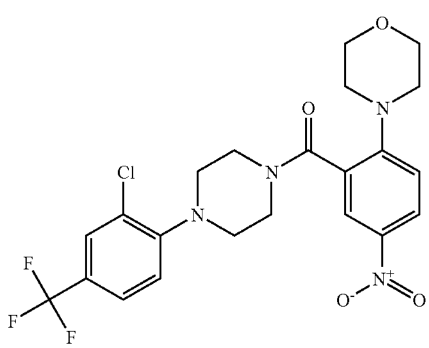 | 498.9 | [4-(2-Chloro-4-trifluoromethyl-phenyl)-piperazin-1-yl]-(2-morpholin-4-yl-5-nitro-phenyl)-methanone | 1-(2-Chloro-4-trifluoromethyl-phenyl)-piperazine and 2-Morpholin-4-yl-5-nitro-benzoyl chloride | 499.2 |

TABLE 1-continued

| No. | Structure | MW | Systematic Name | Starting materials | MW found (MH+) |
|---|---|---|---|---|---|
| 185 | 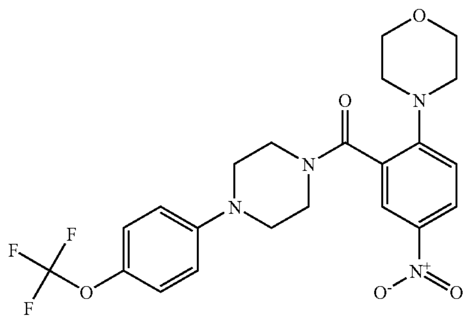 | 480.4 | (2-Morpholin-4-yl-5-nitro-phenyl)-[4-(4-trifluoromethoxy-phenyl)-piperazin-1-yl]-methanone | 1-(4-Trifluoromethoxy-phenyl)-piperazine and 2-Morpholin-4-yl-5-nitro-benzoyl chloride | 481.2 |
| 186 | 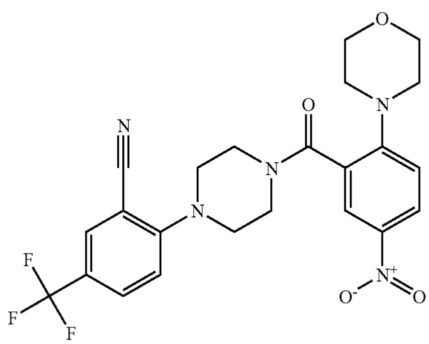 | 489.5 | 2-[4-(2-Morpholin-4-yl-5-nitro-benzoyl)-piperazin-1-yl]-5-trifluoromethyl-benzonitrile | 2-Piperazin-1-yl-5-trifluoromethyl-benzonitrile and 2-Morpholin-4-yl-5-nitro-benzoyl chloride | 490.2 |
| 187 | 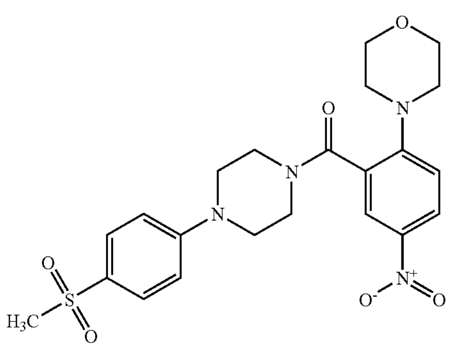 | 474.5 | [4-(4-Methanesulfonyl-phenyl)-piperazin-1-yl]-(2-morpholin-4-yl-5-nitro-phenyl)-methanone | 1-(4-Methanesulfonyl-phenyl)-piperazine and 2-Morpholin-4-yl-5-nitro-benzoyl chloride | 475.1 |
| 188 | 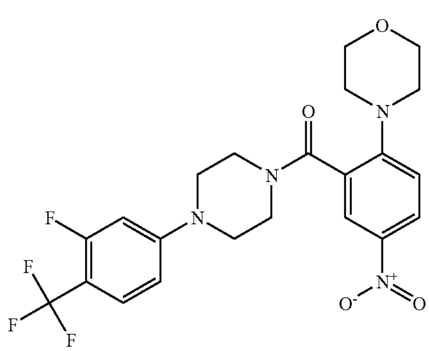 | 482.4 | [4-(3-Fluoro-4-trifluoromethyl-phenyl)-piperazin-1-yl]-(2-morpholin-4-yl-5-nitro-phenyl)-methanone | 1-(3-Fluoro-4-trifluoromethyl-phenyl)-piperazine and 2-Morpholin-4-yl-5-nitro-benzoyl chloride | 483.2 |

TABLE 1-continued

| No. | Structure | MW | Systematic Name | Starting materials | MW found (MH+) |
|---|---|---|---|---|---|
| 189 | 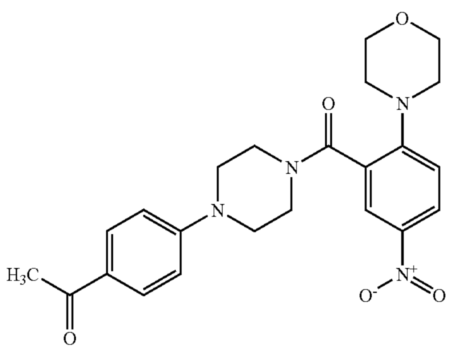 | 438.5 | 1-{4-[4-(2-Morpholin-4-yl-5-nitro-benzoyl)-piperazin-1-yl]-phenyl}-ethanone | 1-{4-[4-(2-Fluoro-5-nitro-benzoyl)-piperazin-1-yl]-phenyl}-ethanone and morpholine | 439.3 |
| 190 | 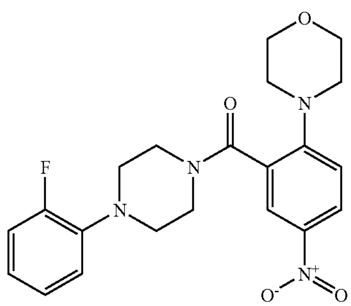 | 414.4 | [4-(2-Fluoro-phenyl)-piperazin-1-yl]-(2-morpholin-4-yl-5-nitro-phenyl)-methanone | (2-Fluoro-5-nitro-phenyl)-[4-(2-fluoro-phenyl)-piperazin-1-yl]-methanone and morpholine | 415.2 |
| 191 | 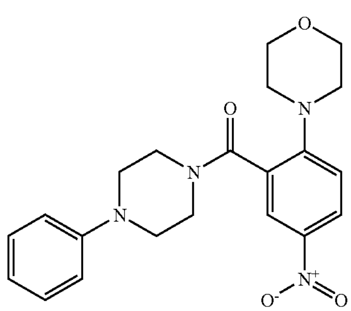 | 396.4 | (2-Morpholin-4-yl-5-nitro-phenyl)-(4-phenyl-piperazin-1-yl)-methanone | (2-Fluoro-5-nitro-phenyl)-(4-phenyl-piperazin-1-yl)-methanone and morpholine | 397.3 |
| 192 | 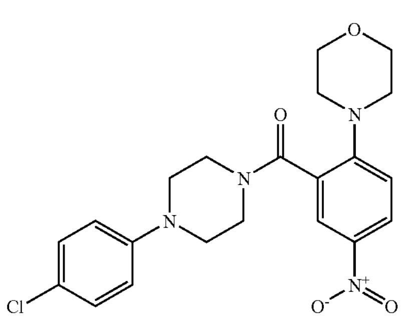 | 430.9 | [4-(4-Chloro-phenyl)-piperazin-1-yl]-(2-morpholin-4-yl-5-nitro-phenyl)-methanone | 2-morpholin-4-yl-5-nitro-benzoyl chloride and 4-chloro-phenyl-piperazine | 449.2 |

TABLE 1-continued

| No. | Structure | MW | Systematic Name | Starting materials | MW found (MH+) |
|---|---|---|---|---|---|
| 193 | 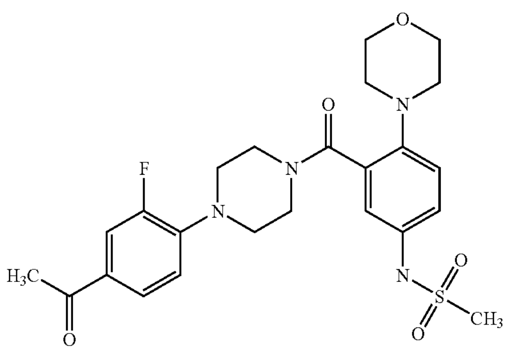 | 504.6 | N-{3-[4-(4-Acetyl-2-fluoro-phenyl)-piperazine-1-carbonyl]-4-morpholin-4-yl-phenyl}-methanesulfonamide | 1-{4-[4-(5-Amino-2-morpholin-4-yl-benzoyl)-piperazin-1-yl]-3-fluoro-phenyl}-ethanone and methanesulfonyl chloride | 505.3 |
| 194 | 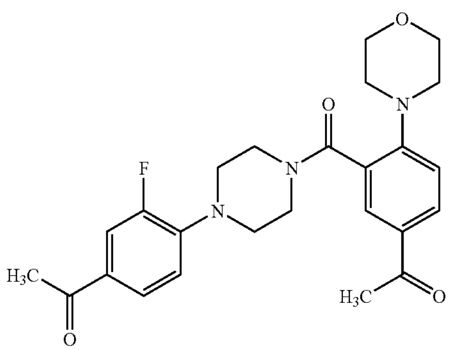 | 453.5 | 1-{4-[4-(5-Acetyl-2-morpholin-4-yl-benzoyl)-piperazin-1-yl]-3-fluoro-phenyl}-ethanone | 1-{4-[4-(5-Bromo-2-morpholin-4-yl-benzoyl)-piperazin-1-yl]-3-fluoro-phenyl}-ethanone and tributyl(1-ethoxyvinyl)tin | 454.2 |
| 195 | 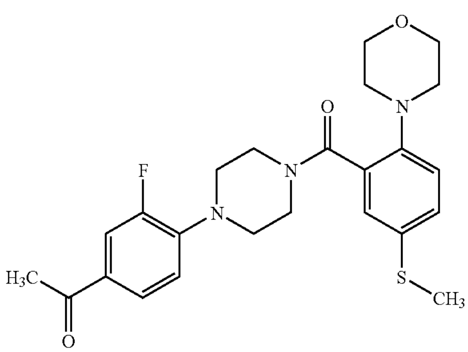 | 457.6 | 1-{3-Fluoro-4-[4-(5-methylsulfanyl-2-morpholin-4-yl-benzoyl)-piperazin-1-yl]-phenyl}-ethanone | 5-Methylsulfanyl-2-morpholin-4-yl-benzoic acid and 1-(3-Fluoro-4-piperazin-1-yl-phenyl)-ethanone | 458.2 |
| 196 | 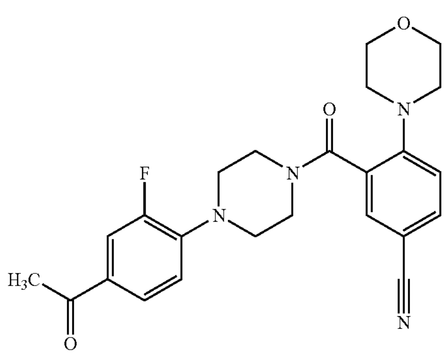 | 436.5 | 3-[4-(4-Acetyl-2-fluoro-phenyl)-piperazine-1-carbonyl]-4-morpholin-4-yl-benzonitrile | 3-[4-(4-Acetyl-2-fluoro-phenyl)-piperazine-1-carbonyl]-4-bromo-benzonitrile and morpholine | 437.2 |

TABLE 1-continued

| No. | Structure | MW | Systematic Name | Starting materials | MW found (MH+) |
|---|---|---|---|---|---|
| 197 | 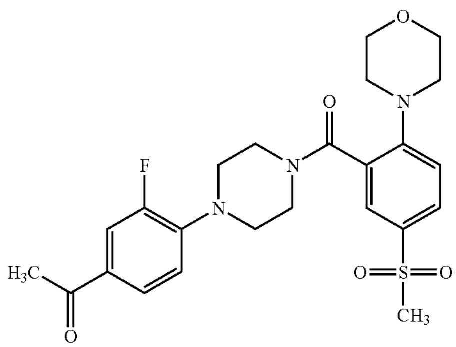 | 489.6 | 1-{3-Fluoro-4-[4-(5-methylsulfonyl-2-morpholin-4-yl-benzoyl)-piperazin-1-yl]-phenyl}-ethanone | 1-{4-[4-(2-Chloro-5-methanesulfonyl-benzoyl)-piperazin-1-yl]-3-fluoro-phenyl}-ethanone and morpholine | 490.2 |
| 198 | 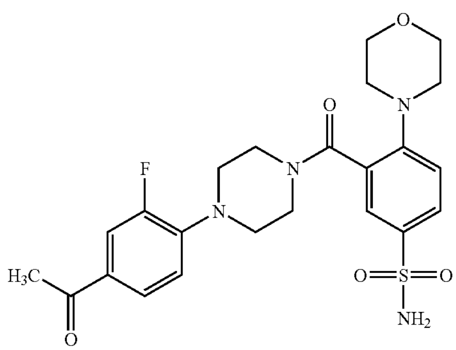 | 490.6 | 3-[4-(4-Acetyl-2-fluoro-phenyl)-piperazine-1-carbonyl]-4-morpholin-4-yl-benzenesulfonamide | 3-[4-(4-Acetyl-2-fluoro-phenyl)-piperazine-1-carbonyl]-4-chloro-benzenesulfonamide and morpholine | 489.4 |
| 199 | 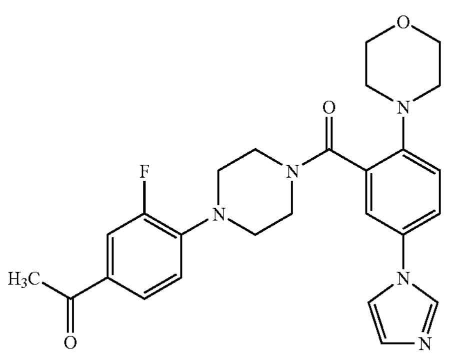 | 477.5 | 1-{3-Fluoro-4-[4-(5-imidazol-1-yl-2-morpholin-4-yl-benzoyl)-piperazin-1-yl]-phenyl}-ethanone | 1-{4-[4-(5-Bromo-2-morpholin-4-yl-benzoyl)-piperazin-1-yl]-3-fluoro-phenyl}-ethanone and imidazole | 478.4 |
| 200 | 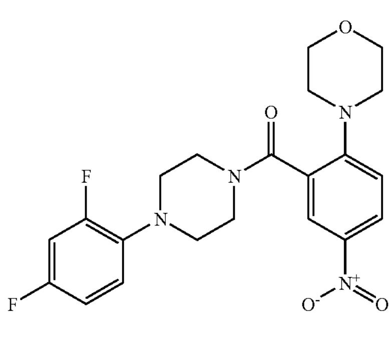 | 432.4 | [4-(2,4-Difluoro-phenyl)-piperazin-1-yl]-(2-morpholin-4-yl-5-nitro-phenyl)-methanone | 2-Morpholin-4-yl-5-nitro-benzoyl chloride and 1-(2,4-difluorophenyl)-piperazine | 433.4 |

TABLE 1-continued

| No. | Structure | MW | Systematic Name | Starting materials | MW found (MH+) |
|---|---|---|---|---|---|
| 201 | 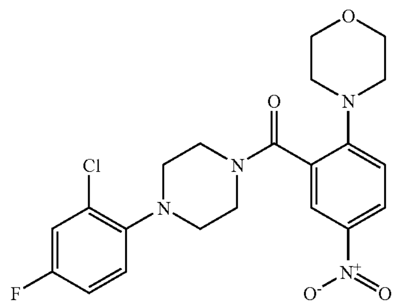 | 448.9 | [4-(2-Chloro-4-fluoro-phenyl)-piperazin-1-yl]-(2-morpholin-4-yl-5-nitro-phenyl)-methanone | 2-Morpholin-4-yl-5-nitro-benzoyl chloride and 1-(2-Chloro-4-fluoro-phenyl)-piperazine | 449.2 |
| 202 | 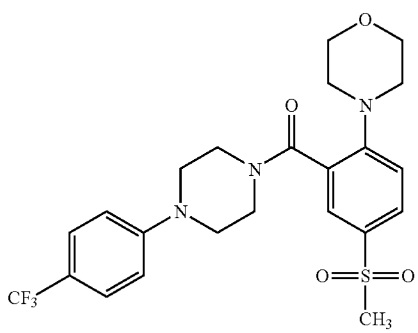 | | 5-Methanesulfonyl-2-morpholin-4-yl-phenyl)-[4-(4-trifluoromethyl-phenyl)piperazin-1-yl]-methanone | Morpholine and (2-Chloro-5-methanesulfonyl-phenyl)-[4-(4-trifluoromethyl-phenyl)-piperazin-1-yl]methanone | 497.5 |
| 203 | 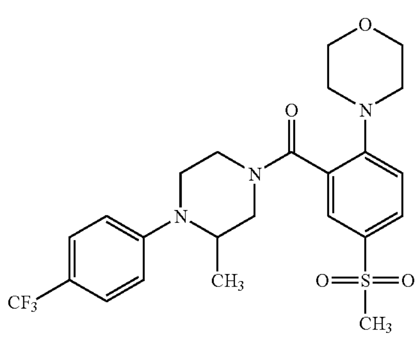 | | rac-5-Methanesulfonyl-2-morpholin-4-yl-phenyl)-[3-methyl-4-(4-trifluoromethyl-phenyl)-piperazin-1-yl]-methanone | Morpholine and (2-iodo-5-methanesulfonyl-phenyl)-[3-methyl-4-(4-trifluoromethyl-phenyl)-piperazin-1-yl]methanone | 512.3 |
| 204 | 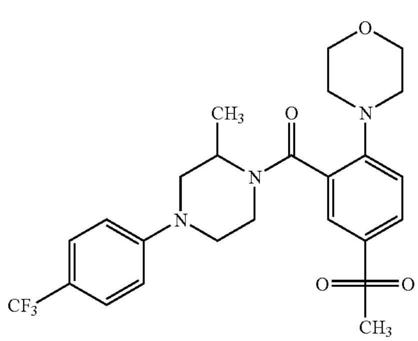 | | rac-5-Methanesulfonyl-2-morpholin-4-yl-phenyl)-[2-methyl-4-(4-trifluoromethyl-phenyl)-piperazin-1-yl]-methanone | rac-4-(5-Methanesulfonyl-2-morpholin-4-yl-benzoyl)-3-methyl-piperazine-1-carboxylic acid tert-butylester and trifluoroacetic acid then 1-Bromo-4-trifluoromethyl-benzene | 512.3 |

Example 205

4-[4-(2-Morpholin-4-yl-5-nitro-benzoyl)-piperazin-1-yl]-benzoic acid butyl ester The title compound was prepared according to the procedure described for example 46 from 4-piperazin-1-yl-benzoic acid butyl ester (CAS: 86620-18-0) and 2-Morpholin-4-yl-5-nitro-benzoyl chloride (example B) (yield: 16%, MS (m/e): 497.3 (M+H, 100%)

Example BU rac-2-(3-Hydroxymethyl-pyrrolidin-1-yl)-5-methanesulfonyl-benzoic acid

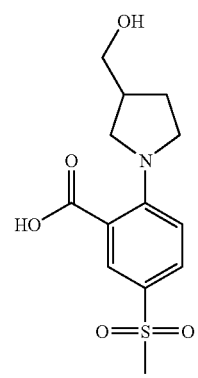

The title compound was synthesised according to the procedure described for the synthesis of 5-Methanesulfonyl-2-pyrrolidin-1-yl-benzoic acid (Example Y) from 2-Chloro-5-methanesulfonyl-benzoic acid and rac-pyrrolidin-3-yl-methanol and obtained in 39% yield. MS (m/e): 298.1 (M−H, 100%).

Example BV

5-Methanesulfonyl-2-piperidin-1-yl-benzoic acid

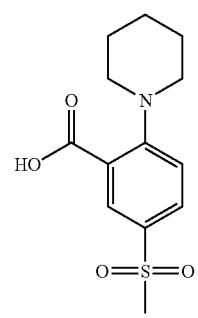

The title compound was synthesised according to the procedure described for the synthesis of 5-Methanesulfonyl-2-pyrrolidin-1-yl-benzoic acid (Example Y) from 2-Chloro-5-methanesulfonyl-benzoic acid and piperidine and obtained in 78% yield. MS (m/e): 282.0 (M−H$^+$100%)

Example BW rac-2-(3-Hydroxy-piperidin-1-yl)-5-methanesulfonyl-benzoic acid

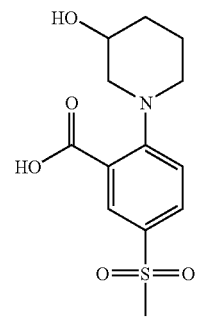

The title compound was synthesised according to the procedure described for the synthesis of 5-Methanesulfonyl-2-pyrrolidin-1-yl-benzoic acid (Example Y) from 2-Chloro-5-methanesulfonyl-benzoic acid and rac-3-hydroxy-piperidine and obtained in 9% yield. MS (m/e): 298.1 (M−H 100%).

Example BX rac-2-(3-Hydroxymethyl-pyrrolidin-1-yl)-5-methylsulfamoyl-benzoic acid

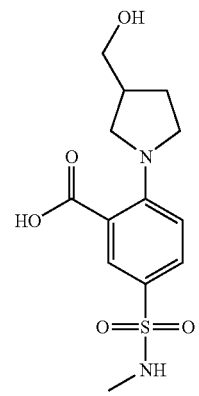

The title compound was synthesised according to the procedure described for the synthesis of 5-Methanesulfonyl-2-pyrrolidin-1-yl-benzoic acid (Example S) from 2-Chloro-5- methylsulfamoyl-benzoic acid and rac-pyrrolidin-3-yl-methanol and obtained in 25% yield. MS (m/e): 313.0 MH– (100%).

Example BY

5-Methylsulfamoyl-2-piperidin-1-yl-benzoic acid

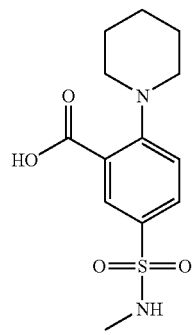

The title compound was synthesised according to the procedure described for the synthesis of 5-Methanesulfonyl-2-pyrrolidin-1-yl-benzoic acid (Example S) from 2-Chloro-5-methylsulfamoyl-benzoic acid and piperidine and obtained in 48% yield. MS (m/e): 297.4 MH–(100%).

Example BZ rac-2-(3-Hydroxy-piperidin-1-yl)-5-methylsulfamoyl-benzoic acid

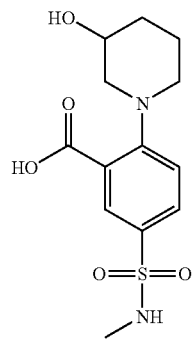

The title compound was synthesised according to the procedure described for the synthesis of 5-Methanesulfonyl-2-pyrrolidin-1-yl-benzoic acid (Example S) from 2-Chloro-5-methylsulfamoyl-benzoic acid and rac-3-hydroxy-piperidine and obtained in 15% yield. MS (m/e): 312.9 (MH− 100%).

Example CA

2-Pyrrolidin-1-yl-5-sulfamoyl-benzoic acid

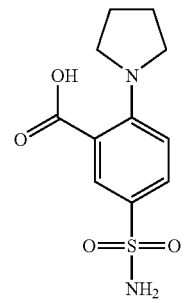

The title compound was synthesised according to the procedure described for the synthesis of 5-Methanesulfonyl-2-pyrrolidin-1-yl-benzoic acid (Example S) from 2-Chloro-5-sulfamoyl-benzoic acid (CAS: 97-04-1; Basu; D.-G.; J. Indian Chem. Soc.; 16; 1939; 100, 106) and pyrrolidine and obtained in 19% yield. MS (m/e): 269.4 (MH− 100%).

Example CB

2-Morpholin-4-yl-5-sulfamoyl-benzoic acid

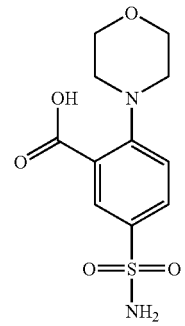

The title compound was synthesised according to the procedure described for the synthesis of 5-Methanesulfonyl-2-pyrrolidin-1-yl-benzoic acid (Example S) from 2-Chloro-5-sulfamoyl-benzoic acid (CAS: 97-04-1; Basu; D.-G.; J. Indian Chem. Soc.; 16; 1939; 100, 106) and morpholine and obtained in 85% yield. MS (m/e): 285.1 (MH+ 100%).

According to the procedure described for the synthesis of Example 123 further derivatives have been synthesised from acid derivatives and piperazine derivatives and comprise Examples 206-279 in Table 2.

TABLE 2

| No. | Structure | MW | Systematic Name | Starting materials | MW found (MH+) |
|---|---|---|---|---|---|
| 206 | 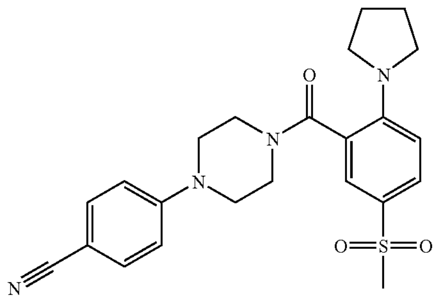 | 438.5 | 4-[4-(5-Methane sulfonyl-2-pyrrolidin-1-yl-benzoyl)-piperazin-1-4]-benzonitrile | 4-Piperazin-1-yl-benzonitrile (commercial) and 5-Methane-sulfonyl-2-pyrrolidin-1-yl-benzoic acid (Example Y) | 439.3 |
| 207 | 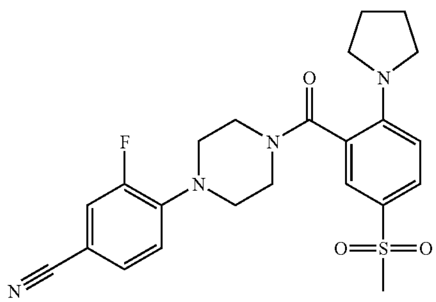 | 456.5 | 3-Fluoro-4-[4-(5-methanesulfonyl-2-pyrrolidin-1-yl-benzoyl)-piperazin-1-yl]-benzonitrile | 3-Fluoro-4-piperazin-1-yl-benzonitrile (WO9625414) and 5-Methanesulfonyl-2-pyrrolidin-1-yl-benzoic acid (Example Y) | 457.3 |
| 208 | 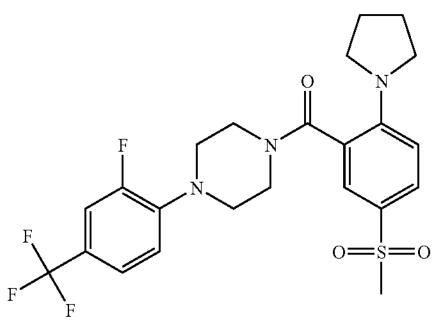 | 499.5 | [4-(2-Fluoro-4-trifluoro-methyl-phenyl)-piperazin-1-yl]-(5-methanesulfonyl-2-pyrrolidin-1-yl-phenyl)-methanone | 1-(2-Fluoro-4-trifluoromethyl-phenyl)-piperazine (example H) and 5-Methane sulfonyl-2-pyrrolidin-1-yl-benzoic acid (Example Y) | 500.2 |
| 209 | 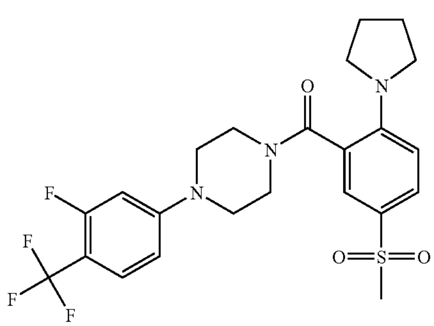 | 499.5 | [4-(3-Fluoro-4-trifluoromethyl-phenyl)-piperazin-1-yl]-(5-methanesulfonyl-2-pyrrolidin-1-yl-phenyl)-methanone | 1-(3-Fluoro-4-trifluoromethyl-phenyl)-piperazine (example BC) and 5-Methanesulfonyl-2-pyrrolidin-1-yl-benzoic acid (Example Y) | 500.2 |

TABLE 2-continued

| No. | Structure | MW | Systematic Name | Starting materials | MW found (MH+) |
|---|---|---|---|---|---|
| 210 | 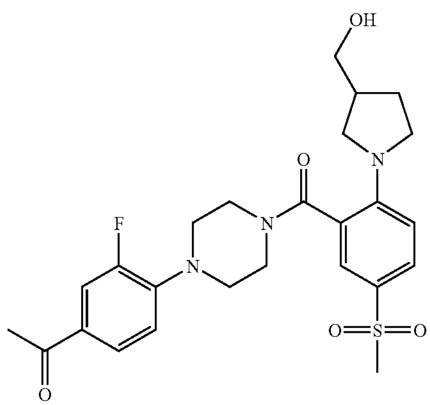 | 503.6 | rac-1-(3-Fluoro-4-{4-[2-(3-hydroxymethyl-pyrrolidin-1-yl)-5-methanesulfonyl-benzoyl]-piperazin-1-yl}-phenyl)-ethanone | 1-(3-Fluoro-4-piperazin-1-yl-phenyl)-ethanone (WO9714690) and rac-2-(3-Hydroxymethyl-pyrrolidin-1-yl)-5-methanesulfonyl-benzoic acid (example BU) | 504.2 |
| 211 | 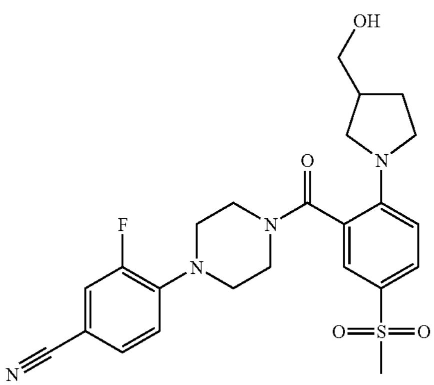 | 486.6 | rac-3-Fluoro-4-{4-[2-(3-hydroxymethyl-pyrrolidin-1-yl)-5-methanesulfonyl-benzoyl]-piperazin-1-yl}-benzonitrile | 3-Fluoro-4-piperazin-1-yl-benzonitrile (WO9625414) and rac-2-(3-Hydroxymethyl-pyrrolidin-1-yl)-5-methanesulfonyl-benzoic acid (example BU) | 487.3 |
| 212 | 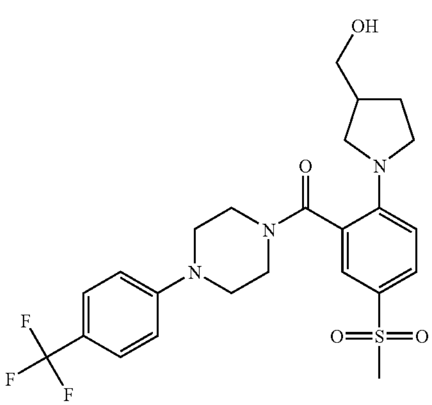 | 511.6 | rac-[2-(3-Hydroxy methyl-pyrrolidin-1-yl)-5-methanesulfonyl-phenyl]-[4-(4-trifluoro methyl-phenyl)-piperazin-1-yl]-methanone | 1-(4-Trifluoromethyl-phenyl)-piperazine (commercial) and rac-2-(3-Hydroxymethyl-pyrrolidin-1-yl)-5-methanesulfonyl-benzoic acid (example BU) | 512.4 |

TABLE 2-continued

| No. | Structure | MW | Systematic Name | Starting materials | MW found (MH+) |
|---|---|---|---|---|---|
| 213 | 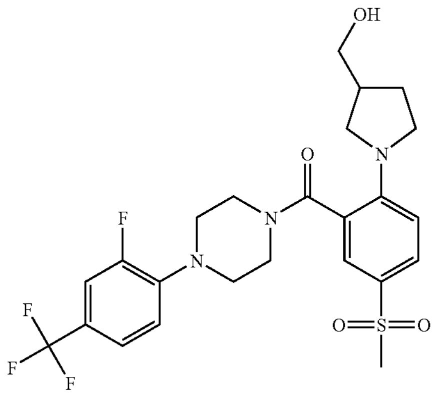 | 529.6 | rac-[4-(2-Fluoro-4-trifluoromethyl-phenyl)-piperazin-1-yl]-[2-(3-hydroxymethyl-pyrrolidin-1-yl)-5-methanesulfonyl-phenyl]-methanone | 1-(2-Fluoro-4-trifluoromethyl-phenyl)-piperazine (example H) and rac-2-(3-Hydroxymethyl-pyrrolidin-1-yl)-5-methanesulfonyl-benzoic acid (example BU) | 530.1 |
| 214 | 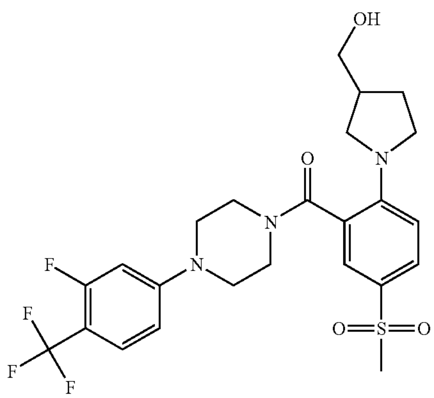 | 529.6 | rac-[4-(3-Fluoro-4-trifluoromethyl-phenyl)-piperazin-1-yl]-[2-(3-hydroxymethyl-pyrrolidin-1-yl)-5-methanesulfonyl-phenyl]-methanone | 1-(3-Fluoro-4-trifluoromethyl-phenyl)-piperazine (example BC) and rac-2-(3-Hydroxymethyl-pyrrolidin-1-yl)-5-methanesulfonyl-benzoic acid (example BU) | 530.1 |
| 215 | 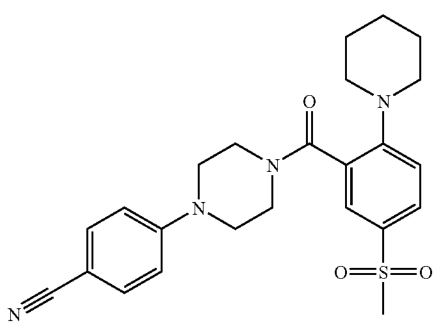 | 452.6 | 4-[4-(5-Methanesulfonyl-2-piperidin-1-yl-benzoyl)-piperazin-1-yl]-benzonitrile | 4-Piperazin-1-yl-benzonitrile (commercial) and 5-Methanesulfonyl-2-piperidin-1-yl-benzoic acid (example BV) | 453.2 |
| 216 | 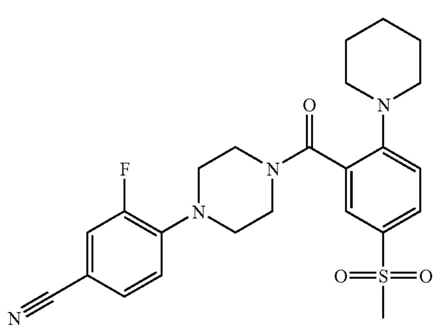 | 470.6 | 3-Fluoro-4-[4-(5-methanesulfonyl-2-piperidin-1-yl-benzoyl)-piperazin-1-yl]-benzonitrile | 3-Fluoro-4-piperazin-1-yl-benzonitrile (WO9625414) and 5-Methanesulfonyl-2-piperidin-1-yl-benzoic acid (example BV) | 471.3 |

TABLE 2-continued

| No. | Structure | MW | Systematic Name | Starting materials | MW found (MH+) |
|---|---|---|---|---|---|
| 217 | 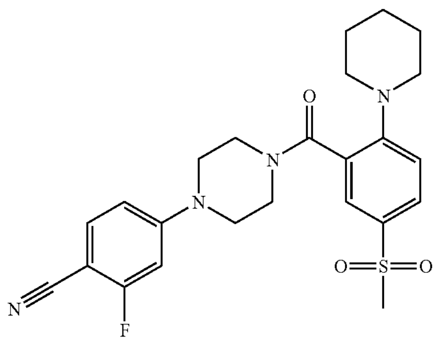 | 470.6 | 2-Fluoro-4-[4-(5-methanesulfonyl-2-piperidin-1-yl-benzoyl)-piperazin-1-yl]-benzonitrile | 2-Fluoro-4-piperazin-1-yl-benzonitrile (WO9808835) and 5-Methanesulfonyl-2-piperidin-1-yl-benzoic acid (example BV) | 471.3 |
| 218 | 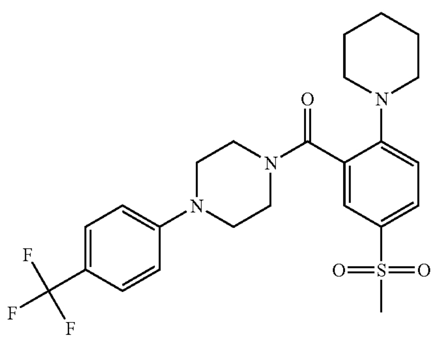 | 495.6 | (5-Methanesulfonyl-2-piperidin-1-yl-phenyl)-[4-(4-trifluoromethyl-phenyl)-piperazin-1-yl]-methanone | 1-(4-Trifluoromethyl-phenyl)-piperazine (commercial) and 5-Methane sulfonyl-2-piperidin-1-yl-benzoic acid (example BV) | 496.3 |
| 219 | 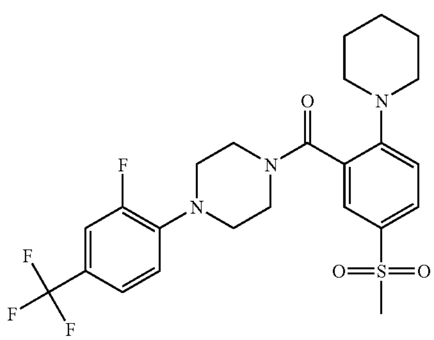 | 513.6 | [4-(2-Fluoro-4-trifluoromethyl-phenyl)piperazin-1-yl]-(5-methanesulfonyl-2-piperidin-1-yl-phenyl)-methanone | 1-(2-Fluoro-4-trifluoromethyl-phenyl)-piperazine (example H) and 5-Methane sulfonyl-2-piperidin-1-yl-benzoic acid (example BV) | 514.3 |
| 220 | 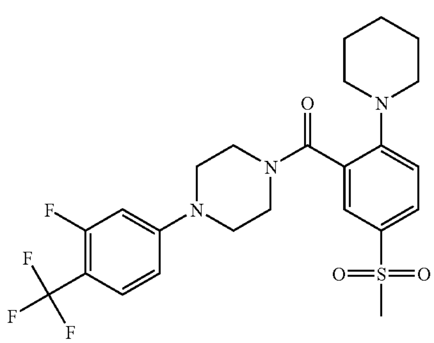 | 513.6 | [4-(3-Fluoro-4-trifluoromethyl-phenyl)piperazin-1-yl]-(5-methanesulfonyl-2-piperidin-1-yl-phenyl)-methanone | 1-(3-Fluoro-4-trifluoromethyl-phenyl)-piperazine (example BC) and 5-Methane sulfonyl-2-piperidin-1-yl-benzoic acid (example BV) | 514.3 |

TABLE 2-continued

| No. | Structure | MW | Systematic Name | Starting materials | MW found (MH+) |
|---|---|---|---|---|---|
| 221 | 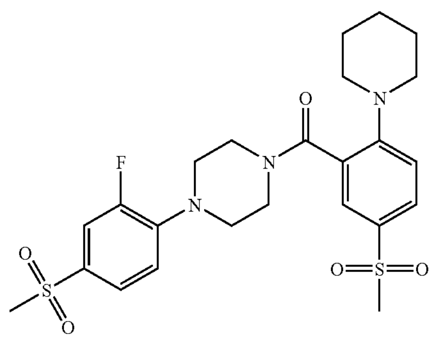 | 523.6 | [4-(2-Fluoro-4-methane sulfonyl-phenyl) piperazin-1-yl]-(5-methanesulfonyl-2-piperidin-1-yl-phenyl)-methanone | 1-(2-Fluoro-4-methane sulfonyl-phenyl)-piperazine (commercial) and 5-Methane sulfonyl-2-piperidin-1-yl-benzoic acid (example BV) | 524.3 |
| 222 | 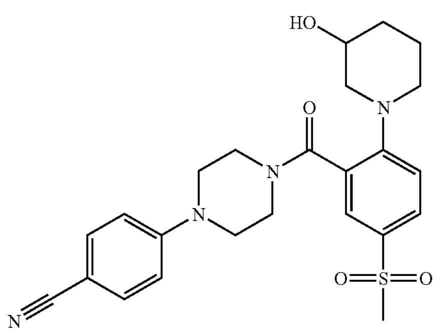 | 468.6 | rac-4-{4-[2-(3-Hydroxy-piperidin-1-yl)-5-methanesulfonylbenzoyl]-piperazin-1-yl}benzo-nitrile | 4-Piperazin-1-yl-benzonitrile (commercial) and rac-2-(3-Hydroxy-piperidin-1-yl)-5-methanesulfonyl-benzoic acid (example BW) | 469.2 |
| 223 | 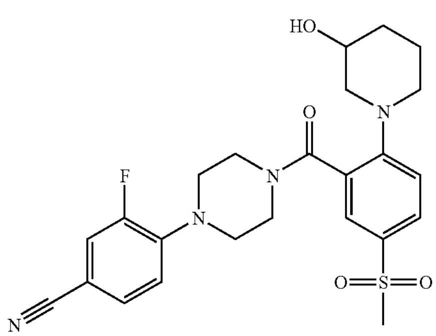 | 486.6 | rac-Fluoro-4-{4-[2-(3-hydroxy-piperidin-1-yl)-5-methanesulfonyl-benzoyl]-piperazin-1-yl}-benzonitrile | 3-Fluoro-4-piperazin-1-yl-benzonitrile (WO9625414) and rac-2-(3-Hydroxy-piperidin-1-yl)-5-methanesulfonyl-benzoic acid (example BW) | 487.3 |
| 224 | 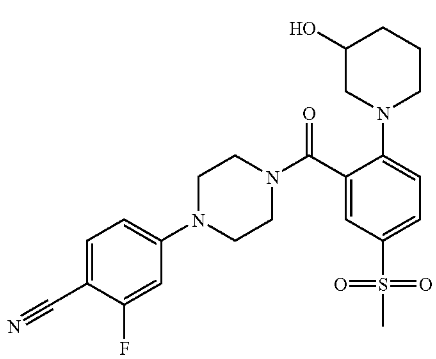 | 486.6 | rac-2-Fluoro-4-{4-[2-(3-hydroxy-piperidin-1-yl)-5-methanesulfonyl-benzoyl]-piperazin-1-yl}-benzonitrile | 2-Fluoro-4-piperazin-1-yl-benzonitrile (WO9808835) and rac-2-(3-Hydroxy-piperidin-1-yl)-5-methane sulfonyl-benzoic acid (example BW) | 487.3 |

TABLE 2-continued

| No. | Structure | MW | Systematic Name | Starting materials | MW found (MH+) |
|---|---|---|---|---|---|
| 225 | 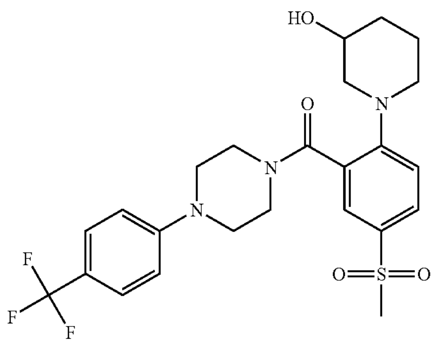 | 511.6 | rac-[2-(3-Hydroxy-piperidin-1-yl)-5-methanesulfonyl-phenyl]-[4-(4-trifluoromethyl-phenyl)-piperazin-1-yl}-methanone | 1-(4-Trifluoromethyl-phenyl)-piperazine (commercial) and rac-2-(3-Hydroxy-piperidin-1-yl)-5-methanesulfonyl-benzoic acid (example BW) | 512.4 |
| 226 | 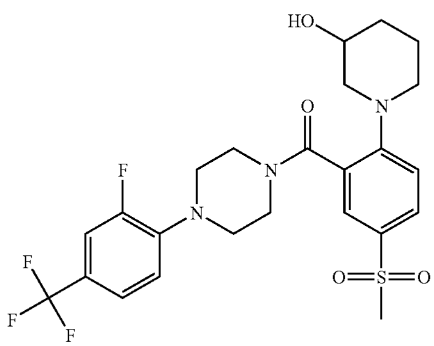 | 529.6 | rac-[4-(2-Fluoro-4-trifluoromethyl-phenyl)-piperazin-1-yl]-[2-(3-hydroxy-piperidin-1-yl)-5-methanesulfonyl-phenyl]-methanone | 1-(2-Fluoro-4-trifluoromethyl-phenyl)-piperazine (example H) and rac-2-(3-Hydroxy-piperidin-1-yl)-5-methanesulfonyl-benzoic acid (example BW) | 530.1 |
| 227 | 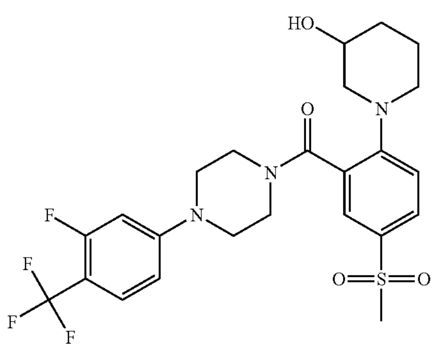 | 529.6 | rac-[4-(3-Fluoro-4-trifluoromethyl-phenyl)-piperazin-1-yl]-[2-(3-hydroxy-piperidin-1-yl)-5-methanesulfonyl-phenyl]-methanone | 1-(3-Fluoro-4-trifluoromethyl-phenyl)-piperazine (example BC) and rac-2-(3-Hydroxy-piperidin-1-yl)-5-methanesulfonyl-benzoic acid (example BW) | 530.1 |
| 228 | 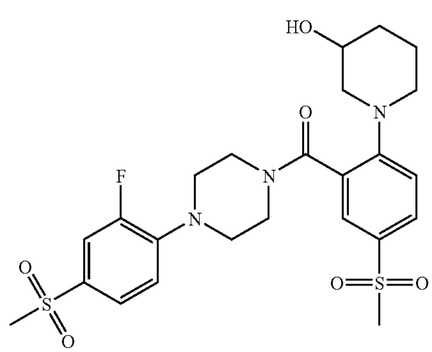 | 539.6 | rac-[4-(2-Fluoro-4-methanesulfonyl-phenyl)-piperazin-1-yl]-[2-(3-hydroxy-piperidin-1-yl)-5-methanesulfonyl-phenyl]-methanone | 1-(2-Fluoro-4-methanesulfonyl-phenyl)-piperazine(commercial) and rac-2-(3-Hydroxy-piperidin-1-yl)-5-methanesulfonyl-benzoic acid (example BW) | 540.3 |

TABLE 2-continued

| No. | Structure | MW | Systematic Name | Starting materials | MW found (MH+) |
|---|---|---|---|---|---|
| 229 | 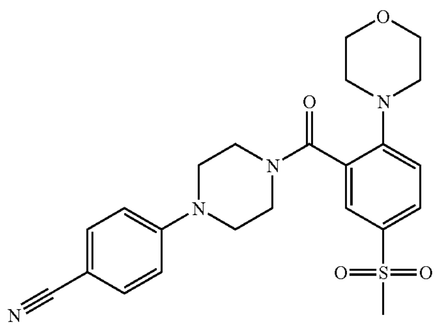 | 454.5 | 4-[4-(5-Methanesulfonyl-2-morpholin-4-yl-benzoyl)-piperazin-1-yl]-benzonitrile | 4-Piperazin-1-yl-benzonitrile (commercial) and 5-Methane sulfonyl-2-morpholin-4-yl-benzoic acid (example AG) | 455.2 |
| 230 | 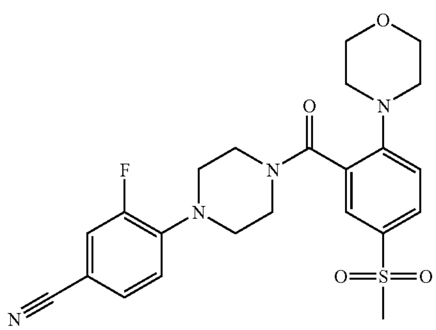 | 472.5 | 3-Fluoro-4-[4-(5-methanesulfonyl-2-morpholin-4-yl-benzoyl)-piperazin-1-yl]-benzonitrile | 3-Fluoro-4-piperazin-1-yl-benzonitrile (WO9625414) and 5-Methanesulfonyl-2-morpholin-4-yl-benzoic acid (example AG) | 473.2 |
| 231 | 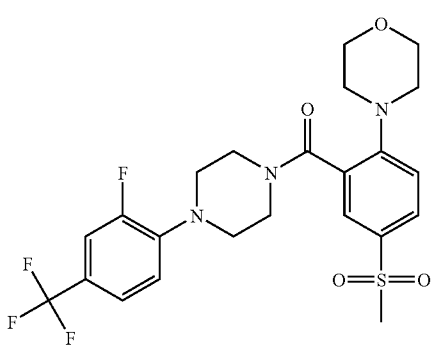 | 515.5 | [4-(2-Fluoro-4-trifluoromethyl-phenyl)-piperazin-1-yl]-(5-methanesulfonyl-2-morpholin-4-yl-phenyl)-methanone | 1-(2-Fluoro-4-trifluoromethyl-phenyl)-piperazine (example H) and 5-Methane sulfonyl-2-morpholin-4-yl-benzoic acid (example AG) | 516.2 |
| 232 | 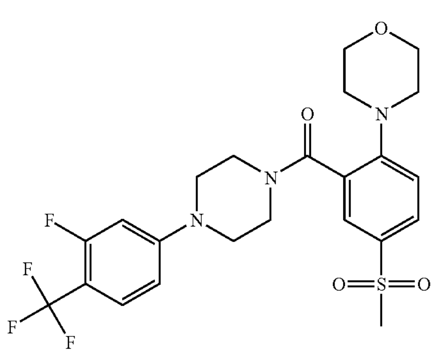 | 515.5 | [4-(3-Fluoro-4-trifluoromethyl-phenyl) piperazin-1-yl]-(5-methanesulfonyl-2-morpholin-4-yl-phenyl)-methanone | 1-(3-Fluoro-4-trifluoromethyl-phenyl)-piperazine (example BC) and 5-Methane sulfonyl-2-morpholin-4-yl-benzoic acid (example AG) | 516.2 |

TABLE 2-continued

| No. | Structure | MW | Systematic Name | Starting materials | MW found (MH+) |
|---|---|---|---|---|---|
| 233 | 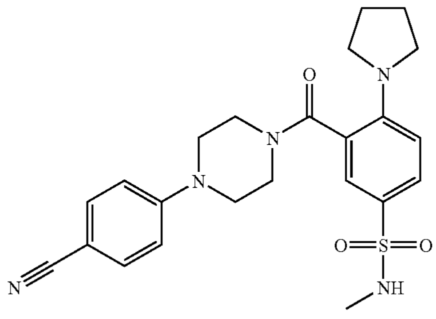 | 453.6 | 3-[4-(4-Cyano-phenyl)-piperazine-1-carbonyl]-N-methyl-4-pyrrolidin-1-yl-benzenesulfonamide | 4-Piperazin-1-yl-benzonitrile (commercial) and 5-Methyl sulfamoyl-2-pyrrolidin-1-yl-benzoic acid (example AC) | 454.3 |
| 234 | 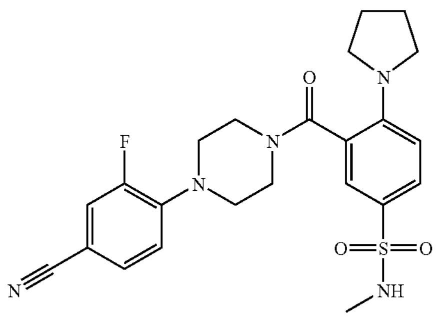 | 471.6 | 3-[4-(4-Cyano-2-fluoro-phenyl)-piperazine-1-carbonyl]-N-methyl-4-pyrrolidin-1-yl-benzenesulfonamide | 3-Fluoro-4-piperazin-1-yl-benzonitrile (WO9625414) and 5-Methylsulfamoyl-2-pyrrolidin-1-yl-benzoic acid (example AC) | 472.3 |
| 235 | 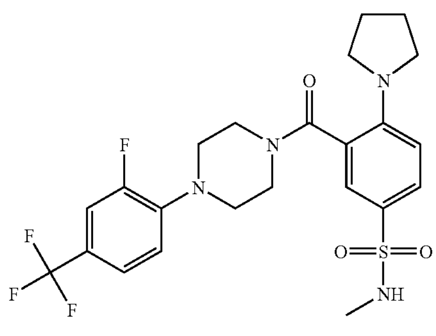 | 514.5 | 3-[4-(2-Fluoro-4-trifluoromethyl-phenyl)-piperazine-1-carbonyl]-N-methyl-4-pyrrolidin-1-yl-benzenesulfonamide | 1-(2-Fluoro-4-trifluoromethyl-phenyl)-piperazine (example H) and 5-Methyl sulfamoyl-2-pyrrolidin-1-yl-benzoic acid (example AC) | 515.3 |
| 236 | 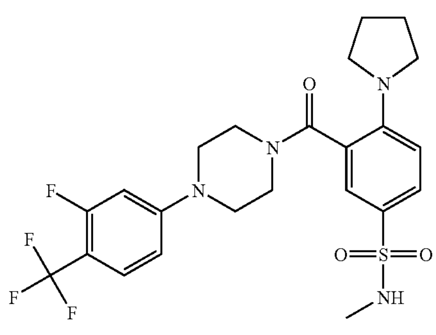 | 514.5 | 3-[4-(3-Fluoro-4-trifluoromethyl-phenyl)-piperazine-1-carbonyl]-N-methyl-4-pyrrolidin-1-yl-benzenesulfonamide | 1-(3-Fluoro-4-trifluoromethyl-phenyl)-piperazine (example BC) and 5-Methyl sulfamoyl-2-pyrrolidin-1-yl-benzoic acid (example AC) | 515.3 |

TABLE 2-continued

| No. | Structure | MW | Systematic Name | Starting materials | MW found (MH+) |
|---|---|---|---|---|---|
| 237 | 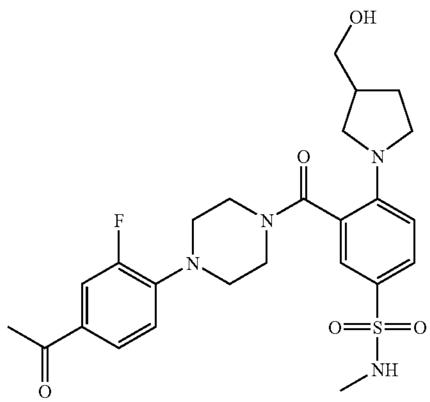 | 518.6 | rac-3-[4-(4-Acetyl-2-fluoro-phenyl)piperazine-1-carbonyl]-4-(3-hydroxymethyl-pyrrolidin-1-yl)-N-methyl-benzene sulfonamide | 1-(3-Fluoro-4-piperazin-1-yl-phenyl)-ethanone (WO9714690) and rac-2-(3-Hydroxymethyl-pyrrolidin-1-yl)-5-methylsulfamoyl-benzoic acid (example BX) | 519.3 |
| 238 | 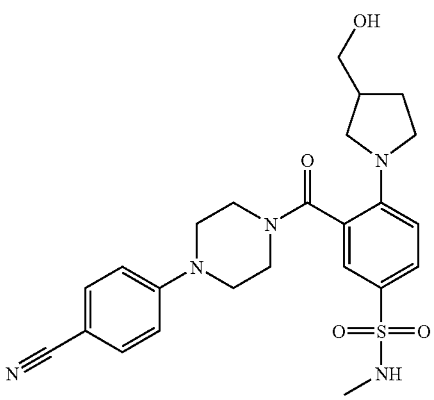 | 483.6 | rac-3-[4-(4-Cyano-phenyl)-piperazine-1-carbonyl]-4-(3-hydroxymethyl-pyrrolidin-1-yl)-N-methyl-benzene sulfonamide | 4-Piperazin-1-yl-benzonitrile (commercial) and rac-2-(3-Hydroxymethyl-pyrrolidin-1-yl)-5-methylsulfamoyl-benzoic acid (example BX) | 484.3 |
| 239 | 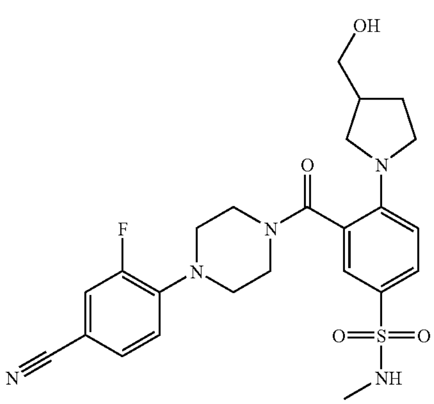 | 501.6 | rac-3-[4-(4-Cyano-2-fluoro-phenyl)-piperazine-1-carbonyl]-4-(3-hydroxymethyl-pyrrolidin-1-yl)-N-methyl-benzene sulfonamide | 3-Fluoro-4-piperazin-1-yl-benzonitrile (WO9625414) and rac-2-(3-Hydroxymethyl-pyrrolidin-1-yl)-5-methyl sulfamoyl-benzoic acid (example BX) | 502.3 |

TABLE 2-continued

| No. | Structure | MW | Systematic Name | Starting materials | MW found (MH+) |
|---|---|---|---|---|---|
| 240 | 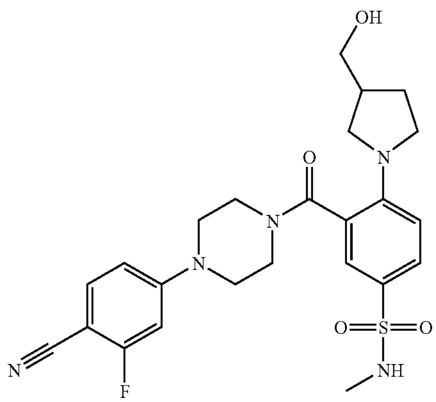 | 501.579 | rac-3-[4-(4-Cyano-3-fluoro-phenyl)-piperazine-1-carbonyl]-4-(3-hydroxymethyl-pyrrolidin-1-yl)-N-methyl-benzene sulfonamide | 2-Fluoro-4-piperazin-1-yl-benzonitrile (WO9808835) and rac-2-(3-Hydroxymethyl-pyrrolidin-1-yl)-5-methyl sulfamoyl-benzoic acid (example BX) | 502.3 |
| 241 | 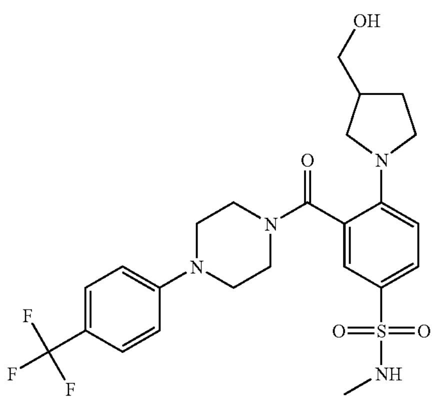 | 526.6 | rac-4-(3-Hydroxymethyl-pyrrolidin-1-yl)-N-methyl-3-[4-(4-trifluoromethyl-phenyl)-piperazine-1-carbonyl]-benzenesulfonamide | 1-(4-Trifluoromethyl-phenyl)-piperazine (commercial) and rac-2-(3-Hydroxymethyl-pyrrolidin-1-yl)-5-methylsulfamoyl-benzoic acid (example BX) | 527.3 |
| 242 | 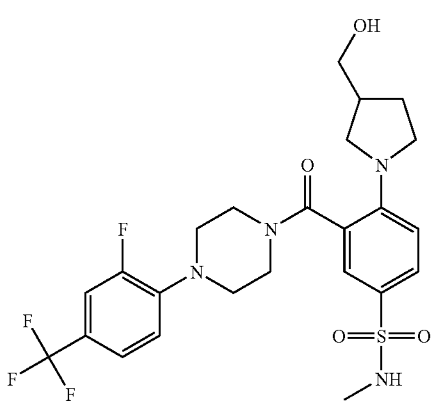 | 544.6 | rac-3-[4-(2-Fluoro-4-trifluoromethyl-phenyl)-piperazine-1-carbonyl]-4-(3-hydroxymethyl-pyrrolidin-1-yl)-N-methyl-benzene sulfonamide | 1-(2-Fluoro-4-trifluoromethyl-phenyl)-piperazine (example H) and rac-2-(3-Hydroxymethyl-pyrrolidin-1-yl)-5-methylsulfamoyl-benzoic acid (example BX) | 545.3 |

TABLE 2-continued

| No. | Structure | MW | Systematic Name | Starting materials | MW found (MH+) |
|---|---|---|---|---|---|
| 243 | 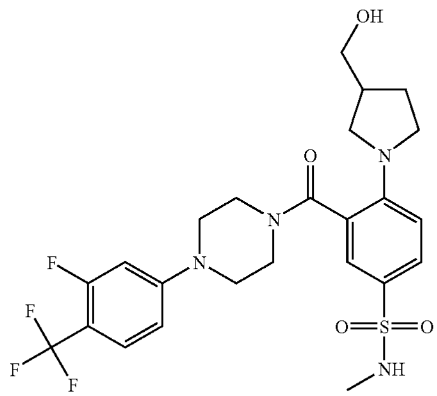 | 544.6 | rac-3-[4-(3-Fluoro-4-trifluoromethyl-phenyl)-piperazine-1-carbonyl]-4-(3-hydroxymethyl-pyrrolidin-1-yl)-N-methyl-benzene sulfonamide | 1-(3-Fluoro-4-trifluoromethyl-phenyl)-piperazine (example BC) and rac-2-(3-Hydroxymethyl-pyrrolidin-1-yl)-5-methyl sulfamoyl-benzoic acid (example BX) | 545.3 |
| 244 | 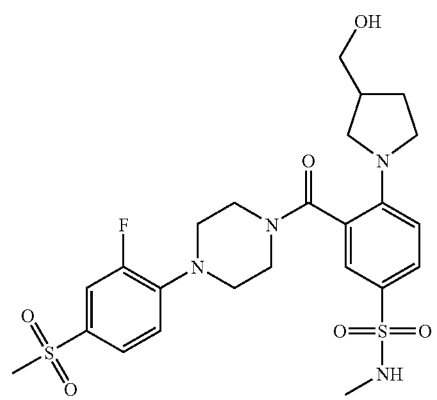 | 554.7 | rac-3-[4-(2-Fluoro-4-methanesulfonyl-phenyl)-piperazine-1-carbonyl]-4-(3-hydroxymethyl-pyrrolidin-1-yl)-N-methyl-benzene sulfonamide | 1-(2-Fluoro-4-methanesulfonyl-phenyl)-piperazine (commercial) and rac-2-(3-Hydroxy-methyl-pyrrolidin-1-yl)-5-methylsulfamoyl-benzoic acid (example BX) | 555.2 |
| 245 | 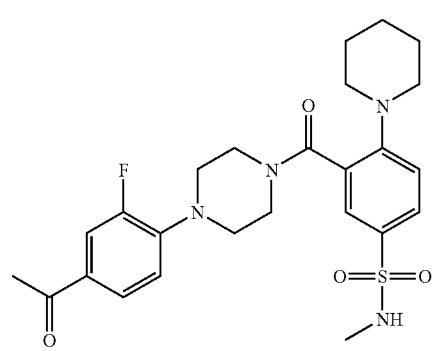 | 502.6 | 3-[4-(4-Acetyl-2-fluoro-phenyl)-piperazine-1-carbonyl]-N-methyl-4-piperidin-1-yl-benzenesulfonamide | 1-(3-Fluoro-4-piperazin-1-yl-phenyl)-ethanone (WO9714690) and 5-Methylsulfamoyl-2-piperidin-1-yl-benzoic acid (example BY) | 503.2 |
| 246 | 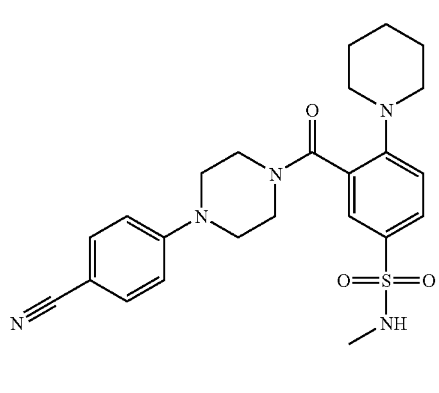 | 467.6 | 3-[4-(4-Cyano-phenyl)-piperazine-1-carbonyl]-N-methyl-4-piperidin-1-yl-benzenesulfonamide | 4-Piperazin-1-yl-benzo-nitrile (commercial) and 5-Methylsulfamoyl-2-piperidin-1-yl-benzoic acid (example BY) | 468.2 |

TABLE 2-continued

| No. | Structure | MW | Systematic Name | Starting materials | MW found (MH+) |
|---|---|---|---|---|---|
| 247 | 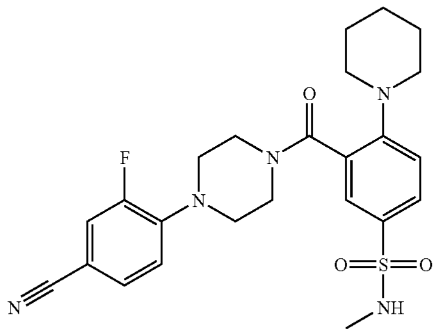 | 485.6 | 3-[4-(4-Cyano-2-fluoro-phenyl)-piperazine-1-carbonyl]-N-methyl-4-piperidin-1-yl-benzenesulfonamide | 3-Fluoro-4-piperazin-1-yl-benzonitrile (WO9625414) and 5-Methylsulfamoyl-2-piperidin-1-yl-benzoic acid (example BY) | 486.3 |
| 248 | 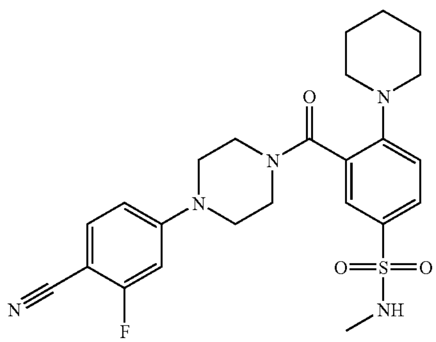 | 485.58 | 3-[4-(4-Cyano-3-fluoro-phenyl)-piperazine-1-carbonyl]-N-methyl-4-piperidin-1-yl-benzenesulfonamide | 2-Fluoro-4-piperazin-1-yl-benzonitrile (WO9808835) and 5-Methylsulfamoyl-2-piperidin-1-yl-benzoic acid (example BY) | 486.3 |
| 249 | 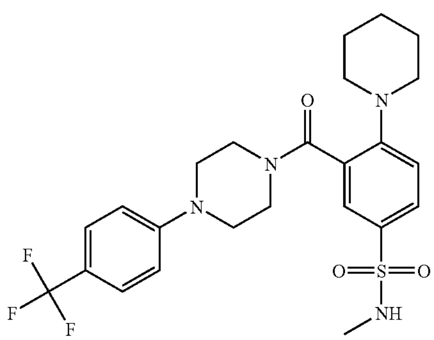 | 510.6 | N-Methyl-4-piperidin-1-yl-3-[4-(4-trifluoromethyl-phenyl)-piperazine-1-carbonyl]-benzenesulfonamide | 1-(4-Trifluoromethyl-phenyl)-piperazine (commercial) and 5-Methyl sulfamoyl-2-piperidin-1-yl-benzoic acid (example BY) | 511.4 |
| 250 | 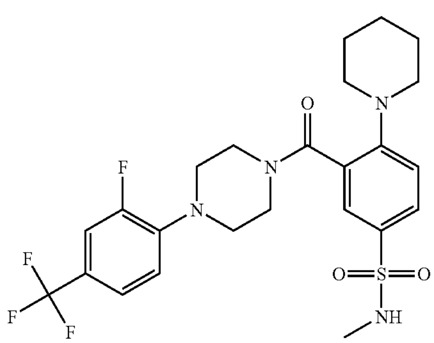 | 528.6 | 3-[4-(2-Fluoro-4-trifluoromethyl-phenyl)-piperazine-1-carbonyl]-N-methyl-4-piperidin-1-yl-benzenesulfonamide | 1-(2-Fluoro-4-trifluoromethyl-phenyl)-piperazine (example H) and 5-Methylsulfamoyl-2-piperidin-1-yl-benzoic acid (example BY) | 529.2 |

TABLE 2-continued

| No. | Structure | MW | Systematic Name | Starting materials | MW found (MH+) |
|---|---|---|---|---|---|
| 251 | 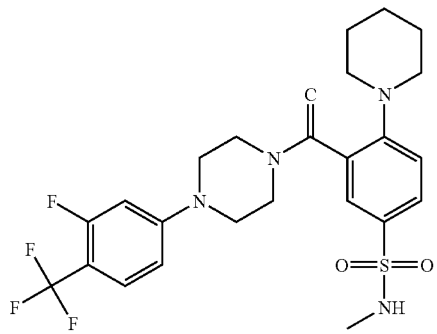 | 528.6 | 3-[4-(3-Fluoro-4-trifluoromethyl-phenyl)-piperazine-1-carbonyl]-N-methyl-4-piperidin-1-yl-benzenesulfonamide | 1-(3-Fluoro-4-trifluoromethyl-phenyl)-piperazine (example BC) and 5-Methylsulfamoyl-2-piperidin-1-yl-benzoic acid (example BY) | 529.2 |
| 252 | 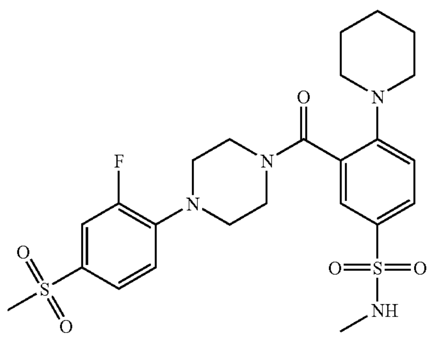 | 538.7 | 3-[4-(2-Fluoro-4-methanesulfonyl-phenyl)-piperazine-1-carbonyl]-N-methyl-4-piperidin-1-yl-benzenesulfonamide | 1-(2-Fluoro-4-methanesulfonyl-phenyl)-piperazine (commercial) and 5-Methylsulfamoyl-2-piperidin-1-yl-benzoic acid (example BY) | 539.3 |
| 253 | 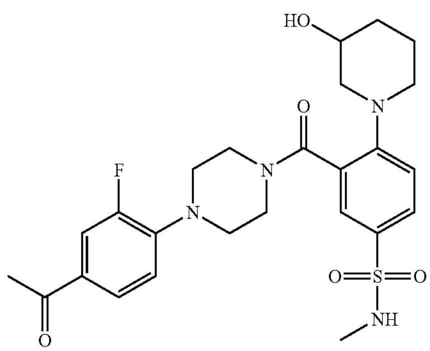 | 518.6 | rac-3-[4-(4-Acetyl-2-fluoro-phenyl)-piperazine-1-carbonyl]-4-(3-hydroxy-piperidin-1-yl)-N-methyl-benzenesulfonamide | 1-(3-Fluoro-4-piperazin-1-yl-phenyl)-ethanone (WO9714690) and rac-2-(3-Hydroxy-piperidin-1-yl)-5-methylsulfamoyl-benzoic acid (example BZ) | 519.3 |
| 254 | 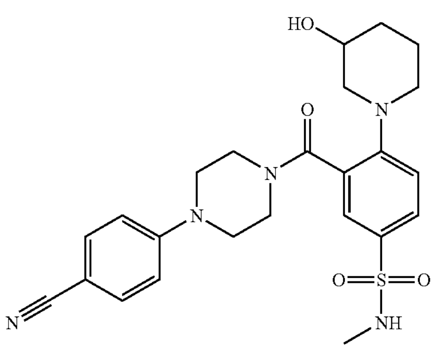 | 483.6 | rac-3-[4-(4-Cyano-phenyl)-piperazine-1-carbonyl]-4-(3-hydroxy-piperidin-1-yl)-N-methyl-benzene sulfonamide | 4-Piperazin-1-yl-benzonitrile (commercial) and rac-2-(3-Hydroxy-piperidin-1-yl)-5-methylsulfamoyl-benzoic acid (example BZ) | 484.3 |

TABLE 2-continued

| No. | Structure | MW | Systematic Name | Starting materials | MW found (MH+) |
|---|---|---|---|---|---|
| 255 | 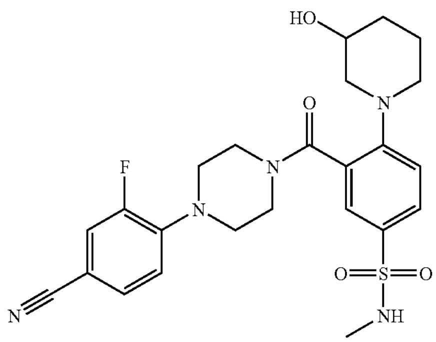 | 501.6 | rac-3-[4-(4-Cyano-2-fluoro-phenyl)-piperazine-1-carbonyl]-4-(3-hydroxy-piperidin-1-yl)-5-methyl-benzene sulfonamide | 3-Fluoro-4-piperazin-1-yl-benzonitrile (WO9625414) and rac-2-(3-Hydroxy-piperidin-1 yl)-5-methyl-sulfamoyl-benzoic acid (example BZ) | 502.3 |
| 256 | 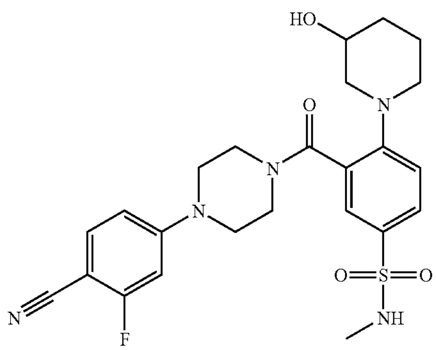 | 501.6 | rac-3-[4-(4-Cyano-3-fluoro-phenyl)-piperazine-1-carbonyl]-4-(3-hydroxy-piperidin-1-yl)-N-methyl-benzene sulfonamide | 2-Fluoro-4-piperazin-1-yl-benzonitrile (WO9808835) and rac-2-(3-Hydroxy-piperidin-1-yl)-5-methyl sulfamoyl-benzoic acid (example BZ) | 502.2 |
| 257 | 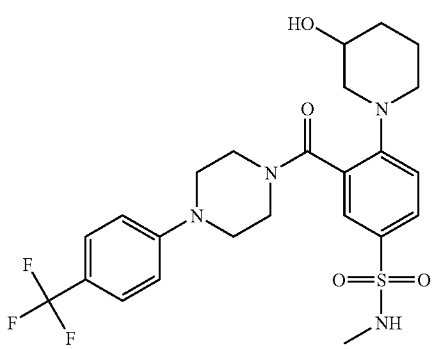 | 526.6 | rac-4-(3-Hydroxy-piperidin-1-yl)-N-methyl-3-[4-(4-trifluoromethyl-phenyl)-piperazine-1-carbonyl]-benzene sulfonamide | 1-(4-Trifluoromethyl-phenyl)-piperazine (commercial) and rac-2-(3-Hydroxy-piperidin-1-yl)-5-methylsulfamoyl-benzoic acid (example BZ) | 527.3 |
| 258 | 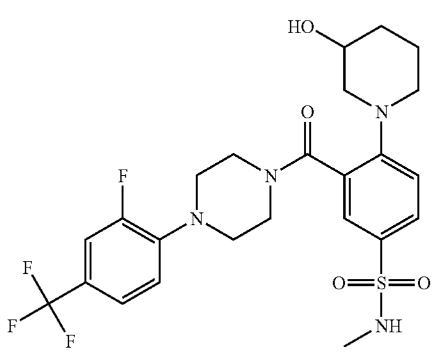 | 544.6 | rac-3-[4-(2-Fluoro-4-trifluoromethyl-phenyl)-piperazine-1-carbonyl]-4-(3-hydroxy-piperidin-1-yl)-N-methyl-benzene sulfonamide | 1-(2-Fluoro-4-trifluoromethyl-phenyl)-piperazine (example H) and rac-2-(3-Hydroxy-piperidin-1 yl)-5-methylsulfamoyl-benzoic acid (example BZ) | 545.3 |

TABLE 2-continued

| No. | Structure | MW | Systematic Name | Starting materials | MW found (MH+) |
|---|---|---|---|---|---|
| 259 | 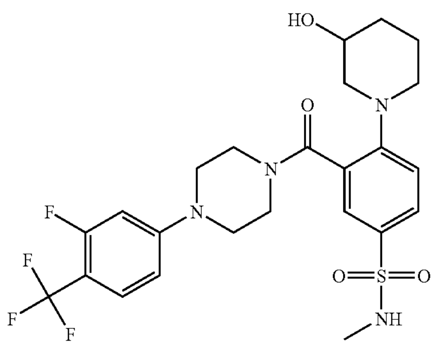 | 544.6 | rac-3-[4-(3-Fluoro-4-trifluoromethyl-phenyl)-piperazine-1-carbonyl]-4-(3-hydroxy-piperidin-1-yl)-N-methyl-benzene sulfonamide | 1-(3-Fluoro-4-trifluoromethyl-phenyl)-piperazine (example BC) and rac-2-(3-Hydroxy-piperidin-1-yl)-5-methylsulfamoyl-benzoic acid (example BZ) | 545.3 |
| 260 | 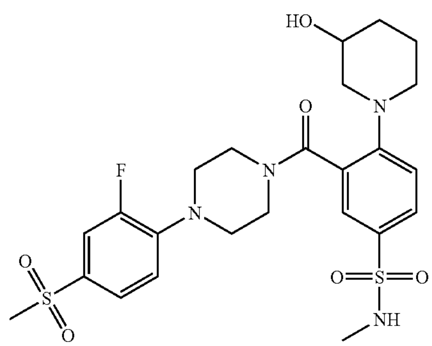 | 554.7 | rac-3-[4-(2-Fluoro-4-methanesulfonyl-phenyl)-piperazine-1-carbonyl]-4-(3-hydroxy-piperidin-1-yl)-N-methyl-benzene sulfonamide | 1-(2-Fluoro-4-methanesulfonyl-phenyl)-piperazine (commercial) and rac-2-(3-Hydroxy-piperidin-1-yl)-5-methylsulfamoyl-benzoic acid (example BZ) | 555.2 |
| 261 | 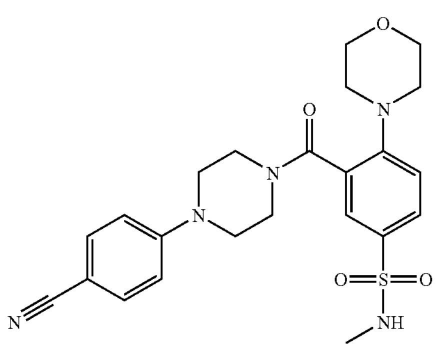 | 469.6 | 3-[4-(4-Cyano-phenyl)-piperazine-1-carbonyl]-N-methyl-4-morpholin-4-yl-benzene sulfonamide | 4-Piperazin-1-yl-benzonitrile (commercial) and 5-Methylsulfamoyl-2-morpholin-4-yl-benzoic acid (example AL) | 470.2 |
| 262 | 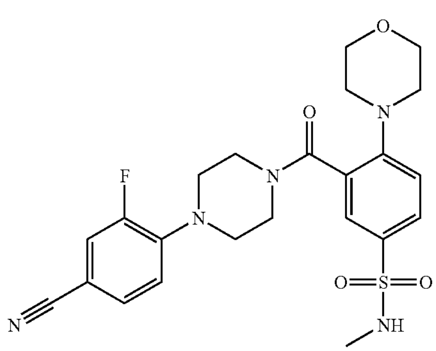 | 487.6 | 3-[4-(4-Cyano-2-fluoro-phenyl)-piperazine-1-carbonyl]-N-methyl-4-morpholin-4-yl-benzene sulfonamide | 3-Fluoro-4-piperazin-1-yl-benzonitrile (WO9625414) and 5-Methylsulfamoyl-2-morpholin-4-yl-benzoic acid (example AL) | 488.2 |

TABLE 2-continued

| No. | Structure | MW | Systematic Name | Starting materials | MW found (MH+) |
|---|---|---|---|---|---|
| 263 | 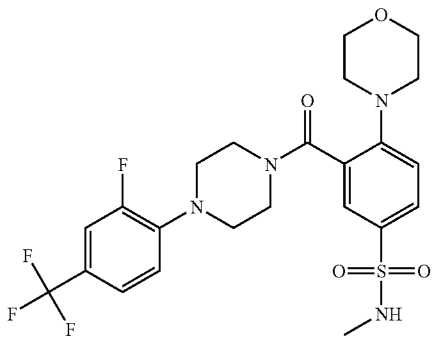 | 530.5 | 3-[4-(2-Fluoro-4-trifluoromethyl-phenyl)-piperazine-1-carbonyl]-N-methyl-4-morpholin-4-yl-benzenesulfonamide | 1-(2-Fluoro-4-trifluoromethyl-phenyl)-piperazine (example H) and 5-Methylsulfamoyl-2-morpholin-4-yl-benzoic acid (example AL) | 531.2 |
| 264 | 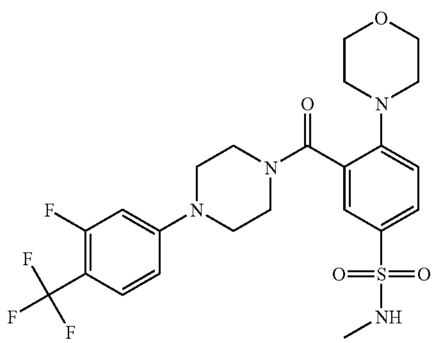 | 530.5 | 3-[4-(3-Fluoro-4-trifluoromethyl-phenyl)-piperazine-1-carbonyl]-N-methyl-4-morpholin-4-yl-benzenesulfonamide | 1-(3-Fluoro-4-trifluoromethyl-phenyl)-piperazine (example BC) and 5-Methylsulfamoyl-2-morpholin-4-yl-benzoic acid (example AL) | 531.2 |
| 265 | 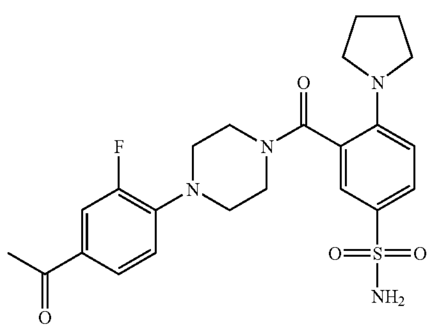 | 474.6 | 3-[4-(4-Acetyl-2-fluoro-phenyl)-piperazine-1-carbonyl]-4-pyrrolidin-1-yl-benzenesulfonamide | 1-(3-Fluoro-4-piperazin-1-yl-phenyl)-ethanone (WO9714690) and 2-Pyrrolidin-1-yl-5 sulfamoyl-benzoic acid (example CA) | 475.2 |
| 266 | 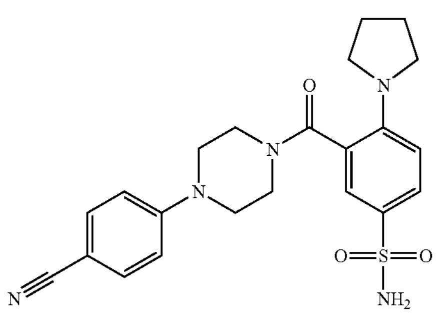 | 439.5 | 3-[4-(4-Cyano-phenyl)-piperazine-1-carbonyl]-4-pyrrolidin-1-yl-benzenesulfonamide | 4-Piperazin-1-yl-benzonitrile (commercial) and 2-Pyrrolidin-1-yl-5-sulfamoyl-benzoic acid (example CA) | 440.3 |

TABLE 2-continued

| No. | Structure | MW | Systematic Name | Starting materials | MW found (MH+) |
|---|---|---|---|---|---|
| 267 | 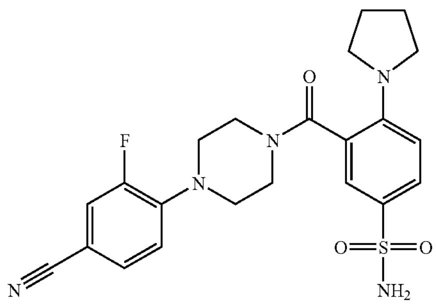 | 457.5 | 3-[4-(4-Cyano-2-fluoro-phenyl)-piperazine-1-carbonyl]-4-pyrrolidin-1-yl-benzenesulfonamide | 3-Fluoro-4-piperazin-1-yl-benzonitrile (WO9625414) and 2-Pyrrolidin-1-yl-5-sulfamoyl-benzoic acid (example CA) | 458.3 |
| 268 | 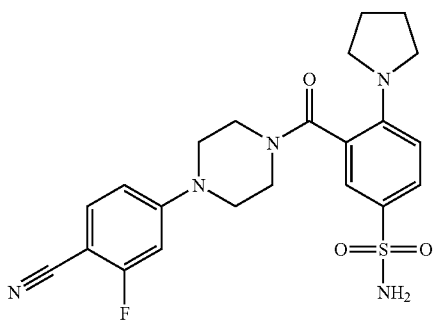 | 457.6 | 3-[4-(4-Cyano-3-fluoro-phenyl)-piperazine-1-carbonyl]-4-pyrrolidin-1-yl-benzenesulfonamide | 2-Fluoro-4-piperazin-1-yl-benzonitrile (WO9808835) and 2-Pyrrolidin-1-yl-5-sulfamoyl-benzoic acid (example CA) | 458.3 |
| 269 | 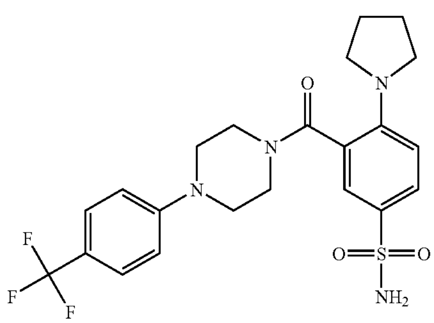 | 482.5 | 4-Pyrrolidin-1-yl-3-[4-(4-trifluoromethyl-phenyl)-piperazine-1-carbonyl]-benzenesulfonamide | 1-(4-Trifluoromethyl-phenyl)-piperazine (commercial) and 2-Pyrrolidin-1-yl-5-sulfamoyl-benzoic acid (example CA) | 483.2 |
| 270 | 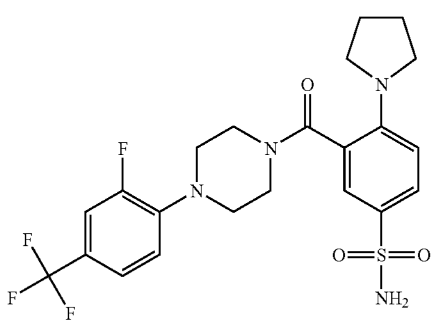 | 500.5 | 3-[4-(2-Fluoro-4-trifluoromethyl-phenyl)-piperazine-1-carbonyl]-4-pyrrolidin-1-yl-enzenesulfonamide | 1-(2-Fluoro-4-trifluoromethyl-phenyl)-piperazine (example H) and 2-Pyrrolidin-1-yl-5-sulfamoyl-benzoic acid (example CA) | 501.2 |

TABLE 2-continued

| No. | Structure | MW | Systematic Name | Starting materials | MW found (MH+) |
|---|---|---|---|---|---|
| 271 | 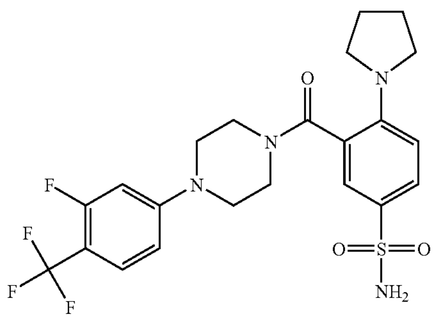 | 500.5 | 3-[4-(3-Fluoro-4-trifluoromethyl-phenyl)-piperazine-1-carbonyl]-4-pyrrolidin-1-yl-enzenesulfonamide | 1-(3-Fluoro-4-trifluoromethyl-phenyl)-piperazine (example BC) and 2-Pyrrolidin-1-yl-5-sulfamoyl-benzoic acid (example CA) | 501.2 |
| 272 | 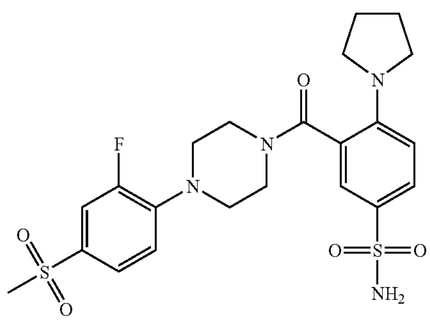 | 510.6 | 3-[4-(2-Fluoro-4-methanesulfonyl-phenyl)-piperazine-1-carbonyl]-4-pyrrolidin-1-yl-benzene sulfonamide | 1-(2-Fluoro-4-methane sulfonyl-phenyl)-piperazine (commercial) and 2-Pyrrolidin-1-yl-5-sulfamoyl-benzoic acid (example CA) | 511.3 |
| 273 | 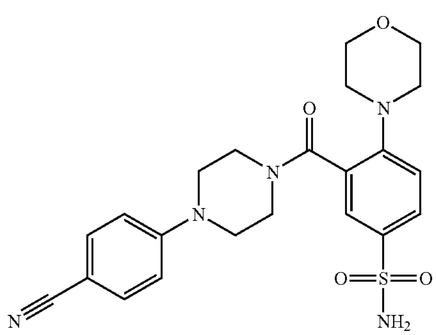 | 455.5 | 3-[4-(4-Cyano-phenyl)-piperazine-1-carbonyl]-4-morpholin-4-yl-benzenesulfonamide | 4-Piperazin-1-yl-benzonitrile (commercial) and 2-Morpholin-4-yl-5-sulfamoyl-benzoic acid (example CB) | 456.2 |
| 274 | 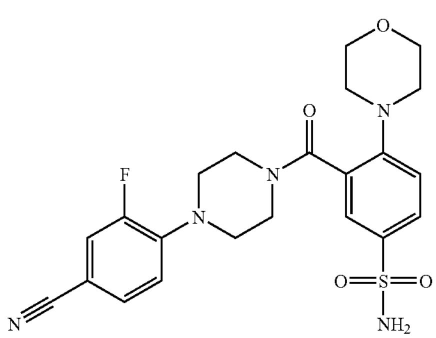 | 473.5 | 3-[4-(4-Cyano-2-fluoro-phenyl)-piperazine-1-carbonyl]-4-morpholin-4-yl-benzenesulfonamide | 3-Fluoro-4-piperazin-1-yl-benzonitrile (WO9625414) and 2-Morpholin-4-yl-5-sulfamoyl-benzoic acid (example CB) | 474.1 |

TABLE 2-continued

| No. | Structure | MW | Systematic Name | Starting materials | MW found (MH+) |
|---|---|---|---|---|---|
| 275 | 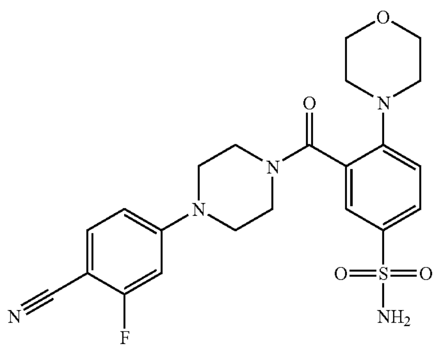 | 473.5 | 3-[4-(4-Cyano-3-fluoro-phenyl)-piperazine-1-carbonyl]-4-morpholin-4-yl-benzenesulfonamide | 2-Fluoro-4-piperazin-1-yl-benzonitrile (WO9808835) and 2-Morpholin-4-yl-5-sulfamoyl-benzoic acid (example CB) | 474.2 |
| 276 | 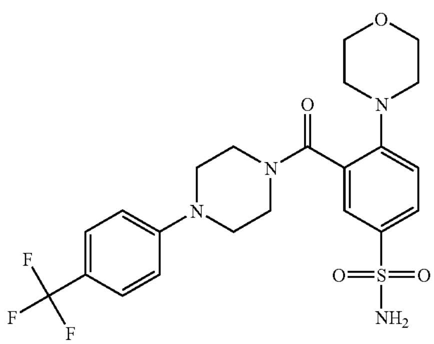 | 498.5 | 4-Morpholin-4-yl-3-[4-(4-trifluoromethyl-phenyl)-piperazine-1-carbonyl]-benzene sulfonamide | 1-(4-Trifluoromethyl-phenyl)-piperazine (commercial) and 2-Morpholin-4-yl-5-sulfamoyl-benzoic acid (example CB) | 499.3 |
| 277 | 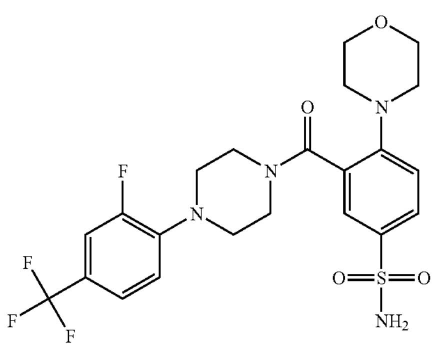 | 516.5 | 3-[4-(2-Fluoro-4-trifluoromethyl-phenyl)-piperazine-1-carbonyl]-4-morpholin-4-yl-benzenesulfonamide | 1-(2-Fluoro-4-trifluoromethyl-phenyl)-piperazine (example H) and 2-Morpholin-4-yl-5-sulfamoyl-benzoic acid (example CB) | 517.2 |
| 278 | 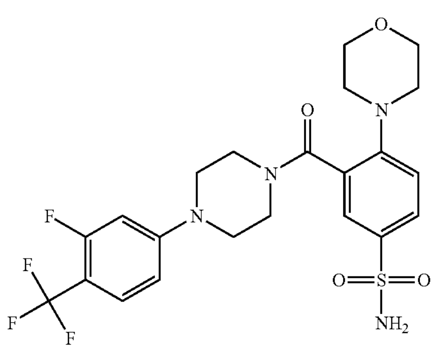 | 516.5 | 3-[4-(3-Fluoro-4-trifluoromethyl-phenyl)-piperazine-1-carbonyl]-4-morpholin-4-yl-benzenesulfonamide | 1-(3-Fluoro-4-trifluoromethyl-phenyl)-piperazine (example BC) and 2-Morpholin-4-yl-5-sulfamoyl-benzoic acid (example CB) | 517.2 |

TABLE 2-continued

| No. | Structure | MW | Systematic Name | Starting materials | MW found (MH+) |
|---|---|---|---|---|---|
| 279 | 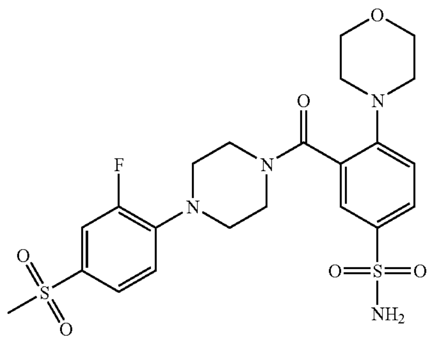 | 526.6 | 3-[4-(2-Fluoro-4-methanesulfonyl-phenyl)-piperazine-1-carbonyl]-4-morpholin-4-yl-benzenesulfonamide | 1-(2-Fluoro-4-methanesulfonyl-phenyl)-piperazine (commercial) and 2-Morpholin-4-yl-5-sulfamoyl-benzoic acid (example CB) | 527.2 |

Example CC 3,4-Difluoro-N-methyl-5-[4-(4-trifluoromethyl-phenyl)-piperazine-1-carbonyl]-benzenesulfonamide

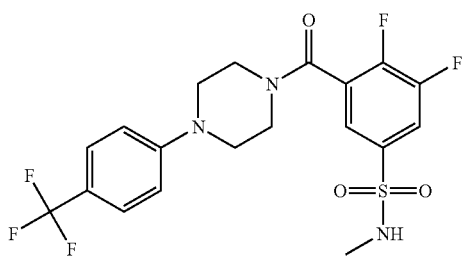

(a) 5-Chlorosulfonyl-2,3-difluoro-benzoic acid

To 2,3-difluoro-benzoic acid (3 g) was added to a solution of chlorosulfonic acid and the reaction mixture was stirred for 2 hours at room temperature. After such time, the reaction mixture was poured onto ice. The resulting solid precipitate was then filtered off and dried in vacuo to yield the title compound as a light grey solid (4.8 g, mp=109-114° C., MS (EI): 256.0 (M+) and was used directly in the next step without any further purification.

(b)-2,3-Difluoro-5-methylsulfamoyl-benzoic acid

To a solution of 5-chlorosulfonyl-2,3-difluoro-benzoic acid (400 mg) in dichloromethane (5 mL) at −10° C. was added a solution of methylamine in ethanol (8M). The reaction mixture was then stirred at −10° C. for 5 minutes and poured over 1N NaOH solution. The aqueous phase was extracted with diethyl ether twice and then acidified with a concentrated solution of HCl. The aqueous phase was then extracted 3 times with a mixture of dichoromethane:ethanol (9:1) and the combined organic layer were dried over sodium sulfate and concentrated in vacuo to yield the title compound as a light brown solid (390 mg, mp=191-194° C., MS (m/e): 250.1 (M−H, 100%).

(c) 3,4-Difluoro-N-methyl-5-[4-(4-trifluoromethyl-phenyl)-piperazine-1-carbonyl]-benzenesulfonamide The title compound was prepared in analogy to Example BO by reaction of 2,3-Difluoro-5-methylsulfamoyl-benzoic acid and 1-(4-trifluoromethylphenyl)piperazine (ABCR F07741NB, [30459-17-7]) to yield the title compound as a light yellow amorpous solid. (m/e): 462.1 (M−H, 100%).

Example CD 2,4-Difluoro-N-methyl-3-[4-(4-trifluoromethyl-phenyl)-piperazine-1-carbonyl]-benzenesulfonamide

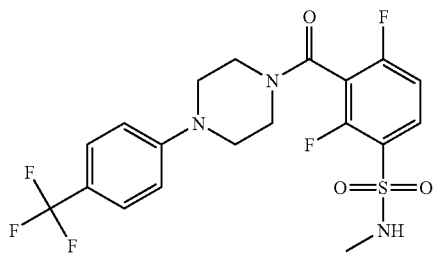

The title compound was prepared in analogy to Example CC using 3-chlorosulfonyl-2,6-difluoro-benzoic acid [142576-91-8] to yield the title compound as a light brown solid (m/e): 462.3 (M−H, 100%).

Example 280

(5-Methanesulfonyl-2-thiomorpholin-4-yl-phenyl)-[4-(4-trifluoromethyl-phenyl)-piperazin-1-yl]-methanone The title compound was prepared according to the procedure described for example 202 from (2-Chloro-5-methanesulfonyl-phenyl)-[4-(4-trifluoromethyl-phenyl)-piperazin-1- yl]-methanone (example BO) and thiomorpholine to yield the title compound as a pale yellow solid. MS (m/e): 514.5 (M+H, 100%).

Example 281

3-Fluoro-N-methyl-4-morpholin-4-yl-5-[4-(4-trifluoromethyl-phenyl)-piperazine-1-carbonyl]-benzenesulfonamide The title compound was prepared according to the procedure described for example 202 from 3,4-Difluoro-N-methyl-5-[4-(4-trifluoromethyl-phenyl)-piperazine-1-carbonyl]-benzenesulfonamide (example CC) and morpholine to yield the title compound as a colourless foam, MS (m/e): 531.1 (M+H, 100%).

Example 282

2-Fluoro-N-methyl-4-morpholin-4-yl-3-[4-(4-trifluoromethyl-phenyl)-piperazine-1-carbonyl]-benzenesulfonamide The title compound was prepared according to the procedure described for example 202 from 2,4-Difluoro-N-methyl-3-[4-(4-trifluoromethyl-phenyl)-piperazine-1-carbonyl]-benzenesulfonamide (example CD) and morpholine to yield the title compound as a colourless foam, MS (m/e): 529.3 (M+H, 100%).

Example CE 2,3-Difluoro-4-piperazin-1-yl-benzonitrile-trifluoroacetic acid

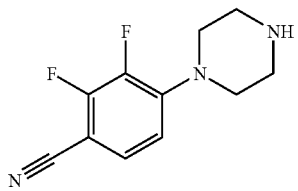 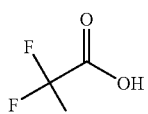

(a) 4-(4-Cyano-2,3-difluoro-phenyl)-piperazine-1-carboxylic acid tert-butyl ester To a solution of N-Boc-piperazine (0.65 g) in DMA (20 mL) was slowly added a solution of 2,3,4-trifluorobenzonitrile (0.49 g) in DMA (10 mL). The reaction mixture was stirred for 2 hours at 80° C. After such time the solvent was removed in vacuo and purified by column chromatography (SiO$_2$) to yield the title compound as white solid (0.76 g).

(b) 2,3-Difluoro-4-piperazin-1-yl-benzonitrile-trifluoro-acetic acid

To a solution of 4-(4-Cyano-2,3-difluoro-phenyl)-piperazine-1-carboxylic acid tert-butyl ester (0.72 g) in dichloromethane (5 mL) was added trifluoroacetic acid and the reaction mixture was stirred at room temperature for 30 minutes. After such time the reaction mixture was concentrated in vacuo to yield the title compound (0.63 g). MS (m/e): 224.3 (M+H$^+$, 100%).

Example CF 2,5-Difluoro-4-piperazin-1-yl-benzonitrile-trifluoroacetic acid

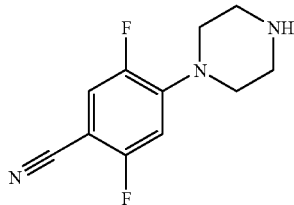 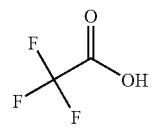

Example CF was prepared in analogy to Example CE using 2,4,5-trifluorobenzonitrile. MS (m/e): 224.3 (M+H$^+$, 100%).

Example CG 3,5-Difluoro-4-piperazin-1-yl-benzonitrile trifluoro-acetic acid

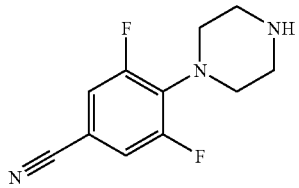 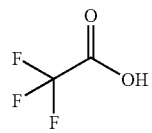

Compound CG was prepared in analogy to compound CE using 3,4,5-trifluorobenzonitrile. MS (m/e): 224.1 (M+H$^+$, 100%).

Example CH 2,6-Difluoro-4-piperazin-1-yl-benzonitrile trifluoro-acetic acid

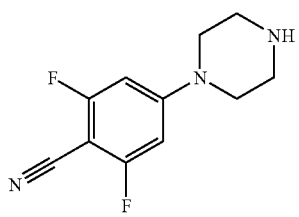 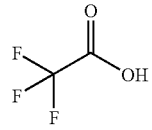

Compound CH was prepared in analogy to compound CE using 2,4,6-trifluorobenzonitrile. MS (m/e): 224.1 (M+H+, 100%).

Example CI 4-piperazin-1-yl-6-trifluoromethyl-pyrimidine trifluoro-acetic acid

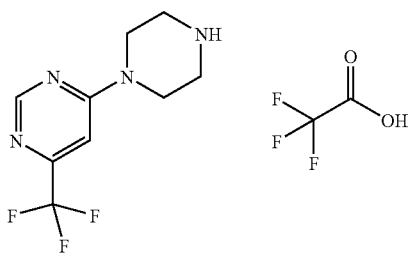

Compound CI was prepared in analogy to compound CE using 4-chloro-6-trifluoromethyl-pyrimidine [37552-81-1]. MS (m/e): 233.1 (M+H+).

Example CJ 2-piperazin-1-yl-5-trifluoromethyl-pyrimidine

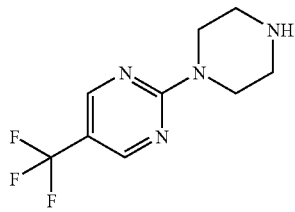

(a) 2-(4-Benzyl-piperazin-1-yl)-5-trifluoromethyl-pyrimidine

To a solution of (3-Dimethylamino-2-trifluoromethyl-allylidene)-dimethyl-ammonium chloride ([176214-18-9], 0.60 g) in acetonitrile (10 mL) was added 4-Benzyl-piperazine-1-carboxamidine hydrochloride ([7773-69-5], 0.66 g) and triethylamine (0.87 mL) and the reaction mixture was stirred for 3 hours at room temperature. After such time the reaction mixture was concentrated in vacuo and purified by column chromatography to yield the title compound as a light yellow solid (0.79 g). MS (m/e): 323.4 (M+H+).

(b) 2-piperazin-1-yl-5-trifluoromethyl-pyrimidine

To a solution of 2-(4-Benzyl-piperazin-1-yl)-5-trifluoromethyl-pyrimidine (0.63 g) in methanol was added Palladium-C (Degussa EL101N; 5%) and the reaction mixture was heated at 60° C. under hydrogen atmosphere. The reaction mixture was then allowed to cool down to room temperature, the catalyst was filtered of and solvent was removed in vacuo to yield the title compound as a colorless solid (0.41 g). MS (m/e): 233.1 (M+H+).

According to the procedure described for the synthesis of Example 123 further derivatives have been synthesised from acid derivatives and piperazine derivatives and comprise Examples 283-289 in Table 3.

TABLE 3

| No. | Structure | MW | Systematic Name | Starting materials | MW found (MH+) |
|---|---|---|---|---|---|
| 283 | 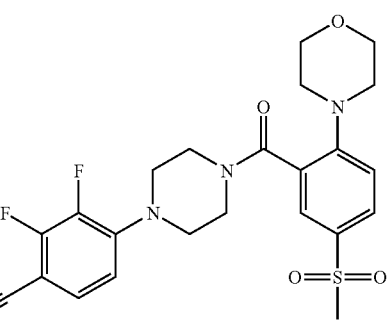 | 490.528 | 2,3-Difluoro-4-[4-(5-methanesulfonyl-2-morpholin-4-yl-benzoyl)-piperazin-1-yl]-benzonitrile | 2,3-Difluoro-4-piperazin-1-yl-benzonitrile-trifluoro-acetic acid (compound CE) and 5-Methanesulfonyl-2-morpholin-4-yl-benzoic acid (example AG) | 491.1 |

TABLE 3-continued

| No. | Structure | MW | Systematic Name | Starting materials | MW found (MH+) |
|---|---|---|---|---|---|
| 284 | 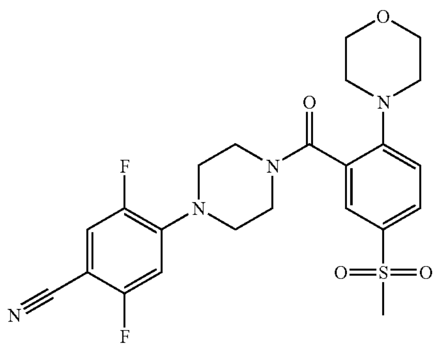 | 490.528 | 2,5-Difluoro-4-[4-(5-methanesulfonyl-2-morpholin-4-yl-benzoyl)-piperazin-1-yl]-benzonitrile | 2,5-Difluoro-4-piperazin-1-yl-benzonitrile-trifluoro-acetic acid (compound CF) and 5-Methanesulfonyl-2-morpholin-4-yl-benzoic acid (example AG) | 491.1 |
| 285 | 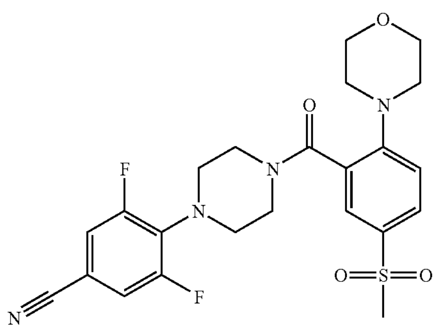 | 490.528 | 3,5-Difluoro-4-[4-(5-methanesulfonyl-2-morpholin-4-yl-benzoyl)-piperazin-1-yl]-benzonitrile | 3,5-Difluoro-4-piperazin-1-yl-benzonitrile trifluoro-acetic acid (compound CG) and 5-Methanesulfonyl-2-morpholin-4-yl-benzoic acid (example AG) | 491.1 |
| 286 | 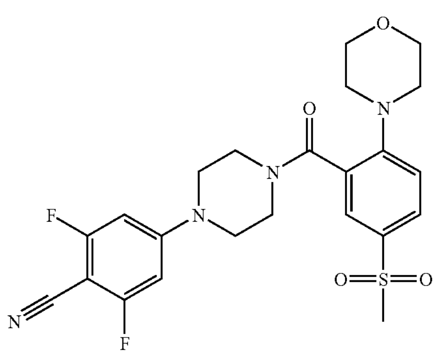 | 490.528 | 2,6-Difluoro-4-[4-(5-methanesulfonyl-2-morpholin-4-yl-benzoyl)-piperazin-1-yl]-benzonitrile | 2,6-Difluoro-4-piperazin-1-yl-benzonitrile trifluoro-acetic acid (compound CH) and 5-Methanesulfonyl-2-morpholin-4-yl-benzoic acid (example AG) | 508.4 (M+NH4+) |
| 287 | 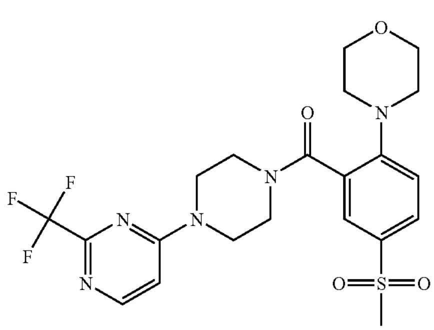 | 499.51 | (5-Methanesulfonyl-2-morpholin-4-yl-phenyl)-[4-(2-trifluoromethyl-pyrimidin-4-yl)-piperazin-1-yl]-methanone | 4-Piperazin-1-yl-2-trifluoromethyl-pyrimidine trifluoro-acetic acid (WO030249) and 5-Methanesulfonyl-2-morpholin-4-yl-benzoic acid (example AG) | 500.4 |

TABLE 3-continued

| No. | Structure | MW | Systematic Name | Starting materials | MW found (MH⁺) |
|---|---|---|---|---|---|
| 288 | 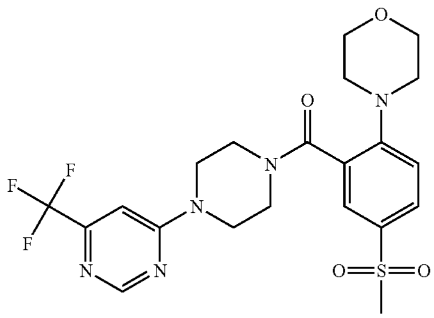 | 499.51 | (5-Methanesulfonyl-2-morpholin-4-yl-phenyl)-[4-(6-trifluoromethyl-pyrimidin-1-yl)-piperazin-1-yl]-methanone | 4-Piperazin-1-yl-6-trifluoromethyl-pyrimidine trifluoro-acetic acid (compound CI) and 5-Methanesulfonyl-2-morpholin-4-yl-benzoic acid (example AG) | 500.3 |
| 289 | 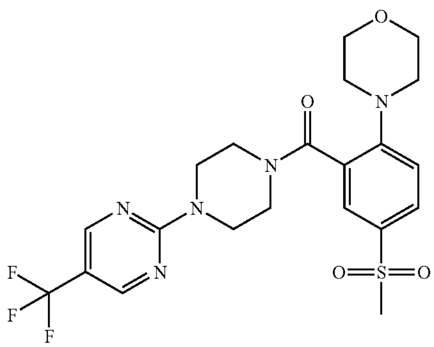 | 499.511 | (5-Methanesulfonyl-2-morpholin-4-yl-phenyl)-[4-(5-trifluoromethyl-pyrimidin-2-yl)-piperazin-1-yl]-methanone | 2-Piperazin-1-yl-5-trifluoromethyl-pyrimidine (compound CJ) and 5-Methanesulfonyl-2-morpholin-4-yl-benzoic acid (example AG) | 500.3 |

Example CK (2-Iodo-5-methanesulfonyl-phenyl)-[4-(4-trifluoromethyl-phenyl)-piperazin-1-yl]-methanone

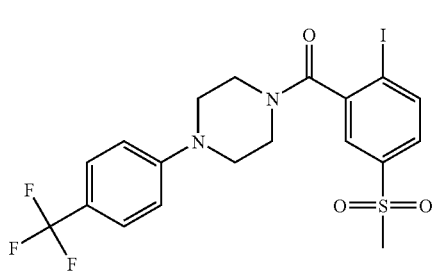

Example CK was prepared in analogy to Example 123 from 2-Iodo-5-methanesulfonyl-benzoic acid (example BQ) and 1-(4-Trifluoromethyl-phenyl)-piperazine (commercial). MS (m/e): 539.1 (M+H⁺, 100%).

Example CL

3-Fluoro-4-[4-(2-iodo-5-methanesulfonyl-benzoyl)-piperazin-1-yl]-benzonitrile

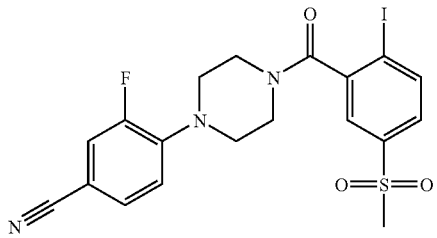

Example CL was prepared in analogy to Example 123 from 2-Iodo-5-methanesulfonyl-benzoic acid (example BQ) and 3-Fluoro-4-piperazin-1-yl-benzonitrile (WO9625414). MS (m/e): 514.0 (M+H⁺, 100%).

Example CM

[4-(2-Fluoro-4-methanesulfonyl-phenyl)-piperazin-1-yl]-(2-iodo-5-methanesulfonyl-phenyl)-methanone

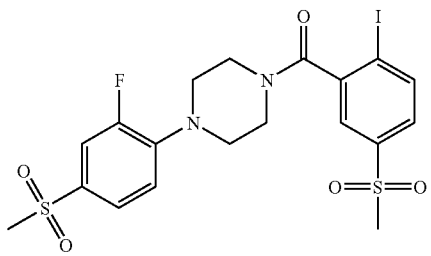

Example CM was prepared in analogy to Example 123 from 2-Iodo-5-methanesulfonyl-benzoic acid (example BQ) and 1-(2-Fluoro-4-methanesulfonyl-phenyl)-piperazine (commercial). MS (m/e): 567.0 (M+H$^+$, 100%).

Example CN

[4-(2-Fluoro-4-trifluoromethyl-phenyl)-piperazin-1-yl]-(2-iodo-5-methanesulfonyl-phenyl)-methanone

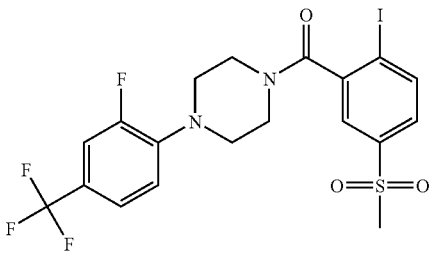

Example CN was prepared in analogy to Example 123 from 2-Iodo-5-methanesulfonyl-benzoic acid (example BQ) and 1-(2-Fluoro-4-trifluoromethyl-phenyl)-piperazine (example H). MS (m/e): 574.2 (M+NH$_4^+$, 100%).

Example CR (5-Bromo-2-morpholin-4-yl-phenyl)-[4-(4-trifluoromethyl-phenyl)-piperazin-1-yl]-methanone

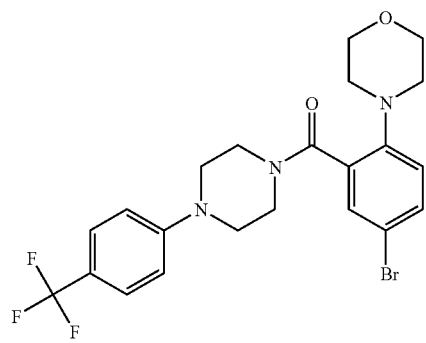

Example CR was prepared in analogy to Example 46 from 5-Bromo-2-morpholin-4-yl-benzoyl chloride (example BI) and 1-(4-Trifluoromethyl-phenyl)-piperazine (commercial). MS (m/e): 500.1 (M+H$^+$, 100%).

Example 290

(2-Imidazol-1-yl-5-methanesulfonyl-phenyl)-[4-(4-trifluoromethyl-phenyl)-piperazin-1-yl]-methanone The title compound was prepared according to the procedure described for example 199 from (2-Iodo-5-methanesulfonyl-phenyl)-[4-(4-trifluoromethyl-phenyl)-piperazin-1-yl]-methanone (compound CK) and imidazole (20%, light grey solid, MS (m/e): 479.2 (M+H, 100%)

Example 291

5-Methanesulfonyl-2-(2-methyl-imidazol-1-yl)-phenyl]-[4-(4-trifluoromethyl-phenyl)-piperazin-1-yl]-methanone The title compound was prepared according to the procedure described for example 199 from (2-Iodo-5-methanesulfonyl-phenyl)-[4-(4-trifluoromethyl-phenyl)-piperazin-1-yl]-methanone (compound CK) and 2-methyl-imidazole (10% yield, yellow solid, MS (m/e): 493.1 (M+H, 100%)

Example 292

[5-Methanesulfonyl-2-(4-methyl-imidazol-1-yl)-phenyl]-[4-(4-trifluoromethyl-phenyl)-piperazin-1-yl]-methanone The title compound was prepared according to the procedure described for example 199 from (2-Iodo-5-methanesulfonyl-phenyl)-[4-(4-trifluoromethyl-phenyl)-piperazin-1-yl]-methanone (compound CK) and 4-Methyl-1H-imidazole (32% yield, white solid, MS (m/e): 493.4 (M+H, 100%)

Example 293

[[5-(2-Cyclopropyl-imidazol-1-yl)-2-morpholin-4-yl-phenyl]-[4-(4-trifluoromethyl-phenyl)-piperazin-1-yl]-methanone The title compound was prepared according to the procedure described for example 199 from (5-Bromo-2-morpholin-4-yl-phenyl)-[4-(4-trifluoromethyl-phenyl)-piperazin-1-yl]-methanone (compound CR) and 2-Cyclopropyl-1H-imidazole (CAS: 89532-38-7) (16% yield, white solid, MS (m/e): 526.3 (M+H, 100%)

Example 294

(5-Methanesulfonyl-2-pyrazol-1-yl-phenyl)-[4-(4-trifluoromethyl-phenyl)-piperazin-1-yl]-methanone In a tube were added successively (2-Iodo-5-methanesulfonyl-phenyl)-[4-(4-trifluoromethyl-phenyl)-piperazin-1-yl]-methanone (compound CK, 0.1 g, 0.19 mmol), pyrazole (15 mg, 0.223 mmol), potassium carbonate (51 mg, 0.37 mmol), CuI (7 mg, 0.037 mmol), Trans-1,2-diaminocyclohexane (9 ul, 0.07 mmol) and dioxane (0.4 ml). The mixture was heated under argon at 120° C. for 24 hours. The reaction mixture was cooled to room temperature and quenched with water/dichloromethane. The aqueous layer was extracted twice with dichloromethane. The organic layers were combined, dried over Na$_2$SO$_4$, filtered and the solvent was

Example 295

[5-Methanesulfonyl-2-(3-methyl-pyrazol-1-yl)-phenyl]-[4-(4-trifluoromethyl-phenyl)-piperazin-1-yl]-methanone The title compound was prepared according to the procedure described for example 294 from (2-Iodo-5-methanesulfonyl-phenyl)-[4-(4-trifluoromethyl-phenyl)-piperazin-1-yl]-methanone (compound CK) and 3-Methyl-1H-pyrazole (15% yield, white solid, MS (m/e): 493.5 (M+H, 100%)

Example 296

[5-Methanesulfonyl-2-(4-methyl-pyrazol-1-yl)-phenyl]-[4-(4-trifluoromethyl-phenyl)-piperazin-1-yl]-methanone The title compound was prepared according to the procedure described for example 294 from (2-Iodo-5-methanesulfonyl-phenyl)-[4-(4-trifluoromethyl-phenyl)-piperazin-1-yl]-methanone (compound CK) and 4-Methyl-1H-pyrazole (43% yield, white solid, MS (m/e): 493.1 (M+H, 100%)

Example 297

3-Fluoro-4-{4-[5-methanesulfonyl-2-(4-methyl-pyrazol-1-yl)-benzoyl]-piperazin-1-yl}-benzonitrile The title compound was prepared according to the procedure described for example 294 from 3-Fluoro-4-[4-(2-iodo-5-methanesulfonyl-benzoyl)-piperazin-1-yl]-benzonitrile (compound CL) and 4-Methyl-1H-pyrazole (20% yield, white foam, MS (m/e): 468.3 (M+H, 100%)

Example 298

[4-(2-Fluoro-4-methanesulfonyl-phenyl)-piperazin-1-yl]-[5-methanesulfonyl-2-(4-methyl-pyrazol-1-yl)-phenyl]-methanone The title compound was prepared according to the procedure described for example 294 from [4-(2-Fluoro-4-methanesulfonyl-phenyl)-piperazin-1-yl]-(2-iodo-5-methanesulfonyl-phenyl)-methanone (compound CM) and 4-Methyl-1H-pyrazole (29% yield, yellow foam, MS (m/e): 521.3 (M+H, 100%)

Example 299

[4-(2-Fluoro-4-trifluoromethyl-phenyl)-piperazin-1-yl]-[5-methanesulfonyl-2-(4-methyl-pyrazol-1-yl)-phenyl]-methanone The title compound was prepared according to the procedure described for example 294 from [4-(2-Fluoro-4-trifluoromethyl-phenyl)-piperazin-1-yl]-(2-iodo-5-methanesulfonyl-phenyl)-methanone (compound CN) and 4-Methyl-1H-pyrazole (30% yield, light brown solid, MS (m/e): 511.2 (M+H, 100%)

Example 300

(5-Methanesulfonyl-2-[1,2,4]triazol-1-yl-phenyl)-[4-(4-trifluoromethyl-phenyl)-piperazin-1-yl]-methanone In a tube were added successively (2-Iodo-5-methanesulfonyl-phenyl)-[4-(4-trifluoromethyl-phenyl)-piperazin-1-yl]-methanone (compound CK, 0.1 g, 0.19 mmol), 1,2,4-triazole (11 mg, 0.155 mmol), potassium phosphate (71 mg, 0.326 mmol), CuI (7 mg, 0.037 mmol), (1R,2R)-diaminomethylcyclohexane (2.3 mg, 0.015 mmol) and DMF (1 ml). The mixture was heated under argon at 120° C. for 24 hours. The reaction mixture was cooled to room temperature and quenched with water/dichloromethane. The aqueous layer was extracted twice with dichloromethane. The organic layers were combined, dried over $Na_2SO_4$, filtered and the solvent was removed in vacuo. The crude oil was chromatographed over silicagel: eluent: heptane/ethylacetate: 0-100% to provide the title compound as a light grey solid (5 mg, 6%), MS (m/e): 480.4 (M+H, 100%)

Example 301

(2-Cyclobutylamino-5-methanesulfonyl-phenyl)-[4-(4-trifluoromethyl-phenyl)-piperazin-1-yl]-methanone A solution of (2-Iodo-5-methanesulfonyl-phenyl)-[4-(4-trifluoromethyl-phenyl)-piperazin-1-yl]-methanone (compound CK, 0.05 g, 0.09 mmol) and of cyclobutylamine (0.1 ml) in dimethylacetamide was heated in a microwave oven (180 deg) for 10 min before being concentrated in vacuo. The residue was dissolve in ethyl acetate, washed with water dried over sodiumsulfate, filtered and concentrated. The residue was purified by column chromatography ($SiO_2$, 5 g, Heptane/EtOAc 0-50%) to give the title compound as a white foam (24 mg, 54%). MS (m/e): 482.5 (M+H$^+$, 100%).

Example 302

[2-(Cyclopropylmethyl-amino)-5-methanesulfonyl-phenyl]-[4-(4-trifluoromethyl-phenyl)-piperazin-1-yl]-methanone The title compound was prepared according to the procedure described for example 301 from (2-Iodo-5-methanesulfonyl-phenyl)-[4-(4-trifluoromethyl-phenyl)-piperazin-1-yl]-methanone (compound CK) and Cyclopropanemethylamine (40% yield, white foam, MS (m/e): 482.5 (M+H, 100%)

Example 303

(2-Isobutylamino-5-methanesulfonyl-phenyl)-[4-(4-trifluoromethyl-phenyl)-piperazin-1-yl]-methanone The title compound was prepared according to the procedure described for example 301 from (2-Iodo-5-methanesulfonyl-phenyl)-[4-(4-trifluoromethyl-phenyl)-piperazin-1-yl]-methanone (compound CK) and Isobutylamine (49% yield, off white foam, MS (m/e): 484.5 (M+H, 100%)

At the top of the first column: removed in vacuo. The crude oil was chromatographed over silicagel: eluent: heptane/ethylacetate: 0-5% to provide the title compound as a light grey powder (19 mg, 21%), MS (m/e): 479.1 (M+H, 100%)

Example 304 rac-{5-Methanesulfonyl-2-[(tetrahydro-furan-2-ylmethyl)-amino]-phenyl}-[4-(4-trifluoromethyl-phenyl)-piperazin-1-yl]-methanone The title compound was prepared according to the procedure described for example 301 from (2-Iodo-5-methanesulfonyl-phenyl)-[4-(4-trifluoromethyl-phenyl)-piperazin-1-yl]-methanone (compound CK) and tetrahydrofurfurylamine (28% yield, MS (m/e): 512.4 (M+H, 100%)

Example CO 1-(6-Trifluoromethyl-pyridin-3-yl)-piperazine

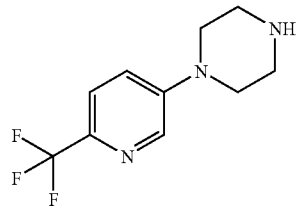

The compound was prepared in analogy to example H from 5-Bromo-2-trifluoromethyl-pyridine [436799-32-5]. MS (m/e): 232.1 (M+H$^+$, 100%)

Example CP 1-(3-Fluoro-5-trifluoromethyl-pyridin-2-yl)-piperazine

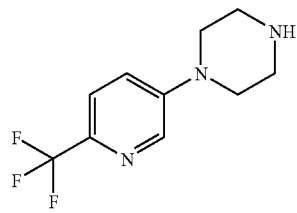

The compound was prepared in analogy to example CE from 2,3-Difluoro-5-trifluoromethyl-pyridine (EP0104715). MS (m/e): 250.2 (MH$^+$, 100%)

Example CO 1-(6-Methyl-pyridin-3-yl)-piperazine

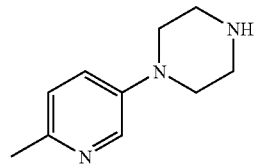

The compound was prepared in analogy to example H from 5-Bromo-2-methyl-pyridine (commercial). MS (m/e): 178.1 (M+H$^+$, 100%)

Example CS 5-piperazin-1-yl-2-trifluoromethyl-pyrimidine

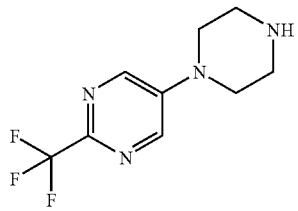

(a) 5-Chloro-2-trifluoromethyl-pyrimidine

To a solution of 38 mmol trifluoroacetamidine in 70 ml acetonitrile was added 37.92 mmol ((Z)-2-Chloro-3-dimethylamino-allylidene)-dimethyl-ammonium hexafluoro phosphate (CAS: 291756-76-8) followed by 45.5 mmol triethylamine. The yellow solution was stirred at room temperature for 5 hours, then poured onto water and extracted 3 times with ether. The combined extracts were dried over sodium sulfate, filtered and distilled at 760 mm Hg to provide the title compound. MS (m/e): 182.2 (M$^+$, 100%)

(b) 4-(2-Trifluoromethyl-pyrimidin-5-yl)-piperazine-1-carboxylic acid tert-butyl ester 0.26 mmol 5-Chloro-2-trifluoromethyl-pyrimidine was added to 0.26 mmol piperazine-1-carboxylic acid tert-butyl ester in 1.5 ml dimethylacetamide and the reaction mixture was stirred at 15° C. for 10 min. in a microwave oven. After such time the reaction mixture was concentrated and the residue was then purified by column chromatography (SiO$_2$, Heptane/EtOAc) to yield the title compound. MS (m/e): 333.2 (M+H$^+$, 100%)

(c) 5-piperazin-1-yl-2-trifluoromethyl-pyrimidine

The title compound was prepared in analogy to Example H from 4-(2-trifluoromethyl-pyrimidin-5-yl)-piperazine-1-carboxylic acid tert-butyl ester MS (m/e): 233.0 (M+H$^+$, 100%)

Example CT 3-piperazin-1-yl-6-trifluoromethyl-pyridazine

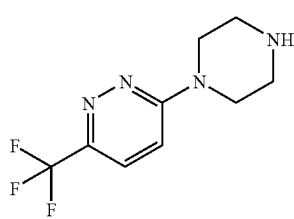

The title compound was prepared in analogy to Example CS (b-c) from 3-Chloro-6-trifluoromethyl-pyridazine (CAS: 258506-68-2). MS (m/e): 233.0 (M+H$^+$, 100%)

Example CU

Dimethyl-(4-piperazin-1-yl-[1,3,5]triazin-2-yl)-amine

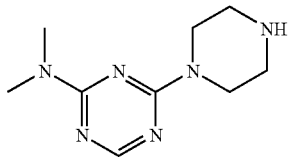

(a) 4-(4-Chloro-[1,3,5]triazin-2-yl)-piperazine-1-carboxylic acid tert-butyl ester A solution of 11 mmol of 2,4-dichlorotriazine (WO 02/083654) in 20 ml of acetonitrile was chilled and treated with 11 mmol of triethylamine and 11 mmol of N-BOC-piperazine. The reaction mixture was stirred for 2 hours at 0° C. then for 2 hours at room temperature. Addition of 100 ml brine and extraction with ethyl acetate yielded the crude product which was purified through trituration in ethyl acetate. MS (m/e): 300.3 (MH+, 100%)

(b) 4-(4-Dimethylamino-[1,3,5]triazin-2-yl)-piperazine-1-carboxylic acid tert-butyl ester A solution of 2 mmol of 4-(4-Chloro-[1,3,5]triazin-2-yl)-piperazine-1-carboxylic acid tert-butyl ester in 15 ml of 2M dimethylamine in methanol was stirred at room temperature for 1 hour. Concentration and purification by chromatography (SiO$_2$; ethyl acetate/cyclohexane 1:1) yielded the title compound as a colorless solid. MS (m/e): 309.1 (MH+, 100%)

(c) Dimethyl-(4-piperazin-1-yl-[1,3,5]triazin-2-yl)-amine

A solution of 1 mmol of 4-(4-Dimethylamino-[1,3,5]triazin-2-yl)-piperazine-1-carboxylic acid tert-butyl ester in 10 ml dichloromethane was chilled and treated with 14 mmol of trifluoroacetic acid. The reaction mixture was heated to 40° C. for 30 min. After cooling, 50 ml of 2M aqueous sodium hydroxide is added. The organic layer was separated, dried and concentrated to yield the title compound as a yellowish oil. MS (m/e): 267.0 (M+CH$_3$COO+, 100%)

Example CV

5'-Trifluoromethyl-3,4,5,6-tetrahydro-2H-[1,2']bi-pyrazinyl

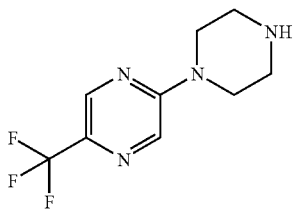

(a) 2-Bromo-5-trifluoromethyl-pyrazine

To a suspension of 0.423 mmol copper (II) bromide in THF (1 ml) was added dropwise 0.51 mmol tert-butylnitrite at 0° C. within 2 minutes. 0.37 mmol 5-Trifluoromethyl-pyrazin-2-ylamine (CAS: 69816-38-2; WO9518097) in solution in THF (0.5 ml) was added dropwise within 5 minutes at 0° C. The mixture was stirred at 0° C. for 1 hour, at room temperature for 21 hours and quenched with water. The aqueous phase was extracted with ether. The combined extracts were dried over sodium sulfate and filtered and concentrated at atmospheric pressure. The residue was then purified by column chromatography (SiO$_2$, ether) to yield the title compound.

(b) 5'-Trifluoromethyl-3,4,5,6-tetrahydro-2H-[1,2] bipyrazinyl

The title compound was prepared in analogy to Example CS (b-c) from 2-Bromo-5-trifluoromethyl-pyrazine MS (m/e): 233.0 (M+H+, 100%)

According to the procedure described for the synthesis of Example 123 further derivatives have been synthesised from acid derivatives and piperazine derivatives and comprise Examples 305-318 in Table 4.

TABLE 4

| No. | Structure | MW | Systematic Name | Starting materials | MW found (MH+) |
|---|---|---|---|---|---|
| 305 | 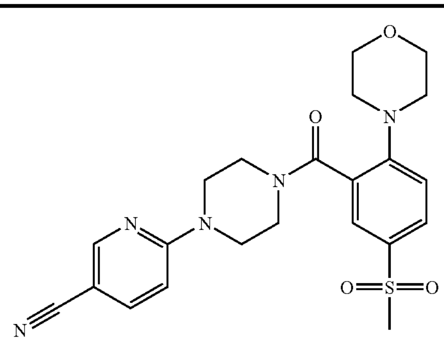 | 455.536 | 6-[4-(5-Methanesulfonyl-2-morpholin-4-yl-benzoyl)-piperazin-1-yl]nicotinonitrile | 6-Piperazin-1-yl nicotinonitrile (commercial) and 5-Methanesulfonyl-2-morpholin-4-yl-benzoic acid (example AG) | 456.5 |

TABLE 4-continued

| No. | Structure | MW | Systematic Name | Starting materials | MW found (MH+) |
|---|---|---|---|---|---|
| 306 | 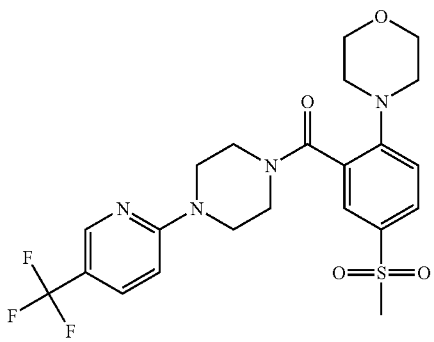 | 498.523 | (5-Methanesulfonyl-2-morpholin-4-yl-phenyl)-[4-(5-trifluoromethyl-pyridin-2-yl)-piperazin-1-yl]-methanone | 1-(5-Trifluoromethyl-pyridin-2-yl)-piperazine (commercial) and 5-Methanesulfonyl-2-morpholin-4-yl-benzoic acid (example AG) | 499.3 |
| 307 | 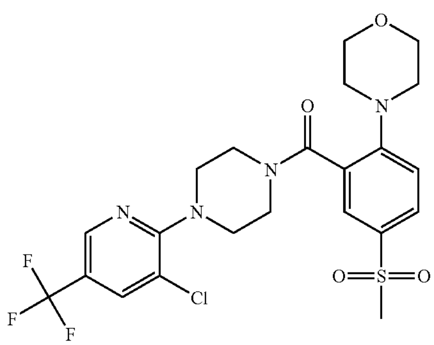 | 532.968 | [4-(3-Chloro-5-trifluoromethyl-pyridin-2yl)-piperazin-1-yl]-(5-methanesulfonyl-2-morpholin-4-yl-phenyl)-methanone | 1-(3-Chloro-5-trifluoromethyl-pyridin-2-yl)-piperazine (commercial) and 5-Methanesulfonyl-2-morpholin-4-yl-benzoic acid (example AG) | 533.4 |
| 308 | 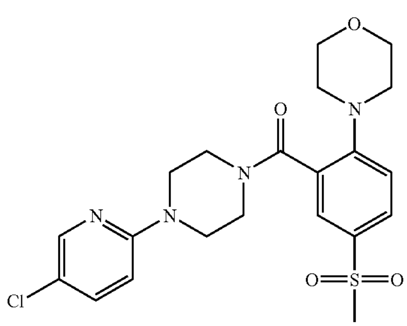 | 464.971 | [4-(5-Chloro-pyridin-2-yl)-piperazin-1-yl]-(5-methanesulfonyl-2-morpholin-4-yl-phenyl)-methanone | 1-(5-Chloro-pyridin-2-yl)-piperazine (WO01062751) and 5-Methanesulfonyl-2-morpholin-4-yl-benzoic acid (example AG) | 465.4 |
| 309 | 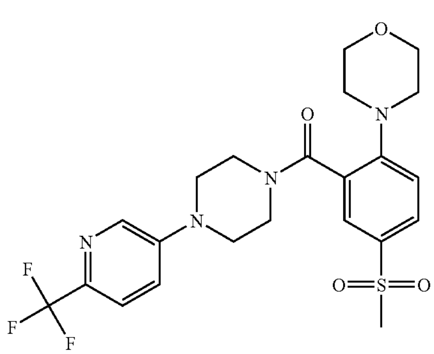 | 498.523 | (5-Methanesulfonyl-2-morpholin-4-yl-phenyl)-[4-(6-trifluoromethyl-pyridin-3-yl)-piperazin-1-yl]-methanone | 1-(6-Trifluoromethyl-pyridin-3-yl)-piperazine (compound CO) and 5-Methanesulfonyl-2-morpholin-yl-benzoic acid (example AG) | 499.4 |

TABLE 4-continued

| No. | Structure | MW | Systematic Name | Starting materials | MW found (MH$^+$) |
|---|---|---|---|---|---|
| 310 | 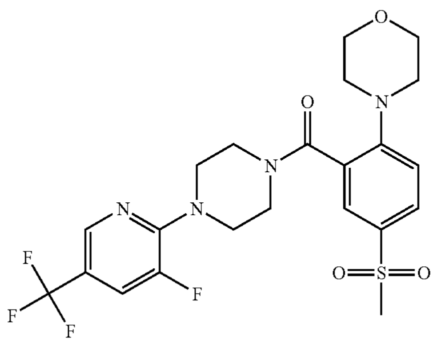 | 516.513 | [4-(3-Fluoro-5-trifluoromethyl-pyridin-2-yl)-piperazin-1-yl]-(5-methane sulfonyl-2-morpholin-4-yl-phenyl)-methanone | 1-(3-Fluoro-5-trifluoro methyl-pyridin-2-yl)-piperazine (compound CP) and 5-Methane sulfonyl-2-morpholin-4-yl-benzoic acid (example AG) | 516.9 |
| 311 | 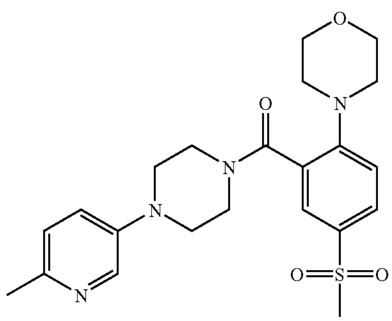 | 444.553 | (5-Methanesulfonyl-2-morpholin-4-yl-phenyl)-[4-(6-methyl-pyridin-3-yl)-piperazin-1-yl]-methanone | 1-(6-Methyl-pyridin-3-yl)-piperazine (compound CQ) and 5-Methane sulfonyl-2-morpholin-4-yl-benzoic acid (example AG) | 445.4 |
| 312 | 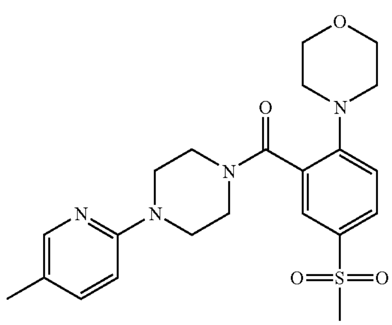 | 444.553 | (5-Methanesulfonyl-2-morpholin-4-yl-phenyl)-[4-(5-methyl-pyridin-2-yl)-piperazin-1-yl]-methanone | 1-(5-Methyl-pyridin-2-yl)-piperazine (WO03032996) and 5-Methanesulfonyl-2-morpholin-4-yl-benzoic acid (example AG) | 445.1 |
| 313 | 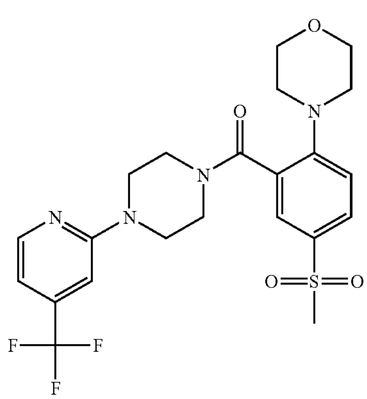 | 498.523 | (5-Methanesulfonyl-2-morpholin-4-yl-phenyl)-[4-(4-trifluoromethyl-pyridin-2-yl)-piperazin-1-yl]-methanone | 1-(4-Trifluoromethyl-pyridin-2-yl)-piperazine (WO02002529) and 5-Methanesulfonyl-2-morpholin-4-yl-benzoic acid (example AG) | 499.1 |

TABLE 4-continued

| No. | Structure | MW | Systematic Name | Starting materials | MW found (MH+) |
|---|---|---|---|---|---|
| 314 | 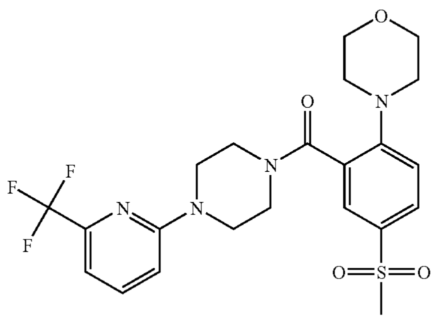 | 498.523 | (5-Methanesulfonyl-2-morpholin-4-yl-phenyl)-[4-(6-trifluoromethyl-pyridin-2-yl)-piperazin-1-yl]-methanone | 1-(6-Trifluoromethyl-pyridin-2-yl)-piperazine (EP 462638) and 5-Methanesulfonyl-2-morpholin-4-yl-benzoic acid (example AG) | 499.1 |
| 315 | 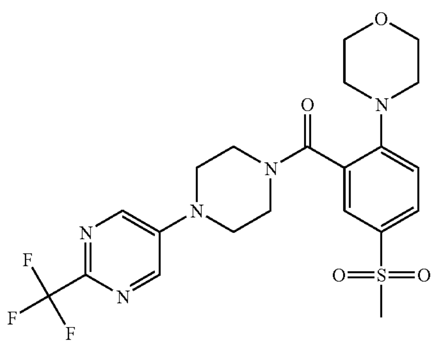 | 499.511 | (5-Methanesulfonyl-2-morpholin-4-yl-phenyl)-[4-(2-trifluoromethyl-pyrimidin-yl)-piperazin-1-yl]-methanone | 5-Piperazin-1-yl-2-trifluoromethyl-pyrimidine (compound CS) and 5-Methanesulfonyl-2-morpholin-4-yl-benzoic acid (example AG) | 500.0 |
| 316 | 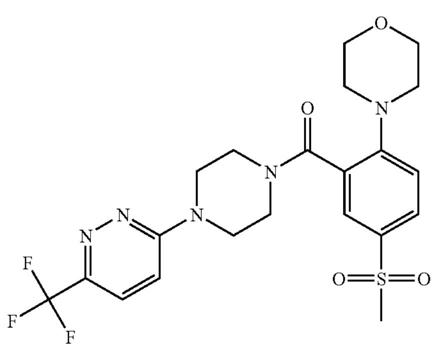 | 499.511 | (5-Methanesulfonyl-2-morpholin-4-yl-phenyl)-[4-(6-trifluoromethyl-pyridazin-3-yl)-piperazin-1-yl]-methanone | 3-Piperazin-1-yl-6-trifluoromethyl-pyridazine (compound CT) and 5-Methanesulfonyl-2-morpholin-4-yl-benzoic acid (example AG) | 500.4 |
| 317 | 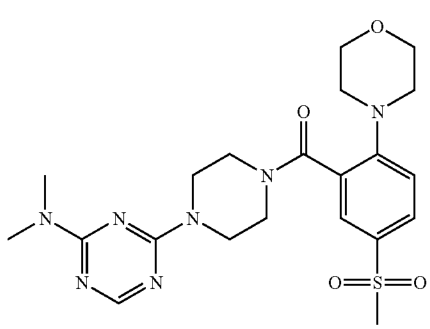 | 475.571 | [4-(4-Dimethylamino[1,3,5]triazin-2-yl) piperazin-1-yl]-(5-methane sulfonyl-2-morpholin-4-yl-phenyl)-methanone | Dimethyl-(4-piperazin-1-yl-[1,3,5]triazin-2-yl)-amine (compound CU) and 5-Methanesulfonyl-2-morpholin-4-yl-benzoic acid (example AG) | 476.1 |

TABLE 4-continued

| No. | Structure | MW | Systematic Name | Starting materials | MW found (MH+) |
|---|---|---|---|---|---|
| 318 | 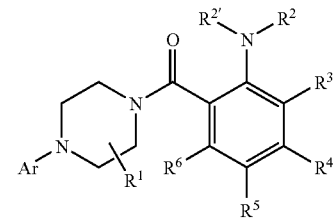 | 499.511 | (5-Methanesulfonyl-2-morpholin-4-yl-phenyl)-(5'-trifluoromethyl-2,3,5,6-tetrahydro[1,2']bipyrazinyl-4-yl)methanone | 5'-Trifluoromethyl-3,4,5,6-tetrahydro-2H-[1,2'] bipyrazinyl (compound CV) and 5-Methane sulfonyl-2-morpholin-4-yl-benzoic acid (example AG) | 500.4 |

Tablet Formulation (Wet Granulation)

| | | mg/tablet | | | |
|---|---|---|---|---|---|
| Item | Ingredients | 5 mg | 25 mg | 100 mg | 500 mg |
| 1. | Compound of formula I | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure

1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

Capsule Formulation

| | | mg/capsule | | | |
|---|---|---|---|---|---|
| Item | Ingredients | 5 mg | 25 mg | 100 mg | 500 mg |
| 1. | Compound of formula I | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure

1. Mix items 1, 2 and 3 in a suitable mixer for 30 minutes.
2. Add items 4 and 5 and mix for 3 minutes.
3. Fill into a suitable capsule.

The invention claimed is:

1. A compound of formula

I wherein

Ar is unsubstituted or substituted 6-membered heteroaryl containing one, two or three nitrogen atoms, and wherein the substituted heteroaryl groups are substituted by one or more substituents selected from the group consisting of hydroxy, halogen, $NO_2$, CN, ($C_1$-$C_6$)-alkyl, ($C_1$-$C_6$)-alkyl substituted by halogen, ($C_1$-$C_6$)-alkoxy, ($C_1$-$C_6$)-alkoxy substituted by halogen, $NR^7R^8$, $C(O)R^9$ and $SO_2R^{10}$;

$R^1$ is hydrogen or ($C_1$-$C_6$)-alkyl;

$R^2$ and $R^{2'}$ are each independently hydrogen,
($CR_2)_n$-hydroxy wherein R is hydrogen or $C_1$-$C_6$-alkyl,
($C_1$-$C_6$)-alkyl,
($C_2$-$C_6$)-alkenyl,
($C_1$-$C_6$)-alkyl substituted by halogen,
$(CH_2)_n$—($C_3$-$C_6$)-cycloalkyl,
$(CH_2)_n$-heterocycloalkyl,
$(CH_2)_n$—O—($C_1$-$C_6$)-alkyl or
$(CH_2)_n$-aryl or $R^2$ and $R^{2'}$ form together with the N atom to which they are attached a heterocycloalkyl ring, optionally containing in addition to the N atom a further heteroatom selected from the group consisting of N, S and O, which rings are unsubstituted or substituted by $(CH_2)_n$-hydroxy, ($C_1$-$C_6$)-alkyl, ($C_1$-$C_6$)-alkoxy, $(CH_2)_n$—O—($C_1$-$C_6$)-alkyl, or $R^2$ and $R^{2'}$ form together with the N atom to which they are attached a 5-membered heteroaryl group, optionally containing in addition to the N atom one, two or three further nitrogen atoms and wherein the heteroaryl group is optionally substituted by ($C_1$-$C_6$)-alkyl;

$R^3$, $R^4$ and $R^6$ are each independently hydrogen, halogen, $(C_1-C_6)$-alkyl or $(C_1-C_6)$-alkoxy;
$R^5$ is $NO_2$, CN, $C(O)R^9$, S—$(C_1-C_6)$-alkyl, $SO_2R^{10}$ or $NR^{11}R^{12}$;
$R^7$ and $R^8$ are each independently hydrogen, $(CH_2)_n$—$(C_3-C_6)$-cycloalkyl or
$(C_1-C_6)$-alkyl, or form together with the N atom to which they are attached a heterocycloalkyl ring, optionally containing in addition to the N atom a further heteroatom, selected from the group consisting of N, S and O;
$R^9$ is hydroxy, $(C_1-C_6)$-alkyl, $(C_3-C_6)$-cycloalkyl, $(C_1-C_6)$-alkoxy or $NR^7R^8$;
$R^{10}$ is $(C_1-C_6)$-alkyl, $(CH_2)_n$—$(C_3-C_6)$-cycloalkyl or $NR^7R^8$;
$R^{11}$ and $R^{12}$ are each independently hydrogen, C(O)—$(C_1-C_6)$-alkyl,
$SO_2$—$(C_1-C_6)$-alkyl, or form together with the N-atom to which they are attached a 5-membered heteroaryl group optionally containing in addition to the N atom one, two or three nitrogen atoms and wherein the heteroaryl group is optionally substituted by halogen, $(C_1-C_6)$-alkyl or $(CH_2)_n(C_3-C_6)$-cycloalkyl;
n is 0, 1 or 2;
wherein the 5-membered heteroaryl group is selected from the group consisting of pyrrolyl 2,5-dihydro-pyrrol-1-yl, imidazolyl, pyrazolyl, triazolyl, and tetrazolyl;
or a pharmaceutically acceptable acid addition salt thereof.

2. A compound of formula

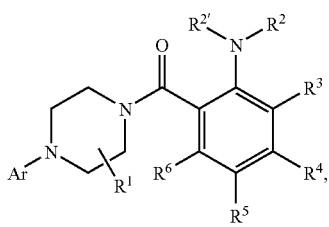

I wherein
Ar is unsubstituted or substituted 6-membered heteroaryl containing one, two or three nitrogen atoms, and wherein the substituted aryl and the substituted heteroaryl groups are substituted by one or more substituents selected from the group consisting of hydroxy, halogen, $NO_2$, CN, $(C_1-C_6)$-alkyl, $(C_1-C_6)$-alkyl substituted by halogen, $(C_1-C_6)$-alkoxy, $(C_1-C_6)$-alkoxy substituted by halogen, $NR^7R^8$, $C(O)R^9$ and $SO_2R^{10}$;
$R^1$ is hydrogen or $(C_1-C_6)$-alkyl;
$R^2$ and $R^{2'}$ are each independently hydrogen,
hydroxy,
$(C_1-C_6)$-alkyl,
$(C_3-C_6)$-alkenyl,
$(C_2-C_6)$-alkyl substituted by halogen,
$(C_3-C_6)$-cycloalkyl,
heterocycloalkyl,
$(C_1-C_6)$-alkyl-$(C_3-C_6)$-cycloalkyl,
$(C_1-C_6)$-alkyl-heterocycloalkyl,
$(C_1-C_6)$-alkyl-C(O)—$R^9$,
$(C_1-C_6)$-alkyl-CN,
$(C_2-C_6)$-alkyl-O—$R^{13}$,
$(C_2-C_6)$-alkyl-$NR^7R^8$,
aryl,
6-membered heteroaryl containing one, two or three nitrogen atoms,
$(C_1-C_6)$-alkyl-aryl or
$(C_1-C_6)$-alkyl-5 or -6-membered heteroaryl containing one, two or three heteroatoms, selected from the group consisting of oxygen, sulphur and nitrogen,
wherein aryl, heterocycloalkyl and heteroaryl are unsubstituted or substituted by one or more substituents selected from the group consisting of hydroxy, halogen, $(C_1-C_6)$-alkyl and $(C_1-C_6)$-alkoxy; or
$R^2$ and $R^{2'}$ form together with the N atom to which they are attached a heterocycloalkyl ring, optionally containing in addition to the N atom a further heteroatom selected from the group consisting of N, S and O, which rings are unsubstituted or substituted by hydroxy, $(C_1-C_6)$-alkyl, $(C_1-C_6)$-alkoxy, $(C_1-C_6)$-alkyl-O—$R^{13}$, or
$R^2$ and $R^{2'}$ form together with the N atom to which they are attached a 5-membered heteroaryl group, optionally containing in addition to the N atom one, two or three further nitrogen atoms and wherein the heteroaryl group is optionally substituted by halogen, $(C_1-C_6)$-alkyl, $(C_1-C_6)$-alkyl substituted by halogen or $(C_3-C_6)$-cycloalkyl;
$R^3$, $R^4$ and $R^6$ are each independently hydrogen, hydroxy, halogen, CN,
$(C_1-C_6)$-alkyl, $(C_1-C_6)$-alkoxy and $NR^7R^8$;
$R^5$ is $NO_2$, CN, $C(O)R^9$, S—$(C_1-C_6)$-alkyl, $SO_2R^{10}$ or $NR^{11}R^{12}$;
$R^7$ and $R^8$ are each independently hydrogen, $(C_1-C_6)$-alkyl-$(C_3-C_6)$-cycloalkyl, $(C_1-C_6)$-alkyl, or $(C_3-C_6)$-cycloalkyl, or form together with the N atom to which they are attached a heterocycloalkyl ring, optionally containing in addition to the N atom a further heteroatom, selected from the group consisting of N, S and O;
$R^9$ is hydroxy, $(C_1-C_6)$-alkyl, $(C_3-C_6)$-cycloalkyl, $(C_1-C_6)$-alkoxy or $NR^7R^8$;
$R^{10}$ is $(C_1-C_6)$-alkyl, $(C_3-C_6)$-cycloalkyl, $(C_1-C_6)$-alkyl-$(C_3-C_6)$-cycloalkyl or $NR^7R^8$;
$R^{11}$ and $R^{12}$ are each independently hydrogen, C(O)—$(C_1-C_6)$-alkyl,
$SO_2$—$(C_1-C_6)$-alkyl, or form together with the N-atom to which they are attached a 5-membered heteroaryl group optionally containing in addition to the N atom one, two or three nitrogen atoms and wherein the heteroaryl group is optionally substituted by halogen,
$(C_1-C_6)$-alkyl, $(C_1-C_6)$-alkyl substituted by halogen, or $(C_3-C_6)$-cycloalkyl;
$R^{13}$ is hydrogen, $(C_1-C_6)$-alkyl or $(C_3-C_6)$-cycloalkyl;
wherein the 5-membered heteroaryl group is selected from the group consisting of pyrrolyl, 2,5-dihydro-pyrrol-1-yl, imidazolyl, pyrazolyl, triazolyl, and tetrazolyl;
or a pharmaceutically acceptable acid addition salt thereof.

3. A compound of formula I-3 according to claim 1

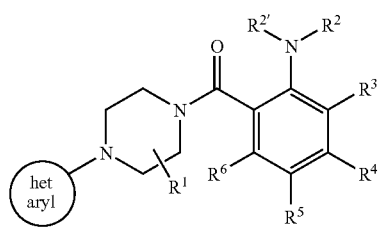

I-3 wherein
hetaryl is a 6-membered heteroaryl containing one, two or three nitrogen atoms, optionally substituted by one or more substituents selected from the group consisting of hydroxy, halogen, NO$_2$, CN, (C$_1$-C$_6$)-alkyl, (C$_1$-C$_6$)-alkyl substituted by halogen, (C$_1$-C$_6$)-alkoxy, (C$_1$-C$_6$)-alkoxy substituted by halogen, NR$^7$R$^8$, C(O)R$^9$ and SO$_2$R$^{10}$;

R$^1$ is hydrogen or (C$_1$-C$_6$)-alkyl;

R$^2$ and R$^{2'}$ are each independently hydrogen,
(CR$_2$)$_n$-hydroxy wherein R is hydrogen or C$_1$-C$_6$-alkyl,
(C$_1$-C$_6$)-alkyl,
(C$_2$-C$_6$)-alkenyl,
(C$_1$-C$_6$)-alkyl substituted by halogen,
(CH$_2$)$_n$—(C$_3$-C$_6$)-cycloalkyl,
(CH$_2$)$_n$-heterocycloalkyl,
(CH$_2$)$_n$—O—(C$_1$-C$_6$)-alkyl or
(CH$_2$)$_n$-aryl;

R$^3$, R$^4$ and R$^6$ are each independently hydrogen, halogen, (C$_1$-C$_6$)-alkyl or (C$_1$-C$_6$)-alkoxy;

R$^5$ is NO$_2$, CN, C(O)R$^9$, S—(C$_1$-C$_6$)-alkyl, SO$_2$R$^{10}$ or NR$^{11}$R$^{12}$;

R$^7$ and R$^8$ are each independently hydrogen, (CH$_2$)$_n$—(C$_3$-C$_6$)-cycloalkyl or (C$_1$-C$_6$)-alkyl, or form together with the N atom to which they are attached a heterocycloalkyl ring, optionally containing in addition to the N atom a further heteroatom selected from the group consisting of N, S and O;

R$^9$ is hydroxy, (C$_1$-C$_6$)-alkyl, (C$_3$-C$_6$)-cycloalkyl, (C$_1$-C$_6$)-alkoxy or NR$^7$R$^8$;

R$^{10}$ is (C$_1$-C$_6$)-alkyl, (CH$_2$)$_n$—(C$_3$-C$_6$)-cycloalkyl or NR$^7$R$^8$;

R$^{11}$ and R$^{12}$ are each independently hydrogen, C(O)—(C$_1$-C$_6$)-alkyl,
SO$_2$—(C$_1$-C$_6$)-alkyl, or form together with the N-atom to which they are attached a 5-membered heteroaryl group optionally containing in addition to the N atom one, two or three nitrogen atoms and wherein the heteroaryl group is optionally substituted by halogen, (C$_1$-C$_6$)-alkyl or (CH$_2$)$_n$(C$_3$-C$_6$)-cycloalkyl;

n is 0, 1 or 2;

or a pharmaceutically acceptable acid addition salt thereof.

4. A compound of formula I-4 according to claim 1

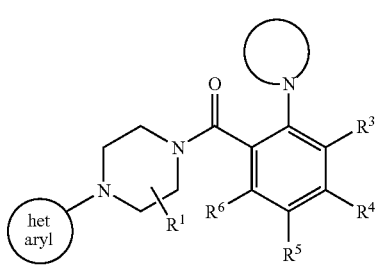

I-4 wherein hetaryl is a 6-membered heteroaryl, containing one, two or three nitrogen atoms, optionally substituted by one or more substituents selected from the group consisting of hydroxy, halogen, NO$_2$, CN, (C$_1$-C$_6$)-alkyl, (C$_1$-C$_6$)-alkyl substituted by halogen, (C$_1$-C$_6$)-alkoxy, (C$_1$-C$_6$)-alkoxy substituted by halogen, NR$^7$R$^8$, C(O)R$^9$ and SO$_2$R$^{10}$;

R$^1$ is hydrogen or (C$_1$-C$_6$)-alkyl;

is a heterocycloalkyl ring, optionally containing in addition to the N atom a further heteroatom selected from the group consisting of N, S and O, which rings are unsubstituted or substituted by (CH$_2$)$_n$-hydroxy, (C$_1$-C$_6$)-alkyl, (C$_1$-C$_6$)-alkoxy, (CH$_2$)$_n$—O—(C$_1$-C$_6$)-alkyl, or is a 5-membered heteroaryl group, optionally containing in addition to the N atom one, two or three further nitrogen atoms and wherein the heteroaryl group is optionally substituted by (C$_1$-C$_6$)-alkyl;

R$^3$, R$^4$ and R$^6$ are each independently hydrogen, halogen, (C$_1$-C$_6$)-alkyl or (C$_1$-C$_6$)-alkoxy;

R$^5$ is NO$_2$, CN, C(O)R$^9$, S—(C$_1$-C$_6$)-alkyl, SO$_2$R$^{10}$ or is NR$^{11}$R$^{12}$;

R$^7$ and R$^8$ are independently from each other hydrogen, (CH$_2$)$_n$—(C$_3$-C$_6$)-cycloalkyl or (C$_1$-C$_6$)-alkyl, or form together with the N atom to which they are attached a heterocycloalkyl ring, optionally containing in addition to the N atom a further heteroatom selected from the group consisting of N, S and O;

R$^9$ is hydroxy, (C$_1$-C$_6$)-alkyl, (C$_3$-C$_6$)-cycloalkyl, (C$_1$-C$_6$)-alkoxy or NR$^7$R$^8$;

R$^{10}$ is (C$_1$-C$_6$)-alkyl, (CH$_2$)$_n$—(C$_3$-C$_6$)-cycloalkyl or NR$^7$R$^8$;

R$^{11}$ and R$^{12}$ are each independently hydrogen, C(O)—(C$_1$-C$_6$)-alkyl,
SO$_2$—(C$_1$-C$_6$)-alkyl, or form together with the N-atom to which they are attached a 5-membered heteroaryl group optionally containing in addition to the N atom one, two or three nitrogen atoms and wherein the heteroaryl group is optionally substituted by halogen, (C$_1$-C$_6$)-alkyl or (CH$_2$)$_n$(C$_3$-C$_6$)-cycloalkyl;

n is 0, 1 or 2;

or a pharmaceutically acceptable acid addition salt thereof.

5. A compound of formula I-4 according to claim 4, which is selected from (2-morpholin-4-yl-5-nitro-phenyl)-[4-(5-trifluoromethyl-pyridin-2-yl)-piperazin-1-yl]-methanone,

[4-(3-chloro-5-trifluoromethyl-pyridin-2-yl)-piperazin-1-yl]-(2-morpholin-4-yl-5-nitro-phenyl)-methanone, 6-[4-(2-morpholin-4-yl-5-nitro-benzoyl)-piperazin-1-yl]-nicotinonitrile,

[4-(3-chloro-pyridin-2-yl)-piperazin-1-yl]-(2-morpholin-4-yl-5-nitro-phenyl)-methanone, (2-morpholin-4-yl-5-nitro-phenyl)-[4-(4-trifluoromethyl-pyridin-2-yl)-piperazin-1-yl]-methanone, (2-morpholin-4-yl-5-nitro-phenyl)-[4-(6-trifluoromethyl-pyridin-2-yl)-piperazin-1-yl]-methanone,

[4-(5-bromo-pyrimidin-2-yl)-piperazin-1-yl]-(2-morpholin-4-yl-5-nitro-phenyl)-methanone, and

[4-(6-chloro-5-trifluoromethyl-pyridin-2-yl)-piperazin-1-yl]-(2-morpholin-4-yl-5-nitro-phenyl)-methanone.

6. A compound of formula I-4 according to claim 4, which is selected from (5-methanesulfonyl-2-morpholin-4-yl-phenyl)-[4-(2-trifluoromethyl-pyrimidin-4-yl)-piperazin-1-yl]-methanone, (5-methanesulfonyl-2-morpholin-4-yl-phenyl)-[4-(6-trifluoromethyl-pyrimidin-4-yl)-piperazin-1-yl]-methanone, (5-methanesulfonyl-2-morpholin-4-yl-phenyl)-[4-(5-trifluoromethyl-pyrimidin-2-yl)-piperazin-1-yl]-methanone, 6-[4-(5-methanesulfonyl-2-morpholin-4-yl-benzoyl)-piperazin-1-yl]-nicotinonitrile, (5-methanesulfonyl-2-morpholin-4-yl-phenyl)-[4-(5-trifluoromethyl-pyridin-2-yl)-piperazin-1-yl]-methanone,

[4-(3-chloro-5-trifluoromethyl-pyridin-2-yl)-piperazin-1-yl]-(5-methanesulfonyl-2-morpholin-4-yl-phenyl)-methanone,

[4-(5-chloro-pyridin-2-yl)-piperazin-1-yl]-(5-methanesulfonyl-2-morpholin-4-yl-phenyl)-methanone, (5-methanesulfonyl-2-morpholin-4-yl-phenyl)-[4-(6-trifluoromethyl-pyridin-3-yl)-piperazin-1-yl]-methanone, and

[4-(3-fluoro-5-trifluoromethyl-pyridin-2-yl)-piperazin-1-yl]-(5-methanesulfonyl-2-morpholin-4-yl-phenyl)-methanone.

7. A compound of formula I-4 according to claim 4, which is selected from (5-methanesulfonyl-2-morpholin-4-yl-phenyl)-[4-(6-methyl-pyridin-3-yl)-piperazin-1-yl]-methanone, (5-methanesulfonyl-2-morpholin-4-yl-phenyl)-[4-(5-methyl-pyridin-2-yl)-piperazin-1-yl]-methanone, (5-methanesulfonyl-2-morpholin-4-yl-phenyl)-[4-(4-trifluoromethyl-pyridin-2-yl)-piperazin-1-yl]-methanone, (5-methanesulfonyl-2-morpholin-4-yl-phenyl)-[4-(6-trifluoromethyl-pyridin-2-yl)-piperazin-1-yl]-methanone, (5-methanesulfonyl-2-morpholin-4-yl-phenyl)-[4-(2-trifluoromethyl-pyrimidin-5-yl)-piperazin-1-yl]-methanone, (5-methanesulfonyl-2-morpholin-4-yl-phenyl)-[4-(6-trifluoromethyl-pyridazin-3-yl)-piperazin-1-yl]-methanone, and

[4-(4-dimethylamino-[1,3,5]triazin-2-yl)-piperazin-1-yl]-(5-methanesulfonyl-2-morpholin-4-yl-phenyl)-methanone.

8. A compound of formula Ia according to claim 2

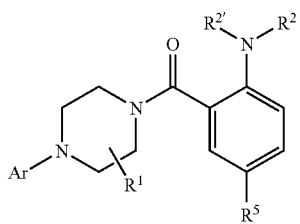

Ia wherein

Ar is unsubstituted or substituted 6-membered heteroaryl, containing one or two nitrogen atoms, and wherein the substituted phenyl and the substituted heteroaryl groups are optionally substituted by one or two substituents selected from the group consisting of halogen, $NO_2$, CN, $(C_1-C_6)$-alkyl, $(C_1-C_6)$-alkyl substituted by halogen, $(C_1-C_6)$-alkoxy, $(C_1-C_6)$-alkoxy substituted by halogen, $NR^7R^8$, $C(O)R^9$ and $SO_2R^{10}$;

$R^1$ is hydrogen or $(C_1-C_6)$-alkyl;

$R^2$ and $R^{2'}$ are each independently hydrogen, hydroxy, $(C_1-C_6)$-alkyl, $(C_3-C_6)$-alkenyl, $(C_3-C_6)$-cycloalkyl, heterocycloalkyl, $(C_1-C_6)$-alkyl-$(C_3-C_6)$-cycloalkyl, $(C_1-C_6)$-alkyl-aryl, or $(C_2-C_6)$-alkyl-O—$R^{13}$, or $R^2$ and $R^{2'}$ form together with the N atom to which they are attached a heterocycloalkyl ring, optionally containing in addition to the N atom a further heteroatom selected from the group consisting of N, S and O, which ring is unsubstituted or substituted by hydroxy, $(C_1-C_6)$-alkyl, $(C_1-C_6)$-alkoxy, or $(C_1-C_6)$-alkyl-O—$R^{13}$, or $R^2$ and $R^{2'}$ form together with the N atom to which they are attached a 5-membered heteroaryl group optionally containing in addition to the N atom one or two nitrogen atoms;

$R^5$ is $NO_2$, CN, $C(O)R^9$, S—$(C_1-C_6)$-alkyl, $SO_2R^{10}$ or $NR^{11}R^{12}$;

$R^7$ and $R^8$ are each independently hydrogen, $(C_1-C_6)$-alkyl-$(C_3-C_6)$-cycloalkyl, or $(C_1-C_6)$-alkyl or form together with the N atom to which they are attached a heterocycloalkyl ring, optionally containing in addition to the N atom a further heteroatom selected from the group consisting of oxygen;

$R^9$ is $(C_1-C_6)$-alkyl, $(C_1-C_6)$-alkoxy or $NR^7R^8$;

$R^{10}$ is $(C_1-C_6)$-alkyl, $(C_1-C_6)$-alkyl-$(C_3-C_6)$-cycloalkyl or $NR^7R^8$;

$R^{11}$ and $R^{12}$ are each independently $SO_2$—$(C_1-C_6)$-alkyl, or form together with the N-atom to which they are attached a 5-membered heteroaryl group containing in addition to the N atom one, two or three nitrogen atoms;

$R^{13}$ is hydrogen or $(C_1-C_6)$-alkyl;

or a pharmaceutically acceptable acid addition salt thereof.

9. A compound of formula Ia, according to claim 2

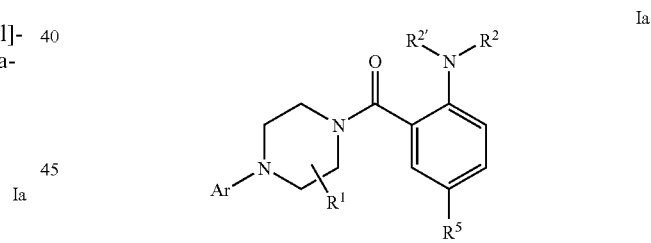

Ia wherein

Ar is unsubstituted or substituted pyridyl or pyrimidinyl, optionally substituted by one or two substituents selected from the group consisting of halogen, $NO_2$, CN, methyl, $CF_3$, methoxy, $OCF_3$, $NH_2$, $C(O)CH_3$, $C(O)OCH_3$, $C(O)OCH_2CH_3$, $SO_2NH_2$ and $SO_2CH_3$;

$R^1$ is hydrogen or methyl;

$R^2$ and $R^{2'}$ are each independently hydrogen, hydroxy, $(C_1-C_6)$-alkyl, —$CH_2CH=CH_2$, —$CH_2CH_2OH$, —CH($CH_3$)$CH_2OH$, cyclopropyl, cyclopentyl, cyclohexyl, tetrahydropyranyl, —$CH_2$-cyclopropyl, or $(CH_2)_2OCH_3$, benzyl, or $R^2$ and $R^{2'}$ form together with the N atom to which they are attached a heterocycloalkyl ring selected from the group consisting of morpholinyl, thiomorpholinyl, azetidinyl, pyrrolidinyl, piperidinyl and azepanyl, which ring is unsubstituted or substituted by hydroxy, methyl, methoxy, ethoxy, or $CH_2OH$, or R² and R²' form together with the N atom to which they are attached a 5-membered heteroaryl ring selected from the group consisting of imidazolyl, triazolyl and di-hydropyrrolyl;

R⁵ is NO₂, CN, —C(O)NH₂, —C(O)NHCH₃, —C(O)N(CH₃)₂, —C(O)CH₃, —SCH₃, —SO₂—(C₁-C₆)-alkyl, —SO₂—NH—(C₁-C₆)-alkyl, —SO₂—N—[(C₁-C₆)-alkyl]₂, —SO₂NH₂, —NHSO₂CH₃, —SO₂—NHCH₂-cycloalkyl, —SO₂—CH₂-cycloalkyl, —SO₂-pyrrolidin-1-yl, —SO₂-morpholidin-1-yl, imidazolyl or tetrazolyl, or a pharmaceutically acceptable acid addition salt thereof.

10. A compound of formula I, according to claim 2, wherein R² and R²' form together with the N atom to which they are attached a morpholine or thiomorpholine ring.

11. A compound of formula I, according to claim 2, wherein R² and R²' form together with the N atom to which they are attached a pyrrolidin- or 2,5-dihydropyrrol ring.

12. A compound of formula I, according to claim 2, wherein R² and R²' form together with the N atom to which they are attached a piperidine ring.

13. A compound of formula I, according to claim 2, wherein R² and R²' form together with the N atom to which they are attached an azepane ring.

14. A compound of formula I, according to claim 2, wherein R² or R²' is CH₂-cycloalkyl or cycloalkyl.

15. A compound of formula I, according to claim 2, wherein one of R² and R²' is (C₁-C₆)-alkyl and the other is hydrogen, or both of R² and R²' are (C₁-C₆)-alkyl.

16. A compound of formula I, according to claim 2, wherein one of R² and R²' is (C₂-C₆)-alkenyl and the other is (C₁-C₆)-alkyl.

17. A composition comprising a pharmaceutically acceptable carrier and a compound of formula I

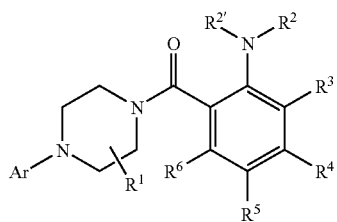

I wherein

Ar is unsubstituted or substituted 6-membered heteroaryl containing one, two or three nitrogen atoms, and wherein the substituted aryl and the substituted heteroaryl groups are substituted by one or more substituents selected from the group consisting of hydroxy, halogen, NO₂, CN, (C₁-C₆)-alkyl, (C₁-C₆)-alkyl substituted by halogen, (C₁-C₆)-alkoxy, (C₁-C₆)-alkoxy substituted by halogen, NR⁷R⁸, C(O)R⁹ and SO₂R¹⁰;

R¹ is hydrogen or (C₁-C₆)-alkyl;

R² and R²' are each independently hydrogen,
(CR₂)ₙ-hydroxy wherein R is hydrogen or C₁-C₆-alkyl,
(C₁-C₆)-alkyl,
(C₂-C₆)-alkenyl,
(C₁-C₆)-alkyl substituted by halogen,
(CH₂)ₙ—(C₃-C₆)-cycloalkyl,
(CH₂)ₙ-heterocycloalkyl,
(CH₂)ₙ—O—(C₁-C₆)-alkyl or
(CH₂)ₙ-aryl or R² and R²' form together with the N atom to which they are attached a heterocycloalkyl ring, optionally containing in addition to the N atom a further heteroatom selected from the group consisting of N, S and O, which rings are unsubstituted or substituted by (CH₂)ₙ-hydroxy, (C₁-C₆)-alkyl, (C₁-C₆)-alkoxy, (CH₂)ₙ—O—(C₁-C₆)-alkyl, or R² and R²' form together with the N atom to which they are attached a 5-membered heteroaryl group, optionally containing in addition to the N atom one, two or three further nitrogen atoms and wherein the heteroaryl group is optionally substituted by (C₁-C₆)-alkyl;

R³, R⁴ and R⁶ are each independently hydrogen, halogen, (C₁-C₆)-alkyl or (C₁-C₆)-alkoxy;

R⁵ is NO₂, CN, C(O)R⁹, S—(C₁-C₆)-alkyl, SO₂R¹⁰ or NR¹¹R¹²;

R⁷ and R⁸ are each independently hydrogen, (CH₂)ₙ—(C₃-C₆)-cycloalkyl or (C₁-C₆)-alkyl, or form together with the N atom to which they are attached a heterocycloalkyl ring, optionally containing in addition to the N atom a further heteroatom, selected from the group consisting of N, S and O;

R⁹ is hydroxy, (C₁-C₆)-alkyl, (C₃-C₆)-cycloalkyl, (C₁-C₆)-alkoxy or NR⁷R⁸;

R¹⁰ is (C₁-C₆)-alkyl, (CH₂)ₙ—(C₃-C₆)-cycloalkyl or NR⁷R⁸;

R¹¹ and R¹² are each independently hydrogen, C(O)—(C₁-C₆)-alkyl,

SO₂—(C₁-C₆)-alkyl, or form together with the N-atom to which they are attached a 5-membered heteroaryl group optionally containing in addition to the N atom one, two or three nitrogen atoms and wherein the heteroaryl group is optionally substituted by halogen, (C₁-C₆)-alkyl or (CH₂)ₙ(C₃-C₆)-cycloalkyl;

n is 0, 1 or 2;

wherein the 5-membered heteroaryl group is selected from the group consisting of pyrrolyl, 2,5-dihydro-pyrrol-1-yl, imidazolyl, pyrazolyl, triazolyl, and tetrazolyl;

or a pharmaceutically acceptable acid addition salt thereof and a pharmaceutically acceptable carrier.

18. A process for preparation of a compound of formula I comprising reacting a compound of formula

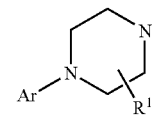

II with a compound of formula

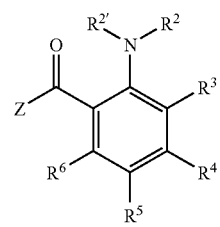

III to produce a compound of formula

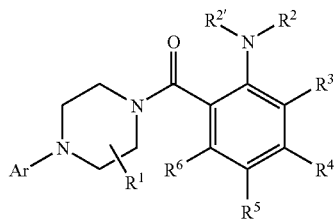

wherein Z is OH or halogen and the other substituents are as defined in claim 1.

19. A process for preparation of a compound of formula I comprising reacting a compound of formula

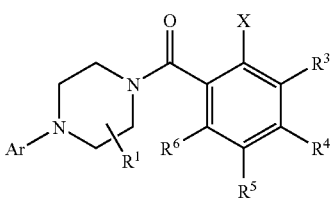

with a compound of formula

R²R²'NH to produce a compound of formula

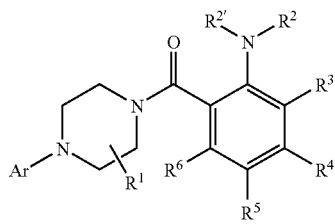

wherein X is halogen and the other substituents are as defined in claim 1.

20. A process for preparation of a compound of formula I comprising reacting a compound of formula

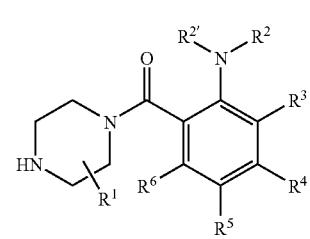

with a compound of formula

ArX to produce a compound of formula

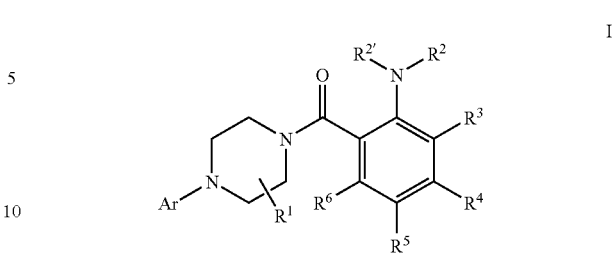

wherein X is halogen and the other substituents are as defined in claim 1.

21. A process for preparation of a compound of formula I comprising reacting a compound of formula

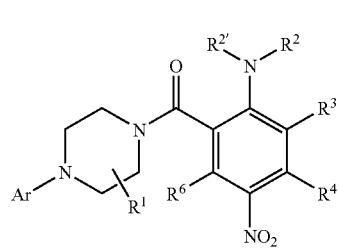

with hydrogen on Pd/C to produce a compound of formula

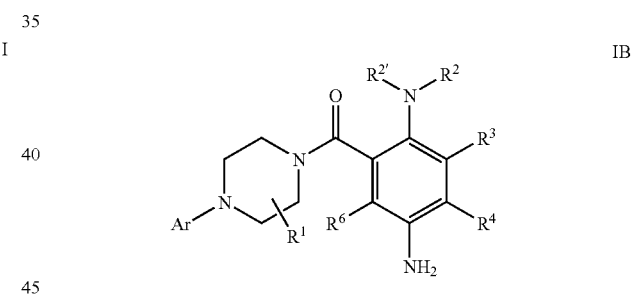

wherein the substituents are as defined in claim 1.

22. A process for preparation of a compound of formula I comprising reacting a compound of formula

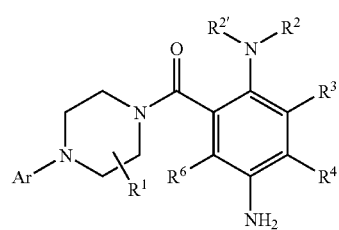

with a compound of formula

R¹⁴AX to produce a compound of formula

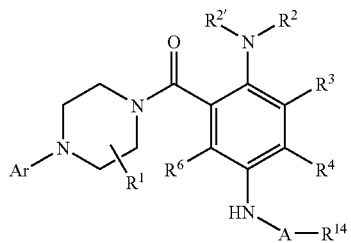

wherein X is halogen, A is —C(O)— or —SO$_2$—, R$^{14}$ is (C$_1$-C$_6$)-alkyl and the other substituents are as defined in claim 1.

23. A process for preparation of a compound of formula I comprising reacting a compound of formula

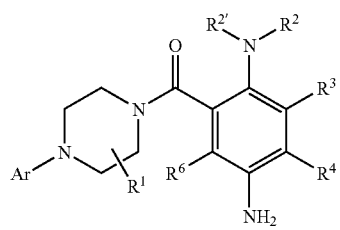

with a compound of formula

to produce a compound of formula

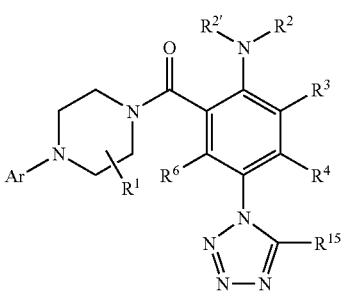

wherein R$^{15}$ is hydrogen halogen, (C$_1$-C$_6$)-alkyl, (C$_1$-C$_6$)-alkyl substituted by halogen or (C$_3$-C$_6$)-cycloalkyl and the other substituents are as defined in claim 1.

24. A process for preparation of a compound of formula I comprising reacting a compound of formula

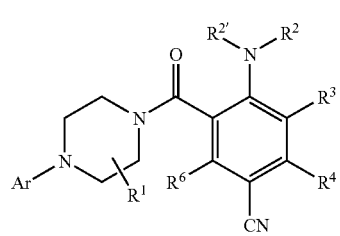

with a base to produce a compound of formula

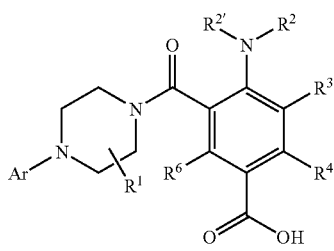

wherein the substituents are as defined in claim 1.

25. A process for preparation of a compound of formula I comprising reacting a compound of formula

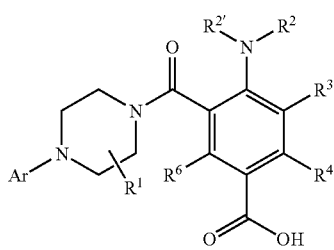

with a compound of formula

to produce a compound of formula

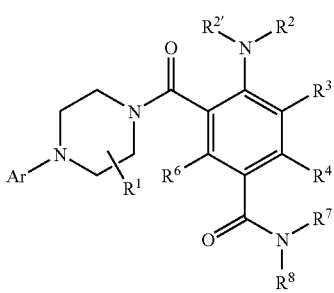

wherein the substituents are as defined in claim 1.

26. A process for preparation of a compound of formula I comprising reacting a compound of formula

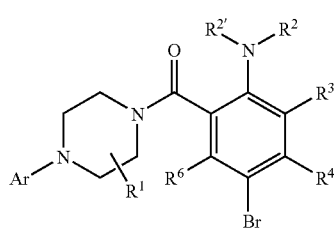

with a compound of formula

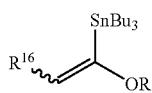

to produce a compound of formula

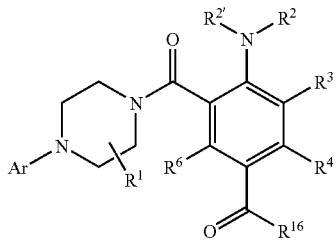

wherein R is $(C_1-C_6)$-alkyl, $R^{16}$ is $(C_1-C_6)$-alkyl or $(C_3-C_6)$-cycloalkyl and the other substituents are as defined in claim 1.

27. A process for preparation of a compound of formula I comprising reacting a compound of formula

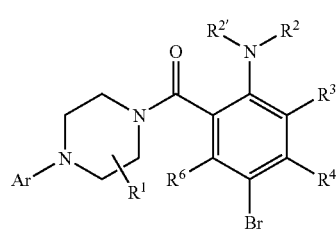

with a compound of formula

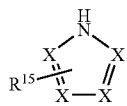

to produce a compound of formula

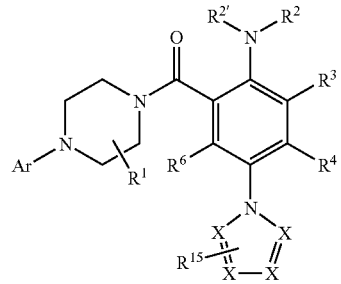

wherein X is CH or N and the heteroaryl ring is selected from the group consisting of imidazole, pyrazole or triazole, $R^{15}$ is hydrogen halogen, $(C_1-C_6)$-alkyl, $(C_1-C_6)$-alkyl substituted by halogen or $(C_3-C_6)$-cycloalkyl and the other substituents are as defined in claim 1.

28. A method of treating schizophrenia, comprising administering to a patient having schizophrenia a therapeutically effective amount of a compound of formula I

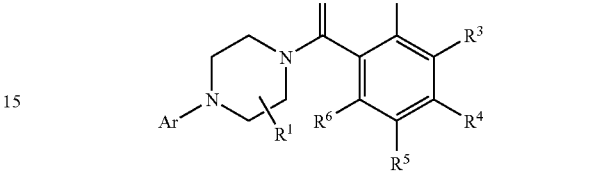

wherein

Ar is unsubstituted or substituted 6-membered heteroaryl containing one, two or three nitrogen atoms, and wherein the substituted aryl and the substituted heteroaryl groups are substituted by one or more substituents selected from the group consisting of hydroxy, halogen, $NO_2$, CN, $(C_1-C_6)$-alkyl, $(C_1-C_6)$-alkyl substituted by halogen, $(C_1-C_6)$-alkoxy, $(C_1-C_6)$-alkoxy substituted by halogen, $NR^7R^8$, $C(O)R^9$ and $SO_2R^{10}$;

$R^1$ is hydrogen or $(C_1-C_6)$-alkyl;

$R^2$ and $R^{2'}$ are each independently hydrogen,
$(CR_2)_n$-hydroxy wherein R is hydrogen or $C_1-C_6$)-alkyl,
$(C_1-C_6)$-alkyl,
$(C_2-C_6)$-alkenyl,
$(C_1-C_6)$-alkyl substituted by halogen,
$(CH_2)_n$—$(C_3-C_6)$-cycloalkyl,
$(CH_2)_n$-heterocycloalkyl,
$(CH_2)_n$—O—$(C_1-C_6)$-alkyl or
$(CH_2)_n$-aryl or $R^2$ and $R^{2'}$ form together with the N atom to which they are attached a heterocycloalkyl ring, optionally containing in addition to the N atom a further heteroatom selected from the group consisting of N, S and O, which rings are unsubstituted or substituted by $(CH_2)_n$-hydroxy, $(C_1-C_6)$-alkyl, $(C_1-C_6)$-alkoxy, $(CH_2)_n$—O—$(C_1-C_6)$-alkyl, or $R^2$ and $R^{2'}$ form together with the N atom to which they are attached a 5-membered heteroaryl group, optionally containing in addition to the N atom one, two or three further nitrogen atoms and wherein the heteroaryl group is optionally substituted by $(C_1-C_6)$-alkyl;

$R^3$, $R^4$ and $R^6$ are each independently hydrogen, halogen, $(C_1-C_6)$-alkyl or $(C_1-C_6)$-alkoxy;

$R^5$ is $NO_2$, CN, $C(O)R^9$, S—$(C_1-C_6)$-alkyl, $SO_2R^{10}$ or $NR^{11}R^{12}$;

$R^7$ and $R^8$ are each independently hydrogen, $(CH_2)_n$—$(C_3-C_6)$-cycloalkyl or
$(C_1-C_6)$-alkyl, or form together with the N atom to which they are attached a heterocycloalkyl ring, optionally containing in addition to the N atom a further heteroatom, selected from the group consisting of N, S and O;

$R^9$ is hydroxy, $(C_1-C_6)$-alkyl, $(C_3-C_6)$-cycloalkyl, $(C_1-C_6)$-alkoxy or $NR^7R^8$;

$R^{10}$ is $(C_1$-$C_6)$-alkyl, $(CH_2)_n$—$(C_3$-$C_6)$-cycloalkyl or $NR^7R^8$;

$R^{11}$ and $R^{12}$ are each independently hydrogen, $C(O)$—$(C_1$-$C_6)$-alkyl, $SO_2$—$(C_1$-$C_6)$-alkyl, or form together with the N-atom to which they are attached a 5-membered heteroaryl group optionally containing in addition to the N atom one, two or three nitrogen atoms and wherein the heteroaryl group is optionally substituted by halogen, $(C_1$-$C_6)$-alkyl or $(CH_2)_n(C_3$-$C_6)$-cycloalkyl;

n is 0, 1 or 2;

wherein the 5-membered heteroaryl group is selected from the group consisting of pyrrolyl, 2,5-dihydro-pyrrol-1-yl, imidazolyl, pyrazolyl, triazolyl, and tetrazolyl;

or a pharmaceutically acceptable acid addition salt thereof.

* * * * *